United States Patent
Frank et al.

(10) Patent No.: US 10,130,590 B2
(45) Date of Patent: Nov. 20, 2018

(54) METHODS OF TREATING CANCER WITH ATOVAQUONE-RELATED COMPOUNDS

(71) Applicant: DANA-FARBER CANCER INSTITUTE, INC., Boston, MA (US)

(72) Inventors: David Frank, Lexington, MA (US); Michael Xiang, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days.

(21) Appl. No.: 15/025,934

(22) PCT Filed: Sep. 30, 2014

(86) PCT No.: PCT/US2014/058203
§ 371 (c)(1),
(2) Date: Mar. 30, 2016

(87) PCT Pub. No.: WO2015/050844
PCT Pub. Date: Apr. 9, 2015

(65) Prior Publication Data
US 2016/0296480 A1    Oct. 13, 2016

Related U.S. Application Data

(60) Provisional application No. 61/885,164, filed on Oct. 1, 2013.

(51) Int. Cl.
| | |
|---|---|
| *A61K 31/122* | (2006.01) |
| *C12Q 1/6886* | (2018.01) |
| *G01N 33/574* | (2006.01) |
| *G01N 33/50* | (2006.01) |
| *A61K 45/06* | (2006.01) |

(52) U.S. Cl.
CPC ............ *A61K 31/122* (2013.01); *A61K 45/06* (2013.01); *C12Q 1/6886* (2013.01); *G01N 33/5017* (2013.01); *G01N 33/57496* (2013.01); *C12Q 2600/106* (2013.01); *C12Q 2600/158* (2013.01); *G01N 2800/52* (2013.01); *G01N 2800/7028* (2013.01)

(58) Field of Classification Search
CPC .. A61K 31/122; A61K 45/06; A61K 2300/00; C12Q 1/6886; C12Q 2600/106; C12Q 2600/158; G01N 2800/52; G01N 2800/7028; G01N 33/5017; G01N 33/57496
USPC ........................................................ 514/682
See application file for complete search history.

(56) References Cited

U.S. PATENT DOCUMENTS

| | | |
|---|---|---|
| 4,046,722 A | 9/1977 | Rowland |
| 4,046,784 A | 9/1977 | Gipson |
| 4,331,647 A | 5/1982 | Goldenberg |
| 4,348,376 A | 9/1982 | Goldenberg |
| 4,361,544 A | 11/1982 | Goldenberg |
| 4,444,744 A | 4/1984 | Goldenberg |
| 4,460,459 A | 7/1984 | Shaw et al. |
| 4,460,561 A | 7/1984 | Goldenberg |
| 4,468,457 A | 8/1984 | Goldenberg |
| 4,624,846 A | 11/1986 | Goldenberg |
| 4,671,958 A | 6/1987 | Rodwell |
| 4,814,470 A | 3/1989 | Colin |
| 4,818,709 A | 4/1989 | Primus |
| 4,857,653 A | 7/1989 | Colin |
| 4,924,011 A | 5/1990 | Denis |
| 5,290,957 A | 3/1994 | Correa |
| 5,292,921 A | 3/1994 | Correa |
| 5,332,567 A | 7/1994 | Goldenberg |
| 5,438,072 A | 8/1995 | Bobee |
| 5,443,953 A | 8/1995 | Hansen |
| 5,541,297 A | 7/1996 | Hansen |
| 5,587,493 A | 12/1996 | Bouchard |
| 5,601,825 A | 2/1997 | Hansen |
| 5,637,288 A | 6/1997 | Goldenberg |
| 5,677,427 A | 10/1997 | Goldenberg |
| 5,686,578 A | 11/1997 | Goldenberg |
| 5,698,178 A | 12/1997 | Goldenberg |
| 5,789,554 A | 8/1998 | Leung |
| 5,922,302 A | 7/1999 | Goldenberg |
| 6,187,287 B1 | 2/2001 | Leung |
| 6,319,500 B1 | 11/2001 | Goldenberg |

(Continued)

FOREIGN PATENT DOCUMENTS

| | | |
|---|---|---|
| EP | 0 253 738 | 1/1988 |
| WO | WO 91/17976 | 11/1991 |

(Continued)

OTHER PUBLICATIONS

Xiang et al., "Gene expression-based discovery of atovaquone as a STAT3 inhibitor and anticancer agent", Aug. 2016, Blood, 128(14), pp. 1845-1853.*
Kim et al., "Co-treatment with the anti-malarial drugs mefloquine and primaquine highly sensitizes drug-resistant cancer cells by increasing P-gp inhibition", 2013, Biochemical and Biophysical Research Communications, vol. 441, Issue 3, pp. 655-660. (Year: 2013).*
Alvarez et al., *Identification of a genetic signature of activated signal transducer and activator of transcription 3 in human tumors.* Cancer research 65(12):5054-5062 (2005).

(Continued)

*Primary Examiner* — My-Chau T. Tran
(74) *Attorney, Agent, or Firm* — Fish & Richardson P.C.

(57) ABSTRACT

Described herein are, inter alia, methods for decreasing the growth of a cancer cell, the method comprising delivering to a target cancer cell a growth-inhibitory amount of an atovaquone-related compound, wherein, prior to the delivery, an increased level of activation of the mTOR pathway in the cancer compared to a control level of activation of the mTOR pathway has been found. Also provided are methods for determining the susceptibility of cancer to treatment with an atovaquone-related compound and for assessing the success of therapy with such a compound.

47 Claims, 35 Drawing Sheets

Specification includes a Sequence Listing.

(56) References Cited

U.S. PATENT DOCUMENTS

| | | | |
|---|---|---|---|
| 2009/0148859 | A1 | 6/2009 | Liotta et al. |
| 2010/0137246 | A1 | 6/2010 | Hyde et al. |
| 2011/0144043 | A1 | 6/2011 | Frank et al. |
| 2011/0318336 | A1 | 12/2011 | Petricoin et al. |

FOREIGN PATENT DOCUMENTS

| | | |
|---|---|---|
| WO | WO 93/00928 | 1/1993 |
| WO | WO 93/00929 | 1/1993 |
| WO | WO 96/01815 | 1/1996 |
| WO | WO 96/39154 | 12/1996 |
| WO | WO 97/03211 | 1/1997 |
| WO | 2013/082105 | 6/2013 |

OTHER PUBLICATIONS

Aoki et al., *Inhibition of STAT3 signaling induces apoptosis and decreases survivin expression in primary effusion lymphoma*. Blood 101(4):1535-1542 (2003).
Baggish & Hill, *Antiparasitic agent atovaquone*. Antimicrobial agents and chemotherapy 46(5):1163-1173 (2002).
Barringer et al. *Blunt-end and single-strand ligations by Escherichia coli ligase: influence on an in vitro amplification scheme*, Gene 89(1):117-122 (1990).
Battle et al., *The natural product honokiol induces caspase dependent apoptosis in B-cell chronic lymphocytic leukemia (B-CLL) cells*. Blood 106(2):690-697 (2005).
Battle and Frank, *STAT1 mediates differentiation of chronic lymphocytic leukemia cells in response to Bryostatin 1*, Blood 102(8):3016-3024 (2003).
Beatty, et al. *CD40 agonists alter tumor stroma and show efficacy against pancreatic carcinoma in mice and humans*. Science, 331, 1612-1616 (2011).
Bollrath & Greten *IKK/NF-kappaB and STAT3 pathways: central signaling hubs in inflammation-mediated tumour promotion and metastasis*. EMBO Reports 10(12):1314-1319 (2009).
Bowman T, et al. *STATs in oncogenesis*. Oncogene 19(21):2474-2488 (2000).
Bowman T, et al. *Stat3-mediated Myc expression is required for Src transformation and PDGF-induced mitogenesis*. Proceedings of the National Academy of Sciences of the United States of America 98(13):7319-7324 (2001).
Brady et al. *Therapeutic and diagnostic uses of modified monoclonal antibodies*, Int. J. Rad. Oncol. Biol. Phys. 13(10):1535-1544 (1987).
Bromberg et al. *Stat3 as an oncogene*. Cell 98(3):295-303 (1999).
Burdelya L, et al. *Stat3 activity in melanoma cells affects migration of immune effector cells and nitric oxide-mediated antitumor effects*. J Immunol 174(7):3925-3931 (2005).
Catlett-Falcone R, et al. *Constitutive activation of Stat3 signaling confers resistance to apoptosis in human U266 myeloma cells*. Immunity 10(1):105-115 (1999).
Chehab et al. *Detection of specific DNA sequences by fluorescence amplification: a color complementation assay* Proc. Natl. Acad. Sci. USA, 86: 9178-9182 (1989).
Cheng et al. *Twist is transcriptionally induced by activation of STAT3 and mediates STAT3 oncogenic function*. Journal of biological chemistry 283(21):14665-14673 (2008).
Cho et al. *STAT3 mediates TGF-beta1-induced TWIST1 expression and prostate cancer invasion*. Cancer Letters 336(1):167-73 (2013).
Dechow et al. *Requirement of matrix metalloproteinase-9 for the transformation of human mammary epithelial cells by Stat3-C*. Proceedings of the National Academy of Sciences of the United States of America 101(29):10602-10607 (2004).
Devarajan & Huang, *STAT3 as a central regulator of tumor metastases*. Current Molecular Medicine 9(5):626-633 (2009).
Dhar, et al., *Chemotherapy of Theileria annulata infection with buparvaquone*, Vet. Rec., 119(25-26):635-636 (1986).

Epling-Burnette et al. *Inhibition of STAT3 signaling leads to apoptosis of leukemic large granular lymphocytes and decreased Mcl-1 expression*. Journal of Clinical Investigation 107(3):351-362 (2001).
Ferris, et al. *Tumor antigen-targeted, monoclonal antibody-based immunotherapy: clinical response, cellular immunity, and immunoescape*. J. Clin. Oncol.28, 4390-4399 (2010).
Frank DA *STAT3 as a central mediator of neoplastic cellular transformation*. Cancer letters 251(2):199-210 (2007).
Fukada T, et al. *STAT3 orchestrates contradictory signals in cytokine-induced G1 to S cell-cycle transition*. The EMBO journal 17(22):6670-6677 (1998).
Fukuda A, et al. *Stat3 and MMP7 contribute to pancreatic ductal adenocarcinoma initiation and progression*. Cancer cell 19(4):441-455 (2011).
Gibson et al., *A novel method for real time quantitative RT-PCR*, Genome Res., 10:995-1001 (1996).
Grandis JR, et al. *Constitutive activation of Stat3 signaling abrogates apoptosis in squamous cell carcinogenesis in vivo*. Proceedings of the National Academy of Sciences of the United States of America 97(8):4227-4232 (2000).
Gritsko T, et al. *Persistent activation of stat3 signaling induces survivin gene expression and confers resistance to apoptosis in human breast cancer cells*. Clinical Cancer Research: an Official Journal of the American Association for Cancer Research 12(1):11-19 (2006).
Grivennikov et al., *Immunity, inflammation, and cancer*. Cell 140(6):883-899 (2010).
Groner B, et al. *The function of Stat3 in tumor cells and their microenvironment*. Seminars in cell & developmental biology 19(4):341-350 (2008).
Guatelli et al. *Isothermal, in vitro amplification of nucleic acids by a multienzyme reaction modeled after retroviral replication*, Proc. Nat. Acad. Sci. USA 87(5):1874-1878 (1990).
Hanahan & Weinberg *Hallmarks of cancer: the next generation*. Cell 144(5):646-674 (2001).
Hedvat M, et al. *The JAK2 inhibitor AZD1480 potently blocks Stat3 signaling and oncogenesis in solid tumors*. Cancer cell 16(6):487-497 (2009).
Heid et al., *Real time quantitative PCR*, Genome Res., 10:986-994 (1996).
Heller, MJ, *DNA microarray technology: Devices, Systems, and Applications* Annual Review of Biomedical Engineering, 4:129-153 (2002).
Huang et al., *Stat3 induces oncogenic Skp2 expression in human cervical carcinoma cells*. Biochemical and biophysical research communications 418(1):186-190 (2012).
Hudson, et al., *Novel anti-malarial hydroxynaphthoquinones with potent broad spectrum anti-protozoal activity*, Parasitology, 90(Pt. 1):45-55 (1985).
Itoh et al. *Requirement of STAT3 activation for maximal collagenase-1 (MMP-1) induction by epidermal growth factor and malignant characteristics in T24 bladder cancer cells*. Oncogene 25(8):1195-1204 (2006).
Ivanov et al. *Cooperation between STAT3 and c-jun suppresses Fas transcription*. Molecular cell 7(3):517-528 (2001).
Iwama et al. *Dimeric RFX proteins contribute to the activity and lineage specificity of the interleukin-5 receptor alpha promoter through activation and repression domains*, Mol. Cell. Biol. 19(6):3940-3950 (1999).
Kanda et al. *STAT3 is constitutively activated and supports cell survival in association with survivin expression in gastric cancer cells*. Oncogene 23(28):4921-4929 (2004).
Karni et al., *Inhibition of pp60c-Src reduces Bcl-XL expression and reverses the transformed phenotype of cells overexpressing EGF and HER-2 receptors*. Oncogene 18(33):4654-4662 (1999).
Konnikova et al., *Signal transducer and activator of transcription 3 (STAT3) regulates human telomerase reverse transcriptase (hTERT) expression in human cancer and primary cells*. Cancer Research 65(15):6516-6520 (2005).
Konnikova et al. *Knockdown of STAT3 expression by RNAi induces apoptosis in astrocytoma cells*. BMC Cancer 3:23 (2003).

(56) References Cited

OTHER PUBLICATIONS

Kwoh et al. *Transcription-based amplification system and detection of amplified human immunodeficiency virus type 1 with a bead-based sandwich hybridization format*, Proc. Natl. Acad. Sci. USA 86(4):1173-1177 (1989).
Landegren et al. *A ligase-mediated gene detection technique* Science 241(4869):1077-1080 (1988).
Laplante, et al. *mTOR signaling in growth control and disease*, Cell. 149(2):274-293 (2012).
Laplante et al. *mTOR signaling at a glance*, J Cell Sci, 122:3589-3594 (2009).
Lim & Cao, *Structure, function, and regulation of STAT proteins.* Molecular BioSystems 2(11):536-550 (2006).
Little et al. *Inhibition of fatty acid synthase induces endoplasmic reticulum stress in tumor cells.* Cancer Research 67(3):1262-1269 (2007).
Liu et al. *Salermide up-regulates death receptor 5 expression through the ATF4-ATF3-CHOP axis and leads to apoptosis in human cancer cells.* Journal of Cellular and Molecular Medicine 16(7):1618-1628 (2012).
Lo et al. *Epidermal growth factor receptor cooperates with signal transducer and activator of transcription 3 to induce epithelial-mesenchymal transition in cancer cells via up-regulation of TWIST gene expression.* Cancer Research 67(19):9066-9076 (2007).
Lockhart et al. *Expression monitoring by hybridization to high-density oligonucleotide arrays* Nature Biotechnology, 14: 1675-1680 (1996).
Marotta et al. *The JAK2/STAT3 signaling pathway is required for growth of CD44(+)CD24(−) stem cell-like breast cancer cells in human tumors.* The Journal of Clinical Investigation 121(7):2723-2735 (2011).
Mata et al., *A hexameric phosphorothioate oligonucleotide telomerase inhibitor arrests growth of Burkitt's lymphoma cells in vitro and in vivo*, Appl. Pharmacol. 144(1):189-197 (1997).
Milligan et al., *Current concepts in antisense drug design*, J. Med. Chem. 36(14):1923-1937 (1993).
Mungrue et al. *CHAC1/MGC4504 is a novel proapoptotic component of the unfolded protein response, downstream of the ATF4-ATF3-CHOP cascade.* J Immunol 182(1):466-476 (2009).
Musolino, et al. *Immunoglobulin G fragment C receptor polymorphisms and clinical efficacy of trastuzumab-based therapy in patients with HER-2/neu positive metastatic breast cancer.* J. Clin. Oncol.26, 1789-1796 (2008).
Nelson et al. *Identification of unique STAT5 targets by chromatin immunoprecipitation-based gene identification.* J. Biol. Chem. 279:54724-54730 (2004).
Nelson et al. *Nifuroxazide inhibits survival of multiple myeloma cells by directly inhibiting STAT3.* Blood 112(13):5095-5102 (2008).
Nelson et al. *The STAT5 Inhibitor Pimozide Displays Efficacy in Models of Acute Myelogenous Leukemia Driven by FLT3 Mutations.* Genes & Cancer 3(7-8):503-511 (2012).
Niu et al. *Signal transducer and activator of transcription 3 is required for hypoxia-inducible factor-1alpha RNA expression in both tumor cells and tumor-associated myeloid cells.* Molecular Cancer Research: MCR 6(7):1099-1105 (2008).
Niu et al. *Role of Stat3 in regulating p53 expression and function.* Molecular and Cellular Biology 25(17):7432-7440 (2005).
Niu et al. *Overexpression of a dominant-negative signal transducer and activator of transcription 3 variant in tumor cells leads to production of soluble factors that induce apoptosis and cell cycle arrest.* Cancer Research 61(8):3276-3280 (2001).
Oyadomari & Mori, *Roles of CHOP/GADD153 in endoplasmic reticulum stress.* Cell Death and Differentiation 11(4):381-389 (2004).
Pakala et al. *MTA 1 promotes STAT3 transcription and pulmonary metastasis in breast cancer.* Cancer research, 73(12):3761-70 (2013).
Pastan et al. *Immunotoxins*, Cell 47(5):641-648 (1986).
Puthier et al. *IL-6 up-regulates mcl-1 in human myeloma cells through JAK / STAT rather than ras / MAP kinase pathway.* European Journal of Immunology 29(12):3945-3950 (1999).
Rao et al. *Treatment with panobinostat induces glucose-regulated protein 78 acetylation and endoplasmic reticulum stress in breast cancer cells.* Molecular Cancer Therapeutics 9(4):942-952 (2010).
Samstag et al., *Synthesis and properties of new antisense oligodeoxynucleotides containing benzylphosphonate linkages*, Antisense Nucleic Acid Drug Dev 6(3):153-156 (1996).
Sanchez et al. *Induction of the endoplasmic reticulum stress protein GADD153/CHOP by capsaicin in prostate PC-3 cells: a microarray study.* Biochemical and Biophysical Research Communications 372(4):785-791 (2008).
Satchi-Fainaro et al., *Inhibition of vessel permeability by TNP-470 and its polymer conjugate, caplostatin*, Cancer Cell 7(3):251-261 (2005).
Schardt et al. *Activation of the unfolded protein response is associated with favorable prognosis in acute myeloid leukemia.* Clinical cancer research: an official journal of the American Association for Cancer Research 15(11):3834-3841 (2009).
Schena et al. *Parallel human genome analysis: Microarray-based expression monitoring of 1000 genes* Proc. Natl. Acad. Sci. USA, 93(20):10614-10619 (1996).
Scott et al. *Antibody therapy of cancer*, Nature Reviews Cancer 12(4):278-287 (2012).
Scott, et al. *A Phase I clinical trial with monoclonal antibody ch806 targeting transitional state and mutant epidermal growth factor receptor.* Proc. Natl Acad. Sci. USA, 104:4071-4076 (2007).
Seo et al. *Leukotriene B4 receptor-2 promotes invasiveness and metastasis of ovarian cancer cells through signal transducer and activator of transcription 3 (STAT3)-dependent up-regulation of matrix metalloproteinase 2.* Journal of Biological Chemistry, 287(17):13840-13849 (2012).
Sherry et al. *STAT3 is required for proliferation and maintenance of multipotency in glioblastoma stem cells.* Stem Cells 27(10):2383-2392 (2009).
Shirogane et al. *Synergistic roles for Pim-1 and c-Myc in STAT3-mediated cell cycle progression and antiapoptosis.* Immunity 11(6):709-719 (1999).
Sinibaldi et al. *Induction of p21WAF1/CIP1 and cyclin D1 expression by the Src oncoprotein in mouse fibroblasts: role of activated STAT3 signaling.* Oncogene 19(48):5419-5427 (2000).
Sofer et al. *Regulation of mTOR and cell growth in response to energy stress by REDD1*, Mol. Cell. Biol. 25(14):5834-5845 (2005).
Southern et al., *Detection of specific sequences among DNA fragments separated by gel electrophoresis*, J. Mol. Biol. 98(3):503-517 (1975).
Strauss-Soukup et al., *Effects of neutralization pattern and stereochemistry on DNA bending by methylphosphonate substitutions*, Biochemistry 36(29):8692-8698 (1997).
Subramanian et al. *Gene set enrichment analysis: a knowledge-based approach for interpreting genome-wide expression profiles*, Proc Natl Acad Sci USA 102(43):15545-15550 (2005).
Tsuyada A, et al. *CCL2 mediates cross-talk between cancer cells and stromal fibroblasts that regulates breast cancer stem cells.* Cancer research 72(11):2768-2779 (2012).
Turkson J. et al. *Requirement of Ras/Rac1-mediated p38 and c-Jun N-terminal kinase signaling for Stat3 transcriptional activity induced by the Src oncoprotein.* Mol. Cell. Biol. 19:7519-28 (1999).
Vitetta et al. *Redesigning nature's poisons to create anti-tumor reagents*, Science 238(4830):1098- 1104, (1987).
Walker et al. *STAT5 outcompetes STAT3 to regulate the expression of the oncogenic transcriptional modulator BCL6.* Molecular and Cellular Biology 33(15):2879-90 (2013).
Walker et al. *Reciprocal effects of STAT5 and STAT3 in breast cancer.* Molecular Cancer Research : MCR 7(6):966-976 (2009).
Walker et al., *Microtubule-targeted chemotherapeutic agents inhibit signal transducer and activator of transcription 3 (STAT3) signaling.* Molecular Pharmacology 78(5):903-908 (2010).
Watson et al. *Technology for microarray analysis of gene expression*, Curr Opin Biotechnol 9(6):609-14 (1998).
Weiner, et al., *Monoclonal antibodies: versatile platforms for cancer immunotherapy.* Nature Rev. Immunol.1D(5):317-327 (2010).
Wu and Wallace, *The ligation amplification reaction (LAR)—amplification of specific DNA sequences using sequential rounds of template-dependent ligation*, Genomics 4(4):560 (1989).

(56) References Cited

OTHER PUBLICATIONS

Wu et al. *Gene expression profiling of human breast tissue samples using SAGE-Seq*, Genome Res. 20(12):1730-9. 2 (2010).

Xie et al. *Stat3 activation regulates the expression of matrix metalloproteinase-2 and tumor invasion and metastasis.* Oncogene 23(20):3550-3560 (2004).

Xie et al. *Activation of stat3 in human melanoma promotes brain metastasis.* Cancer Research 66(6):3188-3196 (2006).

Xiong et al. *Roles of STAT3 and ZEB1 proteins in E-cadherin downregulation and human colorectal cancer epithelial-mesenchymal transition.* Journal of Biological Chemistry 287(8):5819-5832 (2012).

Xu et al. *Targeting Stat3 blocks both HIF-1 and VEGF expression induced by multiple oncogenic growth signaling pathways.* Oncogene 24(36):5552-5560 (2005).

Yadav et al. *IL-6 promotes head and neck tumor metastasis by inducing epithelial-mesenchymal transition via the JAKSTAT3-SNAIL signaling pathway.* Molecular Cancer Research 9(12):1658-1667 (2011).

Yahata et al. *Nuclear translocation of phosphorylated STAT3 is essential for vascular endothelial growth factor-induced human dermal microvascular endothelial cell migration and tube formation.* Journal of biological chemistry 278(41):40026-40031 (2003).

Yamashita et al. *Zinc transporter LIVI controls epithelial-mesenchymal transition in zebrafish gastrula organizer.* Nature 429(6989):298-302 (2004).

Yang et al. *Tumor-associated macrophages regulate murine breast cancer stem cells through a novel paracrine EGFR/Stat3/Sox-2 signaling pathway.* Stem Cells 31(2):248-258(2013).

Yokogami et al. *Serine phosphorylation and maximal activation of STAT3 during CNTF signaling is mediated by the rapamycin target mTOR.* Current Biology 10(1):47-50 (2000).

Zhang et al. *Loss of Tsc1/Tsc2 activates mTOR and disrupts PI3K-Akt signaling through downregulation of PDGFR*, J Clin Invest. 112(8):1223-1233 (2003).

Zhang et al. *STAT3 induces transcription of the DNA methyltransferase 1 gene (DNMT1) in malignant T lymphocytes.* Blood 108(3):1058-1064 (2006).

Zhou, J. et al., *Atovaquone Derivatives as Potent Cytotoxic and Apoptosis Inducing Agents*, Bioorg Med Chem Lett. (Sep. 1, 2009), 19(17):5091-5094 (abstract).

Ghosh, AK et al., *Circulating Microvesicles in B-Cell Chronic Lymphocytic Leukemia Can Stimulate Marrow Stromal Cells: Implications for Disease Progression*, Blood (Mar. 4, 2010) 115(9):1755-1764 (p. 2, $2^{nd}$ para; p. 4, $4^{th}$ para).

International Search Report and Written Opinion issued by ISA/US for PCT/US2014/058203 (dated Feb. 2, 2015).

* cited by examiner

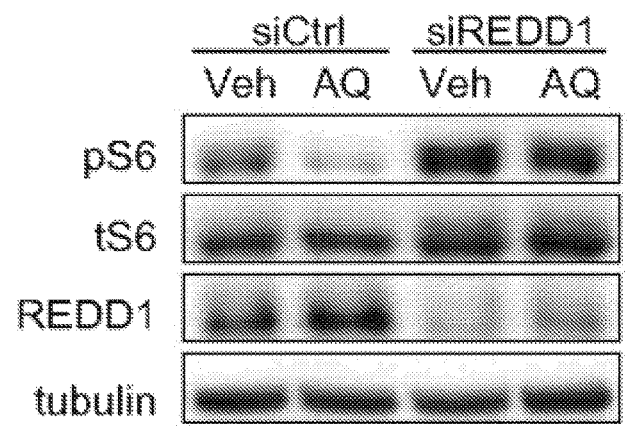
Fig. 31
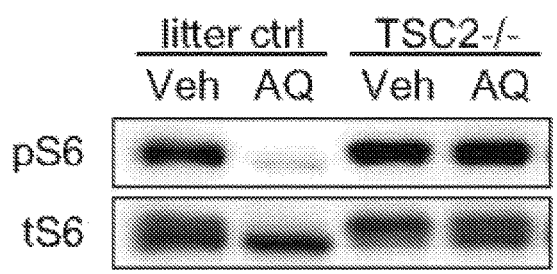 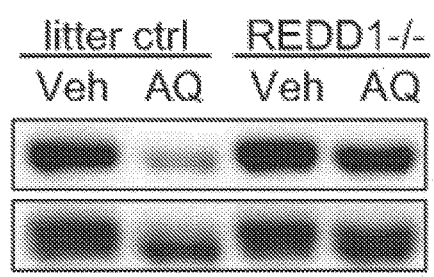
Fig. 32                    Fig. 33

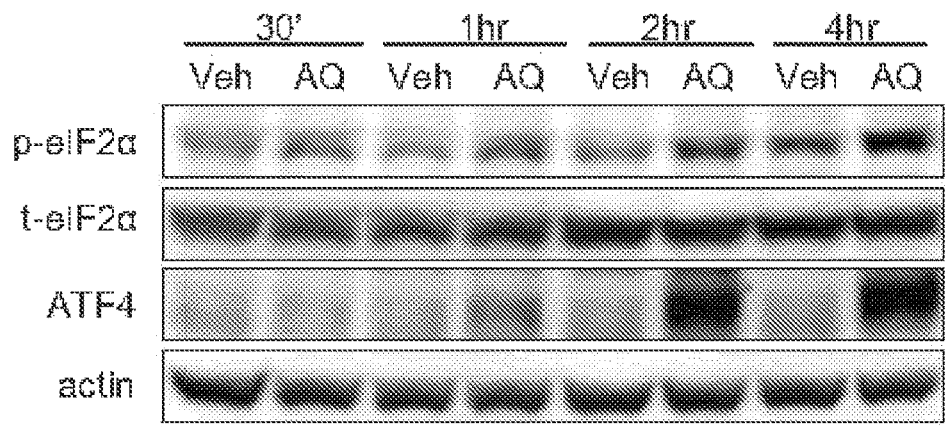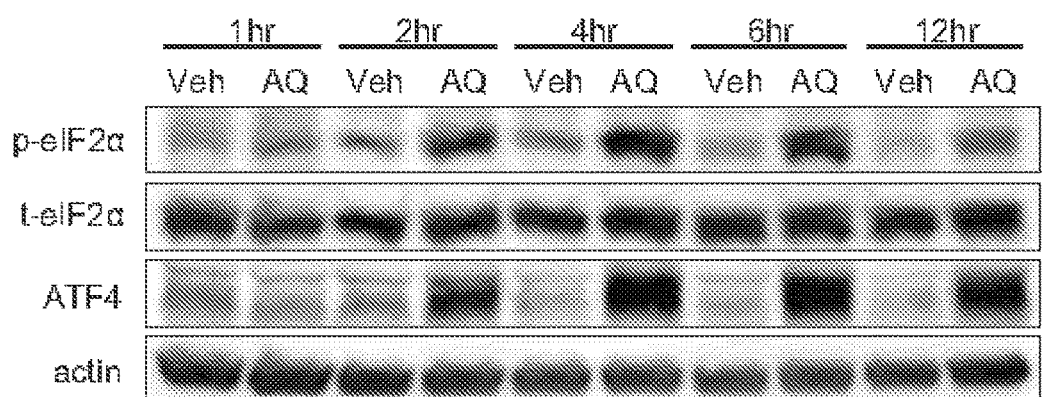
Fig. 36

METHODS OF TREATING CANCER WITH ATOVAQUONE-RELATED COMPOUNDS

STATEMENT REGARDING FEDERALLY SPONSORED RESEARCH OR DEVELOPMENT

This invention was made with government support under grants R01-CA160979 and F30 CA165740-01 awarded by the National Institutes of Health. The United States government has certain rights in the invention.

TECHNICAL FIELD

This disclosure relates generally to the field of molecular biology and, more particularly, to cancer.

BACKGROUND

The transcription factor, signal transducer and activator of transcription 3 (STAT3), is activated inappropriately in a wide range of human cancers, and drives the malignant behavior of cancer cells. Extensive published evidence indicates that inhibition of STAT3 can have a therapeutic effect on cancer cells, while having minimal toxicity to normal tissue. Further, the mTOR pathway is known to be involved in cancer cell growth and survival (see, e.g., Laplante et al. (2012), su Laplante, M. et al. Cell. 2012 Apr. 13; 149(2): 274-293). Although evidence suggests that inhibiting STAT3 or mTOR would be an effective form of cancer therapy (by itself or in conjunction with chemotherapy, immunotherapy, targeted therapy, and/or radiation therapy), it has been extremely difficult to translate these approaches into the clinic.

SUMMARY

As follows from the Background section above, there is a need in the art for novel compositions and methods of inhibiting STAT3 and/or mTOR for the successful treatment of cancer. It is presently discovered that the compound atovaquone inhibits the STAT3 and mTOR signaling pathways, as well as activates the eIF2α/ATF4 pathway, and can be used to inhibit cancer cell growth and prolong survival and prevent relapse in patients being treated with atovaquone. These and other related benefits are presently provided, and discussed in detail below.

In some aspects, provided herein is a method of decreasing the growth of a cancer cell. The method can include delivering to a target cancer cell a growth-inhibitory amount of an atovaquone-related compound, wherein, prior to the delivery, an increased level of activation of the mammalian target of rapamycin (mTOR) pathway in the cancer compared to a control level of activation of the mTOR pathway has been found. In some aspects of the method, prior to the delivery, an increased level of activation of the signal transducer and activator of transcription 3 (STAT3) pathway in the cancer compared to a control level of activation of the STAT3 pathway has been found. In some aspects of the method, the target cancer cell is in a mammalian subject (e.g., a human subject). In some aspects of the method, the delivery to the target cell can include administration of the atovaquone-related compound to the subject. In some aspects of the method, the level of activation of the mTOR pathway in the cancer was detected in a test sample of or from one or more test cells from the cancer and the control level of activation of the mTOR pathway was detected in a control sample of or from one or more control cells. In some aspects of the method, the level of activation of the mTOR pathway in the cancer was detected in microvesicles or exosomes obtained from a test sample of a body fluid of a subject with the cancer and the control level of activation of the mTOR pathway was detected in a microvesicles or exosomes obtained from a control sample of the body fluid. In some aspects of the method, the level of activation of the STAT3 pathway in the cancer was detected in a test sample of or from one or more test cells from the cancer and the control level of activation of the STAT3 pathway was detected in a control sample of or from one or more control cells. In some aspects of the method, the level of activation of the STAT3 pathway in the cancer was detected in microvesicles or exosomes obtained from a test sample of a body fluid of a subject with the cancer and the control level of activation of the STAT3 pathway was detected in a microvesicles or exosomes obtained from a control sample of the body fluid. In some aspects of the method, the body fluid can be blood, lymph, urine, cerebrospinal fluid (CSF), ascites, or pleural fluid. In some aspects of the method, the compound is atovaquone. In some aspects of the method, the compound is buparvaquone or 2-(4-(trans-decahydronaphth-2-yl)butyl)-3-hydoxy-1,4-naphthoquinone (TDBHN). In some aspects of the method, the compound is atovaquone and the growth-inhibitory amount of the atovaquone is in a range of about 10 to about 40 mg/kg per day.

In some aspects, the compound is a substituted hydroxynaphthoquinone compound. In some aspects of the above methods, the substituted hydroxynaphthoquinone is a compound of formula (I):

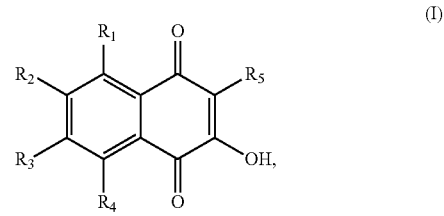

wherein each of $R_1$, $R_2$, $R_3$, and $R_4$, independently, is H or $C_1$-$C_{10}$ alkyl; $R_5$ is $C_1$-$C_{10}$ alkyl optionally substituted with $C_3$-$C_{20}$ cycloalkyl, or $C_3$-$C_{20}$ cycloalkyl optionally substituted with $C_1$-$C_{10}$ alkyl or aryl; and each of $C_3$-$C_{20}$ cycloalkyl and aryl, independently, is optionally substituted with halogen or $C_1$-$C_{10}$ alkyl. In some aspects, $R_5$ is cyclohexyl substituted with aryl, in which aryl is substituted with $C_1$. In some aspects, $R_5$ is methyl substituted with cyclohexyl, in which cycloalkyl is substituted with t-butyl or n-butyl substituted with decahydronaphthyl. In some aspects, the compound of formula (I) is atovaquone, its isomer, buparvaquone, or TDBHN. In some aspects of the method, the substituted hydroxynaphthoquinone is a compound of formula (II):

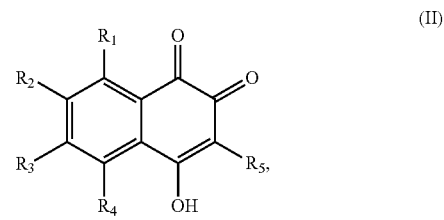

wherein each of $R_1$, $R_2$, $R_3$, and $R_4$, independently, is H or $C_1$-$C_{10}$ alkyl; $R_5$ is $C_1$-$C_{10}$ alkyl optionally substituted with $C_3$-$C_{20}$ cycloalkyl, or $C_3$-$C_{20}$ cycloalkyl optionally substituted with $C_1$-$C_{10}$ alkyl or aryl; and each of $C_3$-$C_{20}$ cycloalkyl and aryl, independently, is optionally substituted with halogen or $C_1$-$C_{10}$ alkyl. In some aspects, $R_5$ is cyclohexyl. In some aspects of the method, the compound of formula (II) is parvaquone.

Also provided herein is a method of determining the susceptibility of a cancer in a subject to the growth-inhibitory effect of an atovaquone-related compound. The method can include assessing the level of activation of the mTOR pathway in a test sample from the subject, identifying the cancer as likely to be susceptible to the growth-inhibitory effect of the atovaquone-related compound if an increased level of activation of the mTOR pathway is detected in the test sample compared to a control level of activation of the mTOR pathway, and identifying the cancer as less likely to be susceptible to the growth-inhibitory effect of the atovaquone-related compound if an increased level activation of the mTOR pathway is not detected in the test sample compared to a control level of activation of the mTOR pathway than if an increased level of activation of the mTOR pathway is detected in the test sample compared to a control level of activation of the mTOR pathway. In some aspects of the method, the method further includes assessing the level of activation of the STAT3 pathway in the test sample or a second test sample from the subject, identifying the cancer as likely to be susceptible to the growth-inhibitory effect of the atovaquone-related compound if an increased level of activation of the STAT3 is detected in the test sample or the second test sample compared to a control level of activation of the STAT3 pathway, and identifying the cancer as less likely to be susceptible to the growth-inhibitory effect of the atovaquone-related compound if an increased level of activation of the STAT3 pathway is not detected in the test sample or the second test sample compared to a control level of activation of the STAT3 pathway than if an increased level of activation of the STAT3 pathway is detected in the test sample or the second test sample compared to a control level of activation of the mTOR pathway. In some aspects of the method, the test sample is a sample of or from one or more cancer cells from the subject. In some aspects of the method, the test sample includes microvesicles or exosomes obtained from a body fluid of the subject. In some aspects of the method, the second test sample is a sample of or from one or more cancer cells from the subject. In some aspects of the method, the second test sample comprises microvesicles or exosomes obtained from a body fluid of the subject. In some aspects of the method, the body fluid can be blood, lymph, urine, cerebrospinal fluid (CSF), ascites, or pleural fluid. In some aspects of the method, the method further includes administering an atovaquone-related compound to the subject if the increased level activation of the mTOR pathway is detected in the test sample. In some aspects of the method, the method further includes administering an atovaquone-related compound to the subject if the increased level of activation of the mTOR pathway is detected in the test sample, if the increased level of activation of the STAT3 pathway is detected in the test sample or the second test sample, or if the increased level activation of the mTOR pathway is detected in the test sample and the increased level of activation of the STAT3 pathway is detected in the test sample or the second test sample. In some aspects of the method, the compound is atovaquone. In some aspects of the method, the compound is buparvaquone or 2-(4-(trans-decahydronaphth-2-yl)butyl)-3-hydoxy-1,4-naphthoquinone (TDBHN). In some aspects, the compound is a substituted hydroxynaphthoquinone compound. In some aspects of the above methods, the substituted hydroxynaphthoquinone is a compound of formula (I):

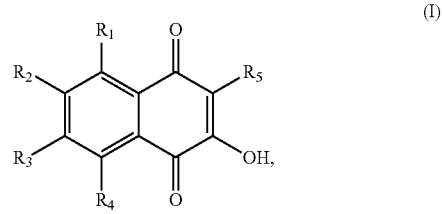

wherein each of $R_1$, $R_2$, $R_3$, and $R_4$, independently, is H or $C_1$-$C_{10}$ alkyl; $R_5$ is $C_1$-$C_{10}$ alkyl optionally substituted with $C_3$-$C_{20}$ cycloalkyl, or $C_3$-$C_{20}$ cycloalkyl optionally substituted with $C_1$-$C_{10}$ alkyl or aryl; and each of $C_3$-$C_{20}$ cycloalkyl and aryl, independently, is optionally substituted with halogen or $C_1$-$C_{10}$ alkyl. In some aspects, $R_5$ is cyclohexyl substituted with aryl, in which aryl is substituted with $C_1$. In some aspects, $R_5$ is methyl substituted with cyclohexyl, in which cycloalkyl is substituted with t-butyl or n-butyl substituted with decahydronaphthyl. In some aspects, the compound of formula (I) is atovaquone, its isomer, buparvaquone, or TDBHN. In some aspects of the method, the substituted hydroxynaphthoquinone is a compound of formula (II):

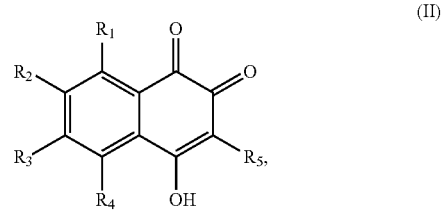

wherein each of $R_1$, $R_2$, $R_3$, and $R_4$, independently, is H or $C_1$-$C_{10}$ alkyl; $R_5$ is $C_1$-$C_{10}$ alkyl optionally substituted with $C_3$-$C_{20}$ cycloalkyl, or $C_3$-$C_{20}$ cycloalkyl optionally substituted with $C_1$-$C_{10}$ alkyl or aryl; and each of $C_3$-$C_{20}$ cycloalkyl and aryl, independently, is optionally substituted with halogen or $C_1$-$C_{10}$ alkyl. In some aspects, $R_5$ is cyclohexyl. In some aspects of the method, the compound of formula (II) is parvaquone.

Also provided herein is a method of assessing the success of cancer cell growth inhibitory therapy with an atovaquone-related compound in a subject. The method can include assessing the level of activation of the mTOR pathway in a test sample from a subject that has been treated with the compound, identifying the treatment as having been successful if the level of activation of the mTOR pathway in the test sample is lower than the level of activation of the mTOR pathway in a control sample, and not identifying the treatment as having been successful if the level of activation of the mTOR pathway in the test sample is not lower than the level of activation of the mTOR pathway in a control sample. In some aspects of the method, the method further includes assessing the level of activation of the STAT3 pathway in the test sample or a second test sample from the subject that has been treated with the compound, identifying the treatment as having been successful if the level of activation of the STAT3 pathway in the test sample or the second test sample is lower than the level of activation of the STAT3 pathway in a control sample or a second control sample, and not identifying the treatment as having been successful if the level of activation of the STAT3 pathway in the test sample or the second test sample is not lower than the level of activation of the STAT3 pathway in the control sample or the second control sample. In some aspects of the method, the test sample is a sample of or from one or more cancer cells from the subject. In some aspects of the method, the test sample comprises microvesicles or exosomes obtained from a body fluid of the subject. In some aspects of the method, the second test sample is a sample of or from one or more cancer cells from the subject. In some aspects of the method, the second sample comprises microvesicles or exosomes obtained from a body fluid of the subject. In some aspects of the method, the control sample or the second control sample was obtained from the subject prior to the treatment with the atovaquone-related compound. In some aspects of the method, the control sample or the second control sample is a sample of or from one or more cancer cells from the subject. In some aspects of the method, the control sample or second control sample includes microvesicles or exosomes obtained from a body fluid of the subject. In some aspects of the method, the body fluid can be blood, lymph, urine, cerebrospinal fluid (CSF), ascites, or pleural fluid. In some aspects of the method, the subject is a mammalian subject. In some aspects of the method, the mammalian subject is a human subject. In some aspects of the method, the compound is atovaquone. In some aspects of the method, the compound is buparvaquone or 2-(4-(trans-decahydronaphth-2-yl)butyl)-3-hydoxy-1,4-naphthoquinone (TDBHN). In some aspects, the compound is a substituted hydroxynaphthoquinone compound. In some aspects of the above methods, the substituted hydroxynaphthoquinone is a compound of formula (I):

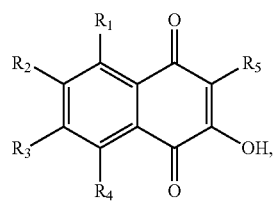

wherein each of $R_1$, $R_2$, $R_3$, and $R_4$, independently, is H or $C_1$-$C_{10}$ alkyl; $R_5$ is $C_1$-$C_{10}$ alkyl optionally substituted with $C_3$-$C_{20}$ cycloalkyl, or $C_3$-$C_{20}$ cycloalkyl optionally substituted with $C_1$-$C_{10}$ alkyl or aryl; and each of $C_3$-$C_{20}$ cycloalkyl and aryl, independently, is optionally substituted with halogen or $C_1$-$C_{10}$ alkyl. In some aspects, $R_5$ is cyclohexyl substituted with aryl, in which aryl is substituted with $C_1$. In some aspects, $R_5$ is methyl substituted with cyclohexyl, in which cycloalkyl is substituted with t-butyl or n-butyl substituted with decahydronaphthyl. In some aspects, the compound of formula (I) is atovaquone, its isomer, buparvaquone, or TDBHN. In some aspects of the method, the substituted hydroxynaphthoquinone is a compound of formula (II):

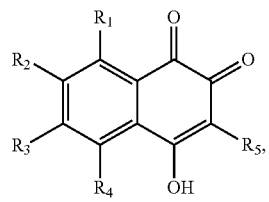

wherein each of $R_1$, $R_2$, $R_3$, and $R_4$, independently, is H or $C_1$-$C_{10}$ alkyl; $R_5$ is $C_1$-$C_{10}$ alkyl optionally substituted with $C_3$-$C_{20}$ cycloalkyl, or $C_3$-$C_{20}$ cycloalkyl optionally substituted with $C_1$-$C_{10}$ alkyl or aryl; and each of $C_3$-$C_{20}$ cycloalkyl and aryl, independently, is optionally substituted with halogen or $C_1$-$C_{10}$ alkyl. In some aspects, $R_5$ is cyclohexyl. In some aspects of the method, the compound of formula (II) is parvaquone.

Also provided herein is a method of treating cancer in a patient. The method can include administering a therapeutically effective amount of an atovaquone-related compound to a patient in need thereof; and, after the administration, monitoring the level of activation of the mTOR pathway in a test sample or two more serial test samples from the patient. In some aspects of the method, the method further includes, after the administration, monitoring the level of activation of the STAT3 pathway in the test sample, the two or more serial test samples, a second test sample or a second set of two or more serial test samples from the patient. In some aspects of the method, the method further includes continuing the treatment if the level of activation of the mTOR pathway in the test sample or the two or more serial test samples is decreased relative to its level of activation in a control sample obtained from the patient prior to treatment. In some aspects of the method, the method further includes continuing the treatment if the level of activation of the STAT3 pathway in the test sample, the two or more serial test samples, the second test sample, or the second set of two or more serial test samples is decreased relative to its level of activation in a control sample obtained from the patient prior to treatment. In some aspects of the method, the test sample or each of the two or more serial test samples is a sample of or from one or more cancer cells from the subject. In some aspects of the method, the test sample or each of the two more serial test samples comprises microvesicles or exosomes obtained from a body fluid of the subject. In some aspects of the method, the second test sample or each of the second set of two or more serial test samples comprises a sample of or from one or more cancer cells from the subject. In some aspects of the method, the second test sample or each of the second set of two or more serial test samples can include microvesicles or exosomes obtained from a body fluid of the subject. In some aspects of the method, the body fluid can be blood, lymph, urine, cerebrospinal fluid (CSF), ascites, or pleural fluid. In some aspects of the method, the patient is a mammalian subject. In some aspects of the method, the mammalian subject is a human subject. In some aspects of the method, the compound is atovaquone. In some aspects of the method, the compound is buparvaquone or 2-(4-(trans-decahydronaphth-2-yl)butyl)-3-hydoxy-1,4-naphthoquinone (TDBHN). In some aspects of the method, the therapeutically effective amount of atovaquone is in a range of about 10 to about 40 mg/kg per day. In some aspects, the compound is a substituted hydroxynaphthoquinone compound. In some aspects of the above methods, the substituted hydroxynaphthoquinone is a compound of formula (I):

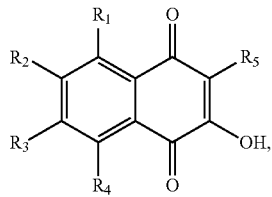

wherein each of $R_1$, $R_2$, $R_3$, and $R_4$, independently, is H or $C_1$-$C_{10}$ alkyl; $R_5$ is $C_1$-$C_{10}$ alkyl optionally substituted with $C_3$-$C_{20}$ cycloalkyl, or $C_3$-$C_{20}$ cycloalkyl optionally substituted with $C_1$-$C_{10}$ alkyl or aryl; and each of $C_3$-$C_{20}$ cycloalkyl and aryl, independently, is optionally substituted with halogen or $C_1$-$C_{10}$ alkyl. In some aspects, $R_5$ is cyclohexyl substituted with aryl, in which aryl is substituted with $C_1$. In some aspects, $R_5$ is methyl substituted with cyclohexyl, in which cycloalkyl is substituted with t-butyl or n-butyl substituted with decahydronaphthyl. In some aspects, the compound of formula (I) is atovaquone, its isomer, buparvaquone, or TDBHN. In some aspects of the method, the substituted hydroxynaphthoquinone is a compound of formula (II):

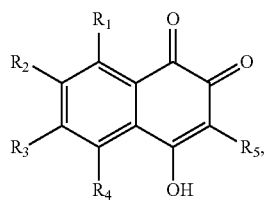

wherein each of $R_1$, $R_2$, $R_3$, and $R_4$, independently, is H or $C_1$-$C_{10}$ alkyl; $R_5$ is $C_1$-$C_{10}$ alkyl optionally substituted with $C_3$-$C_{20}$ cycloalkyl, or $C_3$-$C_{20}$ cycloalkyl optionally substituted with $C_1$-$C_{10}$ alkyl or aryl; and each of $C_3$-$C_{20}$ cycloalkyl and aryl, independently, is optionally substituted with halogen or $C_1$-$C_{10}$ alkyl. In some aspects, $R_5$ is cyclohexyl. In some aspects of the method, the compound of formula (II) is parvaquone. In some aspects of the method, the method can further include administering an additional therapy to the patient. In some aspects of the method, the additional therapy is chemotherapy, immunotherapy, targeted therapy, and/or radiation therapy.

In any of the above-described methods, the level of activation of the mTOR pathway can be determined by detecting the level of phosphorylation of one or more polypeptides selected from the group consisting of mTOR, ribosomal protein S6, S6 kinase, 4E-BP1, eIF2α.

In any of the above-described methods in which the level of activation of the STAT3 pathway is determined, the level of activation of the STAT3 pathway can be determined by detecting the level of one or more of the following markers: STAT3 phosphorylation, nuclear localization of STAT3, STAT3 DNA binding, STAT3-dependent gene expression, and the level of autophosphorylation of JAK family kinases. In some aspects of the method, detecting the level of STAT3 phosphorylation can include determining the level of phosphorylation of tyrosine 705 of human STAT3. In some aspects of the method, detecting STAT3-dependent gene expression comprises determining the expression level of one or more of STAT3 regulated genes encoding polypeptides selected from the group consisting of: myeloid cell leukemia sequence 1 (BCL2-related) (MCL1), jun B proto-oncogene (JUNB), B-cell CLL/lymphoma 6 (BCL6), nuclear factor, interleukin 3 regulated (NFIL3), calpain 2, (m/II) large subunit (CAPN2), early growth response 1 (EGR1), vascular endothelial growth factor A (VEGF), protein tyrosine phosphatase type IVA, member 1 (PTP-CAAX1), Kruppel-like factor 4 (KLF4), exostosin glycosyltransferase 1 (EXT1), Niemann-Pick disease, type C1 (NPC1), p21 protein (Cdc42/Rac)-activated kinase 2 (PAK2), pericentrin (PCNT), fibrinogen-like 2 (FGL2), angiopoietin 1 (ANGPT1), GRB10 interacting GYF protein 1 (GIGYF1) (PERQ1), ceroid-lipofuscinosis, neuronal 6, late infantile, variant (CLN6), Brother of CDO (BOC), cysteine dioxygenase (CDO), BCL2-like 1 (BCL2L1) (BCLX), CYCLIN D1, SURVIVIN, and B-cell CLL/lymphoma 2 (BCL2). In some aspects of the method, the level of STAT3 pathway activation correlates with the level of expression of one or more of the STAT3-regulated genes encoding polypeptides selected from the group consisting of MCL1, JUNB, BCL6, NFIL3, CAPN2, EGR1, VEGF, PTP-CAAX1, KLF4, EXT1, NPC1, PAK2, BCLX, SURVIVIN, and BCL2. In some aspects of the method, the level of STAT3 pathway activation correlates inversely with the level of expression of one or more of the STAT3-regulated genes encoding polypeptides selected from the group consisting of PCNT, FGL2, ANGPT1, PERQ1, CLN6, BOC, and CDO.

Also provided herein is a method of assessing the success of cancer cell growth inhibitory therapy with an atovaquone-related compound in a subject. The method can include assessing the level of activation of the eIF2α/ATF4 pathway in a test sample from a subject that has been treated with the compound, identifying the treatment as having been successful if the level of activation of the eIF2α/ATF4 pathway in the test sample is increased relative to the level of activation of the eIF2α/ATF4 pathway in a control sample, and not identifying the treatment as having been successful if the level of activation of the eIF2α/ATF4 pathway in the test sample is not increased relative to the level of activation of the eIF2α/ATF4 pathway in a control sample. In some aspects of the method, the method further includes determining the level of expression of CHOP and/or CHAC1 and/or REDD1. In some aspects of the method, the method can further include determining the level of mTOR and/or STAT3 activation. In some aspects of the method, the test sample is a sample of or from one or more cancer cells from the subject. In some aspects of the method, the test sample comprises microvesicles or exosomes obtained from a body fluid of the subject. In some aspects of the method, the second test sample is a sample of or from one or more cancer cells from the subject. In some aspects of the method, the second test sample can include microvesicles or exosomes obtained from a body fluid of the subject. In some aspects of the method, the control sample or the second control sample was obtained from the subject prior to the treatment with the atovaquone-related compound. In some aspects of the method, the control sample or the second control sample is a sample of or from one or more cancer cells from the subject. In some aspects of the method, the control sample or second control sample can include microvesicles or exosomes obtained from a body fluid of the subject. In some aspects of the method, the body fluid can be blood, lymph, urine, cerebrospinal fluid (CSF), ascites, or pleural fluid. In some aspects of the method, the subject is a mammalian subject (e.g., human subject). In some aspects of the method, the compound is atovaquone. In some aspects of the method, the compound is buparvaquone or 2-(4-(trans-decahydronaphth-2-yl)butyl)-3-hydoxy-1,4-naphthoquinone (TDBHN). In some aspects, the compound is a substituted hydroxynaphthoquinone compound. In some aspects of the above methods, the substituted hydroxynaphthoquinone is a compound of formula (I):

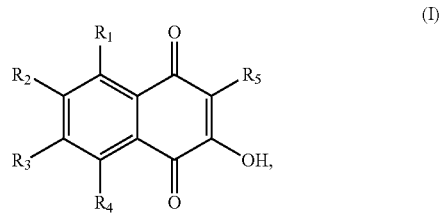

wherein each of $R_1$, R2, R3, and R4, independently, is H or $C_1$-$C_{10}$ alkyl; $R_5$ is $C_1$-$C_{10}$ alkyl optionally substituted with $C_3$-$C_{20}$ cycloalkyl, or $C_3$-$C_{20}$ cycloalkyl optionally substituted with $C_1$-$C_{10}$ alkyl or aryl; and each of $C_3$-$C_{20}$ cycloalkyl and aryl, independently, is optionally substituted with halogen or $C_1$-$C_{10}$ alkyl. In some aspects, $R_5$ is cyclohexyl substituted with aryl, in which aryl is substituted with $C_1$. In some aspects, $R_5$ is methyl substituted with cyclohexyl, in which cycloalkyl is substituted with t-butyl or n-butyl substituted with decahydronaphthyl. In some aspects, the compound of formula (I) is atovaquone, its isomer, buparvaquone, or TDBHN. In some aspects of the method, the substituted hydroxynaphthoquinone is a compound of formula (II):

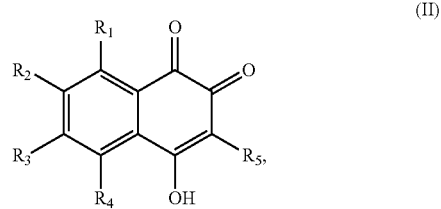

wherein each of $R_1$, R2, R3, and R4, independently, is H or $C_1$-$C_{10}$ alkyl; $R_5$ is $C_1$-$C_{10}$ alkyl optionally substituted with $C_3$-$C_{20}$ cycloalkyl, or $C_3$-$C_{20}$ cycloalkyl optionally substituted with $C_1$-$C_{10}$ alkyl or aryl; and each of $C_3$-$C_{20}$ cycloalkyl and aryl, independently, is optionally substituted with halogen or $C_1$-$C_{10}$ alkyl. In some aspects, $R_5$ is cyclohexyl. In some aspects of the method, the compound of formula (II) is parvaquone.

Also provided herein is a method of treating cancer in a patient. The method can include administering a therapeutically effective amount of an atovaquone-related compound to a patient in need thereof; and, after the administration, monitoring the level of activation of the eIF2α/ATF4 pathway in a test sample or two or more serial test samples from the patient. In some aspects of the method, the method further includes determining the level of expression of CHOP and/or CHAC1 and/or REDD1. In some aspects of the method, the method further includes, after the administration, monitoring the level of activation of the STAT3 pathway in the test sample, the two or more serial test samples, a second test sample or a second set of two or more serial test samples from the patient. In some aspects of the method, the method further includes, after the administration, monitoring the level of activation of the mTOR pathway in the test sample, the two or more serial test samples, a second test sample or a second set of two or more serial test samples from the patient. In some aspects of the method, the method further includes continuing the treatment if the level of activation of the eIF2α/ATF4 pathway in the test sample or the two or more serial test samples is increased relative to its level of activation in a control sample obtained from the patient prior to treatment. In some aspects of the method, the method further includes continuing the treatment if the level of activation of the STAT3 pathway in the test sample, the two or more serial test samples, the second test sample, or the second set of two or more serial test samples is decreased relative to its level of activation in a control sample obtained from the patient prior to treatment. In some aspects of the method, the method further includes continuing the treatment if the level of activation of the mTOR pathway in the test sample, the two or more serial test samples, the second test sample, or the second set of two or more serial test samples is decreased relative to its level of activation in a control sample obtained from the patient prior to treatment. In some aspects of the method, the test sample or each of the two or more serial test samples is a sample of or from one or more cancer cells from the subject. In some aspects of the method, the test sample or each of the two more serial test samples comprises microvesicles or exosomes obtained from a body fluid of the subject. In some aspects of the method, the second test sample or each of the second set of two or more serial test samples comprises a sample of or from one or more cancer cells from the subject. In some aspects of the method, the second test sample or each of the second set of two or more serial test samples can includes microvesicles or exosomes obtained from a body fluid of the subject. In some aspects of the method, the body fluid can be blood, lymph, urine, cerebrospinal fluid (CSF), ascites, or pleural fluid. In some aspects of the method, the patient is a mammalian subject (e.g., human subject). In some aspects of the method, the compound is atovaquone. In some aspects of the method, the compound is buparvaquone or 2-(4-(trans-decahydronaphth-2-yl)butyl)-3-hydoxy-1,4-naphthoquinone (TDBHN). In some aspects of the method, the therapeutically effective amount of atovaquone is in a range of about 10 to about 40 mg/kg per day. In some aspects of the method, the method further includes administering an additional therapy to the patient. In some aspects of the method, the additional therapy is selected from the group consisting of chemotherapy, immunotherapy, targeted therapy, and/or radiation therapy.

In any of the above-disclosed methods, the cancer can be a hematological tumor such as, e.g., acute myeloid leukemia, chronic myeloid leukemia, Hodgkin lymphoma, non-Hodgkin lymphoma, multiple myeloma, acute lymphoblastic leukemia, or chronic lymphocytic leukemia.

In any of the above-disclosed methods, the cancer can be a solid tumor selected from the group consisting of breast cancer, melanoma, lung cancer, ovarian cancer, pancreatic cancer, colorectal cancer, prostate cancer, brain cancer, gastroesophageal cancer, and kidney cancer.

Unless otherwise defined, all technical and scientific terms used herein have the same meaning as commonly understood by one of ordinary skill in the art to which this disclosure pertains. In case of conflict, the present document, including definitions, will control.

All publications, patent applications, patents, and other references mentioned herein are incorporated by reference in their entirety. The materials, methods, and examples disclosed herein are illustrative only and not intended to be limiting.

The details of one or more embodiments of the disclosure are set forth in the accompanying drawings and the description below. Preferred methods and materials are described below, although methods and materials similar or equivalent to those described herein can also be used in the practice or testing of the present disclosure. Other features, objects, and advantages of the disclosure will be apparent from the description and drawings, and from the claims.

DESCRIPTION OF DRAWINGS

FIG. 31 contains photographs of Western blots of lysates of SKBR3 cells transfected with control (siCtrl) or REDD1 siRNA (siREDD1) for 48 hours, then treated with vehicle (Veh) atovaquone (AQ, 25 µM) for 4 hours. Lysates were immunoblotted for phospho (p) and total (t) S6, as well as REDD1, and tubulin.

FIG. 32 contains photographs of Western blots of lysates of TSC2 null (TSC2−/−) murine embryonic fibroblasts (MEFs), alongside their respective littermate control MEFs ("litter ctrl"), that were treated with atovaquone (25 µM) for 2.5 hours. The lysates were immunoblotted for phospho (p) and total (t) S6.

FIG. 33 contains photographs of Western blots of lysates of REDD1 null (REDD1−/−) murine embryonic fibroblasts (MEFs) alongside their respective littermate control MEFs ("litter ctrl") that were treated with atovaquone (25 µM) for 2.5 hours. The lysates were immunoblotted for phospho (p) and total (t) S6.

FIG. 36 contains photographs of Western blots of lysates of K562 cells (upper panel) and SKBR cells (lower panel) treated for the indicated time period ("hr"=hour(s)) with vehicle (Veh) or atovaquone (AQ, 20 µM for K562 cells and 25 µM for SKBR cells) immunoblotted for phospho (p) and total (t) eIF2α, as well as for ATF4 and actin.

DETAILED DESCRIPTION

Overview

Figure 1:
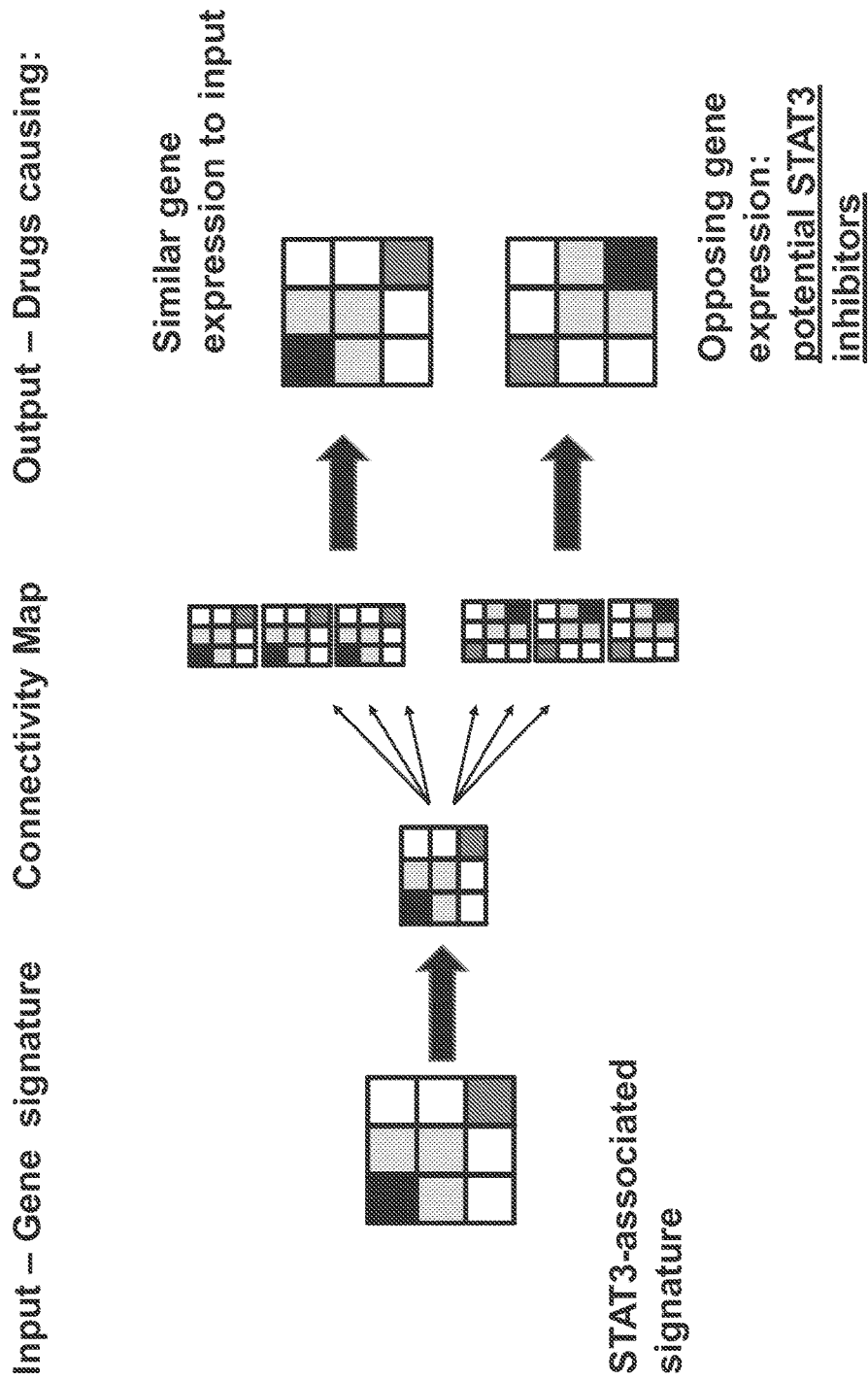
FIG. 1 is an overview of the strategy used to identify drugs that are potential STAT3 inhibitors based on gene expression. The Connectivity Map was queried with the 12-gene STAT3-associated signature (represented by a square grid with a particular shading pattern). Drugs that induced an opposing gene expression pattern (relative to STAT3) were identified as potential STAT3 inhibitors. In this schematic diagram, each grid represents a quantitative gene expression microarray. The darkness of each square represents the amount of expression of each STAT3 signature gene. A drug that causes a grid pattern that is the opposite of the input STAT3-associated gene signature would be a potential STAT3 inhibitor.

As discussed above, despite the importance of STAT3 in cancer, clinically available therapies to inhibit STAT3 are presently limited. As described herein, the FDA-approved drug atovaquone has been discovered to be a novel STAT3 inhibitor. The present Examples demonstrate that atovaquone induced a gene expression signature that opposed the gene expression signature of STAT3. Further, at concentrations readily achieved in human plasma, atovaquone inhibited STAT3 phosphorylation, transcriptional activity, and STAT3-dependent cancer cell viability. Additionally, it has been discovered that atovaquone activates a branch of the unfolded protein response (UPR) involving the eIF2α/ATF4 pathway, and inhibits mammalian target of rapamycin (mTOR) pathway by inducing DNA-damage-inducible transcript 4 (DDIT4) (also known as Regulated in Development and DNA Damage Responses-1 (REDD1)). REDD1 is causally responsible for inhibition of the mTOR pathway. The mTOR signaling pathway senses and integrates a variety of environmental cues to regulate organismal growth and homeostasis. The pathway regulates many major cellular processes and is implicated in an increasing number of pathological conditions, including cancer. Importantly, higher atovaquone exposure was also discovered herein to be associated with improved disease-free survival in patients who underwent hematopoietic stem cell transplant for hematological malignancies. It has been determined in in vitro studies that the atovaquone-related compounds, buparvaquone and 2-(4-(trans-decahydronaphth-2-yl)butyl)-3-hydroxy-1,4-naphthoquinone (an analog available from Sigma-Aldrich) have similar effects as atovaquone (see, Example 8, below). These results establish atovaquone, as well as other atovaquone-related compounds, as novel STAT3 and mTOR inhibitors and anti-cancer therapeutics. Thus, provided herein are methods of treating cancer with atovaquone-related compounds. Moreover, also provided herein, based on the elucidation of the pathways and responses that are modulated by atovaquone, are novel methods for determining whether a particular cancer is susceptible to treatment with an atovaquone-related compound, as well as methods for monitoring whether such treatments are effective.

Definitions

As used herein, "atovaquone-related compound" means atovaquone as well as compounds that have the same type activity of atovaquone (i.e., functional analogs of atovaquone), including the ability to inhibit the mammalian target of rapamycin (mTOR) pathway, to inhibit the activated signal transducer and activator of transcription 3 (STAT3) pathway, and to induce activation of the eIF2α/ATF4 pathway. Typically, but not necessarily, atovaquone-related compounds are structural analogs of atovaquone (e.g., buparvaquone and 2-(4-(trans-decahydronaphth-2-yl)butyl)-3-hydroxy-1,4-naphthoquinone). Methods for determining whether mTOR and/or STAT3 pathways are/is inhibited, e.g., in a cancer cell, are known in the art, and described in detail below. Non-limiting examples of atovaquone-related compounds include, e.g., atovaquone, buparvaquone, parvaquone and 2-(4-(trans-decahydronaphth-2-yl)butyl)-3-hydroxy-1,4-naphthoquinone (TDBHN).

As used herein, a cell (in vitro or in vivo) that has an "activated signal transducer and activator of transcription 3 (STAT3) pathway," means that a cell expresses active STAT3 such that the STAT3 dimerizes and translocates to the nucleus where it acts as a transcription activator. Markers of activated STAT3 pathway (e.g., expression or downregulation of specific genes and/or a specific gene expression profile) are known in the art, and exemplary markers are described in detail, below. As used herein, a cell (in vitro or in vivo) that has an "increased level of activation of the STAT3 pathway," is one in which STAT3 activation is increased relative to a control (e.g., a cell in which it is known that the STAT3 pathway is not activated).

As used herein, a cell (in vitro or in vivo) that has an "activated mammalian target of rapamycin (mTOR) pathway," means that the cell expresses mTOR with active kinase and/or phospho-transferase activity." The mTOR signaling pathways are known in the art, and described, e.g., in Laplante, M. et al. Cell. 2012 Apr. 13; 149(2): 274-293; and Laplante et al. (Oct. 15, 2009 J Cell Sci 122, 3589-3594). As used herein, a cell (in vitro or in vivo) that has an "increased level of activation of the mTOR pathway," is one in which mTOR activation is increased relative to a control (e.g., a cell in which it is known that the mTOR pathway is not activated).

As used herein, a cell (in vitro or in vivo) that has an "activated eIF2α/ATF4 pathway," is one in which eIF2α is phosphorylated and ATF4 is expressed. As used herein, a cell (in vitro or in vivo) that has an "increased level of activation of the eIF2α/ATF4 pathway," has increased levels of phosphorylated eIF2α and increased expression levels of ATF4, relative to a control (e.g., a cell in which it is known that the eIF2α/ATF4 pathway is not activated). The level of expression of REDD1, CHOP and/or CHAC1 can also be increased relative to a control in a cell that has an increased level of activation of the eIF2α/ATF4 pathway.

As used herein "decreasing the growth of a cancer cell" includes inhibiting the proliferation of a cancer cell and/or killing a cancer cell by, for example, the induction of necrosis or of apoptosis of the cancer cell. As used herein, a "growth inhibitory amount," e.g., of an atovaquone-related compound means an amount of the compound sufficient to decrease the growth of a cancer cell, as defined above. A growth inhibitory amount can be a "therapeutically effective" amount. The terms "therapeutically effective" and "effective amount," used interchangeable, refer to that quantity of a composition, compound or pharmaceutical formulation that is sufficient to reduce or eliminate at least one symptom of a disease or condition specified herein, e.g., cancer. When a combination of active ingredients is administered, the effective amount of the combination may or may not include amounts of each ingredient that would have been effective if administered individually. The dosage of the therapeutic formulation will vary, depending upon the nature of the disease or condition, the patient's medical history, the frequency of administration, the manner of administration, the clearance of the agent from the host, and the like. The initial dose may be larger, followed by smaller maintenance doses. The dose may be administered, e.g., weekly, biweekly, daily, semi-weekly, etc., to maintain an effective dosage level. Therapeutically effective dosages can be determined stepwise by combinations of approaches such as (i) characterization of effective doses of the composition or compound in in vitro cell culture assays using tumor cell growth and/or survival as a readout followed by (ii) characterization in animal studies using tumor growth inhibition and/or animal survival as a readout, followed by (iii) characterization in human trials using enhanced tumor growth inhibition and/or enhanced cancer survival rates as a readout.

As used herein, "delivering to a target cancer cell" in the context of an atovaquone related compound means causing a cancer cell to come into contact with the compound. In vivo, this can be achieved by various routes of administration, depending on the location of the target cell (e.g., systemic delivery, direct intratumoral delivery, mucosal delivery, etc.). It can also mean conjugating the compound to an agent that specifically targets a cancer cell (e.g., an antibody specific for a cancer cell surface marker). In vitro, delivery of a compound to a target cancer cell can be achieved by adding the compound to the cell culture media, using liposomes, etc. "Delivering to a target cell" can, but does not necessarily, include delivery to the interior of the target cell.

As used herein, a sample that is "of or from one or more cells" (e.g., of or from one or more cancer cells or of or from one or more control cells), means that the sample can be derived from the cell or cells (the sample can be, e.g., a cell lysate, nucleic acid, protein, or other product obtained from and/or prepared from the cells) or can be the cells themselves.

As used herein, a cancer that is "susceptible" to a therapy disclosed herein means that the cancer cell, as a result of exposure to the therapy (e.g., treatment with an atovaquone-related compound), will have decreased growth and/or survival.

As used herein, "prior to treatment" means from any time after cancer develops in the subject to immediately before or at the same time as administration of the first treatment with an atovaquone-related compound.

As used herein, "administering an additional therapy" in the context of administering an atovaquone-related compound means administering the atovaquone-related compound and at least one additional therapy that is not atovaquone. Administering an atovaquone-related compound and an additional therapy is also referred to herein as a "combination therapy." Additional therapies can include an additional treatment for cancer (e.g., chemotherapy (e.g., administering a chemotherapeutic agent), administering a biologic agent, e.g., antigen, vaccine, antibody etc., administering a cytokine, radiation therapy, immunotherapy, and/or surgery, etc.). Such combination therapy can be sequential therapy wherein the patient is treated first with one therapy and then the other, and so on, or all therapies can be administered simultaneously. In either case, these therapies are said to be coadministered. It is to be understood that "coadministered" does not necessarily mean that the drugs and/or therapies are administered in a combined form (i.e., they may be administered separately or together to the same or different sites at the same or different times).

As used herein, the "expression level" of a gene, such as, e.g., MCL1, JUNB, BCL6, NFIL3, CAPN2, EGR1, VEGF, PTPCAAX1, KLF4, EXT1, NPC1, PAK2, PCNT, FGL2, ANGPT1, PERQ1, CLN6, BOC, CDO, BCLX, SURVIVIN, BCL2. etc., means the mRNA and/or protein expression level of the gene in a sample (e.g., the level of the polypeptide encoded by the gene can be detected by immunoassay), which can be determined by any suitable method known in the art, such as, but not limited to Northern blot, polymerase chain reaction (PCR), e.g., quantitative real-time, "QPCR", Western blot, immunoassay (e.g., ELISA), immunohistochemistry, cell immunostaining and fluorescence activated cell sorting (FACS), etc.

As used herein, the term "subject" means any animal, including any vertebrate including any mammal, and, in particular, a human, and can also be referred to, e.g., as an individual or patient. A non-human mammal can be, for example, without limitation a non-human primate (such as a monkey, baboon, gorilla, or orangutan), a bovine animal, a horse, a whale, a dolphin, a sheep, a goat, a pig, a dog, a feline animal (such as a cat), a rabbit, a guinea pig, a hamster, a gerbil, a rat, or a mouse. Non-mammalian vertebrates include without limitation, a bird, a reptile, or a fish.

As used herein, "treating" or "treatment" of a state, disorder or condition includes: (1) preventing or delaying the appearance of clinical or sub-clinical symptoms of the state, disorder or condition developing in a mammal that may be afflicted with or predisposed to the state, disorder or condition but does not yet experience or display clinical or subclinical symptoms of the state, disorder or condition; and/or (2) inhibiting the state, disorder or condition, i.e., arresting, reducing or delaying the development of the disease or a relapse thereof (in case of maintenance treatment) or at least one clinical or sub-clinical symptom thereof; and/or (3) relieving the disease, i.e., causing regression of the state, disorder or condition or at least one of its clinical or sub-clinical symptoms; and/or (4) causing a decrease in the severity of one or more symptoms of the disease. The benefit to a subject to be treated is either statistically significant or at least perceptible to the patient or to the physician.

As used herein, the term "treating cancer" means causing a partial or complete decrease in the rate of growth of a tumor, and/or in the size of the tumor and/or in the rate of local or distant tumor metastasis, and/or the overall tumor burden in a subject, and/or any decrease in tumor survival, in the presence of an inhibitor (e.g., an atovaquone-related compound) described herein.

As used herein, the term "preventing a disease" (e.g., preventing cancer) in a subject means for example, to stop the development of one or more symptoms of a disease in a subject before they occur or are detectable, e.g., by the patient or the patient's doctor. Preferably, the disease (e.g., cancer) does not develop at all, i.e., no symptoms of the disease are detectable. However, it can also result in delaying or slowing of the development of one or more symptoms of the disease. Alternatively, or in addition, it can result in the decreasing of the severity of one or more subsequently developed symptoms.

As used herein, the phrase "pharmaceutically acceptable" refers to molecular entities and compositions that are generally believed to be physiologically tolerable and do not typically produce an allergic or similar untoward reaction, such as gastric upset, dizziness and the like, when administered to a human. As used herein, the term "pharmaceutically acceptable derivative" means any pharmaceutically acceptable salt, solvate or prodrug, e.g., ester, of an atovaquone-related compound described herein, which upon administration to the recipient is capable of providing (directly or indirectly) a compound described herein, or an active metabolite or residue thereof. Such derivatives are recognizable to those skilled in the art, without undue experimentation. Nevertheless, reference is made to the teaching of Burger's Medicinal Chemistry and Drug Discovery, 5th Edition, Vol 1: Principles and Practice, which is incorporated herein by reference to the extent of teaching such derivatives. Pharmaceutically acceptable derivatives include salts, solvates, esters, carbamates, and/or phosphate esters.

The term "nucleic acid hybridization" refers to the pairing of complementary strands of nucleic acids. The mechanism of pairing involves hydrogen bonding, which may be Watson-Crick, Hoogsteen or reversed Hoogsteen hydrogen bonding, between complementary nucleoside or nucleotide bases (nucleobases) of the strands of nucleic acids. For example, adenine and thymine are complementary nucleobases that pair through the formation of hydrogen bonds. Hybridization can occur under varying circumstances. Nucleic acid molecules are "hybridizable" to each other when at least one strand of one nucleic acid molecule can form hydrogen bonds with the complementary bases of another nucleic acid molecule under defined stringency conditions. Stringency of hybridization is determined, e.g., by (i) the temperature at which hybridization and/or washing is performed, and (ii) the ionic strength and (iii) concentration of denaturants such as formamide of the hybridization and washing solutions, as well as other parameters. Hybridization requires that the two strands contain substantially complementary sequences. Depending on the stringency of hybridization, however, some degree of mismatches may be tolerated. Under "low stringency" conditions, a greater percentage of mismatches are tolerable (i.e., will not prevent formation of an anti-parallel hybrid). See Molecular Biology of the Cell, Alberts et al., 3rd ed., New York and London: Garland Publ., 1994, Ch. 7.

Typically, hybridization of two strands at high stringency requires that the sequences exhibit a high degree of complementarity over an extended portion of their length. Examples of high stringency conditions include: hybridization to filter-bound DNA in 0.5 M NaHPO4, 7% SDS, 1 mM EDTA at 65° C., followed by washing in 0.1×SSC/0.1% SDS (where 1×SSC is 0.15 M NaCl, 0.15 M Na citrate) at 68° C. or for oligonucleotide (oligo) inhibitors washing in 6×SSC/0.5% sodium pyrophosphate at about 37° C. (for 14 nucleotide-long oligos), at about 48° C. (for about 17 nucleotide-long oligos), at about 55° C. (for 20 nucleotide-long oligos), and at about 60° C. (for 23 nucleotide-long oligos).

Conditions of intermediate or moderate stringency (such as, for example, an aqueous solution of 2×SSC at 65° C.; alternatively, for example, hybridization to filter-bound DNA in 0.5 M NaHPO4, 7% SDS, 1 mM EDTA at 65° C. followed by washing in 0.2×SSC/0.1% SDS at 42° C.) and low stringency (such as, for example, an aqueous solution of 2×SSC at 55° C.), require correspondingly less overall complementarity for hybridization to occur between two sequences. Specific temperature and salt conditions for any given stringency hybridization reaction depend on the concentration of the target DNA or RNA molecule and length and base composition of the probe, and are normally determined empirically in preliminary experiments, which are routine (see Southern, J. Mol. Biol. 1975; 98:503; Sambrook et al., Molecular Cloning: A Laboratory Manual, 2nd ed., vol. 2, ch. 9.50, CSH Laboratory Press, 1989; Ausubel et al. (eds.), 1989, Current Protocols in Molecular Biology, Vol. I, Green Publishing Associates, Inc., and John Wiley & Sons, Inc., New York, at p. 2.10.3). An extensive guide to the hybridization of nucleic acids is found in, e.g., Tijssen (1993) Laboratory Techniques in Biochemistry and Molecular Biology—Hybridization with Nucleic Acid Probes part I, chapt 2, "Overview of principles of hybridization and the strategy of nucleic acid probe assays," Elsevier, N.Y. ("Tijssen").

As used herein, the term "standard hybridization conditions" refers to hybridization conditions that allow hybridization of two nucleotide molecules having at least 50% sequence identity. According to a specific embodiment, hybridization conditions of higher stringency may be used to allow hybridization of only sequences having at least 75% sequence identity, at least 80% sequence identity, at least 90% sequence identity, at least 95% sequence identity, or at least 99% sequence identity.

As used herein, the phrase "under hybridization conditions" means under conditions that facilitate specific hybridization of a subset of capture oligonucleotides to complementary sequences present in the cDNA or cRNA. The terms "hybridizing specifically to" and "specific hybridization" and "selectively hybridize to," as used herein refer to the binding, duplexing, or hybridizing of a nucleic acid molecule preferentially to a particular nucleotide sequence under at least moderately stringent conditions, and preferably, highly stringent conditions, as discussed above.

"Polypeptide" and "protein" are used interchangeably and mean any peptide-linked chain of amino acids, regardless of length or post-translational modification.

As used herein, the term "nucleic acid" or "oligonucleotide" refers to a deoxyribonucleotide or ribonucleotide in either single- or double-stranded form. The term also encompasses nucleic-acid-like structures with synthetic backbones. DNA backbone analogues provided by the disclosure include phosphodiester, phosphorothioate, phosphorodithioate, methylphosphonate, phosphoramidate, alkyl phosphotriester, sulfamate, 3'-thioacetal, methylene(methylimino), 3'-N-carbamate, morpholino carbamate, and peptide nucleic acids (PNAs); see Oligonucleotides and Analogues, a Practical Approach, edited by F. Eckstein, IRL Press at Oxford University Press (1991); Antisense Strategies, Annals of the New York Academy of Sciences, Volume 600, Eds. Baserga and Denhardt (NYAS 1992); Milligan (1993) J. Med. Chem. 36:1923-1937; Antisense Research and Applications (1993, CRC Press). PNAs contain non-ionic backbones, such as N-(2-aminoethyl) glycine units. Phosphorothioate linkages are described in WO 97/03211; WO 96/39154; Mata (1997) Toxicol. Appl. Pharmacol. 144:189-197. Other synthetic backbones encompassed by the term include methyl-phosphonate linkages or alternating methyl-phosphonate and phosphodiester linkages (Strauss-Soukup (1997) Biochemistry 36:8692-8698), and benzylphosphonate linkages (Samstag (1996) Antisense Nucleic Acid Drug Dev 6:153-156). The term nucleic acid is used interchangeably with cDNA, cRNA, mRNA, oligonucleotide, probe and amplification product.

Methods for Measuring the Level of Activation of eIF2α/ATF4, mTOR, and STAT3 Pathways Methods are provided herein (e.g., for decreasing cancer cell growth, for treating cancer, for determining the susceptibility of a cancer in a subject to the growth-inhibitory effect of atovaquone, for assessing the efficacy of a cancer treatment, etc.) that comprise delivering an atovaquone-related compound to a cancer cell or a subject with cancer, wherein the cell and/or subject has an "increased level of activation of the mTOR pathway" and/or an "increased level of activation of the STAT3 pathway." In other embodiments, it is desirable to determine whether the level of activation of the mTOR, STAT3 and/or eIF2α/ATF4 pathways has changed (increased or decreased) relative to a control (e.g., a control sample obtained prior to treatment with an atovaquone-related compound). The mTOR, STAT3 and/or eIF2α/ATF4 pathways are known and described in the art. The skilled artisan will appreciate how to determine whether these pathways are activated in a cell and/or subject (e.g., a cancer patient); however, exemplary methods and markers of activation are described below.

In some embodiments, it is desirable to determine (e.g., assay, measure, approximate) the level (e.g., expression or activity), the level of STAT3- and mTOR-regulated genes or any other target gene of interest.

The expression level of the exemplary genes described below can be determined according to any suitable method known in the art. A non-limiting example of such a method includes real-time PCR (RT-PCR), e.g., quantitative RT-PCR (QPCR), which measures the expression level of the mRNA encoding the polypeptide. Real-time PCR evaluates the level of PCR product accumulation during amplification. RNA (or total genomic DNA for detection of germline mutations) is isolated from a sample. RT-PCR can be performed, for example, using a Perkin Elmer/Applied Biosystems (Foster City, Calif.) 7700 Prism instrument. Matching primers and fluorescent probes can be designed for genes of interest using, based on the genes' nucleic acid sequences (e.g., as described above), for example, the primer express program provided by Perkin Elmer/Applied Biosystems (Foster City, Calif.). Optimal concentrations of primers and probes can be initially determined by those of ordinary skill in the art, and control (for example, beta-actin) primers and probes may be obtained commercially from, for example, Perkin Elmer/Applied Biosystems (Foster City, Calif.).

To quantitate the amount of the specific nucleic acid of interest in a sample, a standard curve is generated using a control. Standard curves may be generated using the Ct values determined in the real-time PCR, which are related to the initial concentration of the nucleic acid of interest used in the assay. Standard dilutions ranging from 10-106 copies of the gene of interest are generally sufficient. In addition, a standard curve is generated for the control sequence. This permits standardization of initial content of the nucleic acid of interest in a tissue sample to the amount of control for comparison purposes. Methods of QPCR using TaqMan probes are well known in the art. Detailed protocols for QPCR are provided, for example, for RNA in: Gibson et al., 1996, Genome Res., 10:995-1001; and for DNA in: Heid et al., 1996, Genome Res., 10:986-994; and in Innis et al. (1990) Academic Press, Inc. N.Y.

Expression of mRNA, as well as expression of peptides and other biological factors, can also be determined using microarray, methods for which are well known in the art [see, e.g., Watson et al. Curr Opin Biotechnol (1998) 9: 609-14; "DNA microarray technology: Devices, Systems, and Applications" Annual Review of Biomedical Engineering; Vol. 4: 129-153 (2002); Chehab et al. (1989) "Detection of specific DNA sequences by fluorescence amplification: a color complementation assay" Proc. Natl. Acad. Sci. USA, 86: 9178-9182; Lockhart et al. (1996) "Expression monitoring by hybridization to high-density oligonucleotide arrays" Nature Biotechnology, 14: 1675-1680; and M. Schena et al. (1996) "Parallel human genome analysis: Microarray-based expression monitoring of 1000 genes" Proc. Natl. Acad. Sci. USA, 93:10614-10619; Peptide Microarrays Methods and Protocols; Methods in Molecular Biology; Volume 570, 2009, Humana Press; and Small Molecule Microarrays Methods and Protocols; Series: Methods in Molecular Biology, Vol. 669, Uttamchandani, Mahesh; Yao, Shao Q. (Eds.) 2010, 2010, Humana Press]. For example, mRNA expression profiling can be performed to identify differentially expressed genes, wherein the raw intensities determined by microarray are log 2-transformed and quantile normalized and gene set enrichment analysis (GSEA) is performed according, e.g., to Subramanian et al. (2005) Proc Natl Acad Sci USA 102:15545-15550).

Other suitable amplification methods include, but are not limited to, ligase chain reaction (LCR) (see Wu and Wallace (1989) Genomics 4:560, Landegren et al. (1988) Science 241:1077, and Barringer et al. (1990) Gene 89:117), transcription amplification (Kwoh et al. (1989) Proc. Natl. Acad. Sci. USA 86:1173), self-sustained sequence replication (Guatelli et al. (1990) Proc. Nat. Acad. Sci. USA 87:1874), dot PCR, and linker adapter PCR, etc.

Methods for determining DNA binding, e.g., STAT3 binding to DNA in the nucleus, are known in the art, and include, e.g., measured binding in vivo by chromatin immunoprecipitation (ChIP), and measured in vitro by electrophoretic mobility shift assay (EMSA). For example, for EMSA, the LightShift EMSA Kit (Pierce) can be used according to the manufacturer's protocol. STAT binding reactions can be performed as described (e.g., in Battle T E & Frank D A (2003) STAT1 mediates differentiation of chronic lymphocytic leukemia cells in response to Bryostatin 1. Blood 102(8):3016-3024) using 5'-biotinylated 25 bp probes. The ChIP method is described, e.g., in Nelson E A, et al. Identification of unique STAT5 targets by chromatin immunoprecipitation-based gene identification. J. Biol. Chem. 2004; 279:54724-54730.

Other methods for detecting gene expression (e.g., mRNA levels) include Serial Analysis of Gene Expression applied to high-throughput sequencing (SAGEseq), as described in Wu Z J et al. Genome Res. 2010 December; 20(12):1730-9. 2.

Methods for detecting the expression levels of polypeptides are also known in the art. Non-limiting examples of suitable methods for detecting expression levels of gene products (i.e., polypeptides) described herein include, e.g., flow cytometry, immunoprecipitation, Western blot (see, e.g., Battle T E, Arbiser J, & Frank D A (2005) The natural product honokiol induces caspase-dependent apoptosis in B-cell chronic lymphocytic leukemia (B-CLL) cells. Blood 106(2):690-697), ELISA (enzyme-linked immunosorbent assay) and/or immunohistochemistry.

eIF2α/ATF4 Pathway

It is presently discovered that atovaquone-related compounds activate certain components of the unfolded protein response (UPR). In particular, it was demonstrated in the present Examples that atovaquone induced Eukaryotic Initiation Factor 2 alpha (eIF2α) phosphorylation and expression of Activating transcription factor 4 (tax-responsive enhancer element B67) (ATF4) (i.e., the EFIα/ATF4 pathway), but not other branches of the UPR. Moreover, expression of CCAAT/-enhancer-binding protein homologous protein (CHOP), cation transport regulator-like protein 1 (CHAC1) and Regulated in Development and DNA Damage Responses-1 (REDD1) were increased following activation of the pathway.

While broad UPR activation has variable effects in cancer, the EFIα/ATF4 pathway has been shown to promote apoptosis in numerous cancer contexts (see, e.g., Little J L, et al. (2007) Inhibition of fatty acid synthase induces endoplasmic reticulum stress in tumor cells. Cancer Research 67(3):1262-1269; Liu G, et al. (2012) Salermide up-regulates death receptor 5 expression through the ATF4-ATF3-CHOP axis and leads to apoptosis in human cancer cells. Journal of Cellular and Molecular Medicine 16(7):1618-1628; Oyadomari S & Mori M (2004) Roles of CHOP/GADD153 in endoplasmic reticulum stress. Cell Death and Differentiation 11(4):381-389; Rao R, et al. (2010) Treatment with panobinostat induces glucose-regulated protein 78 acetylation and endoplasmic reticulum stress in breast cancer cells. Molecular Cancer Therapeutics 9(4):942-952; and Sanchez A M, et al. (2008) Induction of the endoplasmic reticulum stress protein GADD153/CHOP by capsaicin in prostate PC-3 cells: a microarray study. Biochemical and Biophysical Research Communications 372(4):785-791). Atovaquone strongly upregulates CHOP with no effect on levels of BiP, supporting the role of the EFIα/ATF4 pathway in atovaquone-mediated apoptosis. CHAC1, an EFIα/ATF4 target gene consistently upregulated by atovaquone, is also proapoptotic (Mungrue Ind., et al. (2009) CHAC1/MGC4504 is a novel proapoptotic component of the unfolded protein response, downstream of the ATF4-ATF3-CHOP cascade. J Immunol 182(1):466-476). Thus, atovaquone inhibits the viability of cancer cells through STAT3-related and STAT3-independent mechanisms.

Thus, in certain aspects, effective inhibition of tumor growth and/or treatment of cancer using an atovaquone-related compound can be determined/monitored by determining whether the levels of eIF2α phosphorylation and/or ATF4 (i.e., the eIF2α/ATF4 pathway) are increased, decreased, or not increased or not decreased, relative to a control.

Thus, in some embodiments, methods of assessing the success of cancer cell growth inhibitory therapy with an atovaquone-related compound in a subject are provided, wherein the method comprises: (a) assessing the level of activation of the eIF2α/ATF4 pathway in a test sample from a subject that has been treated with the compound, (b) identifying the treatment as having been successful if the level of activation of the eIF2α/ATF4 pathway in the test sample is increased relative to the level of activation of the eIF2α/ATF4 pathway in a control sample, and (c) not identifying the treatment as having been successful if the level of activation of the eIF2α/ATF4 pathway in the test sample is not increased and/or decreased relative to the level of activation of the eIF2α/ATF4 pathway in a control sample. In some embodiments, the method further comprises determining the level of expression of CHOP, CHAC1 and/or REDD1, wherein increased expression of one or both of the genes or the polypeptides encoded by these genes correlates with activation of the eIF2α/ATF4 pathway. CHAC1 is a target gene of CHOP (see, Mungrue Ind., Pagnon J, Kohannim O, Gargalovic P S, & Lusis A J (2009) CHAC1/MGC4504 is a novel proapoptotic component of the unfolded protein response, downstream of the ATF4-ATF3-CHOP cascade. J Immunol 182(1):466-476). In some aspects, the method comprises determining the level of phosphorylation of eIF2α, wherein its increased phosphorylation correlates with activation of the eIF2α/ATF4 pathway. In other aspects, the method comprises determining the expression level of ATF4, wherein increased expression of ATF4 gene or the polypeptide encoded by ATF4 correlates with activation of the eIF2α/ATF4 pathway.

The level of activation or any relative change (e.g., compared to a prior measurement) in the level of activation of the eIF2α/ATF4 pathway in a cell (e.g., a cancer cell) can be determined by detecting, for example, the expression level of one or more of the genes involved in the eIF2α/ATF4 pathway, such as, but not limited to, the genes encoding REDD1, DNA-damage-inducible transcript 3 (DDIT3) (also known as CHOP), activating transcription factor 3 (ATF3), cation transport regulator homolog 1 (CHAC1), and activating transcription factor 4 (ATF4).

The expression levels of these genes can be determined by any suitable method known in the art. For example, the nucleic and amino acid sequences for these genes are known and can be used to determine whether the genes are expressed. By way of non-limiting example, the GenBank® Accession numbers for the human nucleic acid sequences of these genes, as well as the human amino acid sequences encoded by those genes are set forth in Table 1, below:

TABLE 1

GenBank ® Accession Nos.

| Gene Name | Nucleic Acid GenBank ® No. | SEQ ID NO. | Amino Acid GenBank ® No. | SEQ ID NO. |
|---|---|---|---|---|
| REDD1 | NM_019058 | 1 | NP_061931 | 2 |
| CHOP | NM_001195053 | 3 | NP_001181982 | 4 |
| ATF3 | NM_001030287 | 5 | NP_001025458 | 6 |
| CHAC1 | BC019625 | 7 | AAH19625.1 | 8 |
| ATF4 | NM_001675 | 9 | NP_001666 | 10 |

Phosphorylation of eIF2α can be determined by any method known in the art. For example, Western blot, using an antibody specific for the phosphorylated form of eIF2α can be used. Expression levels of CHOP, CHAC1, ATF4 and REDD1 can be determined using Q-PCR for measuring gene expression, and by ELISA for measuring protein expression. Methods for designing primers for Q-PCR, based on the known nucleic acid sequences of these proteins (see, e.g., Table 1, above), are known in the art. Antibodies for detecting, e.g., by ELISA, Western blot, flow cytometry, and/or immunohistochemistry, are commercially available. For example, REDD1 antibody is available from Proteintech, antibody recognizing eIF2α (total and phosphorylated form) are available from Cell Signaling Technology, antibody recognizing full-length and cleaved ATF6 is available from Abcam, CHOP-specific antibodies are available, e.g., from Thermo Scientific (Pierce Antibody) (Rockford, Ill.).

mTOR Pathway

It is presently discovered that atovaquone-related compounds are potent inhibitors of the mTOR signaling pathway, or "mTOR pathway." The mTOR pathway is known to be involved in cancer cell growth and survival (see, e.g., the comprehensive review by Laplante et al. (2012), supra). The mTOR protein is a 289-kDa serine-threonine kinase that belongs to the phospho-inositide 3-kinase (PI3K)-related kinase family and is conserved throughout evolution. mTOR nucleates at least two distinct multi-protein complexes, mTOR complex 1 (mTORC1) and mTOR complex 2 (mTORC2).

The nucleic acid and amino acid sequences for human mTOR are known and have the following GenBank® Accession Nos.: NM_004958 (mRNA) (SEQ ID NO: 11) and NP_004949 (amino acid) (SEQ ID NO: 12).

In some aspects, the methods disclosed herein encompass determining whether the mTOR pathway is activated in a cell and/or whether its level of activation is increased, decreased, or not increased or not decreased (relative to a control). The mTOR pathway has been extensively studied for decades, and there is a large body of literature describing the many components of the mTOR pathway. Thus, the skilled artisan will understand how to determine whether an mTOR pathway is activated and/or whether its level of activation is increased, decreased, or not increased, or not decreased (e.g., relative to a control), e.g., by looking for presence of one or more known markers of the activated pathway. While these markers are well known in the art, a brief review is provided, below.

Protein synthesis is the best characterized process controlled by mTORC1. mTORC1 directly phosphorylates the translational regulators eukaryotic translation initiation factor 4E (eIF4E) binding protein 1 (4E-BP1) and S6 kinase 1 (S6K1), which, in turn, promote protein synthesis. The phosphorylation of 4E-BP1 prevents its binding to the cap-binding protein eIF4E, enabling it to participate in the formation of the eIF4F complex which is required for the initiation of cap-dependent translation. The activation of S6K1 leads, through a variety of effectors, to an increase in mRNA biogenesis, as well as translational initiation and elongation. S6K1 was originally thought to control the translation of an abundant subclass of mRNAs characterized by an oligopyrimidine tract at the 5' end (5' TOP mRNAs) and which encode most of the protein components of the translational machinery. Although mTOR itself is key for the translational control of 5'TOP mRNAs, S6K1 and its substrate ribosomal protein S6 are not required for this process and so how mTORC1 controls the translation of these mRNAs remains unknown.

mTORC1 also upregulates the protein synthesis machinery in other ways: (1) it activates the regulatory element tripartite motif-containing protein-24 (TIF-1A), which promotes its interaction with RNA Polymerase I (Pol I) and the expression of ribosomal RNA (rRNA); and (2) mTORC1 phosphorylates and inhibits Maf1, a Pol III repressor, and so induces 5S rRNA and transfer RNA (tRNA) transcription. The overall role of mTORC1 in the regulation of mRNA translation is highly significant because specific, active-site inhibitors of mTOR that completely inhibit mTORC1 function, significantly reduce overall rates of protein synthesis in proliferating cells in culture.

In addition to regulating the production of proteins, mTORC1 also controls the synthesis of lipids required for proliferating cells to generate membranes. To a large extent, mTORC1 acts through the sterol regulatory element binding protein 1/2 (SREBP1/2) transcription factors that control the expression of numerous genes involved in fatty acid and cholesterol synthesis. The inactive SREBPs reside on the endoplasmic reticulum (ER) and their proteolytic processing in response to insulin or sterol depletion releases an active form that travels to the nucleus to activate transcription. mTORC1 inhibition reduces SREBP1/2 levels as well as processing and markedly lowers the expression of lipogenic genes. mTORC1 appears to regulate SREBP function through several mechanisms, including, at least in some cell types, through S6K1. In addition, mTORC1 phosphorylates Lipin-1, preventing it from entering the nucleus and suppressing SREBP1/2 function and levels. mTORC1 also promotes the expression and activity of peroxisome proliferator-activated receptor γ (PPAR-γ), the master regulator of adipogenesis. mTORC1 also positively regulates cellular metabolism and ATP production.

mTORC1 increases glycolytic flux by activating the transcription and the translation of hypoxia inducible factor 1α (HIF1α), a positive regulator of many glycolytic genes. mTORC1 also increases mitochondrial DNA content and the expression of genes involved in oxidative metabolism, in part, it is thought, by mediating the nuclear association between PPAR-γ coactivator 1α (PGC1α) and the transcription factor Ying-Yang 1 (YY1), which positively regulate mitochondrial biogenesis and oxidative function.

mTORC1 also promotes growth by negatively regulating autophagy, the central degradative process in cells. Autophagy is required for the recycling of damaged organelles and for the organismal and cellular adaptation to nutrient starvation. Upon mTORC1 inhibition, autophagosomes form which then engulf cytoplasmic proteins and organelles and fuse with lysosomes, leading to the degradation of cell components and the recycling of cellular building blocks. In mammals, mTORC1 directly phosphorylates and suppresses ULK1/Atg13/FIP200 (unc-51-like kinase 1/mammalian autophagy-related gene 13/focal adhesion kinase family-interacting protein of 200 kDa), a kinase complex required to initiate autophagy. As with the control of protein and lipid synthesis, mTORC1 is likely to impact autophagy through several mechanisms. For example, mTORC1 regulates death associated protein 1 (DAP1), a suppressor of autophagy and, in a recent analysis of the mTOR-dependent phosphoproteome, WIPI2, a mammalian ortholog of Atg18—a regulator of early autophagosome formation in yeast—emerged as a potential mTOR effector.

mTORC2 controls several members of the AGC subfamily of kinases including Akt, serum- and glucocorticoid-induced protein kinase 1 (SGK1), and protein kinase C-α (PKC-α). Akt regulates cellular processes such as metabolism, survival, apoptosis, growth, and proliferation through the phosphorylation of several effectors. mTORC2 directly activates Akt by phosphorylating its hydrophobic motif (Ser473), a site required for its maximal activation. Defective Akt-Ser473 phosphorylation associated with mTORC2 depletion impairs the phosphorylation of some Akt targets, including forkhead box O1/3a (FoxO1/3a), while other Akt targets like TSC2 and GSK3-β remain unaffected. The fact that Akt activity is not completely abolished in cells lacking mTORC2 likely explains these results. mTORC2 also directly activates SGK1, a kinase controlling ion transport and growth. In contrast to Akt, SGK-1 activity is completely blocked by the loss of mTORC2. Because SGK1 controls FoxO1/3a phosphorylation on residues also phosphorylated by Akt, loss of SGK1 activity is probably responsible for the reduction in FoxO1/3a phosphorylation in mTORC2-depleted cells. PKC-α is the third AGC kinase activated by mTORC2. Along with other effectors such as paxilin and Rho GTPases, the activation of PKC-α by mTORC2 regulates cell shape in cell type-specific fashion by affecting the actin cytoskeleton.

Several observations support the importance of mTOR pathway in cancer pathogenesis. Many components of the PI3K signaling pathway, which is upstream of both mTORC1 and mTORC2, are mutated in human cancers. Additionally, the loss of p53, a very common event in cancer, promotes mTORC1 activation. In addition, several familial cancer syndromes arise from mutations in genes encoding proteins that lie upstream of the mTOR complexes, including Tsc1/2, serine threonine kinase 11 (Lkb1), Pten, and neurofibromatosis type 1 (Nf1). Oncogenic activation of mTOR signaling induces several processes required for cancer cell growth, survival, and proliferation.

In certain embodiments, the methods described herein encompass assessing the level of and/or relative changes in the level of activation of the mTOR pathway (e.g., in a test sample, e.g. of or from a cancer cell). Non-limiting examples of cancers in which the level of mTOR pathway activation is known to be increased include, e.g., endometrial, renal cell, prostate, non-small cell lung, neuroendocrine cancers, as well as glioblastoma multiforme, multiple myeloma, non-Hodgkin lymphoma, chronic myelogenous leukemia, chronic lymphocytic leukemia, acute lymphoblastic leukemia, and acute myeloid leukemia. The skilled artisan will appreciate that the level of mTOR pathway is also increased in other cancers not listed herein; however, such cancers are also encompassed by the present disclosure.

In some embodiments, the level of activation and/or any relative change (e.g., compared to a prior measurement) in the level of activation of the mTOR pathway can be determined by detecting, for example, the level of phosphorylation of one or more polypeptides mTOR, ribosomal protein S6 (S6), S6 kinase (S6K), 4E-BP1, and eIF2α. Further, mTOR is known to phosphorylate STAT3 on serine 727 and increase its transcriptional activity [see, e.g., Yokogami K, et al. (2000) Serine phosphorylation and maximal activation of STAT3 during CNTF signaling is mediated by the rapamycin target mTOR. Current Biology: CB 10(1):47-50]. Thus, phosphoSTAT3 (pSTAT3) is also a marker of activated mTOR pathway.

Methods for measuring the expression levels of phosphorylated polypeptides are known in the art. For example, Western blotting using antibodies specific for phosphorylated forms, as well as non-phosphorylated forms, or total polypeptide (phosphorylated and non-phosphorylated), are commercially available. The presence and/or levels of phosphorylated polypeptides can be compared to the total levels of the polypeptide. Exemplary, non-limiting examples of commercially-available antibodies for detecting markers of activated mTOR pathway are listed in Table 2, below:

TABLE 2

Antibodies for Detecting Total (t) and Phosphorylated (p) Forms of Markers of Activated mTOR Pathway

| Polypeptide | Commercially Available Antibody - Catalog # |
| --- | --- |
| t-mTOR | Cell Signaling Technology - 2972 |
| p-mTOR | Cell Signaling Technology - 2976 |
| t-S6 | Cell Signaling Technology - 2217 |
| p-S6 | Cell Signaling Technology - 2215 |
| t-S6K | Cell Signaling Technology - 2708 |
| p-S6K | Cell Signaling Technology - 9234 |
| t-4E-BP1 | Cell Signaling Technology - 9451 |
| P-4E-BP1 | Cell Signaling Technology - 9452 |
| t-eIF2α | Cell Signaling Technology - 5324 |
| p-eIF2α | Cell Signaling Technology - 9721 |
| t-STAT3 | Santa Cruz Biotechnology - sc-7179 |
| phospho-Y705 STAT3 | Cell Signaling Technology - 9131 See, also, Frank DA, Mahajan S, & Ritz J (1997) B lymphocytes from patients with chronic lymphocytic leukemia contain signal transducer and activator of transcription (STAT) 1 and STAT3 constitutively phosphorylated on serine residues. The Journal of Clinical Investigation 100(12): 3140-3148. |

Table legend:
"t" in column 1 = total;
"p" in column 1 = phospho

STAT3 Pathway

It is presently discovered that atovaquone-related compounds are potent inhibitors of signal transducer and activator of transcription 3 (STAT3). While not intending to bound by theory or any particular mechanism of action, it is demonstrated herein that atovaquone is not a kinase inhibitor, but instead downregulates cell-surface gp130 expression, which is required for STAT3 activation in multiple contexts. An abundance of evidence establishes STAT3 as a central oncogenic mediator. STAT3 activation is transient and tightly-controlled in normal cells, but is often constitutively activated in numerous tumor types to drive target genes regulating growth, survival, invasion, and angiogenesis. A major source of STAT3 activation in malignancy is the cytokine IL-6 (interleukin-6), which signals through a complex of IL-6Rα (interleukin-6 receptor α) and gp130 to activate Janus kinases (JAKs) and induce phosphorylation of STAT3. The importance of IL-6-driven STAT3 activation has been demonstrated in multiple tumor types, including breast, lung, liver, prostate, pancreatic, colon, head and neck, multiple myeloma, and melanoma. The source of IL-6 can be paracrine—derived from non-neoplastic stromal or inflammatory cells—or autocrine, produced by tumor cells.

STAT3 is activated by a plethora of oncogenic kinases and growth factors, and it is specifically required for transformation by v-Src and mutant c-Kit. Conversely, loss of STAT3 inhibits tumor formation in multiple cell types (see, Frank D A (2007) STAT3 as a central mediator of neoplastic cellular transformation. Cancer letters 251(2):199-210)). Moreover, a constitutively-active variant of STAT3, termed STAT3C, is sufficient for neoplastic transformation and induces tumorigenic target genes such as cyclin D1, Bcl-X, and c-Myc (38). STAT3C has cysteine residues introduced near the C-terminus that form intermolecular disulfide bridges, promoting dimerization and transcriptional activity. In addition to transformation and tumor initiation, STAT3 is also critical to tumor maintenance and progression. For example, inhibition of constitutively-active STAT3 in multiple tumor models and cancer cell lines leads to apoptosis (see, Devarajan E & Huang S (2009) STAT3 as a central regulator of tumor metastases. Current Molecular Medicine 9(5):626-633).

STAT3 has numerous targets, and knowledge of how STAT3 acts on these targets can be taken advantage of to determine whether or not the STAT3 pathway is activated (e.g., in a cell, e.g., a cancer cell, e.g., in a cancer patient). The activity of STAT3 and markers of STAT3 activation are known in the art; non-limiting examples are described for various cancers below.

For example, the effects of STAT3 are mediated by the direct regulation of diverse target genes involving all of the hallmarks of cancer (see, Hanahan D & Weinberg R A (2011) Hallmarks of cancer: the next generation. Cell 144 (5):646-674). Also, the significance of STAT3 in tumor-stromal interactions is increasingly gaining attention. Uncontrolled proliferation, one of the first cancer hallmarks to be recognized, is advanced by STAT3 at many levels. STAT3 induces cyclin D1 (see, Bromberg J F, et al. (1999) Stat3 as an oncogene. Cell 98(3):295-303; and Sinibaldi D, et al. (2000) Induction of p21WAF1/CIP1 and cyclin D1 expression by the Src oncoprotein in mouse fibroblasts: role of activated STAT3 signaling. Oncogene 19(48):5419-5427), which is critical for G1/S phase transition, as well as cyclins D2/D3/A and the phosphatase cdc25A (see, Fukada T, et al. (1998) STAT3 orchestrates contradictory signals in cytokine-induced G1 to S cell-cycle transition. The EMBO journal 17(22):6670-6677). Moreover, genome-wide profiling of STAT3-regulated genes identified Egr1 and JunB as further targets promoting cell cycle entry (see, e.g., Frank D A (2007) STAT3 as a central mediator of neoplastic cellular transformation. Cancer Letters 251(2):199-210). Also, STAT3 antagonizes the cell cycle inhibitors p21 and p27 by direct transcriptional repression (Fukada et al., supra) and by upregulating Skp2, which mediates their ubiquitin-mediated degradation (see, Huang H, Zhao W, & Yang D (2012) Stat3 induces oncogenic Skp2 expression in human cervical carcinoma cells. Biochemical and biophysical research communications 418(1):186-190).

STAT3 induction of c-Myc, a pleiotropic protein with key roles in cancer growth and proliferation, is required for v-Src transformation and PDGFR-induced mitogenesis (Bowman T, et al. (2001) Stat3-mediated Myc expression is required for Src transformation and PDGF-induced mitogenesis. Proceedings of the National Academy of Sciences of the United States of America 98(13):7319-7324). Moreover, the kinases Pim-1 and Pim-2 are STAT3 targets, and ectopic expression of Pim-1 with c-Myc fully rescues loss of cell cycle progression after STAT3 inhibition (Shirogane T, et al. (1999) Synergistic roles for Pim-1 and c-Myc in STAT3-mediated cell cycle progression and antiapoptosis. Immunity 11(6): 709-719). Finally, STAT3 fosters limitless replicative potential by directly inducing telomerase (Konnikova L, Simeone M C, Kruger M M, Kotecki M, & Cochran B H (2005) Signal transducer and activator of transcription 3 (STAT3) regulates human telomerase reverse transcriptase (hTERT) expression in human cancer and primary cells. Cancer Research 65(15):6516-6520).

STAT3 also enhances cancer cell survival. While STAT3 regulates Bcl-2 and mediates chemotherapy resistance, STAT3 regulation of Bcl-X has been better studied. STAT3 is required for Bcl-X expression by EGFR in head and neck squamous cell carcinoma (HNSCC), HER2 in breast cancer, and IL-6 in multiple myeloma (see, Grandis J R, et al. (2000) Constitutive activation of Stat3 signaling abrogates apoptosis in squamous cell carcinogenesis in vivo. Proceedings of the National Academy of Sciences of the United States of America 97(8):4227-4232; Karni R, Jove R, & Levitzki A (1999) Inhibition of pp60c-Src reduces Bcl-XL expression and reverses the transformed phenotype of cells overexpressing EGF and HER-2 receptors. Oncogene 18(33):4654-4662; Catlett-Falcone R, et al. (1999) Constitutive activation of Stat3 signaling confers resistance to apoptosis in human U266 myeloma cells. Immunity 10(1):105-115; and Bowman T, et al. (2000) STATs in oncogenesis. Oncogene 19(21):2474-2488). Mcl-1, a related STAT3 target, collaborates with Bcl-X to resist Fas-mediated cell death, particularly in hematological cancers (Catlett-Falcone R, et al., supra, Epling-Burnette P K, et al. (2001) Inhibition of STAT3 signaling leads to apoptosis of leukemic large granular lymphocytes and decreased Mcl-1 expression. The Journal of Clinical Investigation 107(3):351-362; and Puthier D, et al. (1999) IL-6 up-regulates mcl-1 in human myeloma cells through JAK/STAT rather than ras/MAP kinase pathway. European Journal of Immunology 29(12):3945-3950).

Survivin is another anti-apoptotic protein induced by STAT3 in various settings, including astrocytoma, breast cancer, gastric cancer, and primary effusion lymphoma (see, e.g., Konnikova L, et al. (2003) Knockdown of STAT3 expression by RNAi induces apoptosis in astrocytoma cells. BMC Cancer 3:23; Gritsko T, et al. (2006)). Persistent activation of stat3 signaling induces survivin gene expression and confers resistance to apoptosis in human breast cancer cells. Clinical Cancer Research: an Official Journal of the American Association for Cancer Research 12(1):11-19; Kanda N, et al. (2004) STAT3 is constitutively activated and supports cell survival in association with survivin expression in gastric cancer cells. Oncogene 23(28):4921-4929; and Aoki Y, Feldman G M, & Tosato G (2003) Inhibition of STAT3 signaling induces apoptosis and decreases survivin expression in primary effusion lymphoma. Blood 101(4): 1535-1542). Inhibiting STAT3 reduces levels of these survival factors and causes apoptosis, which is reversed by their enforced expression, demonstrating the importance of these downstream effectors (see, Bowman T et al., supra, Gritsko T, et al., supra, Aoki Y. et al., supra, and Lim C P & Cao X (2006) Structure, function, and regulation of STAT proteins. Molecular BioSystems 2(11):536-550).

Additionally, STAT3 transcriptional repression of pro-apoptotic Fas, TNF-α, and p53 facilitates tumor escape from normal death signals (see, Niu G, et al. (2005) Role of Stat3 in regulating p53 expression and function. Molecular and Cellular Biology 25(17):7432-7440, Ivanov V N, et al. (2001) Cooperation between STAT3 and c-jun suppresses Fas transcription. Molecular cell 7(3):517-528; and Niu G, et al. (2001) Overexpression of a dominant-negative signal transducer and activator of transcription 3 variant in tumor cells leads to production of soluble factors that induce apoptosis and cell cycle arrest. Cancer Research 61(8):3276-3280). Self-renewal and resistance to apoptosis are traits of cancer stem cells (CSC), and not surprisingly, STAT3 has been linked to the CSC phenotype. In fact, LIF activation of STAT3 is critical to pluripotency in embryonic stem cells. The STAT3 target genes KLF4 and BCL6 inhibit differentiation (see, Frank et al., supra), while another STAT3 target, DNA methyltransferase I (see, Zhang Q, et al. (2006) STAT3 induces transcription of the DNA methyltransferase 1 gene (DNMT1) in malignant T lymphocytes. Blood 108(3):1058-1064), functions to maintain both hematopoietic and leukemic stem cells. CSCs in glioblastoma and breast cancer require STAT3 activation (see, Marotta L L, et al. (2011) The JAK2/STAT3 signaling pathway is required for growth of CD44(+)CD24(−) stem cell-like breast cancer cells in human tumors. The Journal of Clinical Investigation 121 (7):2723-2735; and Sherry M M, et al. (2009) STAT3 is required for proliferation and maintenance of multipotency in glioblastoma stem cells. Stem Cells 27(10):2383-2392) resulting from IL-6 or EGFR (Yang J, et al. (2013) Tumor-associated macrophages regulate murine breast cancer stem cells through a novel paracrine EGFR/Stat3/Sox-2 signaling pathway. Stem Cells 31(2):248-258).

Also, trastuzumab (HER-2-specific monoclonal antibody) resistance in HER2+ breast tumors occurs by IL-6-driven expansion of stem-like cells. In other cases, STAT3 activation in CSCs is due to Runx1-mediated silencing of SOCS family members. STAT3 additionally promotes CSCs via tumor-stromal interactions. Breast cancer cells secrete factors that activate STAT3 in cancer-associated fibroblasts, which respond by producing CCL2 to induce CSC phenotypes in breast cancer cells (see, Tsuyada A, et al. (2012) CCL2 mediates cross-talk between cancer cells and stromal fibroblasts that regulates breast cancer stem cells. Cancer research 72(11):2768-2779).

STAT3 activation is associated with aggressive clinical behavior and poor prognosis. Interestingly, inhibiting STAT3 can prevent tumor growth in mice without affecting growth of cancer cells in vitro (Hedvat M, et al. (2009) The JAK2 inhibitor AZD1480 potently blocks Stat3 signaling and oncogenesis in solid tumors. Cancer cell 16(6):487-497; and Xie T X, et al. (2004) Stat3 activation regulates the expression of matrix metalloproteinase-2 and tumor invasion and metastasis. Oncogene 23(20):3550-3560). The ability to migrate, invade, and eventually metastasize is a malignant hallmark that enables cancer cells to grow and spread in vivo. Thus, STAT3 has been found to intimately regulate these processes, and in particular, many matrix metalloproteinases (MMPs) are under transcriptional control of STAT3. For example, STAT3 regulation of MMP-2 promotes invasion and metastasis in melanoma and ovarian cancer cells (see, Xie T X et al., supra; Xie T X, et al. (2006) Activation of stat3 in human melanoma promotes brain metastasis. Cancer Research 66(6):3188-3196; and Seo J M, et al. (2012) Leukotriene B4 receptor-2 promotes invasiveness and metastasis of ovarian cancer cells through signal transducer and activator of transcription 3 (STAT3)-dependent up-regulation of matrix metalloproteinase 2. The Journal of Biological Chemistry 287(17):13840-13849), while MMP-7 is critical to pancreatic cancer progression (see, Fukuda A, et al. (2011) Stat3 and MMPI contribute to pancreatic ductal adenocarcinoma initiation and progression. Cancer cell 19(4):441-455).

STAT3 and c-Jun cooperatively induce MMP-1 and MMP-10 in bladder cancer cells to increase motility and tumor formation in mice (see, Itoh M, et al. (2006) Requirement of STAT3 activation for maximal collagenase-1 (MMP-1) induction by epidermal growth factor and malignant characteristics in T24 bladder cancer cells. Oncogene 25(8):1195-1204). Moreover, STAT3C transformation of immortalized breast epithelial cells requires MMP-9, whose expression correlates with STAT3 activation in primary breast cancers (Dechow T N, et al. (2004) Requirement of matrix metalloproteinase-9 for the transformation of human mammary epithelial cells by Stat3-C. Proceedings of the National Academy of Sciences of the United States of America 101(29):10602-10607).

Besides MMPs, genes linked to epithelial-mesenchymal transition (EMT) are regulated by STAT3. For instance, STAT3 directly promotes Snail expression while also inducing LIV1, a zinc transporter essential for Snail nuclear localization (see, Yamashita S, et al. (2004) Zinc transporter LIVI controls epithelial-mesenchymal transition in zebrafish gastrula organizer. Nature 429(6989):298-302; and Yadav A, et al. (2011) IL-6 promotes head and neck tumor metastasis by inducing epithelial-mesenchymal transition via the JAK-STAT3-SNAIL signaling pathway. Molecular Cancer Research: MCR 9(12):1658-1667.=).

Twist is another key EMT gene upregulated by STAT3 (see, Cheng G Z, et al. (2008) Twist is transcriptionally induced by activation of STAT3 and mediates STAT3 oncogenic function. The Journal of biological chemistry 283(21): 14665-14673; Pakala S B, et al. (2013) MTA1 promotes STAT3 transcription and pulmonary metastasis in breast cancer. Cancer research; and Cho K H, et al. (2013) STAT3 mediates TGF-beta1-induced TWIST1 expression and prostate cancer invasion. Cancer Letters.). STAT3 mediates EGFR-stimulated Twist expression, E-cadherin downregulation and human colorectal cancer epithelial-mesenchymal transition (EMT), and motility, and levels of Twist correlate with EGFR and STAT3 phosphorylation in primary breast tumors (see, Lo H W, et al. (2007) Epidermal growth factor receptor cooperates with signal transducer and activator of transcription 3 to induce epithelial-mesenchymal transition in cancer cells via up-regulation of TWIST gene expression. Cancer Research 67(19):9066-9076).

In colorectal carcinoma, STAT3 may promote EMT by inducing ZEB1, a repressor of E-cadherin. Transformation of immortalized prostate epithelial cells by STAT3C involves upregulation of integrin β6 and its ligands fibronectin and tenascin C, which produce an EMT phenotype. Reciprocally, HER2 interaction with integrin 134 activates STAT3 to cause loss of epithelial adhesion and polarity. STAT3 also modulates the cytoskeleton to promote migration through both transcriptional and non-transcriptional mechanisms. Angiogenesis is another process crucial to tumor growth in vivo but is not readily assayed in vitro. STAT3 induction of MMPs may facilitate angiogenesis (Xiong H, et al. (2012) Roles of STAT3 and ZEB1 proteins in E-cadherin downregulation and human colorectal cancer epithelial-mesenchymal transition. The Journal of Biological Chemistry 287(8):5819-5832), in addition to their role in motility.

The pro-angiogenic factor VEGF (vascular endothelial growth factor) is a STAT3 target gene. In multiple cancer models, STAT3 regulation of VEGF enhances tumor vascularity, growth, and metastasis in vivo; inhibiting STAT3 or VEGF does the opposite. Interestingly, STAT3 activation in endothelial cells is critical to assuming the angiogenic phenotype (Yahata Y, et al. (2003) Nuclear translocation of phosphorylated STAT3 is essential for vascular endothelial growth factor-induced human dermal microvascular endothelial cell migration and tube formation. The Journal of biological chemistry 278(41):40026-40031) and derives from VEGF itself, alongside other factors secreted by both tumor cells and tumor-infiltrating myeloid cells. Thus, STAT3 activation in tumor cells spreads to stromal cells, fostering tumor growth from multiple cellular compartments. STAT3 in both tumor and stroma can also modulate VEGF indirectly by upregulating HIF-1α, which stimulates VEGF transcription (Xu Q, et al. (2005) Targeting Stat3 blocks both HIF-1 and VEGF expression induced by multiple oncogenic growth signaling pathways. Oncogene 24(36):5552-5560; and Niu G, et al. (2008) Signal transducer and activator of transcription 3 is required for hypoxia-inducible factor-1alpha RNA expression in both tumor cells and tumor-associated myeloid cells. Molecular Cancer Research: MCR 6(7):1099-1105).

Tumor growth in vivo requires evading immune destruction. Here, too, the actions of STAT3 in multiple cellular compartments are synergistic, functioning to dampen the immune response and promote tumor tolerance. In both cancer cells and cancer-associated fibroblasts, STAT3 curbs the secretion of chemoattractants and pro-inflammatory cytokines such as TNF-α and IFN-β, while inducing the secretion of immunosuppressive IL-6, IL-10, and TGF-β (see, Burdelya L, et al. (2005) Stat3 activity in melanoma cells affects migration of immune effector cells and nitric oxide-mediated antitumor effects. J Immunol 174(7):3925-3931; Groner B, et al. (2008) The function of Stat3 in tumor cells and their microenvironment. Seminars in cell & developmental biology 19(4):341-350; and Bollrath J & Greten F R (2009) IKK/NF-kappaB and STAT3 pathways: central signaling hubs in inflammation-mediated tumour promotion and metastasis. EMBO Reports 10(12):1314-1319). Furthermore, the maturation and function of immunological cells is impaired by STAT3 activation, which can result from STAT3-dependent secretion of paracrine factors by tumor cells.

In some aspects, determining whether the STAT3 pathway is activated and/or determining whether the level of activation of the STAT3 pathway, e.g., in a cell, is increased, decreased, or not increased, or not decreased, relative to a control (e.g., a cell in which it is known that the STAT3 pathway is not activated, and or a control reference value), includes assessing the levels of STAT3-dependent gene expression. Determining STAT3-dependent gene expression includes determining the expression level of one or more STAT3-regulated genes and/or the level of one or more polypeptides encoded by STAT3-regulated gene(s). The list of STAT3-regulated genes is lengthy, and known in the art. Thus, a complete list of STAT3-regulated genes is not disclosed herein. However, non-limiting examples of STAT3-regulated genes include, e.g., myeloid cell leukemia sequence 1 (BCL2-related) (MCL1), jun B proto-oncogene (JUNB), B-cell CLL/lymphoma 6 (BCL6), nuclear factor, interleukin 3 regulated (NFIL3), calpain 2, (m/II) large subunit (CAPN2), early growth response 1 (EGR1), vascular endothelial growth factor A (VEGF), protein tyrosine phosphatase type IVA, member 1 (PTPCAAX1), Kruppel-like factor 4 (gut) (KLF4), exostosin glycosyltransferase 1 (EXT1), Niemann-Pick disease, type C1 (NPC1), p21 protein (Cdc42/Rac)-activated kinase 2 (PAK2), pericentrin (PCNT), fibrinogen-like 2 (FGL2), angiopoietin 1 (AN- GPT1), GRB10 interacting GYF protein 1 (GIGYF1)(also known as PERQ1), ceroid-lipofuscinosis, neuronal 6, late infantile, variant (CLN6), Brother of CDO (BOC), cysteine dioxygenase (CDO), BCL2-like 1 (BCL2L1) (BCLX), CYCLIN D1, baculoviral IAP repeat containing 5 (BIRC5) (also known as SURVIVIN), and B-cell CLL/lymphoma 2 (BCL2) (this exemplary group of genes is referred to herein as "STAT3-regulated genes") (see also, Alvarez J V, et al. (2005) Identification of a genetic signature of activated signal transducer and activator of transcription 3 in human tumors. Cancer research 65(12):5054-5062). Thus, in some embodiments, the level of STAT3 pathway activation correlates with the level of expression of one or more of the STAT3-regulated genes encoding polypeptides including, e.g., MCL1, JUNB, BCL6, NFIL3, CAPN2, EGR1, VEGF, PTPCAAX1, KLF4, EXT1, NPC1, PAK2, BCLX, SURVIVIN, and BCL2 (this group of genes is referred to herein collectively as "STAT3 upregulated genes"). In some embodiments, the level of STAT3 pathway activation correlates inversely with the level of expression of one or more of the STAT3-regulated genes encoding polypeptides including, e.g., PCNT, FGL2, ANGPT1, PERQ1, CLN6, BOC, and CDO (this group of genes is referred to herein collectively as "STAT3 downregulated genes.

The GenBank® Accession Nos. for the human nucleic acid sequences of these genes, as well as the human amino acid sequences encoded by those genes are set forth in Table 3, below:

TABLE 3

GenBank ® Accession Nos.

| Gene Name | Nucleic Acid GenBank ® No. | SEQ ID NO: | Amino Acid GenBank ® No. | SEQ ID NO.: |
|---|---|---|---|---|
| MCL1 | NM_001197320 | 13 | NP_001184249 | 14 |
| JUNB | NM_002229 | 15 | NP_002220 | 16 |
| BCL6 | NM_001130845 | 17 | NP_001124317 | 18 |
| NFIL3 | NM_005384 | 19 | NP_005375 | 20 |
| CAPN2 | NM_001146068 | 21 | NP_001139540 | 22 |
| EGR1 | NM_001964 | 23 | NP_001955 | 24 |
| VEGF | NM_001025366 | 25 | NP_001020537 | 26 |
| PTPCAAX1 | NM_003463 | 27 | NP_003454 | 28 |
| KLF4 | NM_004235 | 29 | NP_004226 | 30 |
| EXT1 | NM_000127 | 31 | NP_000118 | 32 |
| NPC1 | NM_000271 | 33 | NP_000262 | 34 |
| PAK2 | NM_002577 | 35 | NP_002568 | 36 |
| PCNT | NM_006031 | 37 | NP_006022 | 38 |
| FGL2 | NM_006682 | 39 | NP_006673 | 40 |
| ANGPT1 | NM_001146 | 41 | NP_001137 | 42 |
| PERQ1 | NM_022574 | 43 | NP_072096 | 44 |
| CLN6 | NM_017882 | 45 | NP_060352 | 46 |
| BOC | NM_033254 | 47 | NP_150279 | 48 |
| CDO | NM_001801.2 | 49 | NP_001792.2 | 50 |
| BCLX, | NM_138578 | 51 | NP_612815.1 | 52 |
| CYCLIN D1 | NM_053056 | 53 | NP_444284.1 | 54 |
| SURVIVIN | NM_001168 | 55 | NP_001159 | 56 |
| BCL2 | NM_000633 | 57 | NP_000624 | 58 |

Furthermore, in other embodiments, the level of activation of the STAT3 pathway is determined by detecting STAT3 phosphorylation, nuclear localization of STAT3, STAT3 DNA binding, and/or cell surface expression of the protein gp130 (CD130).

In some aspects, the STAT3 phosphorylation comprises phosphorylation of tyrosine 705 of human STAT3. Antibodies for detecting phosphorylation of tyrosine 705 of human STAT3 and gp130 are commercially available, e.g., from Cell Signaling Technology and Santa Cruz Biotechnology.

Methods for determining STAT3 phosphorylation are known in the art, e.g., Western blot. Methods for determining cell surface expression of markers such as gp130 are also known in the art (e.g., flow cytometry), and are described in Example 1, below.

STAT3 DNA binding can be determined by, e.g., electrophoretic mobility shift assay (EMSA), as described in Turkson J. et al. Requirement of Ras/Rac1-mediated p38 and c-Jun N-terminal kinase signaling for Stat3 transcriptional activity induced by the Src oncoprotein. Mol. Cel. Biol. 1999; 19:7519-28. STAT3 DNA binding can also be measured by chromatin immunoprecipitation (ChIP) as described, e.g., in Walker S R et al. STAT5 outcompetes STAT3 to regulate the expression of the oncogenic transcriptional modulator BCL6. Molecular and Cellular Biology 2013; 33:2879-90.

Any of the above markers or combinations of two or more thereof can be used to determine whether the STAT3 pathway is active in a test sample (e.g., in a cancer cell and/or subject with cancer).

Atovaquone-Related Compounds

Provided herein are atovaquone-related compounds and methods of their use. Atovaquone-related compounds include atovaquone itself, as well as other compounds that have both STAT3 and mTOR inhibitory activities. Examples of atovaquone-related compounds include substituted hydroxynaphthoquinone compounds. Suitable substituents on substituted hydroxynaphthoquinone compounds include halogen (e.g., F, Cl, Br, or I), $C_1$-$C_{10}$ alkyl, $C_3$-$C_{20}$ cycloalkyl, or aryl. In some embodiments, substituents such as $C_3$-$C_{20}$ cycloalkyl and aryl can be optionally further substituted with halogen or $C_1$-$C_{10}$ alkyl.

In some embodiments, a substituted hydroxynaphthoquinone can be a compound of formula (I):

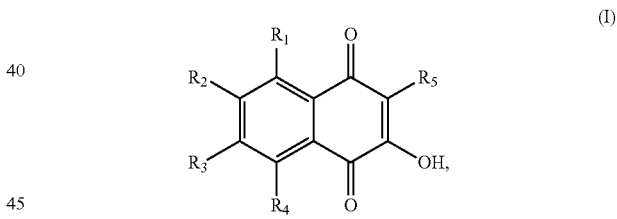

in which each of $R_1$, $R_2$, $R_3$, and $R_4$, independently is H or $C_1$-$C_{10}$ alkyl; $R_5$ is $C_1$-$C_{10}$ alkyl optionally substituted with $C_3$-$C_{20}$ cycloalkyl, or $C_3$-$C_{20}$ cycloalkyl optionally substituted with $C_1$-$C_{10}$ alkyl or aryl; and each of $C_3$-$C_{20}$ cycloalkyl and aryl, independently, is optionally substituted with halogen (e.g., F, Cl, Br, or I) or $C_1$-$C_{10}$ alkyl.

A subset of the compounds of formula (I) are those in which $R_5$ is cyclohexyl substituted with aryl (e.g., phenyl), in which aryl is substituted with Cl. In such compounds, each of $R_1$, $R_2$, $R_3$, and $R_4$ can be H. Examples of such compounds include atovaquone and its cis-isomer.

Another subset of the compounds of formula (I) are those in which $R_5$ is methyl substituted with cyclohexyl, in which cycloalkyl is substituted with t-butyl or $R_5$ is n-butyl substituted with decahydronaphthyl. In such compounds, each of $R_1$, $R_2$, $R_3$, and $R_4$ can be H. Examples of such compounds include buparvaquone and TCBHN described below.

In some embodiments, a substituted hydroxynaphthoquinone can be a compound of formula (II):

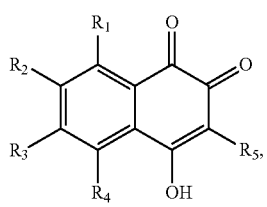

(II)

in which each of $R_1$, $R_2$, $R_3$, and $R_4$, independently is H or $C_1$-$C_{10}$ alkyl; $R_5$ is $C_1$-$C_{10}$ alkyl optionally substituted with $C_3$-$C_{20}$ cycloalkyl, or $C_3$-$C_{20}$ cycloalkyl optionally substituted with $C_1$-$C_{10}$ alkyl or aryl; and each of $C_3$-$C_{20}$ cycloalkyl and aryl, independently, is optionally substituted with halogen or $C_1$-$C_{10}$ alkyl.

A subset of the compounds of formula (I) are those in which $R_5$ is cyclohexyl. In such compounds, each of $R_1$, $R_2$, $R_3$, and $R_4$ can be H. An example of such compounds is parvaquone described below.

Atovaquone is commercially available (trade name: Mepron]. It is an antiprotozoal agent with the chemical name trans-2-[4-(4-chlorophenyl)cyclohexyl]-3-hydroxy-1,4-naphthalenedione. Mepron is formulation as a suspension for oral administration. Each teaspoonful (5 mL) contains 750 mg of atovaquone and the inactive ingredients benzyl alcohol, flavor, poloxamer 188, purified water, saccharin sodium, and xanthan gum.

Other atovaquone-related compounds encompassed herein include atovaquone's isomer (cis-2-[4-(4-chlorophenyl)cyclohexyl]-3-hydroxy-1,4-naphthoquinone), buparvaquone (2((4-tert-butylcyclohexyl)methyl)-3-hydroxy-1,4-naphthoquinone) (Hudson, A. T., et al.: Parasitology, 90, 45 (1985), Dhar, S., et al.: Vet. Rec., 119, 635 (1986)), parvaquone (3-cyclohexyl-4-hydroxy-naphthalene-1,2-dione), and 2-(4-(trans-decahydronaphth-2-yl)butyl)-3-hydoxy-1,4-naphthoquinone (TDBHN).

Also encompassed herein are analogs of the above-disclosed atovaquone-related compounds. Analogs encompassed herein have both STAT3 and mTOR inhibitory activities and, typically, although not necessarily, are structurally related to atovaquone. Methods for designing analogs are also known in the art. The desired activities of the analogs (i.e., both STAT3 and mTOR inhibitory activities and/or ability to induce activation of the eIF2α/ATF4 pathway) can be determined using, e.g., in vitro cell-based or in vivo assays described in detail above (e.g., Q-PCR, immunoprecipitation, Western blot, ELISA, etc.).

The atovaquone-related compounds described herein include the compounds themselves, as well as their pharmaceutically acceptable derivatives, such as salts, prodrugs, and solvates of the atovaquone-related compounds.

A salt of an atovaquone-related compound, for example, can be formed between an anion and a positively charged group (e.g., amino) on the compound. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on the compound. Suitable cations include sodium ion, potassium ion, magnesium ion, calcium ion, and an ammonium cation such as tetramethylammonium ion. The salts of the atovaquone-related compounds described herein also include those containing quaternary nitrogen atoms.

Examples of prodrugs of the atovaquone-related compounds described herein include esters and other derivatives, which, upon administration to a subject, are capable of providing active atovaquone-related compounds. A solvate refers to a complex formed between an active atovaquone-related compound and a pharmaceutically acceptable solvent. Examples of pharmaceutically acceptable solvents include water, ethanol, isopropanol, ethyl acetate, acetic acid, and ethanolamine.

Also within the scope of this disclosure is a pharmaceutical composition containing one or more of the atovaquone-related compounds described herein for use in treating cancer, and the use of such a composition for the manufacture of a medicament for the just-mentioned treatment.

Uses of Atovaquone-Related Compounds

It is presently discovered that atovaquone-related compounds inhibit STAT3 and mTOR pathways, as well as induce activation of the eIF2α/ATF4 pathway, and can be used for the treatment of cancer, as well as related benefits (e.g., determining whether a cancer is susceptible to treatment with an atovaquone-related compound, methods of monitoring efficacy of treatment with an atovaquone-related compound, etc.)

Cancers that can be treated according to the methods disclosed herein include, but are not limited to cancers with increased levels of activation of the STAT3 and/or mTOR pathways. Non-limiting examples included, e.g., solid such as breast cancer, melanoma, lung cancer, ovarian cancer, pancreatic cancer, colorectal cancer, prostate cancer, brain cancer, gastroesophageal cancer, kidney cancer; endometrial cancer, non-small cell lung cancer, neuroendocrine cancers, as well as glioblastoma multiforme, or a hematological cancer such as acute myeloid leukemia, chronic myeloid leukemia, Hodgkin lymphoma, non-Hodgkin lymphoma, multiple myeloma, acute lymphoblastic leukemia, and chronic lymphocytic leukemia.

Provided herein are methods of decreasing the growth of a cancer cell, the method comprising delivering to a target cancer cell a growth-inhibitory amount of an atovaquone-related compound (e.g., atovaquone, TDBHN, parvaquone, buparvaquone, etc.) (e.g., administering the compound to a cancer cell (e.g., a mammalian, e.g., human, cancer cell) or to a subject (e.g., mammal, e.g., human, subject) with cancer), wherein, prior to the delivery, an increased level of activation of the mTOR pathway in the cancer (e.g., in a test cell of or from the cancer) compared to a control level of activation of the mTOR pathway (e.g., in a control sample of or from a control cell) has been found. Further, in some aspects, prior to the delivery, an increased level of activation of the STAT3 pathway in the cancer compared to a control level of activation of the STAT3 pathway has also been found. An increased level of activation of the mTOR and/or STAT3 pathways means that level of expression of the one or more of the markers used to determine that the pathway is activated (described above) is upregulated by at least 2, 3, 4, 5, 6, 7, 8, 9, 10, 20, 30, 40, 50, 75, or 100-fold or more relative to a control level.

In some aspects, suitable control levels include, e.g., a predetermined value based on the expression level of the relevant marker(s) in one or more cancer-free individuals. Alternatively, or, in addition, the control level can be simultaneously or sequentially (either before or after) determined when the level in cancer is determined, e.g. in the same assay in which the cancer is tested, wherein the results are directly compared. A control level can also be the level in a sample (e.g., exosomes and/or microvesicles from a body fluid or a sample of or from one or more cancer cells) obtained from a subject prior to treatment with an atovaquone-related compound. Moreover, a control level can be the level in a sample of the tissue from the subject in which the cancer is located but in which no cancer cells are detectable, in a sample of the same tissue but in a different organ of the subject, or in a sample from the subject of a different tissue.

Also provided herein are methods of determining the susceptibility of a cancer (e.g., the cancers described above) in a subject to the growth-inhibitory effect of an atovaquone-related compound (e.g., atovaquone), the method comprising, assessing the level of activation of the mTOR pathway in a test sample from the subject, identifying the cancer as likely to be susceptible to the growth-inhibitory effect of atovaquone if an increased level of activation of the mTOR pathway is detected in the test sample compared to a control level of activation of the mTOR pathway, and identifying the cancer as less likely to be susceptible to the growth-inhibitory effect of atovaquone if an increased level activation of the mTOR pathway is not detected in the test sample compared to a control level of activation of the mTOR pathway than if an increased level of activation of the mTOR pathway is detected in the test sample compared to a control level of activation of the mTOR pathway. In some aspects, the method further comprises assessing the level of activation of the STAT3 pathway in the test sample or a second test sample from the subject, identifying the cancer as likely to be susceptible to the growth-inhibitory effect of atovaquone if an increased level of activation of the STAT3 is detected in the test sample or the second test sample compared to a control level of activation of the STAT3 pathway, and identifying the cancer as less likely to be susceptible to the growth-inhibitory effect of atovaquone if an increased level of activation of the STAT3 pathway is not detected in the test sample or the second test sample compared to a control level of activation of the STAT3 pathway than if an increased level of activation of the STAT3 pathway is detected in the test sample or the second test sample compared to a control level of activation of the mTOR pathway. In further aspects, the methods can further comprise administering an atovaquone-related compound to the subject if the increased level activation of the mTOR pathway is detected in the test sample. In some aspects, the method comprises administering an atovaquone-related compound to the subject if the increased level of activation of the mTOR pathway is detected in the test sample, if the increased level of activation of the STAT3 pathway is detected in the test sample or the second test sample, or if the increased level activation of the mTOR pathway is detected in the test sample and the increased level of activation of the STAT3 pathway is detected in the test sample or the second test sample.

In some aspects, the test sample is a sample of or from one or more cancer cells from the subject. In some aspects, the second test sample is a sample of or from one or more cancer cells from the subject.

In some aspects, the level of activation of the mTOR pathway is determined to be increased in the test sample relative to a control sample if the difference is at least 2, 3, 4, 5, 6, 7, 8, 9, or 10-fold. By way of non-limiting example, in one embodiment, if the expression level of REDD1, CHOP, ATF3, CHAC1, and/or ATF4 is at least 2, 3, 4, 5, 6, 7, 8, 9, or 10-fold increased in the test sample relative to the control, then it is determined that the mTOR pathway is increased, and the cancer cell is susceptible to treatment with an atovaquone-related compound. As another non-limiting example, if the level of phosphorylation of one or more of the following polypeptides: mTOR, ribosomal protein S6, S6 kinase, 4E-BP1, eIF2α, is at least 2, 3, 4, 5, 6, 7, 8, 9, or 10-fold increased in a test sample, relative to a control sample then it is determined that the mTOR pathway is increased, and the cancer cell is susceptible to treatment with an atovaquone-related compound. Methods for determining the level of activation of the mTOR pathway (e.g., by determining the expression levels of one or more of the markers described above), are described above.

In some aspects, the level of activation of the STAT3 pathway is determined to be increased in the test sample relative to a control sample if the difference is at least 2, 3, 4, 5, 6, 7, 8, 9, or 10-fold. By way of non-limiting example, in one embodiment, if the expression level of MCL1, JUNB, BCL6, NFIL3, CAPN2, EGR1, VEGF, PTPCAAX1, KLF4, EXT1, NPC1, PAK2, BCLX, SURVIVIN, and/or BCL2 is at least 2, 3, 4, 5, 6, 7, 8, 9, or 10-fold increased in the test sample relative to the control, then it is determined that the STAT3 pathway is increased, and the cancer cell is susceptible to treatment with an atovaquone-related compound. By way of non-limiting example, in one embodiment, if the expression level of PCNT, FGL2, ANGPT1, PERQ1, CLN6, BOC, and/or CDO is at least 2, 3, 4, 5, 6, 7, 8, 9, or 10-fold decreased in the test sample relative to the control, then it is determined that the STAT3 pathway is increased, and the cancer cell is susceptible to treatment with an atovaquone-related compound. As another non-limiting example, if the level of phosphorylation of STAT3 is at least 2, 3, 4, 5, 6, 7, 8, 9, or 10-fold increased in a test sample, relative to a control sample then it is determined that the STAT3 pathway is increased, and the cancer cell is susceptible to treatment with an atovaquone-related compound. Moreover, if nuclear localization of STAT-3, STAT-3 DNA binding, and/or STAT3-dependent gene expression is at least 2, 3, 4, 5, 6, 7, 8, 9, or 10-fold increased, then it is determined that the STAT3 pathway is increased, and the cancer cell is susceptible to treatment with an atovaquone-related compound.

Methods for determining the level of activation of the mTOR pathway and/or STAT3 pathway (e.g., by determining the expression levels of one or more of the markers described above), are described above.

In other aspects, provided herein are methods of assessing the success of cancer cell growth inhibitory therapy with an atovaquone-related compound (e.g., atovaquone) in a subject, the method comprising, assessing the level of activation of the mTOR pathway in a test sample from a subject that has been treated with the compound, identifying the treatment as having been successful if the level of activation of the mTOR pathway in the test sample is lower than the level of activation of the mTOR pathway in a control sample, and not identifying the treatment as having been successful if the level of activation of the mTOR pathway in the test sample is not lower than the level of activation of the mTOR pathway in a control sample. In some aspects, the method further comprises assessing the level of activation of the STAT3 pathway in the test sample or a second test sample from the subject that has been treated with the compound, identifying the treatment as having been successful if the level of activation of the STAT3 pathway in the test sample or the second test sample is lower than the level of activation of the STAT3 pathway in a control sample or a second control sample, and not identifying the treatment as having been successful if the level of activation of the STAT3 pathway in the test sample or the second test sample is not lower than the level of activation of the STAT3 pathway in the control sample or the second control sample.

In some aspects, the test sample is a sample of or from one or more cancer cells from the subject. In some aspects, the control sample or the second control sample was obtained from the subject prior to the treatment with the atovaquone-related compound.

Also provided herein are methods of assessing the success of cancer cell growth inhibitory therapy with an atovaquone-related compound in a subject are provided, wherein the method comprises: (a) assessing the level of activation of the eIF2α/ATF4 pathway in a test sample from a subject that has been treated with the compound, (b) identifying the treatment as having been successful if the level of activation of the eIF2α/ATF4 pathway in the test sample is increased relative to the level of activation of the eIF2α/ATF4 pathway in a control sample, and (c) not identifying the treatment as having been successful if the level of activation of the eIF2α/ATF4 pathway in the test sample is not increased relative to the level of activation of the eIF2α/ATF4 pathway in a control sample. In some embodiments, the method further comprises determining the level of expression of CHOP and/or CHAC1 and/or REDD1, wherein increased expression of one or both of the genes or the polypeptides encoded by these genes correlates with activation of the eIF2α/ATF4 pathway. In some aspects, the level of activation of the eIF2α/ATF4 pathway is determined to be increased in the test sample relative to a control sample if the difference is at least 2, 3, 4, 5, 6, 7, 8, 9, or 10-fold. In some aspects, the method comprises determining the level of phosphorylation of eIF2α, wherein its increased phosphorylation correlates with activation of the eIF2α/ATF4 pathway. In some aspects, the level of phosphorylation is determined to be increased relative to the control (e.g., a sample obtained prior to treatment with an atovaquone-related compound), if the level of phosphorylated protein is increased by at least 2, 3, 4, 5, 6, 7, 8, 9, or 10-fold. In other aspects, the method comprises determining the expression level of ATF4, wherein increased expression of ATF4 or the polypeptide encoded by ATF4 correlates with activation of the eIF2α/ATF4 pathway. In some aspects, the level of expression of ATF4 is determined to be increased relative to the control (e.g., a sample obtained prior to treatment with an atovaquone-related compound), if the level of expression of ATF4 is increased by at least 2, 3, 4, 5, 6, 7, 8, 9, or 10-fold.

In some aspects, the level of expression of CHOP is determined to be increased relative to the control (e.g., a sample obtained prior to treatment with an atovaquone-related compound), if the level of expression of CHOP is increased by at least 2, 3, 4, 5, 6, 7, 8, 9, or 10-fold.

In some aspects, the level of expression of CHAC1 is determined to be increased relative to the control (e.g., a sample obtained prior to treatment with an atovaquone-related compound), if the level of expression of CHAC1 is increased by at least 2, 3, 4, 5, 6, 7, 8, 9, or 10-fold.

In some aspects, the level of expression of REDD1 is determined to be increased relative to the control (e.g., a sample obtained prior to treatment with an atovaquone-related compound), if the level of expression of REDD1 is increased by at least 2, 3, 4, 5, 6, 7, 8, 9, or 10-fold.

Also provided herein are methods of treating cancer in a patient, the method comprising: administering a therapeutically effective amount of an atovaquone-related compound to a patient in need thereof; and, after the administration, monitoring the level of activation of the mTOR pathway in a test sample or two more serial test samples from the patient. In some aspects, the method further comprises, after the administration, monitoring the level of activation of the STAT3 pathway in the test sample, the two or more (e.g., three, four, five, six, seven, eight, nine, ten, or more) serial test samples, a second test sample or a second set of two or more serial test samples from the patient. In some aspects, the method further comprises continuing the treatment if the level of activation of the mTOR pathway in the test sample or the two or more serial test samples is decreased relative to its level of activation in a control sample obtained from the patient prior to treatment. In some aspects, the method further comprises continuing the treatment if the level of activation of the STAT3 pathway in the test sample, the two or more serial test samples, the second test sample, or the second set of two or more serial test samples is decreased relative to its level of activation in a control sample obtained from the patient prior to treatment. In some embodiments, these treatment methods can follow or be followed by steps including, e.g., diagnosing the patient (e.g., with cancer) and/or making a prognosis and/or determining whether the treatment method (e.g., treatment with an atovaquone-related compound) is likely to be successful for treating the cancer (e.g., if the cancer is likely susceptible to treatment with the atovaquone-related compound), as described herein.

In other aspects, also provided herein are methods of treating cancer in a patient, the method comprising: administering a therapeutically effective amount of an atovaquone-related compound to a patient in need thereof; and, after the administration, monitoring the level of activation of the eIF2α/ATF4 pathway in a test sample or two or more serial test samples from the patient. In some aspects, the method further comprises determining the level of expression of CHOP and/or CHAC1 and/or REDD1. In some aspects, the method further comprises, after the administration, monitoring the level of activation of the STAT3 pathway in the test sample, the two or more serial test samples, a second test sample or a second set of two or more serial test samples from the patient. In some aspects, the method further comprises, after the administration, monitoring the level of activation of the mTOR pathway in the test sample, the two or more serial test samples, a second test sample or a second set of two or more serial test samples from the patient. In some aspects, the method further comprises continuing the treatment if the level of activation of the eIF2α/ATF4 pathway and/or the expression level of CHOP and/or CHAC1 and/or REDD1 in the test sample or the two or more serial test samples is increased (e.g., by at least 2, 3, 4, 5, 6, 7, 8, 9, 10, 20, 30, 40, 50, 75, or 100-fold or more) relative to its level of activation in a control sample obtained from the patient prior to treatment. In some aspects, the method further comprises continuing the treatment if the level of activation of the STAT3 pathway in the test sample, the two or more serial test samples, the second test sample, or the second set of two or more serial test samples is decreased relative to its level of activation in a control sample obtained from the patient prior to treatment. In some aspects, the method further comprises continuing the treatment if the level of activation of the mTOR pathway in the test sample, the two or more serial test samples, the second test sample, or the second set of two or more serial test samples is decreased relative to its level of activation in a control sample obtained from the patient prior to treatment. Serial sets of test samples as disclosed herein can be taken at any frequency (e.g., every hour, every 12 hours, once a day, every other day, once a week, once a month, once every two, three, four, five, six, or nine months, or once a year) for as long as considered necessary (e.g., a day, several days, a week, a month, 6 months, a year, or longer). Moreover, times between taking of the samples can the same or different.

In some aspects, the test sample or each of the two or more serial test samples is a sample of or from one or more cancer cells from the subject. In some aspects, the second set of two or more serial test samples comprises a sample of or from one or more cancer cells from the subject. In other aspects, the control sample is obtained from non-autologous mammalian cancer cells (preferably of the same species as the test sample) known to have activated mTOR and/or STAT3 pathway(s) and/or known to not have activated eIF2α/ATF4 pathway.

In some aspects, the cancer cell growth inhibitory therapy or cancer treatment (i.e., "the treatment") is identified as having been successful if the level of activation of the mTOR pathway in the test sample is decreased, relative to the control sample, by at least 2-fold, at least 3-fold, at least 5-fold, at least 10-fold, or more. By way of non-limiting example, in one embodiment, if the expression level of REDD1, CHOP, ATF3, CHAC1, and/or ATF4 is at least 2, 3, 4, 5, 6, 7, 8, 9, or 10-fold increased in the test sample relative to the control, then it is determined that the treatment has been successful. As another non-limiting example, if the level of phosphorylation of one or more of the following polypeptides: mTOR, ribosomal protein S6, S6 kinase, 4E-BP1, eIF2α, at least 2, 3, 4, 5, 6, 7, 8, 9, or 10-fold decreased in the test sample, relative to the control sample then it is determined that the has been successful. Methods for determining the level of activation of the mTOR pathway (e.g., by determining the expression levels of one or more of the markers described above), are described above.

In some aspects, the treatment is identified as having been successful if the level of activation of the STAT3 pathway in the test sample is decreased, relative to the control sample, by at least 2-fold, at least 3-fold, at least 5-fold, at least 10-fold, or more. In some aspects, the level of activation of the STAT3 pathway is determined to be increased in the test sample relative to a control sample if the difference is at least 2, 3, 4, 5, 6, 7, 8, 9, or 10-fold. If the level of the STAT3 pathway is not increased in a test sample relative to a control sample, then it is not determined that the treatment with an atovaquone-related compound has been successful (or it is determined that it has not been successful). By way of non-limiting example, in one embodiment, if the expression level of MCL1, JUNB, BCL6, NFIL3, CAPN2, EGR1, VEGF, PTPCAAX1, KLF4, EXT1, NPC1, PAK2, BCLX, SURVIVIN, and/or BCL2 is at least 2, 3, 4, 5, 6, 7, 8, 9, or 10-fold decreased in the test sample relative to the control sample, then it is determined that the treatment has been successful. If the levels of MCL1, JUNB, BCL6, NFIL3, CAPN2, EGR1, VEGF, PTPCAAX1, KLF4, EXT1, NPC1, PAK2, BCLX, SURVIVIN, and/or BCL2 are not decreased in a test sample relative to a control sample, then it is not determined that the treatment with an atovaquone-related compound has been successful (or it is determined that it has not been successful). By way of non-limiting example, in one embodiment, if the expression level of PCNT, FGL2, ANGPT1, PERQ1, CLN6, BOC, and/or CDO is at least 2, 3, 4, 5, 6, 7, 8, 9, or 10-fold increased in the test sample relative to the control sample, then it is determined that the treatment has been successful. If the levels of the PCNT, FGL2, ANGPT1, PERQ1, CLN6, BOC, and/or CDO is not increased in a test sample relative to a control sample, then it is not determined that the treatment with an atovaquone-related compound has been successful (or it is determined that it has not been successful). As another non-limiting example, if the level of phosphorylation of STAT3 is at least 2, 3, 4, 5, 6, 7, 8, 9, or 10-fold decreased in the test sample, relative to the control sample, then it is determined that treatment has been successful. If the level of STAT3 phosphorylation is not increased in a test sample relative to a control sample, then it is not determined that the treatment with an atovaquone-related compound has been successful (or it is determined that it has not been successful). Moreover, if nuclear localization of STAT-3, STAT-3 DNA binding, STAT3-dependent gene expression, and/or cell surface expression of the protein gp130 (CD130) is at least 2, 3, 4, 5, 6, 7, 8, 9, or 10-fold decreased, then it is determined that the treatment has been successful. If the level of the nuclear localization of STAT-3, STAT-3 DNA binding, STAT3-dependent gene expression, and/or cell surface expression of the protein gp130 (CD130) is not increased in a test sample relative to a control sample, then it is not determined that the treatment with an atovaquone-related compound has been successful (or it is determined that it has not been successful).

In another aspect, the effect of an atovaquone-related compound in a subject is determined by determining whether the levels of eIF2α phosphorylation and ATF4 are increased relative to a control sample. If the levels of phospho-eIF2α and/or ATF4 are increased (e.g., at least 2-fold, at least 3-fold, at least 4-fold, at least 5-fold, at least 10-fold, or more) in a test sample relative to a control sample then the treatment with an atovaquone-related compound is expected to have the desired therapeutic effect (e.g., inhibition of the mTOR pathway, e.g. treatment of cancer). If the levels of phospho-eIF2α and/or ATF4 are not increased in a test sample relative to a control sample, then it is not determined that the treatment with an atovaquone-related compound has had the desired therapeutic effect (inhibition of the mTOR pathway, e.g. treatment of cancer), or it is determined that it has not had the desired therapeutic effect). In some embodiments, if the levels of CHOP and/or CHAC1 and/or REDD1 are increased (e.g., at least 2-fold, at least 3-fold, at least 4-fold, at least 5-fold, at least 10-fold, or more) in a test sample relative to a control sample, then it is determined that the treatment with an atovaquone-related compound has been successful. If the level of CHOP and/or CHAC1 and/or REDD1 is not increased in a test sample relative to a control sample, then it is not determined that the treatment with an atovaquone-related compound has been successful (or it is determined that it has not been successful).

In any of the above methods, the test sample(s) can be obtained from microvesicles or exosomes obtained from a body fluid of a subject with the cancer and the control sample(s) can be obtained from microvesicles or exosomes obtained from a control sample of the body fluid. In some aspects, the body can be blood, lymph, or urine, or other appropriate body fluid, e.g., cerebrospinal fluid (CSF), ascites, and pleural fluid. In other aspects, the test sample can be obtained from a tumor biopsy.

Any of the above described methods of treatment can further comprise administering to the subject (e.g., a subject in which the efficacy of the treatment with an atovaquone-related compound was determined to be poor or not optimal, or a subject in which initial treatment with an atovaquone-related compound produced tumor-inhibitory effects but the subject subsequently developed resistance to the treatment) an additional therapy for the treatment of cancer. Further, any of the treatment methods described herein can follow or be followed by steps including, e.g., diagnosing the patient (e.g., with cancer) and/or making a prognosis and/or determining whether the treatment method (e.g., treatment with an atovaquone-related compound) is likely to be successful for treating the cancer (e.g., if the cancer is likely susceptible to treatment with the atovaquone-related compound), as described herein.

In other embodiments, the methods can comprise recording the results in a database or medical history (e.g., medical records) of the subject, selecting the subject for increased monitoring or periodically monitoring the health of the subject (e.g., for development or changes in the signs or symptoms of the breast cancer, e.g., tumor development and/or changes in tumor size (e.g., increased or decreased size), such as e.g., clinical exam, mammography, MRI, or other suitable imaging or other diagnostic method(s) known in the art. In other embodiments, the methods can comprise using a PCR machine to determine the level of expression of one or more markers of activation of the mTOR and/or STAT3 and/or eIF2α/ATF4 pathways.

In the above-described methods for cancer cell growth inhibitory therapy and treatment of cancer, the method can further comprise administering an additional therapy to the patient. Additional therapies can include an additional treatment for cancer (e.g., chemotherapy (e.g., administering a chemotherapeutic agent), administering a biologic agent, e.g., antigen, vaccine, antibody etc., administering a cytokine, radiation therapy, immunotherapy, and/or surgery, etc.). Such combination therapy can be sequential therapy wherein the patient is treated first with one therapy and then the other, and so on, or all therapies can be administered simultaneously. In either case, these therapies are said to be coadministered. It is to be understood that "coadministered" does not necessarily mean that the drugs and/or therapies are administered in a combined form (i.e., they may be administered separately or together to the same or different sites at the same or different times).

In some embodiments, an atovaquone-related compound can be used for the treatment of cancer, either as initial therapy or as a second-line option if resistance to another therapy (e.g., JAK resistance mutations emerge following JAK inhibitor therapy) develops.

Chemotherapeutic agents, which can be administered in a combination therapy with an atovaquone-related compound, include for example: taxanes such as taxol, taxotere or their analogues; alkylating agents such as cyclophosphamide, isosfamide, melphalan, hexamethylmelamine, thiotepa or dacarbazine; antimetabolites such as pyrimidine analogues, for instance 5-fluorouracil, cytarabine, capecitabine, and gemcitabine or its analogues such as 2-fluorodeoxycytidine; folic acid analogues such as methotrexate, idatrexate or trimetrexate; spindle poisons including vinca alkaloids such as vinblastine, vincristine, vinorelbine and vindesine, or their synthetic analogues such as navelbine, or estramustine and a taxoid; platinum compounds such as cisplatin; epipodophyllotoxins such as etoposide or teniposide; antibiotics such as daunorubicin, doxorubicin, bleomycin or mitomycin, enzymes such as L-asparaginase, topoisomerase inhibitors such as topotecan or pyridobenzoindole derivatives; and various agents such as procarbazine, mitoxantrone, and biological response modifiers or growth factor inhibitors such as interferons or interleukins. Other chemotherapeutic agents include, though are not limited to, a p38/JAK kinase inhibitor, e.g., SB203580; a phospatidyl inositol-3 kinase (PI3K) inhibitor, e.g., LY294002; a MAPK inhibitor, e.g. PD98059; a JAK inhibitor, e.g., AG490; preferred chemotherapeutics such as UCN-01, NCS, mitomycin C (MMC), NCS, and anisomycin; taxoids in addition to those describe above (e.g., as disclosed in U.S. Pat. Nos. 4,857,653; 4,814,470; 4,924,011, 5,290,957; 5,292,921; 5,438,072; 5,587,493; European Patent No. 0 253 738; and PCT Publication Nos. WO 91/17976, WO 93/00928, WO 93/00929, and WO 96/01815. In other embodiments, a cancer therapy can include but is not limited to immunotherapy such as the administration of cytokines and growth factors such as interferon (IFN)-gamma, tumor necrosis factor (TNF)-alpha, TNF-beta, and/or similar cytokines, or an antagonist of a tumor growth factor (e.g., TGF-β and IL-10). Antiangiogenic agents that can be used in the therapy of cancer, include, e.g., endostatin, angiostatin, TNP-470, Caplostatin (Stachi-Fainaro et al., Cancer Cell 7(3), 251 (2005)). Drugs that interfere with intracellular protein synthesis can also be used in the methods of the present disclosure; such drugs are known to those skilled in the art and include puromycin, cycloheximide, and ribonuclease.

For radiation therapy, common sources of radiation used for cancer treatment include, but are not limited to, high-energy photons that come from radioactive sources such as cobalt, cesium, iodine, palladium, or a linear accelerator, proton beams; neutron beams (often used for cancers of the head, neck, and prostate and for inoperable tumors), x or gamma radiation, electron beams, etc.

It is well known that radioisotopes, drugs, and toxins can be conjugated to antibodies or antigen-binding antibody fragments which specifically bind to markers which are produced by or associated with cancer cells, and that such antibody conjugates can be used to target the radioisotopes, drugs or toxins to tumor sites to enhance their therapeutic efficacy and minimize side effects. Examples of these agents and methods are reviewed in Wawrzynczak and Thorpe (in Introduction to the Cellular and Molecular Biology of Cancer, L. M. Franks and N. M. Teich, eds, Chapter 18, pp. 378-410, Oxford University Press. Oxford, 1986), in Immunoconjugates: Antibody Conjugates in Radioimaging and Therapy of Cancer (C. W. Vogel, ed., 3-300, Oxford University Press, N.Y., 1987), in Dillman, R. O. (CRC Critical Reviews in Oncology/Hematology 1:357, CRC Press, Inc., 1984), in Pastan et al. (Cell 47:641, 1986) in Vitetta et al. (Science 238:1098-1104, 1987) and in Brady et al. (Int. J. Rad. Oncol. Biol. Phys. 13:1535-1544, 1987). Other examples of the use of immunoconjugates for cancer and other forms of therapy have been disclosed, inter alia, in U.S. Pat. Nos. 4,331,647, 4,348,376, 4,361,544, 4,468,457, 4,444,744, 4,460,459, 4,460,561 4,624,846, 4,818,709, 4,046,722, 4,671,958, 4,046,784, 5,332,567, 5,443,953, 5,541,297, 5,601,825, 5,637,288, 5,677,427, 5,686,578, 5,698,178, 5,789,554, 5,922,302, 6,187,287, and 6,319,500. In addition, unconjugated antibodies (e.g., antibodies to epidermal growth factor receptors such a HER2/neu) can be used for the treatment of cancer. Exemplary cancer-cell specific antibodies that can be used in the combination therapies disclosed herein are described, for example, in the review by Scott et al. (Nature Reviews Cancer 12, 278-287 (April 2012)). See also, Weiner, L. M., et al. Monoclonal antibodies: versatile platforms for cancer immunotherapy. Nature Rev. Immunol. 10, 317-327 (2010); Beatty, G. L. et al. CD40 agonists alter tumor stroma and show efficacy against pancreatic carcinoma in mice and humans. Science 331, 1612-1616 (2011); Musolino, A. et al Immunoglobulin G fragment C receptor polymorphisms and clinical efficacy of trastuzumab-based therapy in patients with HER-2/neu-positive metastatic breast cancer. J. Clin. Oncol. 26, 1789-1796 (2008); Ferris, R. L., et al. Tumor antigen-targeted, monoclonal antibody-based immunotherapy: clinical response, cellular immunity, and immunoescape. J. Clin. Oncol. 28, 4390-4399 (2010); and Scott, A. M. et al. A Phase I clinical trial with monoclonal antibody ch806 targeting transitional state and mutant epidermal growth factor receptor. Proc. Natl Acad. Sci. USA 104, 4071-4076 (2007).

Other therapies include, e.g., hematopoietic stem cell transplant (HSCT), e.g., for treatment of acute myeloid leukemia (AML) patients and many other cancers.

Formulations, Administration and Dosage

While it is possible to use an inhibitor or agonist disclosed herein for therapy as is, it may be preferable to administer an inhibitor or agonist as a pharmaceutical formulation, e.g., in admixture with a suitable pharmaceutical excipient, diluent, or carrier selected with regard to the intended route of administration and standard pharmaceutical practice. Pharmaceutical formulations comprise at least one active compound, or a pharmaceutically acceptable derivative thereof, in association with a pharmaceutically acceptable excipient, diluent, and/or carrier. The excipient, diluent and/or carrier must be "acceptable," as defined above. The compositions disclosed herein can be formulated for administration in any convenient way for use in human or veterinary medicine.

Compositions and formulations comprising an atovaquone-related compound disclosed herein, can be administered topically, parenterally, orally, by inhalation, as a suppository, or by other methods known in the art. The term "parenteral" includes injection (for example, intravenous, intraperitoneal, epidural, intrathecal, intramuscular, intraluminal, intratracheal or subcutaneous). Exemplary routes of administration include, e.g., intravenous, intraductal, and intratumoral.

Administration of a composition or formulation disclosed herein can be once a day, twice a day, or more often. Frequency may be decreased during a treatment maintenance phase of the disease or disorder, e.g., once every second or third day instead of every day or twice a day. The dose and the administration frequency will depend on the clinical signs, which confirm maintenance of the remission phase, with the reduction or absence of at least one or more preferably more than one clinical signs of the acute phase known to the person skilled in the art. More generally, dose and frequency will depend in part on recession of pathological signs and clinical and subclinical symptoms of a disease condition or disorder contemplated for treatment with the present compounds.

It will be appreciated that the amount of an atovaquone-related compound for use in treatment will vary with the route of administration, the nature of the condition for which treatment is required, and the age, body weight and condition of the patient, and will be ultimately at the discretion of the attendant physician or veterinarian. Compositions will typically contain an effective amount of the active agent(s), alone or in combination. Preliminary doses can be determined according to animal tests, and the scaling of dosages for human administration can be performed according to art-accepted practices.

Length of treatment, i.e., number of days, will be readily determined by a physician treating the subject; however the number of days of treatment may range from 1 day to about 20 days. In some embodiments, an atovaquone-related compound can be administered in multiple "cycles" with rest periods of 7 days between cycles of administration, or, given the minimal toxicity, continuous indefinite treatment with an atovaquone-related compound is also possible. As provided by the present methods, and discussed below, the efficacy of treatment can be monitored during the course of treatment to determine whether the treatment has been successful, or whether additional (or modified) treatment is necessary.

In some embodiments, an atovaquone-related compound, as described herein, can be formulated with at least one additional therapy (e.g., drug therapy, e.g., chemotherapy, immunotherapy, or other cancer therapy involving administration of a drug) described herein. Thus, formulations can comprise combinations of 2 or more, 3 or more, 4 or more, or 5 or more additional therapies. In certain embodiments, the atovaquone-related compound and the additional therapy (drug) are formulated in separate compositions.

In some aspects, a cancer cell growth-inhibitory amount and/or a therapeutically effective amount of atovaquone is in a range of about 0.5 to about 500 mg/kg/day, about 1 to about 250 mg/kg/day, about 5 to about 125 mg/kg/day, about 5 to about 100 mg/kg/day, or about 10 to about 75 mg/kg/day, about 10 to about 50 mg/kg/day, or about 10 to about 40 mg/kg per day.

In one embodiment, the dose of atovaquone is 1500 mg per day.

Kits

In certain embodiments, kits are provided for treating breast cancer. In still other embodiments, kits are provided for determining the efficacy of a cancer therapy.

In some embodiments, the kits comprise an atovaquone-related compound (e.g., atovaquone, buparvaquone, parvaquone, TDBHN, etc.) for use in the treatment of cancer. In other embodiments, the kits comprise reagents for the detection of the expression level of STAT3 and/or mTOR and/or eIF2α/ATF4 pathways and, optionally, an atovaquone-related compound. Such kits can further comprise instructions to administer the atovaquone-related compound to a subject with cancer if the subject has elevated expression levels of the mTOR and/or prior to treatment. The instructions can further comprise directions to serially test (i.e. test at least once more, at least twice more, at least three time more, etc.) samples obtained from the subject following initiation of treatment with the atovaquone related compound to monitor efficacy of the treatment, wherein the instructions instruct the user (e.g., physician) that treatment is effective if the level of activation of the mTOR pathway is decreased relative to its level of activation prior to treatment and/or if the level of activation of the STAT3 pathway is decreased relative to its level of activation prior to treatment and/or if the level of activation of the eIF2α/ATF4 is increased relative to its level of activation prior to treatment. Method for determining changes in the level of activation of these pathways are described in detail above.

The kits, regardless of type, will generally comprise one or more containers into which the biological agents (e.g. inhibitors) are placed and, preferably, suitably aliquotted. The components of the kits may be packaged either in aqueous media or in lyophilized form.

In accordance with the present invention, there may be employed conventional molecular biology, microbiology, recombinant DNA, immunology, cell biology and other related techniques within the skill of the art. See, e.g., Sambrook et al., (2001) Molecular Cloning: A Laboratory Manual. 3rd ed. Cold Spring Harbor Laboratory Press: Cold Spring Harbor, N.Y.; Sambrook et al., (1989) Molecular Cloning: A Laboratory Manual. 2nd ed. Cold Spring Harbor Laboratory Press: Cold Spring Harbor, N.Y.; Ausubel et al., eds. (2005) Current Protocols in Molecular Biology. John Wiley and Sons, Inc.: Hoboken, N.J.; Bonifacino et al., eds. (2005) Current Protocols in Cell Biology. John Wiley and Sons, Inc.: Hoboken, N.J.; Coligan et al., eds. (2005) Current Protocols in Immunology, John Wiley and Sons, Inc.: Hoboken, N.J.; Coico et al., eds. (2005) Current Protocols in Microbiology, John Wiley and Sons, Inc.: Hoboken, N.J.;

Coligan et al., eds. (2005) Current Protocols in Protein Science, John Wiley and Sons, Inc.: Hoboken, N.J.; Enna et al., eds. (2005) Current Protocols in Pharmacology John Wiley and Sons, Inc.: Hoboken, N.J.; Hames et al., eds. (1999) Protein Expression: A Practical Approach. Oxford University Press: Oxford; Freshney (2000) Culture of Animal Cells: A Manual of Basic Technique. 4th ed. Wiley-Liss; among others. The Current Protocols listed above are updated several times every year.

The following examples are meant to illustrate, not limit, the invention.

EXAMPLES

Example 1: Materials and Methods

The following are the materials and methods used in the Examples set forth below.

Connectivity Map Analysis

The 12-gene STAT3 signature described in Alvarez J V, et al. ((2005) Identification of a genetic signature of activated signal transducer and activator of transcription 3 in human tumors. Cancer research 65(12):5054-5062) was mapped from murine U74Av2 probes to all corresponding human U133A probes using a file downloaded from dChip (http://www.hsph.harvard.edu/cli/complab/dchip/common%20HG-U133A_MG-U74Av2.xls). Two genes downregulated by STAT3 activation were similarly mapped. The resulting probe lists shown in Table 4, below, were used to query the Connectivity Map. Detailed results were downloaded, and the "up" score was averaged across all instances for each compound; compounds with fewer than 3 instances were excluded.

TABLE 4

| Probe List | |
|---|---|
| Up tags | Down tags |
| 200730_s_at | 202951_at |
| 200731_s_at | 216727_at |
| 200732_s_at | 212811_x_at |
| 200733_s_at | 209610_s_at |
| 200796_s_at | 209611_s_at |
| 200797_s_at | 212810_s_at |
| 200798_x_at | |
| 201473_at | |
| 201693_s_at | |
| 201694_s_at | |
| 201995_at | |
| 202679_at | |
| 203140_at | |
| 203574_at | |
| 205962_at | |
| 208683_at | |
| 208743_s_at | |
| 208875_s_at | |
| 208876_s_at | |
| 208877_at | |
| 208878_s_at | |
| 210512_s_at | |
| 210513_s_at | |
| 211527_x_at | |
| 212171_x_at | |
| 214056_at | |
| 214057_at | |
| 214888_at | |
| 215990_s_at | |

TABLE 4-continued

| Probe List | |
|---|---|
| Up tags | Down tags |
| 220266_s_at | |
| 221841_s_at | |

Cell Lines and Tissue Culture

Mouse embryonic fibroblasts (MEFs) were cultured in DMEM+10% FBS. TSC2-null (see, Zhang et al. J Clin Invest. 2003; 112(8):1223-1233) and REDD1-null (see, Sofer et al. Mol. Cell. Biol. July 2005 vol. 25 no. 14 5834-5845) MEFs, along with MEFs from the littermate controls, were kind gifts from Dr. John Blenis and Dr. Leif Ellisen, respectively. HEL (see, Iwama et al. Mol. Cell. Biol. June 1999 vol. 19 no. 6 3940-3950) was a kind gift of Dr. Daniel G. Tenen and grown in RPMI-1640+10% FBS. OCI-AML2 and OCI-AML3 (see, Grunberger et al. Blood Dec. 1, 2003 vol. 102 no. 12 4153-4158), and MOLM-13 (German Collection of Microorganisms and Cell Cultures (DSMZ, Braunschweig, Germany)) were kind gifts of Dr. James D. Griffin and grown in RPMI-1640+10% FBS. MM.1S (ATCC) was a kind gift of Dr. Kenneth C. Anderson and grown in RPMI-1640+10% FBS. SET2 (see, Koppikar et al. Nature 489, 155-159 (6 Sep. 2012)) was a kind gift of Dr. Ross L. Levine and grown in RPMI-1640+10% FBS. HL60 (ATCC) was a kind gift of Dr. James D. Griffin and grown in RPMI-1640+10% FBS. SKBR3, MDA-MB-468, U266, INA-6, RPMI-8226, K562, and MV-4-11 cells were obtained and cultured as previously reported (see, Nelson E A, et al. (2011) The STAT5 inhibitor pimozide decreases survival of chronic myelogenous leukemia cells resistant to kinase inhibitors. Blood 117(12):3421-3429; Nelson E A, et al. (2008) Nifuroxazide inhibits survival of multiple myeloma cells by directly inhibiting STAT3. Blood 112(13): 5095-5102; Nelson E A, et al. (2012) The STAT5 Inhibitor Pimozide Displays Efficacy in Models of Acute Myelogenous Leukemia Driven by FLT3 Mutations. Genes & Cancer 3(7-8):503-511; Walker S R, Chaudhury M, Nelson E A, & Frank D A (2010) Microtubule-targeted chemotherapeutic agents inhibit signal transducer and activator of transcription 3 (STAT3) signaling. Molecular Pharmacology 78(5):903-908; and Walker S R, Nelson E A, et al. (2009) Reciprocal effects of STAT5 and STAT3 in breast cancer. Molecular Cancer Research: MCR 7(6):966-976). Peripheral blood mononuclear cells (PBMCs) were isolated from healthy donors by Ficoll density gradient centrifugation and maintained in RPMI-1640+10% FBS. All cells were maintained in a humidified incubator at 37° C. with 5% $CO_2$.

Total RNA Isolation

Cell pellets were lysed in 270 µl RLT Plus buffer (Qiagen, Valencia, Calif.)+1% β-mercaptoethanol and processed by QIAshredder and genomic DNA eliminator spin columns. The flow-through solution was mixed with 460 µl 95% ethanol by pipetting up and down, and then run through an RNeasy spin column (Qiagen). The spin column was washed twice with 500 µl RPE buffer (after ethanol addition), spun once again to remove residual ethanol, and then eluted with 50 µl RNase-free water. All spin steps were performed on a benchtop microcentrifuge at room temperature and 14,000 RPM for 1 minute.

Gene Expression Analysis

Total RNA was reverse transcribed using random hexamers and assayed by qRT-PCR as previously described (see, Grivennikov S I, Greten F R, & Karin M (2010) Immunity, inflammation, and cancer. Cell 140(6):883-899). Primer sequences used are shown in Table 5, below.

TABLE 5

Primer Sequences

| Gene | Forward (5'→3') | SEQ ID NO | Reverse (5'→3') | SEQ ID NO |
|---|---|---|---|---|
| 18S rRNA | GTAACCCGTTGAACCCCATT | 59 | CCATCCAATCGGTAGTAGCG | 60 |
| Beta actin | TCCCTGGAGAAGAGCTACGA | 61 | AGCACTGTGTTGGCGTACAG | 62 |
| Pri-miR-146b | ATTCAGGGTTTTGGGGAGAT | 63 | GGGGCTTTCTGAGCTAAAGG | 64 |
| STAT3 | ACCGGCGTCCAGTTCACTACT | 65 | CCGGGATCCTCTGAGAGCTGC | 66 |
| SOCS3 | TCAAGACCTTCAGCTCCAAG | 67 | TGACGCTGAGCGTGAAGAAG | 68 |
| BIRC3 | GGGAAGAGGAGAGAGAAAGAGC | 69 | TCCAGGATTGGAATTACACAAG | 70 |
| NFKB2 | AGAGGGAGGAGGGCCTTTAG | 71 | CAGGTTCTGCTTCCCAGAAT | 72 |
| RELB | AGCATCCTTGGGGAGAGC | 73 | AGGCAGTCACCTCCACCTC | 74 |
| NFKBIE | CTCGCTCACCTACACCCTGT | 75 | CTCATGAATCACTGCCAGGT | 76 |
| IKB alpha | ACGAGCAGATGGTCAAGGAG | 77 | CTTCCATGGTCAGTGCCTTT | 78 |
| A20 | CCTTGGAAGCACCATGTTTG | 79 | TTGTGTGGTTCGAGGCACAT | 80 |
| CCL2 | TGCCCAGTCACCTGCTGTT | 81 | CCCACTTCTGCTTGGGGTCAGC | 82 |
| IL6 | GAAAGCAGCAAAGAGGCACT | 83 | TTTCACCAGGCAAGTCTCCT | 84 |
| RELA | CCACGAGCTTGTAGGAAAGG | 85 | CTGGATGCGCTGACTGATAG | 86 |
| JUNB | AAATGGAACAGCCCTTCT | 87 | TGTAGAGAGAGGCCACCA | 88 |
| MCL1 | GAGACCTTACGACGGGTT | 89 | TTTGATGTCCAGTTTCCG | 90 |
| EGR1 | AGCCCTACGAGCACCTGAC | 91 | AGCGGCCAGTATAGGTGATG | 92 |
| KLF4 | TCCCATCTTTCTCCACGTTC | 93 | AGTCGCTTCATGTGGGAGAG | 94 |
| BCL6 | CTGCAGATGGAGCATGTTGT | 95 | TCTTCACGAGGAGGCTTGAT | 96 |
| BCL3 | CCTCTGGTGAACCTGCCTAC | 97 | TACCCTGCACCACAGCAATA | 98 |
| BCL-X | GGTATTGGTGAGTCGGATCG | 99 | TGCTGCATTGTTCCCATAGA | 100 |
| E-cadherin | CCTGGGACTCCACCTACAGA | 101 | TGTGAGCAATTCTGCTTGGA | 102 |
| Desmoplakin | GGCACCAGCAGGATGTACT | 103 | ATCAAGCAGTCGGAGCAGTT | 104 |
| Vimentin | TCAGAGAGAGGAAGCCGAAA | 105 | ATTCCACTTTGCGTTCAAGG | 106 |
| Cadherin-11 | CAACGGACTATGAAACACAGGA | 107 | GAAAGGGCCATTGCTGATAA | 108 |
| Slug | TCGGACCCACACATTACCTT | 109 | TGACCTGTCTGCAAATGCTC | 110 |
| Cyclin D1 | AGAGGCGGAGGAGAACAAAC | 111 | GGCGGATTGGAAATGAACTT | 112 |
| Survivin | GGACCACCGCATCTCTACAT | 113 | GTCTGGCTCGTTCTCAGTGG | 114 |
| BCL2 | GCCCTGTGGATGACTGAGTA | 115 | AGGGCCAAACTGAGCAGAG | 116 |
| ATF4 | CCAACAACAGCAAGGAGGAT | 117 | GTGTCATCCAACGTGGTCAG | 118 |
| BIP | CACAGTGGTGCCTACCAAGA | 119 | CAGTCAGATCAAAATGTACCCAG | 120 |
| Hsp90B1 | AACGGGCAAGGACATCTCTA | 121 | CGTCGAAGCATGTCTCTGAT | 122 |
| DNAJC3 | CATCTTGAATTGGGCAAGAAA | 123 | AGCCCTCCGATAATAAGCAA | 124 |
| HERP | GCGACTTGGAGCTGAGTGG | 125 | CCAACAACAGCTTCCCAGAAT | 126 |
| Erp72 | AGCAGGTTTGATGTGAGTGG | 127 | TTCTCTGACCTTGGCAACAA | 128 |
| EDEM1 | GTGAAAGCCCTTTGGAACCT | 129 | AGGCCACTCTGCTTTCCAAC | 130 |
| Spliced XBP1 | CTGAGTCCGCAGCAGGTG | 131 | ACTGGGTCCAAGTTGTCCAG | 132 |
| ERdj4 | TTTCACAAGTTGGCCATGAA | 133 | AAGCACTGTGATCCAAGTGTATC | 134 |
| SEC61A1 | AGCAGCAGATGGTGATGAGA | 135 | CCTAGGAAGTCAGCCAGGAC | 136 |
| gp130 (human) | GTCACCTCACACTCCTCCAAG | 137 | TTTGAACAGGTCCAATGATTTC | 138 |
| gp130 (mouse) | GGCACCAGCAGGATGTACT | 139 | ATCAAGCAGTCGGAGCAGTT | 140 |

Table legend:
Abbreviations (for genes not disclosed elsewhere):
"SOCS3": suppressor of cytokine signaling 3;
"BIRC3": baculoviral IAP repeat containing 3;
"NFKB2": Nuclear factor NF-kappa-B p100 subunit;
"NFKBIE": Nuclear factor of kappa light polypeptide gene enhancer in B-cells inhibitor, epsilon;
"IKB alpha": I-kappa-B-alpha;
"CCL2": (C-C motif) ligand 2;
"IL6": interleukin-6;
"BCL3": B-cell CLL/lymphoma 3;
"BIP": Binding immunoglobulin protein;
"Hsp90B1": Heat shock protein 90kDa beta member 1;
"DNAJC3": Endoplasmic reticulum DNA J domain-containing protein 6;
"HERP": Drosophila melanogaster Homocysteine-induced endoplasmic reticulum protein;
"ERP": endoplasmic reticulum protein 72;
"EDEM1": ER degradation enhancer, mannosidase alpha-like 1;
"XBP1": X-box binding protein 1;
"ERdj4": DnaJ (Hsp40) homolog, subfamily B, member 9;
"SEC61A1"; Sec61 alpha 1 subunit;
"gp130": glycoprotein 130.

Gene expression was analyzed in triplicate, normalized by 18S rRNA, and expressed as mean±SEM. For gene expression microarrays, RNA was isolated by Trizol, purified further on RNeasy columns, and profiled using Affymetrix Human Gene 1.0 ST arrays (Affymetrix). Results were deposited under GEO Accession: GSE46575.

Western Blotting, Immunoprecipitation, and Antibodies

Western blotting was performed as previously described (Battle T E, Arbiser J, & Frank D A (2005) The natural product honokiol induces caspase dependent apoptosis in B-cell chronic lymphocytic leukemia (B-CLL) cells. Blood 106(2):690-697). Antibodies to phospho-MAPK (9101), total MAPK (9102), phospho-Y705 STAT3 (9131), phospho-S6 (2215), total S6 (2217), phospho-4E-BP1 (9451), total 4E-BP1 (9644), total RSK (9355), phospho-S6K (9234, 85 used at 1:5000), total S6K (2708), phospho-eIF2α (9721, used at 1:1000), total eIF2α (5324), ATF4 (11815, used at 1:1000), PDGFRβ (3169), IGF1Rβ (9750), EGFR (2232), and HER2 (2242) were from Cell Signaling Technology. Phospho-RSK antibody was from R&D (AF889). Antibodies to total STAT3 (sc-482) and gp130 (sc-656, used at 1:1000) were from Santa Cruz Biotechnology. Phospho-S727 STAT3 antibody was described previously (229). REDD1 antibody was from Proteintech (10638-1-AP, used at 1:1000). Antibody recognizing full-length and cleaved ATF6 was from Abcam (ab122897, used at 1:1000). Antibodies to tubulin (T5168) and beta actin (A5316) were from Sigma. All antibodies were used at 1:10000 dilution for western blot unless otherwise noted. For immunoprecipitations, cells were lysed in 500 µl lysis buffer (0.5% NP-40, 150 mM NaCl, 50 mM Tris pH 7.5, with protease and phosphatase inhibitors freshly added at 1:100 [Pierce, PI78443]) on ice for 15 minutes, then centrifuged for 10 minutes at 14,000 RPM and 4° C. The supernatant was transferred to a new tube and incubated with 10 µl JAK2 antibody (Santa Cruz sc-278) or a mix of two TYK2 antibodies, 10 µl of each (Santa Cruz sc-5271 and Cell Signaling Technology 9312). Immunoprecipitation was performed overnight at 4° C. with rotation. The next day, 75 µl of protein A/G beads (Santa Cruz sc-2003) were washed twice in lysis buffer, then incubated with immunoprecipitates overnight as before. The next day, the beads were spun down (1 min. at 7,500 RPM and 4° C.) and washed 3 times with 650 µl lysis buffer for 10 minutes at 4° C. with rotation, then boiled in 50 µl sample buffer+10% β-mercaptoethanol. For Western blot, 20 µl were loaded per lane. For detection of phospho-tyrosine, a mixture of two pan-phospho-tyrosine antibodies (Cell Signaling Technology 9411 and 9416, 1:1000 of each) was used. Antibody to phospho-Y1007/1008 JAK2 was from Cell Signaling 86 Technology (3771, used at 1:1000). Antibody to phospho-Y570 JAK2 was from Millipore (09-241, used at 1:1000). Luminometric Assays Luciferase reporter cell lines were described previously (186). Firefly luciferase values were normalized by concurrent cell viability. Cell viability was measured as ATP-dependent luminescence by Cell Titer Glo (Promega).

Drug Treatments

For drug treatments, cells were spun down and suspended in fresh media the day prior. Atovaquone (Sigma-Aldrich, A7986) was dissolved at a stock concentration of 12.5 mM and used to treat cells at up to 1:500 dilution (up to 0.2% v/v DMSO final). JAK inhibitor 1 (Millipore 420097) was used at 1 µM, unless indicated otherwise. DTT (Bio-Rad 1610610) was dissolved at 1 M in PBS and used at 1:200 (5 mM final). Tunicamycin (Sigma-Aldrich T7765) was used at 5 µg/ml. Thapsigargin (T9033) was used at 1 µM. Brefeldin A (Millipore 203729) was used at 3 µg/ml. Rapamycin (Millipore 553210) was used at 10-100 µM as indicated. DMSO was used to dissolve all drugs unless otherwise specified.

Flow Cytometry

Annexin V/PI staining was performed using Annexin V:FITC Apoptosis Detection Kit I (BD Biosciences). Staining for cell cycle analysis was performed as previously described (267). Staining for cell-surface receptors was performed in 50 µl PBS+2% FBS with 2 µl antibody to IL6R (BioLegend #352803) or 5 µl antibody to gp130 (BD Biosciences #555757) for 20 minutes on ice in the dark. Cells were washed twice, then resuspended in 300 µl of the same buffer. Samples were analyzed on a BD FACSCanto II machine. Transfection and siRNA Cells were reverse-transfected using Lipofectamine RNAiMAX (Invitrogen); the culture medium was changed 24 hours later. Control siRNA (D-001210-02) and REDD1 siRNA (M-010855-01) were from Thermo Scientific Dharmacon.

Chart Review

Atovaquone start and end dates for approximately 500 AML patients who underwent HSCT at Dana-Farber Cancer Institute from 2006-2012 were obtained by chart review of the electronic medical record with DFCI IRB approval. Atovaquone was administered as a suspension, 750 mg twice daily. Due to the intermittent atovaquone dosing for some patients, a discontinuation for longer than 50 days disqualified subsequent atovaquone treatment from counting toward a patient's total atovaquone exposure. Patients who received more than one HSCT were excluded (4% of total patients).

Example 2: Identification of Atovaquone as a STAT3 Inhibitor

This example describes identification of atovaquone as a STAT3 inhibitor using a Connectivity Map.

Figure 2:
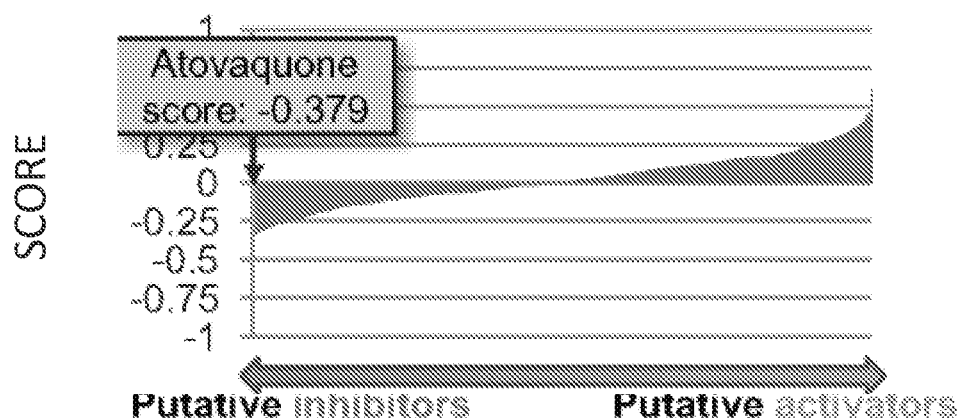
FIG. 2 is a graph showing the results from the Connectivity Map analysis, with more negative scores indicating more dissimilarity with respect to the STAT3 signature (i.e., putative inhibitors of STAT3).
Figure 3:
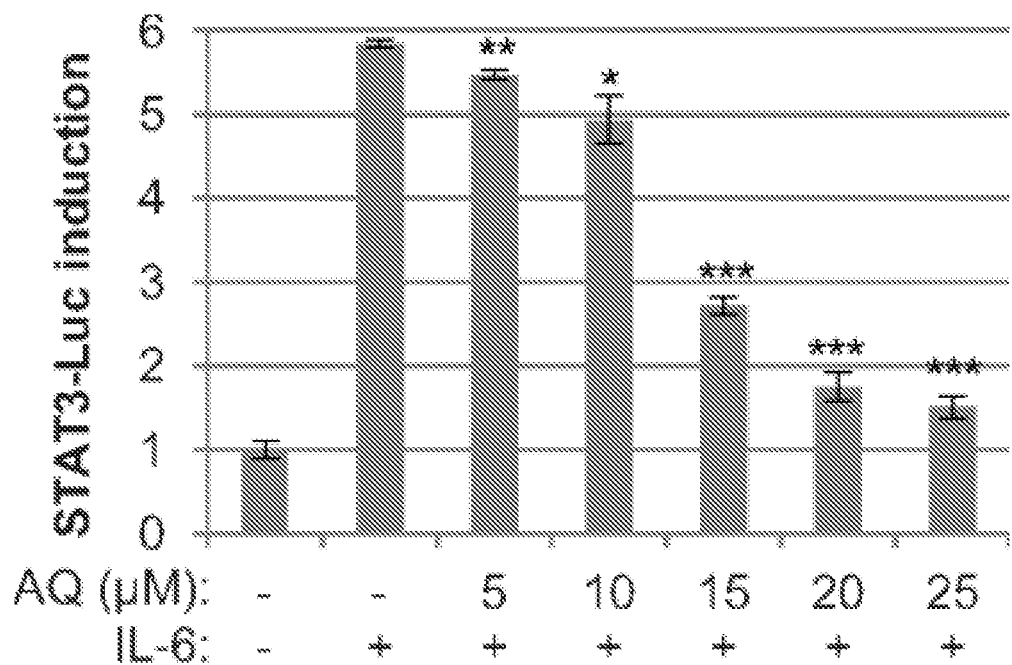
FIG. 3 is a graph quantifying the activity of firefly luciferase in STAT3-luc reporter cells that were pre-treated with atovaquone (AQ) at the indicated concentrations for 1 hour, then stimulated with (+) or without (−) IL-6 (interleukin-6; 10 µg/ml) for 5 hours. P-values (*, $p<0.05$; , $p<0.01$; *, $p<0.001$) are shown relative to IL-6 stimulation in the presence of vehicle alone.

Using a 12-gene signature of STAT3 activation, the Connectivity Map was queried to discover compounds that elicit gene expression changes contrary to the STAT3 signature (FIG. 1). The compound most opposed to the STAT3 signature was atovaquone (FIG. 2). In addition to being the leading hit, atovaquone was attractive for several other reasons. Most importantly, it is already FDA-approved, greatly reducing the cost and latency of bench-to bedside translation. Atovaquone, which is used clinically for infections caused by *Pneumocystis, Toxoplasma*, and *Plasmodium*, inhibits parasitic mitochondrial respiration and is not known to have any effects on mammalian cells (see, Baggish A L & Hill D R (2002) Antiparasitic agent atovaquone. Antimicrobial agents and chemotherapy 46(5):1163-1173). Furthermore, its side effects are minimal, and high plasma concentrations (15-30 µg/ml; 40-80 µM) are readily and routinely achieved in patients (Baggish & Hill, supra). For all these reasons, further investigation was focused on atovaquone as a putative STAT3 inhibitor and anti-cancer drug.

To determine if atovaquone inhibits STAT3, it was tested in a cell-based reporter system of STAT3 transcriptional activity (Nelson E A, et al. (2008) Nifuroxazide inhibits survival of multiple myeloma cells by directly inhibiting STAT3. Blood 112(13):5095-5102). These cells lack basal STAT3 activation; upon IL-6 treatment, STAT3 becomes activated and drives transcription of a STAT3-dependent luciferase reporter gene. The STAT3-luc reporter cells were pre-treated with drug for 1 hour, then stimulated with IL-6 (10 ng/ml) for 5 hr. Activity of firefly luciferase was measured and normalized by cell viability (Cell Titer Glo). Pre-treatment of the cells with atovaquone caused a dose-dependent inhibition of luciferase induction by IL-6, indicating suppression of STAT3 transcriptional activity (FIG.

Figure 4:
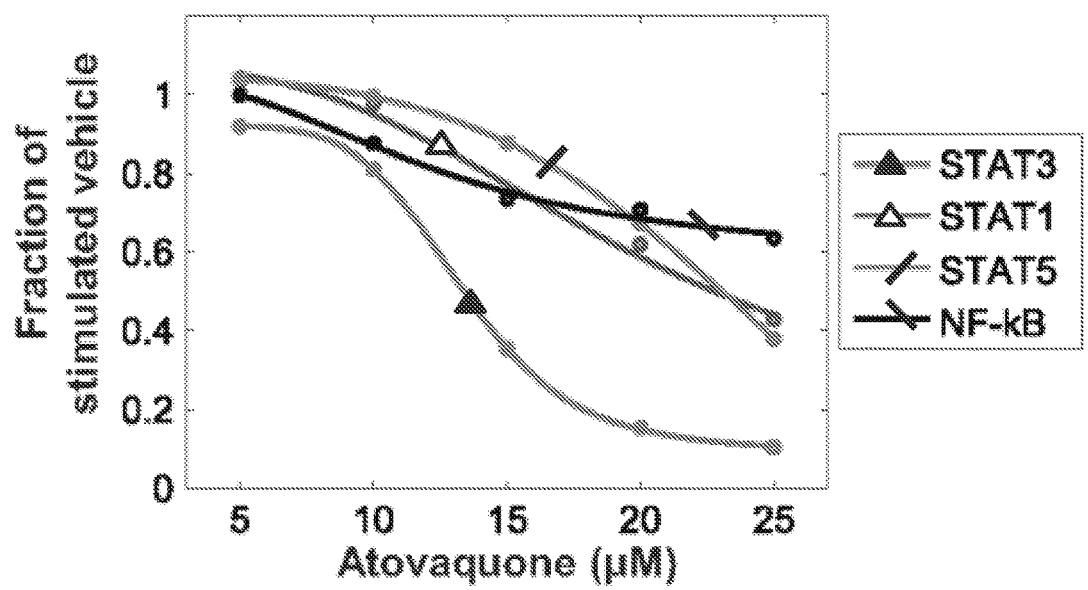
FIG. 4 is a graph comparing the level of inhibition (expressed as the fraction of control (stimulated vehicle)) of the indicated STATs (STAT3, STAT1, STAT5) or NFkB following treatment of STAT3-luc, STAT1-luc and STAT5-luc reporter cells with the indicated concentrations of atovaquone.

3). To determine if atovaquone inhibits STAT3 activity specifically over other transcription factors, it was tested in cell-based reporter systems for STAT1 and STAT5, two other STAT family members, and NF-κB, an unrelated transcription factor. While the activity of these other transcription factors was modestly affected at the higher doses of atovaquone, the effect on STAT3 activity was much greater, indicating specificity for inhibition of STAT3 (FIG. 4). These results demonstrate atovaquone to be a novel STAT3 inhibitor.

Example 3: Mechanisms of Action of Atovaquone

This example demonstrates that atovaquone inhibits STAT3 phosphorylation, expression of endogenous STAT3 target genes, and viability of STAT3-dependent cancer cells.

Figure 5:
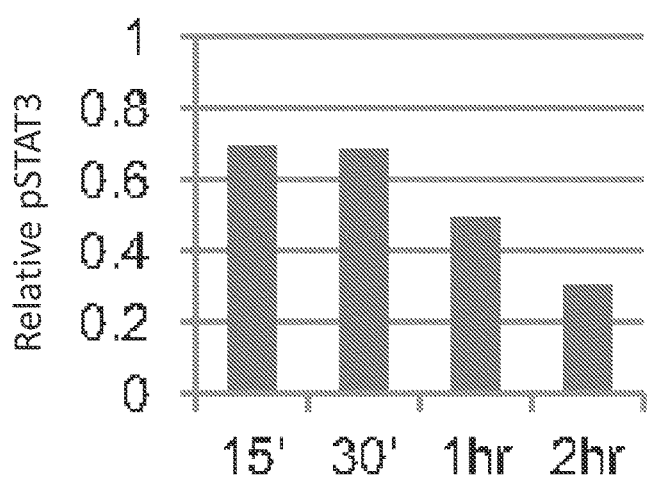
FIG. 5 is a bar graph quantifying the level of phospho-STAT3 (pSTAT3) in STAT3-luc reporter cells pre-treated with atovaquone (20 µM) for 1 hr, and then stimulated with IL-6 (10 µg/ml) for the indicated lengths of time. pSTAT3 levels were normalized to total STAT3 and relative to phospho-STAT3 in the presence of vehicle.
Figure 6:
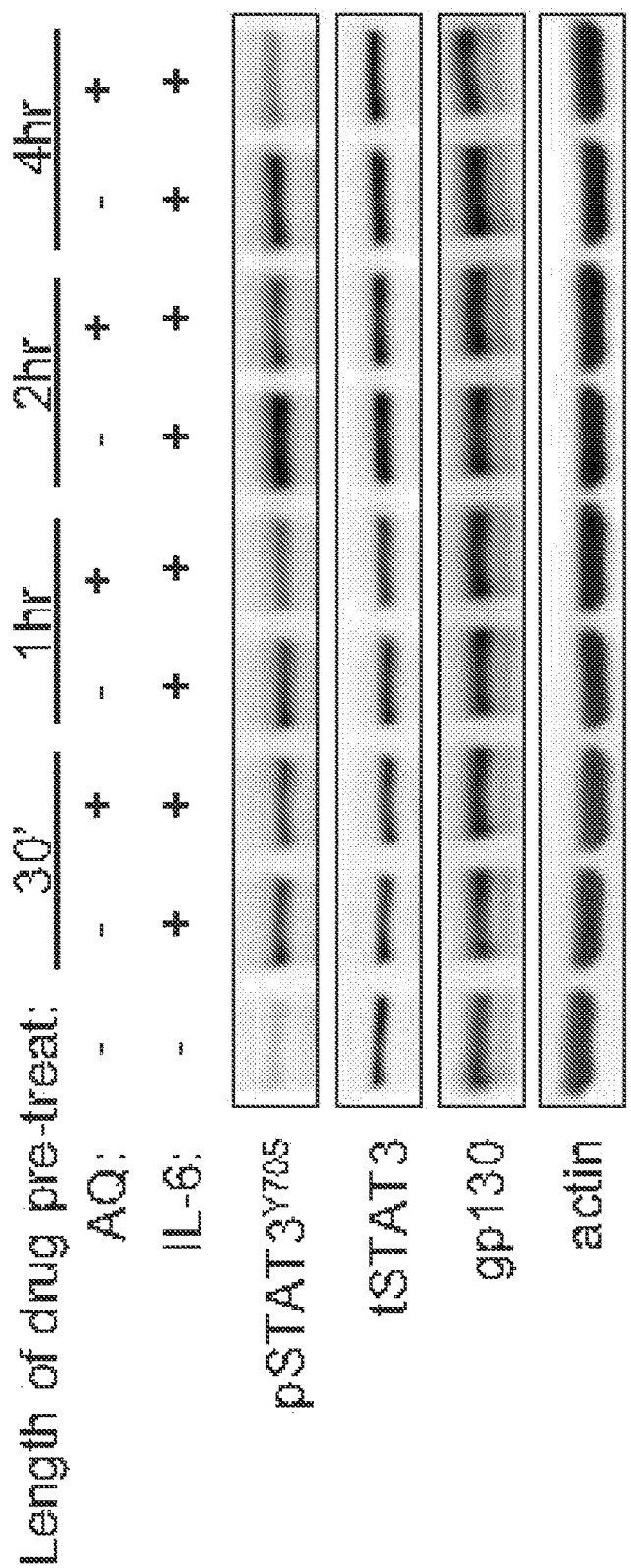
FIG. 6 is an image of a Western blot result for phoshoSTAT3$^{Y705}$ (pSTAT3$^{Y705}$), total STAT3 (tSTAT3), gp130, and actin, in cell lysates obtained from murine embryonic fibroblasts (MEFs) pre-treated with atovaquone (AQ) (25 µM) for the indicated time periods ("hr"=hour), then stimulated with IL-6 (5 µg/ml) and soluble IL-6 receptor (20 ng/ml) for 15 minutes.
Figure 7:
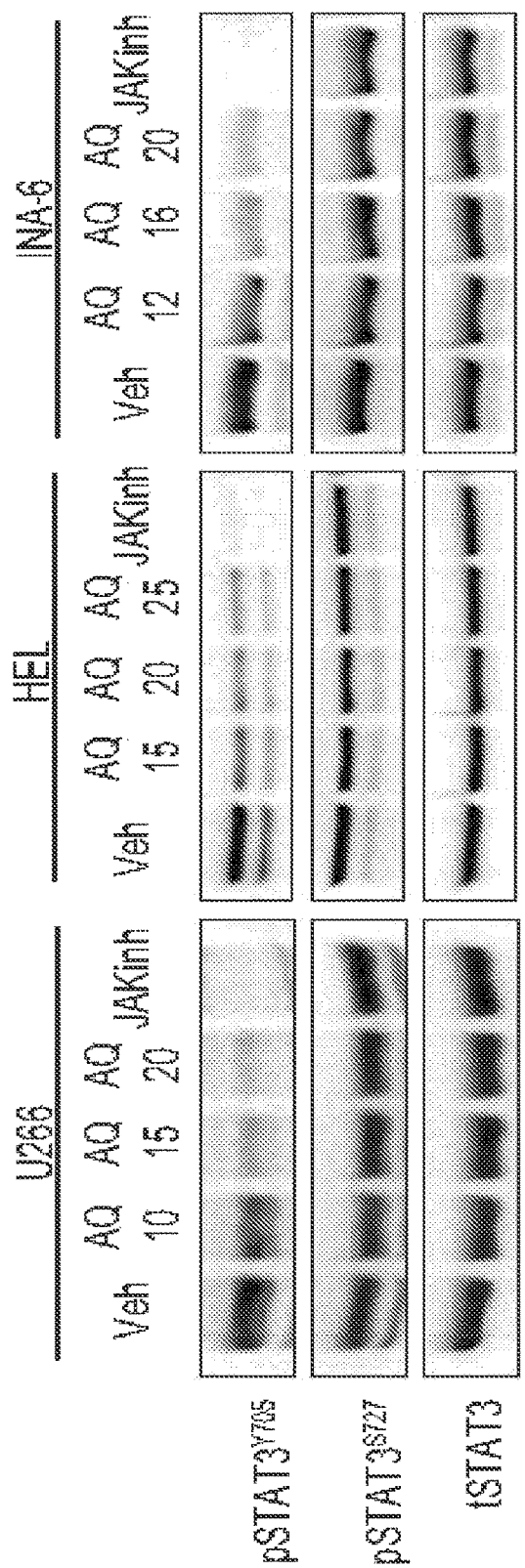
FIG. 7 contains Western blot results for phospho (p) STAT3$^{Y705}$, STAT3$^{S727}$, and total (t) STAT3 in U266, HEL and NA-6 cells treated for 2.5 hours, 6 hours, and 4 hours, respectively, with vehicle or the indicated concentrations of atovaquone (AQ) or 1 µM JAK inhibitor 1.
Figure 8:
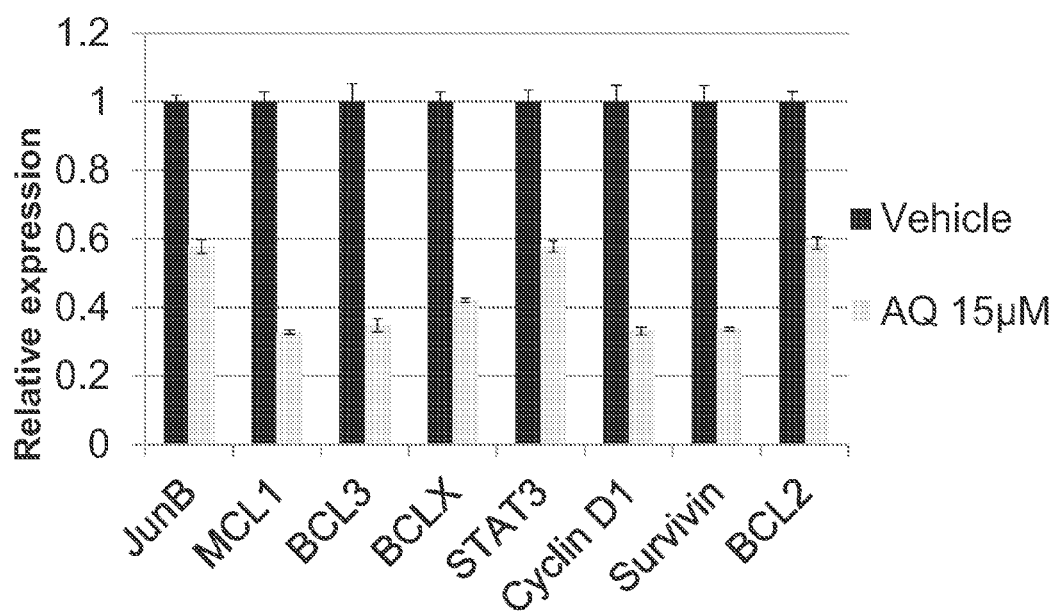
FIG. 8 is a bar graph quantifying the gene expression levels of the indicated endogenous STAT3 target genes following treatment of U266 cells with vehicle or 15 µM atovaquone (AQ) for 6 hours.
Figure 9:
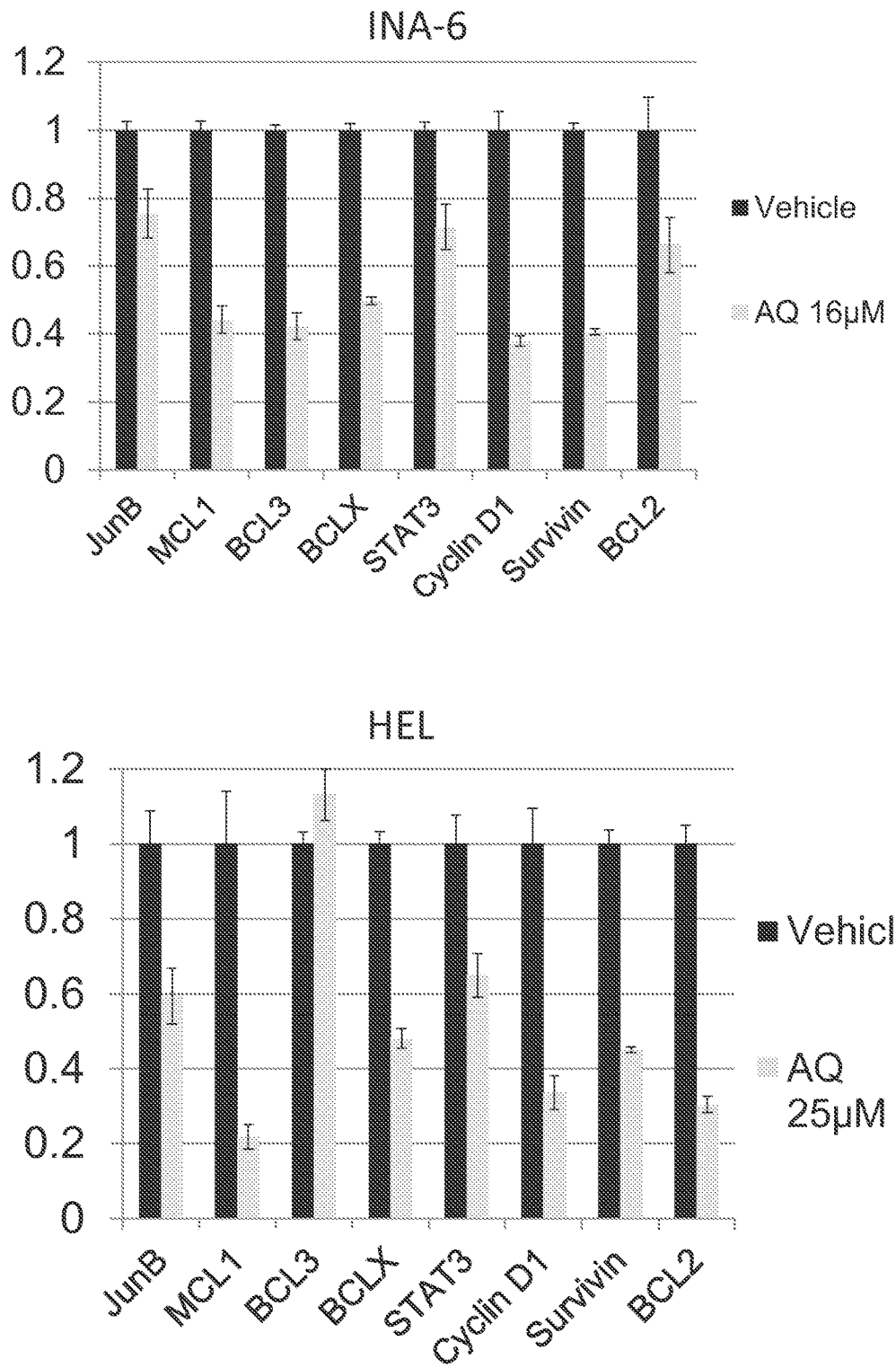
FIG. 9 contains bar graphs quantifying the gene expression levels of the indicated endogenous STAT3 target genes following treatment of INA-6 cells (upper graph) and HEL cells (lower graph) with vehicle or the indicated concentration of atovaquone (AQ) for 6 hours.

The mechanism by which atovaquone inhibits STAT3 was investigated. STAT3-luc reporter cells were pre-treated with atovaquone (20 μM) for 1 hr, and then stimulated with IL-6 (10 ng/ml) for 15 minutes, 30 minutes, 1 hours, or 2 hours. Since STAT3 transcriptional activity is critically dependent on tyrosine phosphorylation, Western blotting was performed to see if atovaquone affected STAT3 phosphorylation. In the STAT3 reporter cells, atovaquone pre-treatment reduced STAT3 tyrosine phosphorylation following IL-6 stimulation (FIG. 5). A similar effect was observed in mouse embryonic fibroblasts (MEF), which were pre-treated with atovaquone (25 μM) for 30 minutes up to four hours, then stimulated with IL-6 (5 ng/ml) and soluble IL-6 receptor (20 μg/ml) for 15 minutes (FIG. 6). Next, atovaquone was used to treat U266 (2.5 hours), HEL (6 hours), or INA-6 cells (4 hours). Atovaquone inhibited constitutive STAT3 tyrosine phosphorylation in multiple cancer cell lines, while STAT3 serine phosphorylation, which is not critical to transcriptional activity, was not affected (FIG. 7). In U266 and INA-6 cells, the source of STAT3 activation is JAK-dependent IL-6 signaling, while in HEL cells, STAT3 is activated by mutant JAK2-V617F. Given that atovaquone inhibits constitutive STAT3 activation in cancer cells, it was asked whether atovaquone inhibits expression of endogenous STAT3 target genes in this context. In U266, INA-6 and HEL cells treated with atovaquone for 6 hours, expression of multiple STAT3 target genes was substantially down-regulated (FIG. 8 and FIG. 9).

Figure 10:
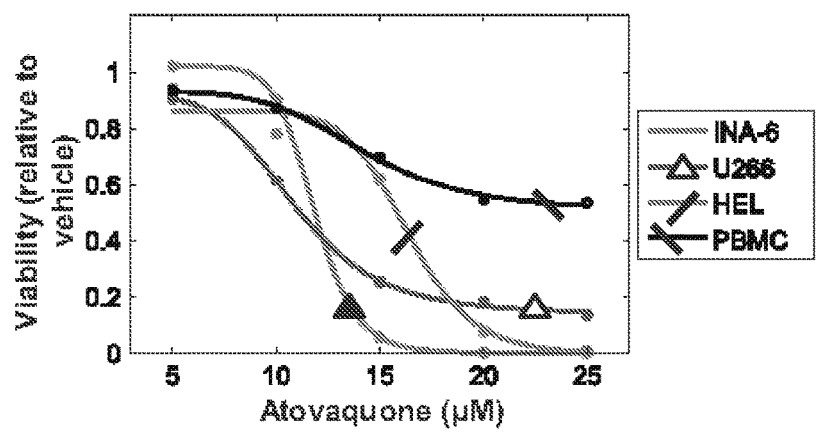
FIG. 10 is a line graph comparing cell viability of hematologic cancer cells INA-6, U266, HEL, which have activated STAT3, with non-malignant peripheral blood mononuclear cells (PBMC) (average of donors), following treatment for 72 hours with the indicated concentrations of atovaquone.
Figure 11:
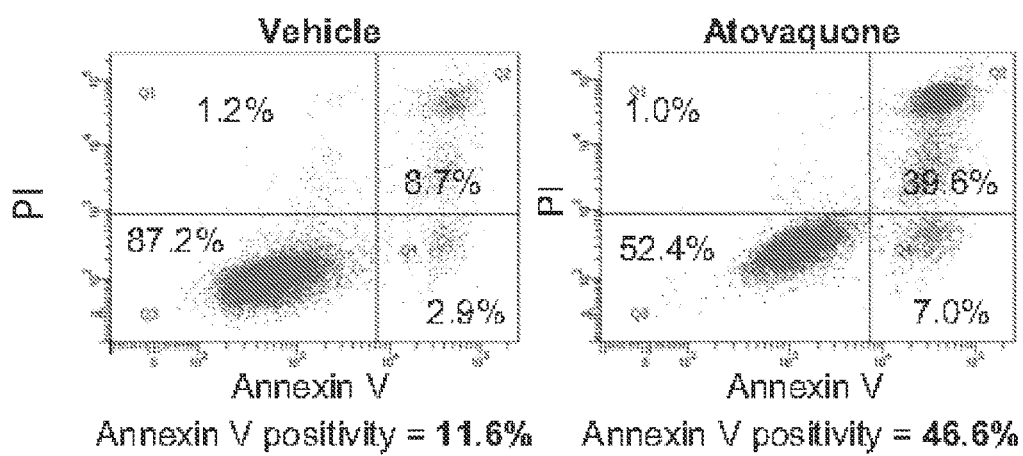
FIG. 11 contains fluorescence flow cytometry (FFC) dot plots of INA-6 cells treated for 24 hours with vehicle (left graph) or 15 µM atovaquone (right graph) and stained with propidium iodine (PI) (Y-axis) and Annexin V antibody (X-axis).
Figure 12:
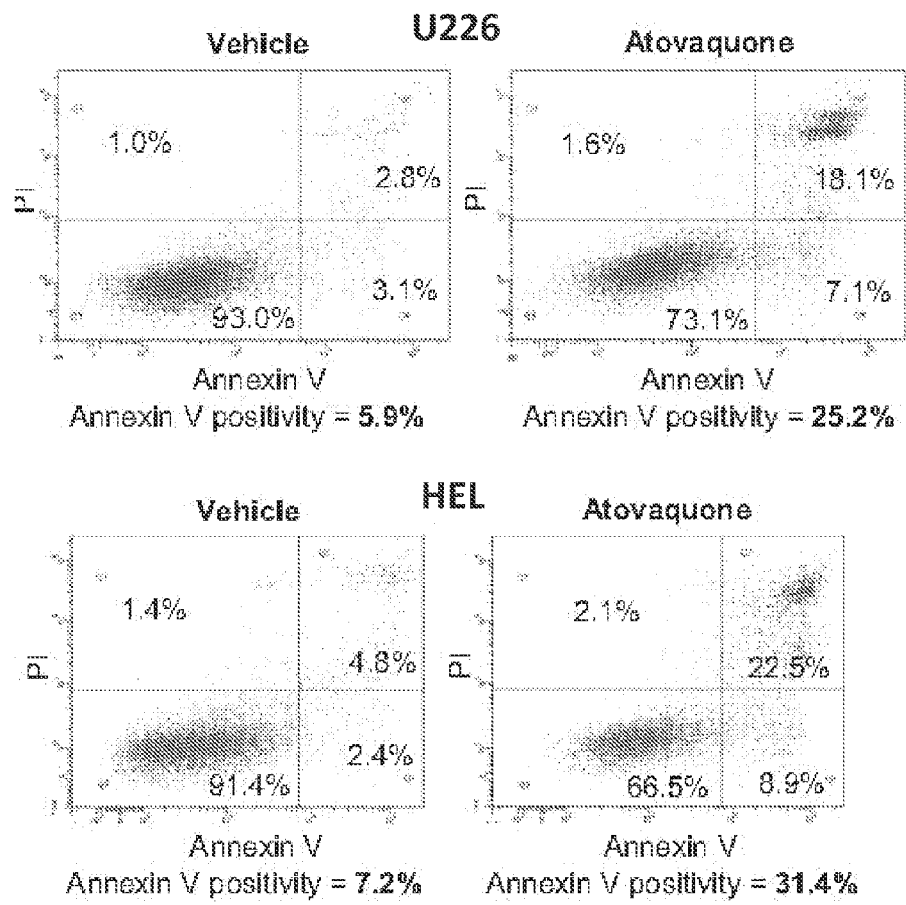
FIG. 12 contains FFC dot plots of U226 cells (upper graphs) and HEL cells (lower graphs) treated for 24 hours with vehicle (left graphs) or 15 µM atovaquone (right graphs) and stained with propidium iodine (PI) (Y-axis) and Annexin V antibody (X-axis).

Next, the effect of atovaquone on the growth and survival of STAT3-dependent cancer cells was examined Survival of the multiple myeloma cell line INA-6 is exquisitely dependent on IL-6 added to culture medium and resultant STAT3 activation. Atovaquone suppressed the viability of INA-6 cells with an $IC_{50}$ of 11.9 μM, with complete loss of viability at higher doses (FIG. 10). The other cell lines with constitutively-active STAT3, U266 and HEL, were also killed by atovaquone. By contrast, the viability of non-malignant peripheral blood mononuclear cells (PBMC) was relatively preserved. To ascertain how atovaquone treatment reduced the viability of STAT3-dependent cancer cells, annexin V and PI staining followed by flow cytometry was performed on INA-6 cells treated with atovaquone (15 μM) for 24 hours and on U266 and HEL cells treated with atovaquone (20 μM) for 48 hours. These experiments revealed that atovaquone was inducing apoptotic cell death (FIG. 11 and FIG. 12).

Figure 13:
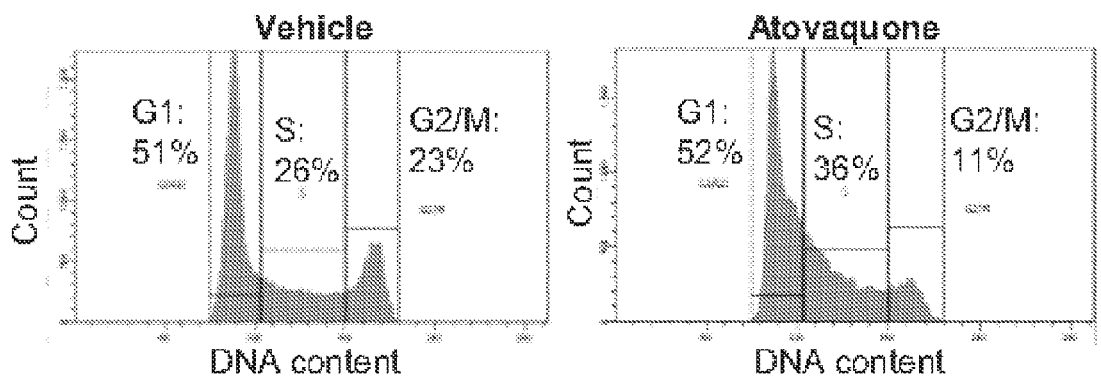
FIG. 13 contains FFC histograms quantifying DNA content (as an indicator of proliferation phase (G1, S and G2/M)) in HEL cells treated for 24 hours with 25 µM atovaquone.

Additionally, it was hypothesized atovaquone inhibits proliferation by disrupting cell cycle progression. An analysis of cell cycle distribution showed that atovaquone decreased the population of cells in G2/M and increased the proportion of cells with lower DNA content in HEL cells treated with atovaquone (25 μM) for 24 hours (FIG. 13). In summary, atovaquone inhibits constitutive STAT3 activation and target gene expression in cancer cells, and reduces their survival and proliferation.

Example 4: Atovaquone Selectively Inhibits Gp130 Cell-Surface Expression

This example demonstrates that atovaquone rapidly induces specific loss of cell-surface gp130, while total gp130 declines secondarily due to protein degradation.

Figure 14A:
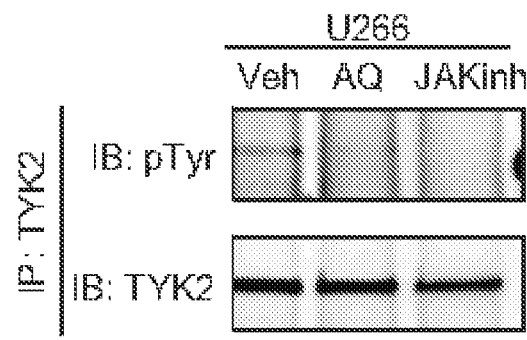
FIG. 14A contains photographs of Western blots for pTyr and pTYK2 following lysis of U266 cells treated with vehicle, atovaquone (15 µM) or JAK inhibitor 1 (1 µM) for 1 hour and immunoprecipitation with TYK2.
Figure 14B:
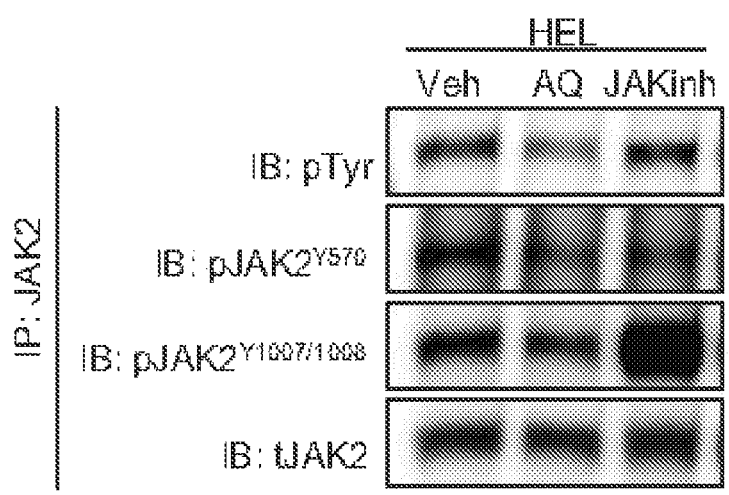
FIG. 14B contains photographs of Western blots for pTyr, pJAK2Y570, pJAK2Y1007/1008 and total JAK2 (tJAK2) following lysis of HEL cells treated with atovaquone (20 µM) or JAK inhibitor 1 (1 µM) for 6 hours, followed by immunoprecipitation to JAK2.
Figure 15:
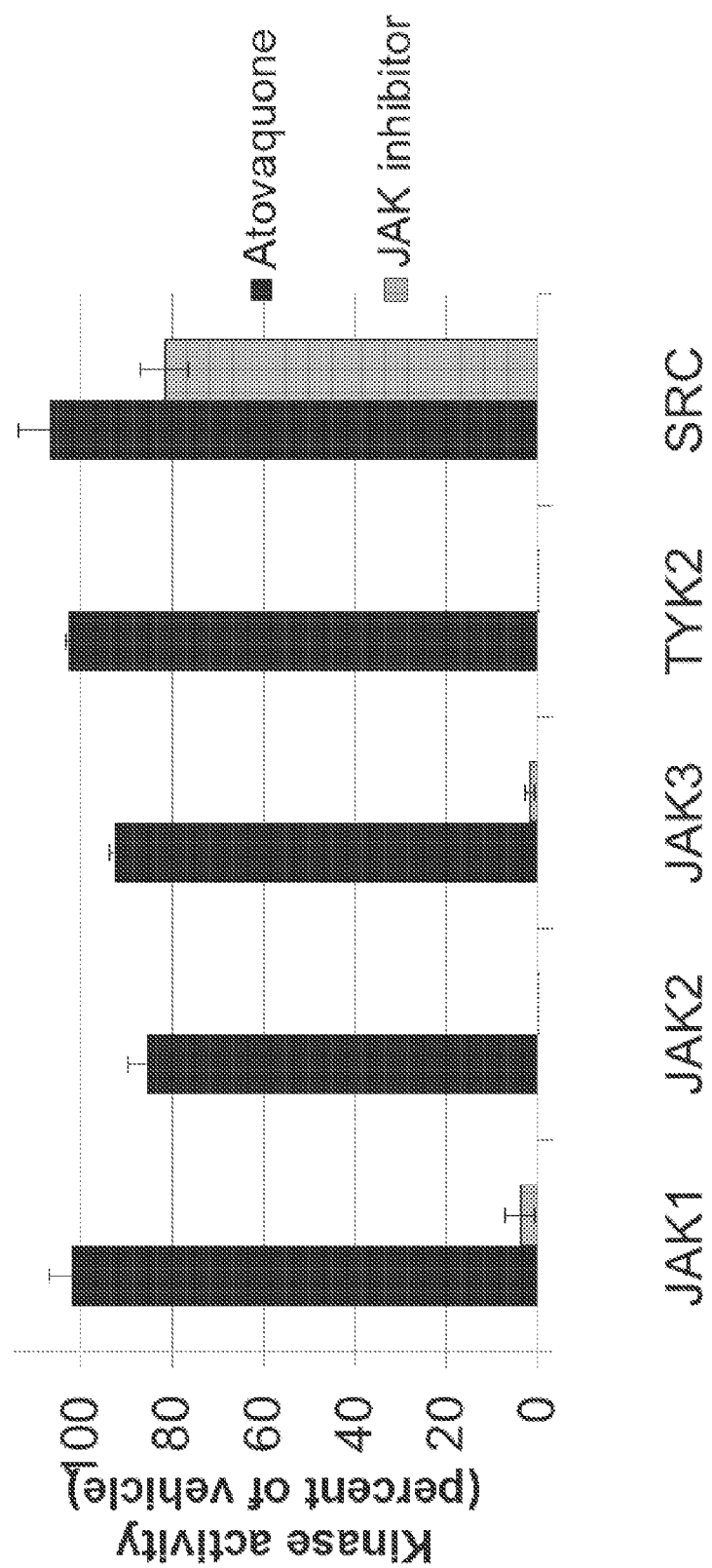
FIG. 15 contains a bar graph quantifying kinase activity (expressed as percent of vehicle) for the indicated kinases (JAK1, JAK2, JAK3, TYK2, SRC) determined using in vitro kinase assays (Invitrogen SelectScreen) and following treatment with atovaquone (AQ) (15 µM) or JAK inhibitor 1 (0.5 µM).

To understand how atovaquone inhibits STAT3 phosphorylation, the possibility that atovaquone decreases the kinase activity of JAKs, which are responsible for STAT3 activation in the systems previously tested was considered. To assess kinase activity, the extent of kinase auto-phosphorylation, which provides a cellular readout of kinase activity, was first analyzed. Atovaquone treatment inhibited the auto-phosphorylation of JAK family members, showing that it diminished JAK kinase activity in cells (FIG. 14A-B). In particular, U266 cells were treated with atovaquone (15 μM) or JAK inhibitor 1(1 μM) for 1 hour, followed by lysis and immunoprecipitation to TYK2. The blot was probed with a pan-phospho-tyrosine antibody (FIG. 14A). Due to technical limitations, tyrosine phosphorylation of other JAK family members was not detected in U266 cells. Next, HEL cells were treated with atovaquone (20 μM) or JAK inhibitor 1 (1 μM) for 6 hours, followed by lysis and immunoprecipitation to JAK2, which was selected because these cells harbor mutant JAK2-V617F. The blot was probed with a pan-phospho-tyrosine antibody, as well as antibodies specific to phospho-Tyr570 and phospho-Tyr1007/1008 (FIG. 14B). Phospho-Tyr570 was previously reported to correlate better with kinase activity, whereas phospho-Tyr1007/1008 is paradoxically induced by certain JAK inhibitors, including JAK inhibitor 1, depending on binding mode In vitro kinase assays of atovaquone with JAK family members showed no inhibition (FIG. 15), ruling out the possibility that atovaquone was a direct JAK inhibitor. Therefore, it was hypothesized that atovaquone inhibits JAKs indirectly by acting on an upstream signaling component required for JAK activity. As receptor-associated kinases, JAK signaling depends upon direct interaction with plasma membrane-localized proteins for scaffolding. This requirement also extends to mutant JAK2-V617F. In particular, JAKs are frequently associated with gp130, a transmembrane protein that participates in the signaling of several cytokines, including IL-6, oncostatin M (OSM), and leukemia inhibitory factor (LIF). By contrast, gp130 is not involved in the signaling of prolactin or IFN-γ, which were used to activate STAT5 and STAT1 in their respective luciferase reporter systems. For these reasons, it was hypothesized that atovaquone inhibits the function or expression of gp130.

Figure 16:
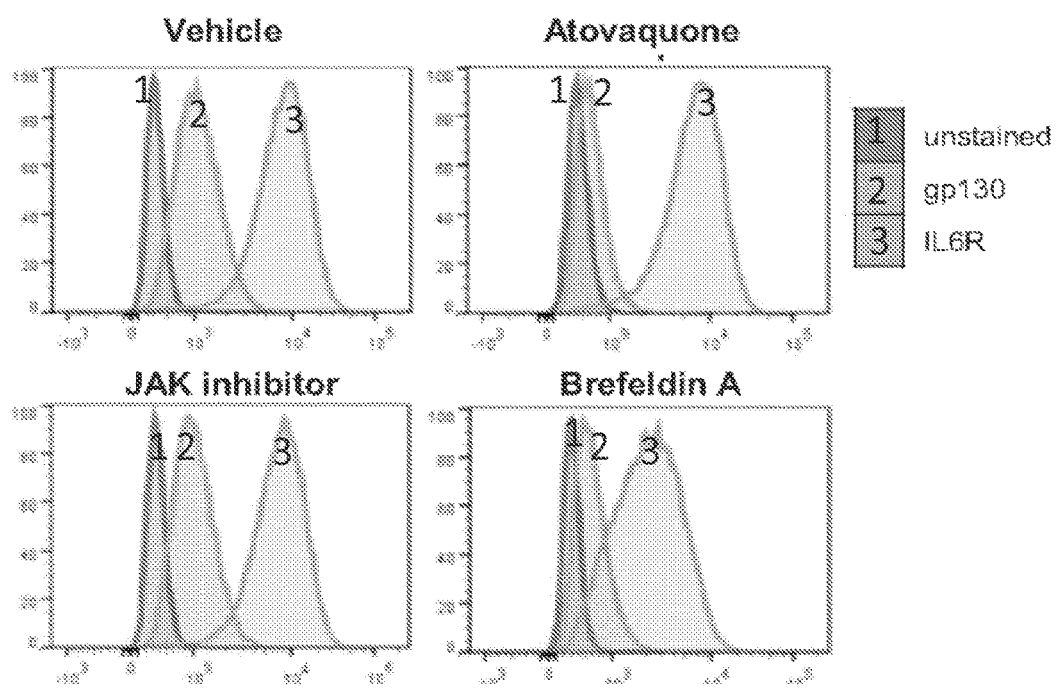
FIG. 16 contains FFC histograms plotting levels of cell surface expression of gp130 and IL-6 receptor (IL6R) on U266 cells treated with vehicle, atovaquone (20 µM), JAK inhibitor 1 (1 µM), or Brefeldin A (3 µg/ml) for 2.5 hours.
Figure 17:
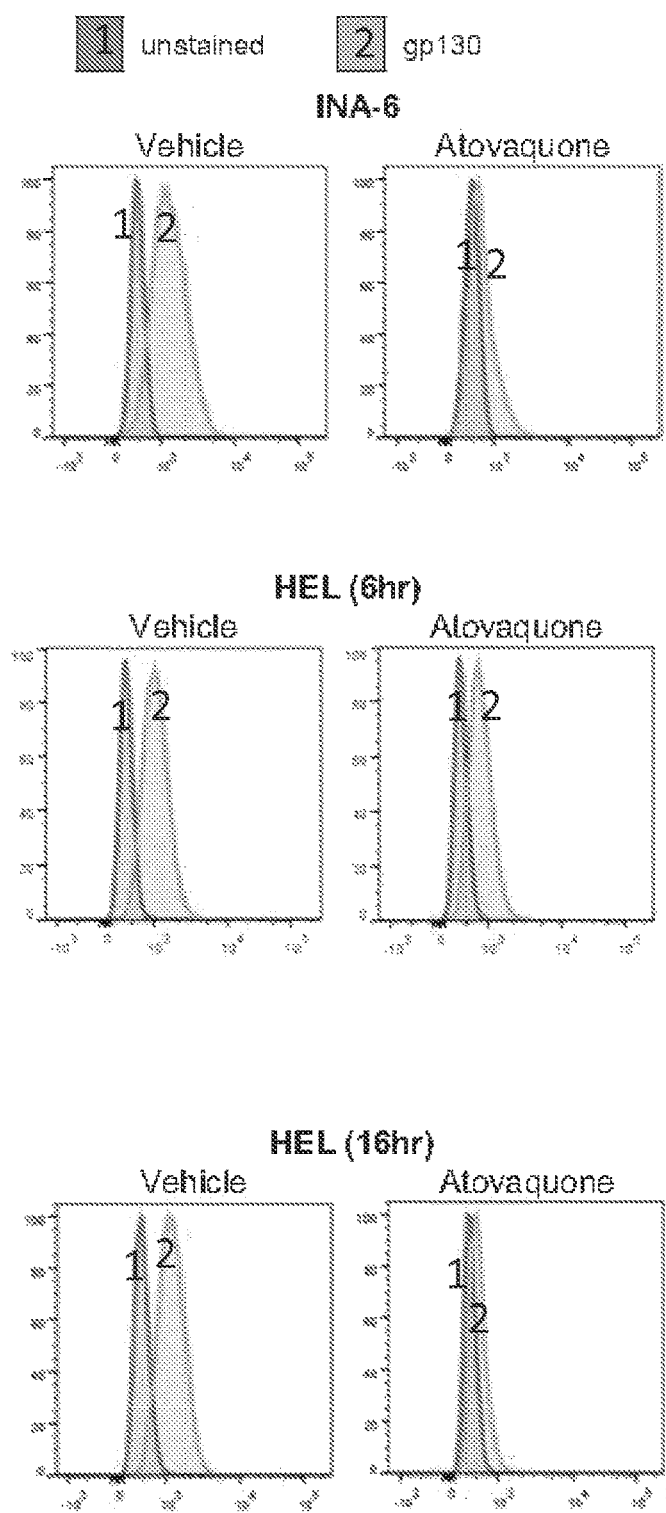
FIG. 17 contains FFC histograms plotting levels of cell surface expression of gp130 determined by flow cytometry in INA-6 cells (upper panel) or HEL cells (mid and lower panels) treated with vehicle or atovaquone (AQ) ((INA-6 cells: 20 µM AQ, for 4 hours; HEL cells: 25 µM AQ, for 6 or 16 hours)).

Flow cytometry was performed to measure the cell-surface expression of gp130 on U266 cells treated with atovaquone (20 μM), JAK inhibitor 1 (1 μM), or brefeldin A (3 μg/ml) for 2.5 hours, in which STAT3 phosphorylation was strongly suppressed by atovaquone. Interestingly, atovaquone substantially downregulated the cell-surface expression of gp130 but not IL-6 receptor (FIG. 16). A pharmacological JAK inhibitor did not affect gp130 expression, indicating this effect was not secondary to inhibition of STAT3 phosphorylation. Lastly, brefeldin A, which inhibits transport of proteins from ER to Golgi, reduced the cell surface expression of both gp130 and IL-6 receptor. Consequently, only atovaquone specifically inhibited the cell-surface expression of gp130. Atovaquone also induced downregulation of cell surface gp130 in INA-6 and HEL cells (FIG. 17).

Figure 18:
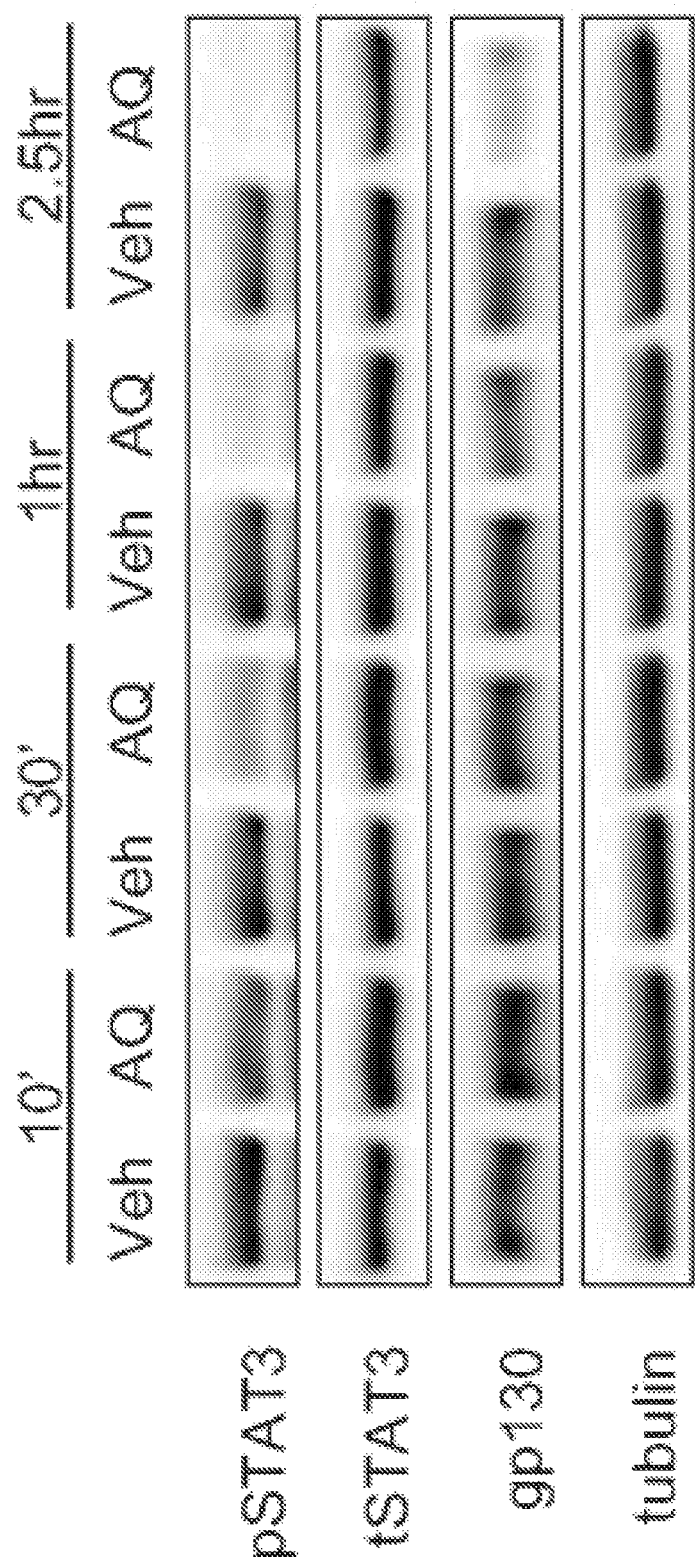
FIG. 18 contains photographs of Western blots of lysates of U266 cells treated with vehicle or 20 µM atovaquone (AQ) for the indicated time period ("hr"=hour(s)). Blots were probed for phospho (p) and total (t) STAT3, as well as gp130, and tubulin.
Figure 19:
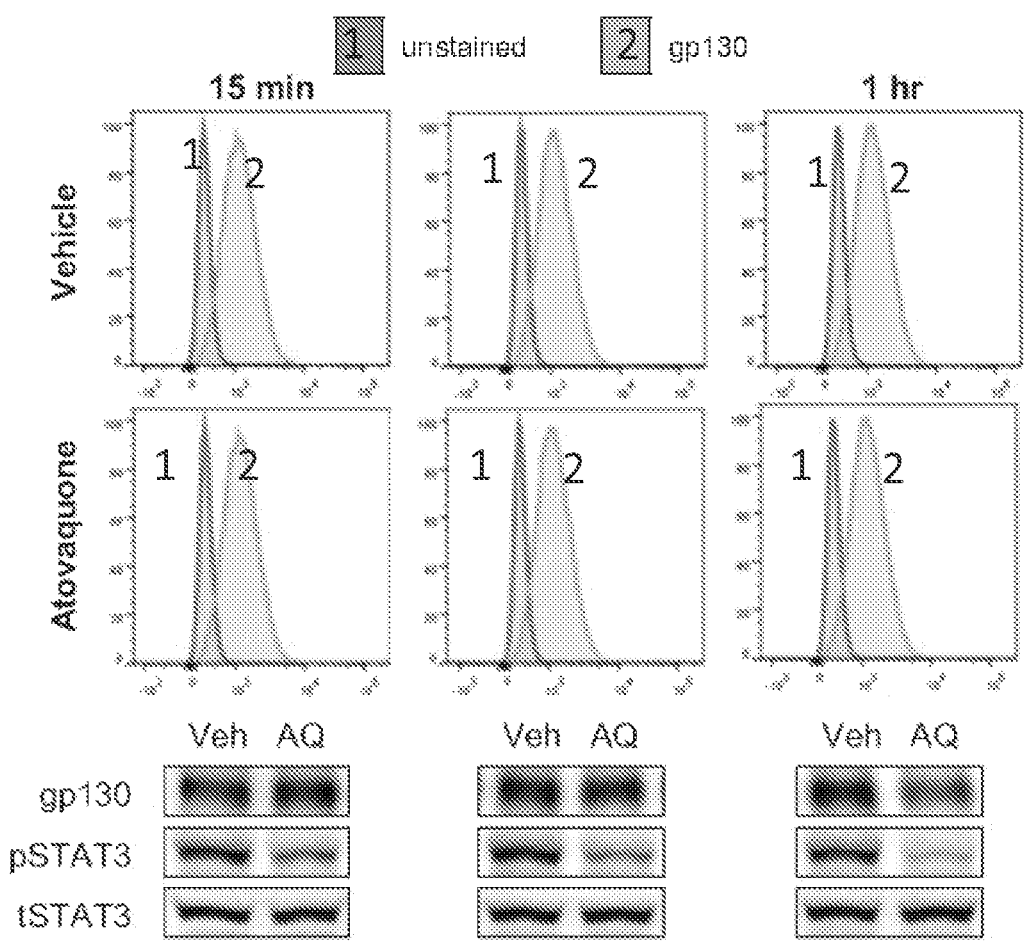
FIG. 19 contains FFC histograms (upper two panels) and photographs of Western blots (lower panel) for gp130 expression (cell surface staining shown in histograms; total protein in Western blot results) in U266 cells treated with vehicle ("Veh") or atovaquone (AQ) at 20 µM.

Since atovaquone reduced gp130 expression at the cell surface, it was asked whether this effect was accompanied by reduced total gp130 in the cell. To address this question, a time course of atovaquone treatment was performed and total cellular gp130 was measured by Western blotting in U266 cells treated with atovaquone at 20 µM. STAT3 phosphorylation was inhibited rapidly, after only 10 minutes, whereas total gp130 was not reduced except at much longer time points (FIG. 18). Thus, it was surmised that atovaquone also rapidly downregulates cell-surface gp130, paralleling STAT3 inhibition and preceding the decrease in total gp130. This was confirmed by a flow cytometric time course experiment that demonstrated atovaquone rapidly inhibits the cell-surface expression of gp130, without affecting total gp130 until much later (FIG. 19). Loss of cell-surface gp130 may be due to decreased entry into the plasma membrane or increased internalization. In either case, the decrease in total gp130 observed at longer time points is likely due to degradation of relatively unstable intracellular gp130.

Figure 20:
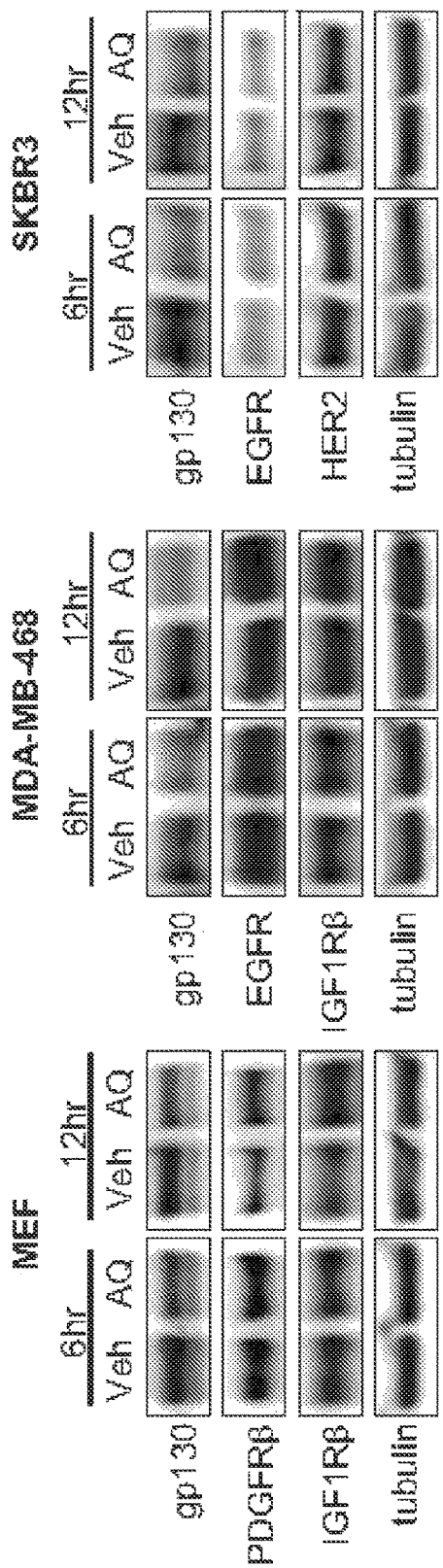
FIG. 20 contains photographs of Western blots for the indicated proteins at the indicated time points (6 or 12 hours) following treatment of the indicated cells (MEF, MDA-MB-468, and SKBR3) with vehicle ("Veh) or 25 µM atovaquone (AQ).
Figure 21:
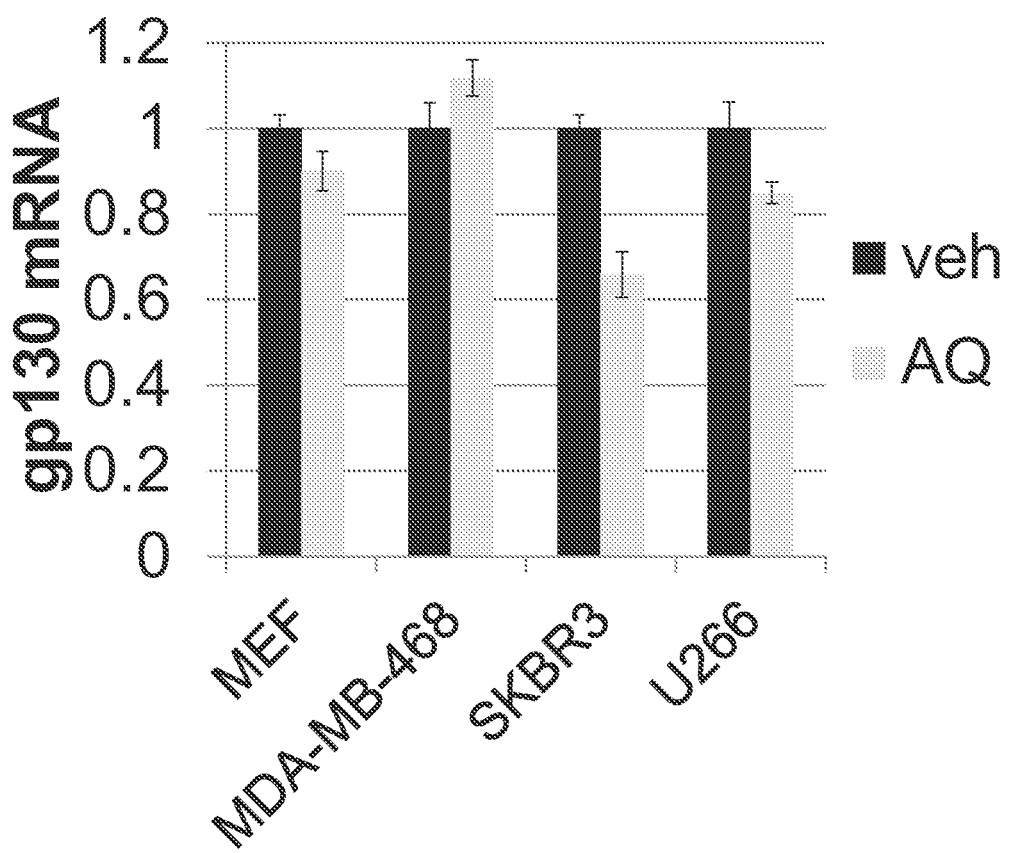
FIG. 21 is a bar graph quantifying gp130 mRNA expression in MEF, MDA-MB, SKBR3 and U266 cells treated for 12 hours with vehicle ("Veh) or 25 µM atovaquone (AQ).

MEF, MDA-MB-468, and SKBR3 cells were treated with atovaquone (25 µM) for 6 or 12 hours, then analyzed by Western blot for expression of gp130 and various other receptors. It was found that atovaquone also induced loss of total gp130 after prolonged treatment in multiple other cell lines, including MEF, SKBR3, and MDA-MB-468 cells (FIG. 20). In contrast, levels of other receptors—such as PDGFR-β, EGFR, HER2, and IGF1R-β—were not affected, again indicating a specific effect on gp130. Also, gp130 mRNA expression was not significantly changed by atovaquone, demonstrating that the decrease in total gp130 occurs post-transcriptionally (FIG. 21). In summary, atovaquone rapidly induces specific loss of cell-surface gp130, while total gp130 declines secondarily due to protein degradation.

Example 5: Atovaquone Inhibits mTOR Activity Through REDD1

This example demonstrates that atovaquone inhibits the mTOR pathway by inducing the expression of REDD1.

Figure 22:
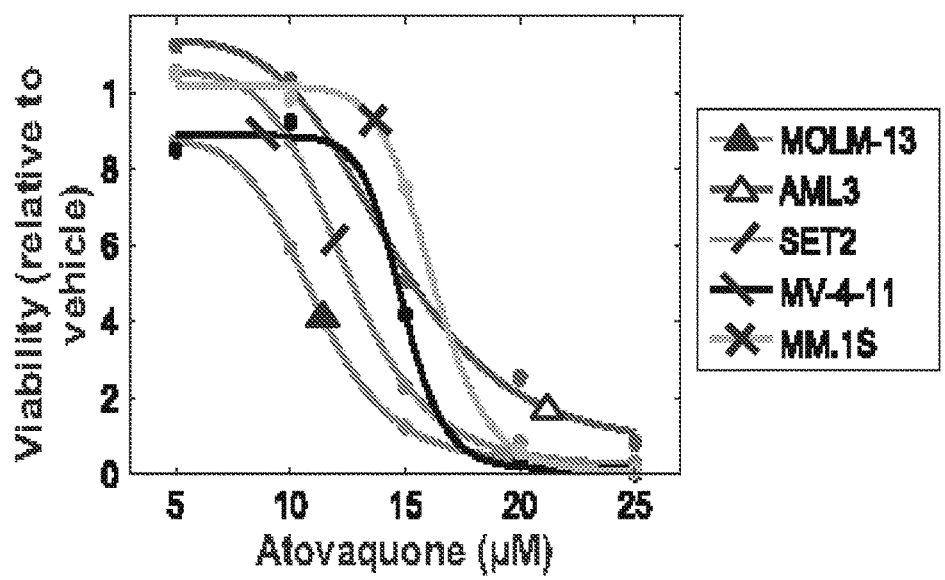
FIG. 22 is a line graph comparing the viability (relative to vehicle) of MOLM-13, AML3, SET2, MV-4-11, and MM.1S cells, which are hematologic cancer cell lines that lack STAT3 activation, following treatment for 72 hours with the indicated concentrations (µM) of atovaquone.
Figure 23:
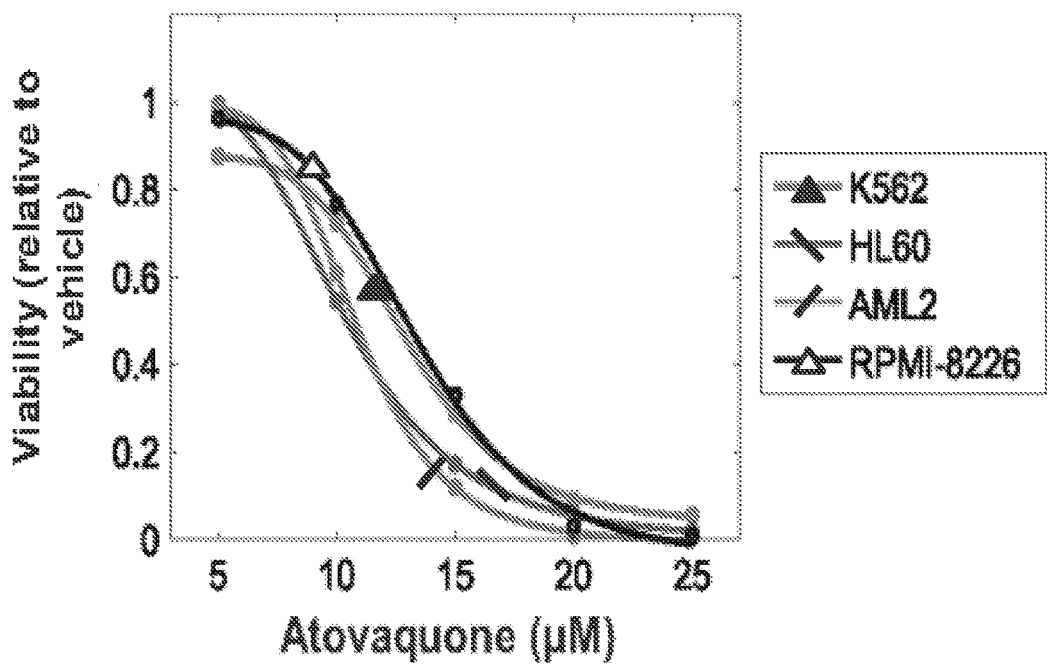
FIG. 23 is a line graph comparing the viability (relative to vehicle) of K562, HL60, AML2 and RPMI-8226 cells, which are hematologic cancer cells that lack constitutive STAT3 activation, following treatment for 72 hours with the indicated concentrations (µM) of atovaquone.
Figure 24:
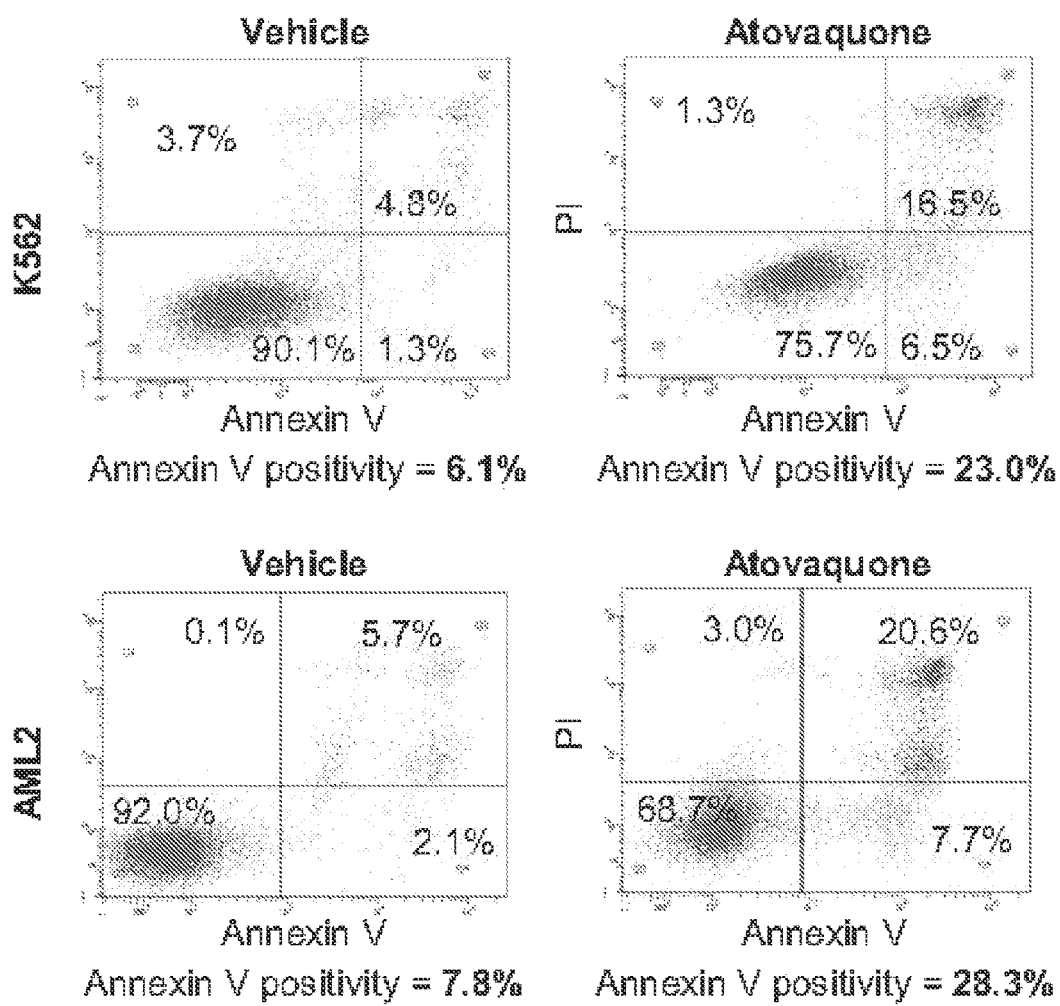
FIG. 24 contains FFC dot plots of K562 cells (upper plots) and AML2 cells (lower plots) treated with vehicle or atovaquone (20 µM and 15 µM, respectively), stained for PI and Annexin V and analyzed by flow cytometry.
Figure 25:
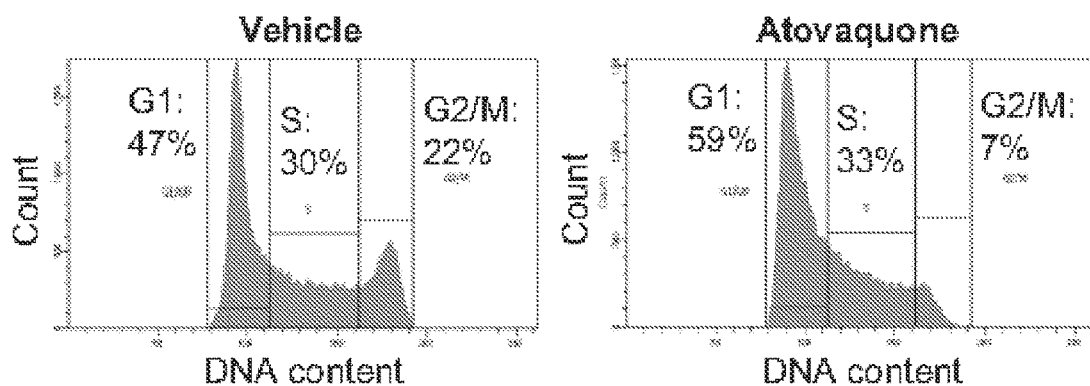
FIG. 25 contains FFC histograms for PI cell cycle analysis of K562 cells treated with vehicle or atovaquone (20 µM) for 24 hours. Cell cycle phases G1, S and G2/M are indicated.

Having characterized the effect of atovaquone on STAT3 and STAT3-dependent cell lines, it was asked if atovaquone had effects on the viability of cells that do not display constitutive STAT3 activation. K562 and AML2 cells treated with atovaquone (20 and 15 µM, respectively) for 48 hours. Interestingly, atovaquone also reduced the viability of various malignant hematological cell lines that lack STAT3 activation (FIG. 22 and FIG. 23). Similar to cells with activated STAT3, the loss of viability occurred through apoptosis and cell cycle arrest (FIG. 24 and FIG. 25). Therefore, it was hypothesized that atovaquone kills cancer cells through STAT3-related and STAT3-independent mechanisms. Accordingly, the hypothesis that atovaquone inhibited another common pathway in cancer pathogenesis was considered. In particular, the mTOR pathway, which is known to be involved in cancer cell growth and survival, was investigated.

Figure 26:
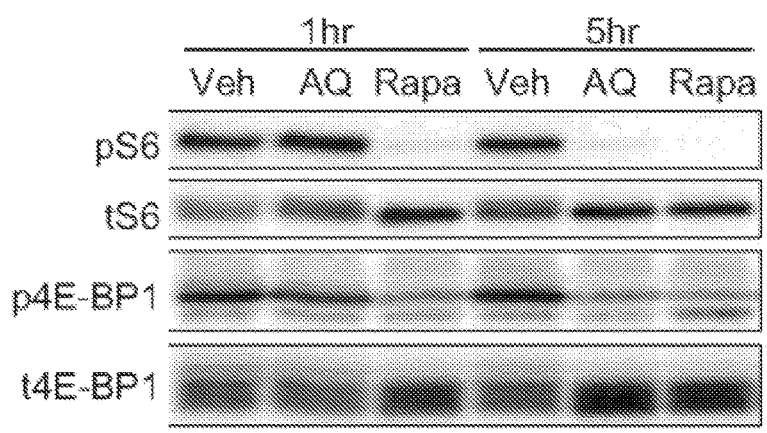
FIG. 26 contains photographs of Western blots of lysates of K562 cells treated with vehicle (Veh), atovaquone (AQ, 20 µM) or rapamycin (Rapa, 10 µM) for 1 hour or 5 hours, and immunoblotted for phospho (p) and total (t) ribosomal protein S6 (S6), and 4E-BP1.
Figure 27:
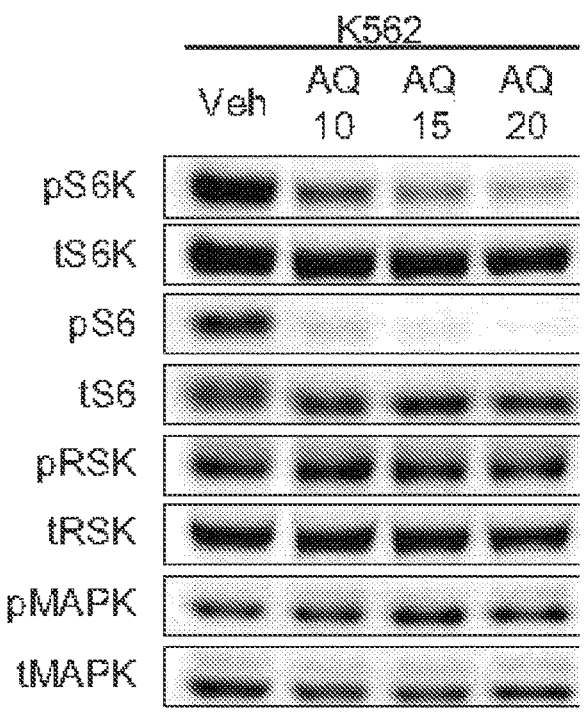
FIG. 27 contains photographs of Western blots of lysates of K562 cells treated for 6 hours with vehicle or the indicated concentrations of atovaquone (AQ) and immunoblotted for phospho (p) and total (t) ribosomal protein S6 kinase (S6K), S6, ribosomal S6 kinase (RSK), and MAP kinase (MAPK).
Figure 28:
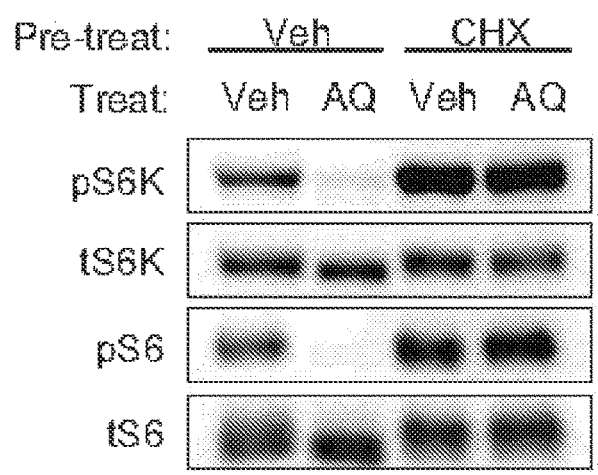
FIG. 28 contains photographs of Western blots of lysates of K562 cells pretreated with vehicle or cycloheximide (CHX, 2 µg/ml) for 1 hour, then treated with vehicle or atovaquone (AQ, 20 µM) for 5 hours. The lysates were immunoblotted for phospho (p) and total (t) S6K and S6.
Figure 29:
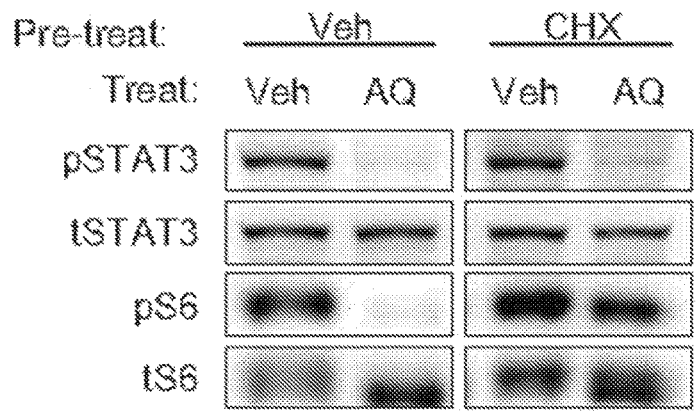
FIG. 29 contains photographs of Western blots of lysates of U266 cells pretreated with vehicle or cycloheximide (CHX, 2 µg/ml) for 1 hour, then treated with vehicle or atovaquone (AQ, 15 µM) for 2.5 hours. The lysates were immunoblotted for phospho (p) and total (t) STAT3 and S6.

K562 cells were treated with atovaquone (20 µM) or rapamycin (10 nM) for 1 hour or 5 hours, then analyzed by Western blot. In K562 cells lacking STAT3 activation, atovaquone inhibited phosphorylation of 4E-BP1, a direct mTOR substrate, and ribosomal protein S6 with efficacy comparable to rapamycin, but only after 5 hours of treatment (FIG. 26). Additionally, atovaquone inhibited phosphorylation of p70S6K, but not p42/44 MAPK, p90RSK, or Akt in K562 cells treated with atovaquone for 6 hours (FIG. 27). Taken together, these findings suggested that inhibition of the mTOR pathway by atovaquone was taking place at the level of mTOR itself. The requirement for prolonged treatment to observe mTOR inhibition raised the possibility that this effect was mediated by an induced factor. To test this hypothesis, cells were pretreated with cycloheximide, a protein synthesis inhibitor. K562 cells were pre-treated with vehicle or cycloheximide (2 µg/ml) for 1 hour, then treated with vehicle or atovaquone (20 µM) for 5 hours. Atovaquone inhibition of S6 phosphorylation in K562 and U266 cells was blocked in the presence of cycloheximide (FIG. 28 and FIG. 29). In contrast, cycloheximide did not affect the inhibition of STAT3 phosphorylation by atovaquone in U266 cells (FIG. 29), consistent with the rapid kinetics of this effect (FIG. 18). Similar results were obtained with actinomycin D, an inhibitor of mRNA synthesis. These results demonstrate that atovaquone inhibition of mTOR, but not STAT3, requires de novo gene expression.

Figure 30:
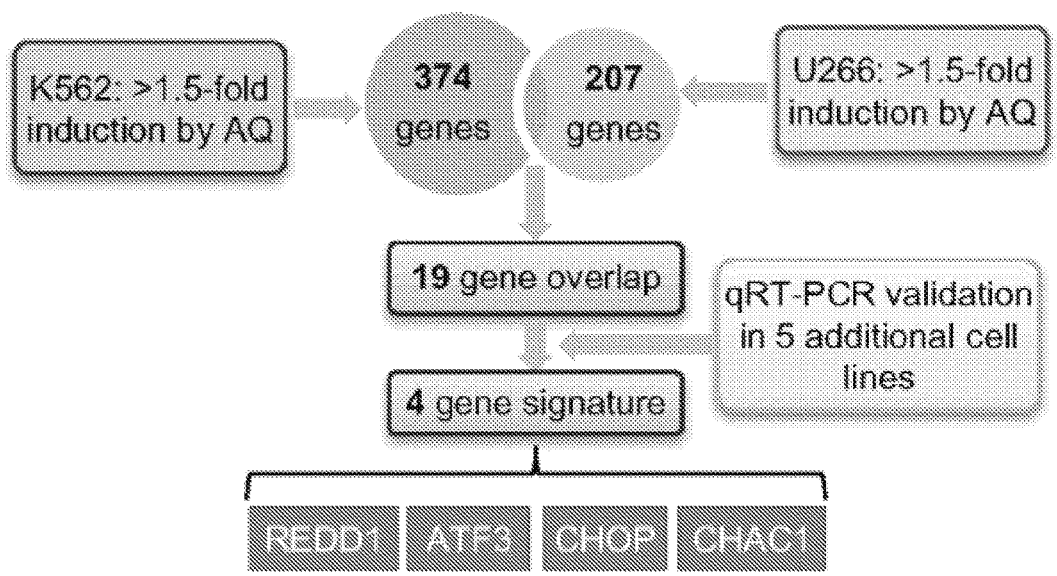
FIG. 30 is a schematic diagram depicting the strategy used to identify the factor upregulated by atovaquone that is responsible for mTOR inhibition ("AQ": atovaquone).

To discover the gene whose induction by atovaquone was responsible for mTOR inhibition, gene expression microarrays were performed in K562 and U266 cells. It was reasoned that induction of the causative factor must be common to all cell lines in which atovaquone inhibits the mTOR pathway. Using a 1.5-fold cutoff, atovaquone upregulated several hundred genes in each cell line; however, only 19 of these genes were upregulated in both K562 and U266 cells. The expression of the 19 genes was then analyzed by qRT-PCR in additional cell lines responsive to atovaquone, resulting in the identification of a set of 4 genes that was consistently induced in all cell lines (FIG. 30). Of these, REDD1 is a known negative regulator of mTOR, whose activity is dependent on the TSC1/2-complex.

To evaluate the role of REDD1, RNA interference was used to knock down its expression in adherent SKBR3 cells, given the relative ease of introducing siRNA into these cells. SKBR3 cells were transfected with control or REDD1 siRNA for 48 hours, then treated with atovaquone (25 µM) for 4 hours. Knocking down REDD1 largely blocked atovaquone inhibition of S6 phosphorylation (FIG. 31). Moreover, atovaquone had no effect on S6 phosphorylation in MEFs with knockout of TSC2 or REDD1 itself following treatment with atovaquone (25 µM) for 2.5 hours (FIG. 32 and FIG. 33). Thus, atovaquone inhibits the mTOR pathway by inducing the expression of REDD1.

Example 6: Atovaquone Selectively Activates the Phospho-eIF2α/ATF4 Branch of the Unfolded Protein Response (UPR)

This example demonstrates that atovaquone inhibition of STAT3 is not secondary to UPR activation.

Figure 34:
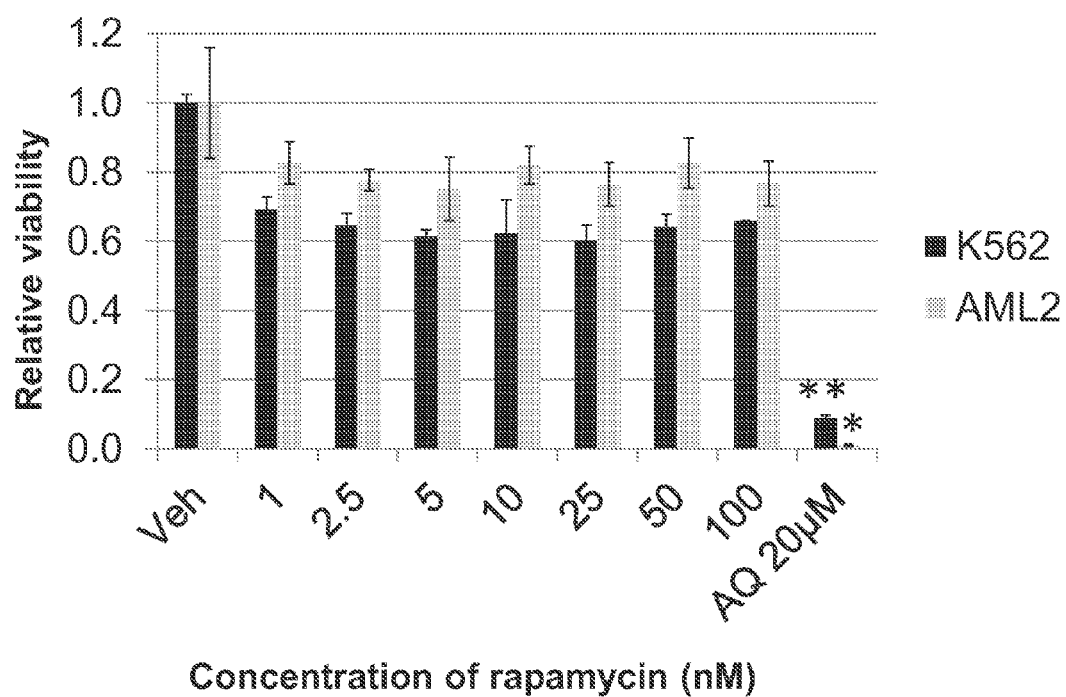
FIG. 34 is a graph quantifying the relative viability of K562 and AML2 cells, which lack STAT3 activation, following treatment for 72 hours with 20 µM atovaquone (AQ) and the indicated concentration of rapamycin, resulting in only a modest viability decrease. P-values (*, $p<0.01$; **, $p<0.0001$) are shown for the viability after 72-hour atovaquone treatment relative to 100 µM rapamycin for each cell line.
Figure 35:
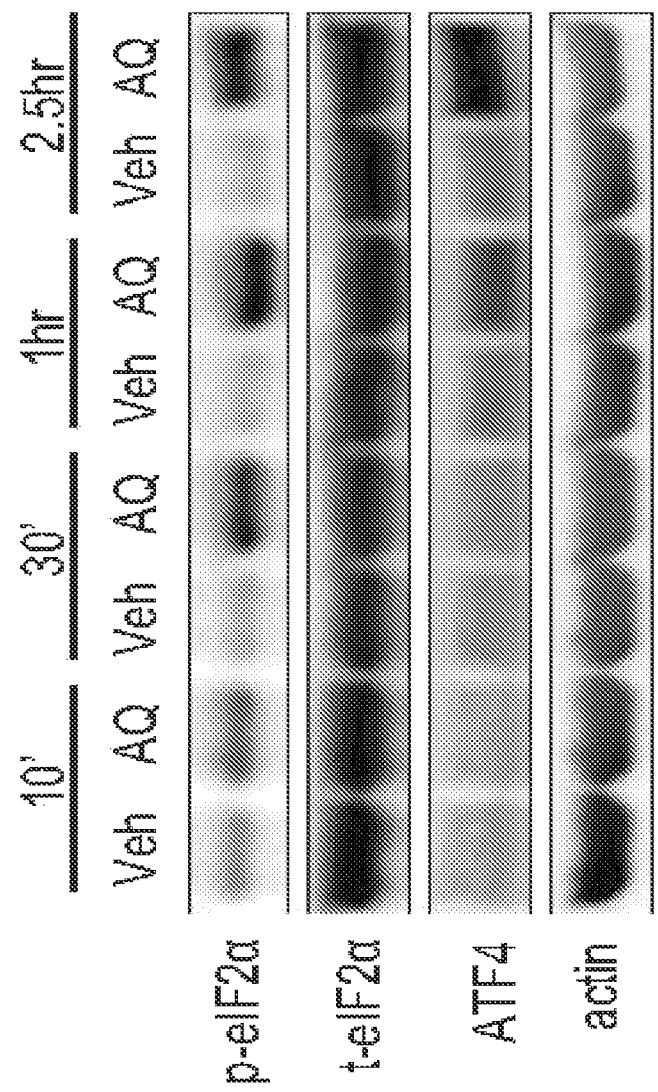
FIG. 35 contains photographs of Western blots of lysates of U266 cells treated with vehicle (Veh) or 20 µM atovaquone (AQ) for the indicated time period ("hr"=hour(s)). The lysates were immunoblotted for phospho (p) and total (t) eIF2α, as well as for ATF4 and actin.
Figure 37:
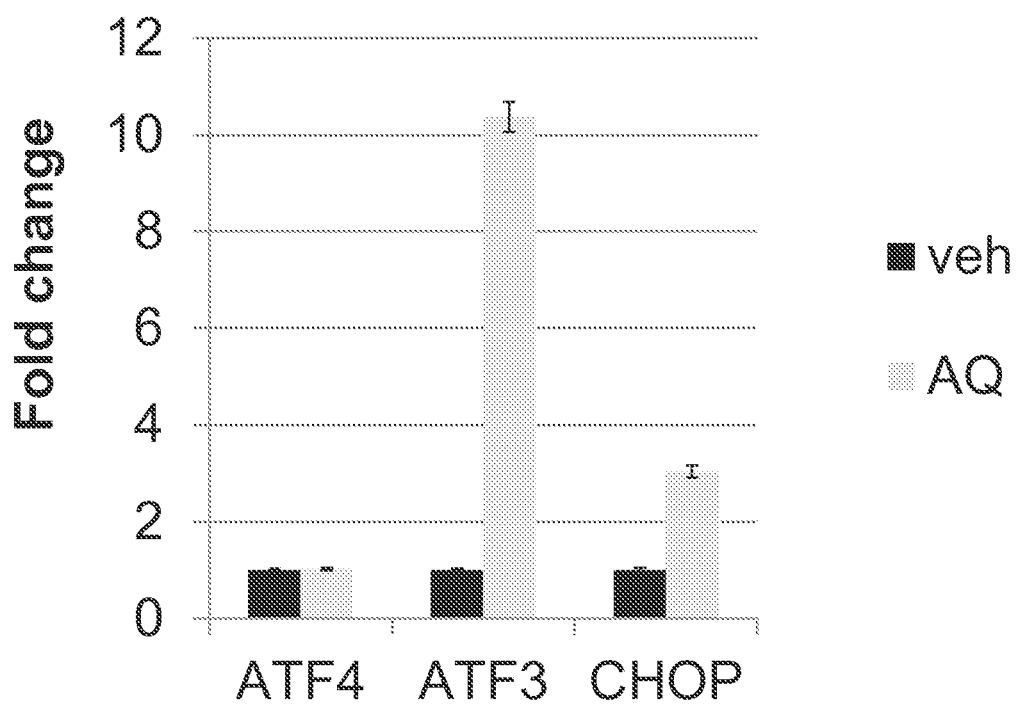
FIG. 37 is a bar graph quantifying the fold change in ATF4 gene expression in U266 cells treated with vehicle (veh) or atovaquone (AQ) at 15 µM for 2 hours.
Figure 38:
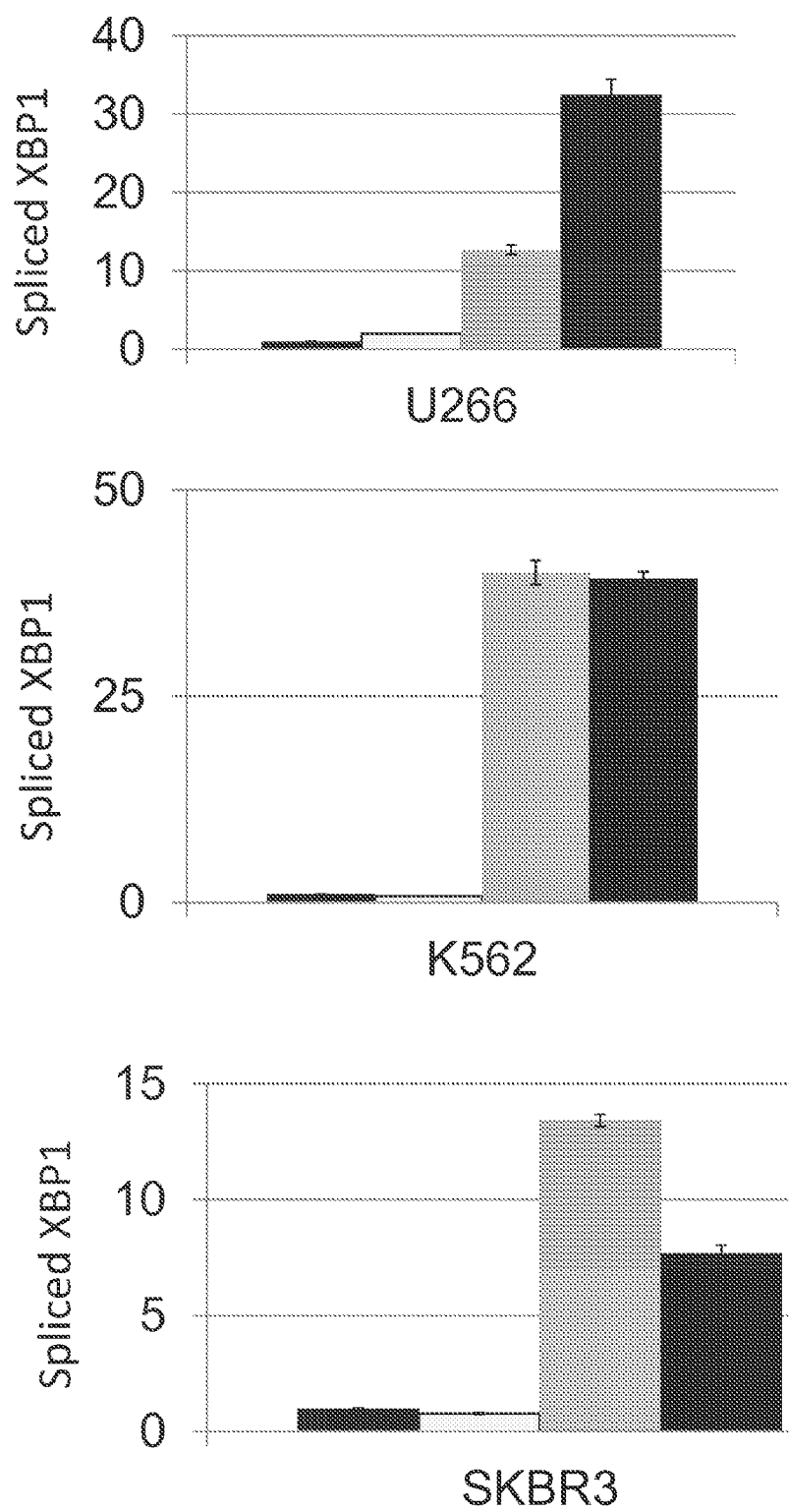
FIG. 38 contains bar graphs quantifying the level of spliced XBP1 in U266, K562, and SKBR3 cells treated, from left to right bar in each graph, with vehicle, atovaquone (20, 20, 25 µM respectively), thapsigargin (1 µM), or tunicamycin (5 µg/ml) for 6 hours.
Figure 39:
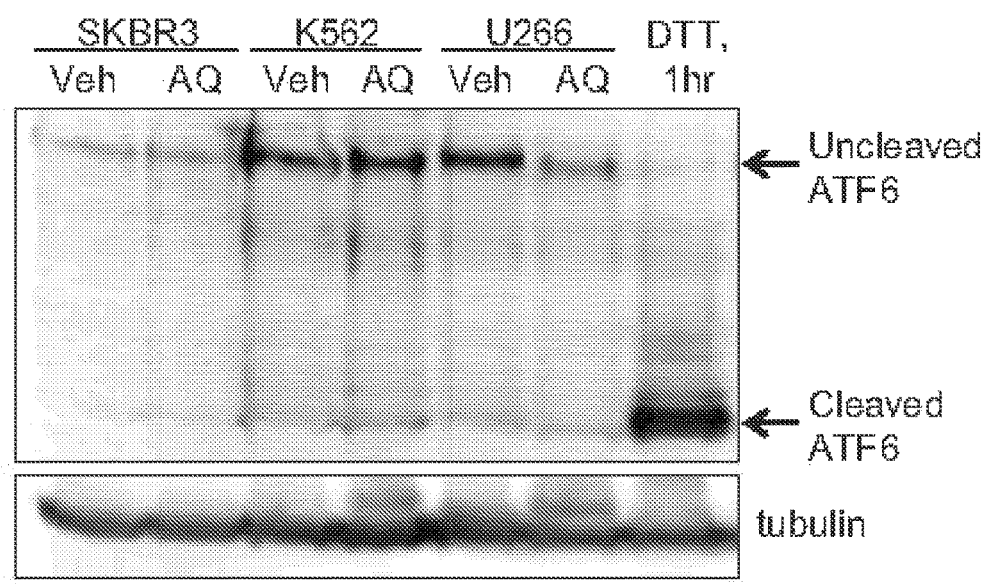
FIG. 39 contains photographs of Western blots of cleaved and uncleaved ATF6 in SKBR3, K562, U266 cells treated with vehicle (Veh) or atovaquone ("AQ": 25, 20, and 20 µM, respectively). The last lane is a positive control, consisting of U266 cells treated with 5 mM DTT for 1 hour. Due to the insolubility of ATF6, all of these samples were prepared by boiling in sample buffer.
Figure 40:
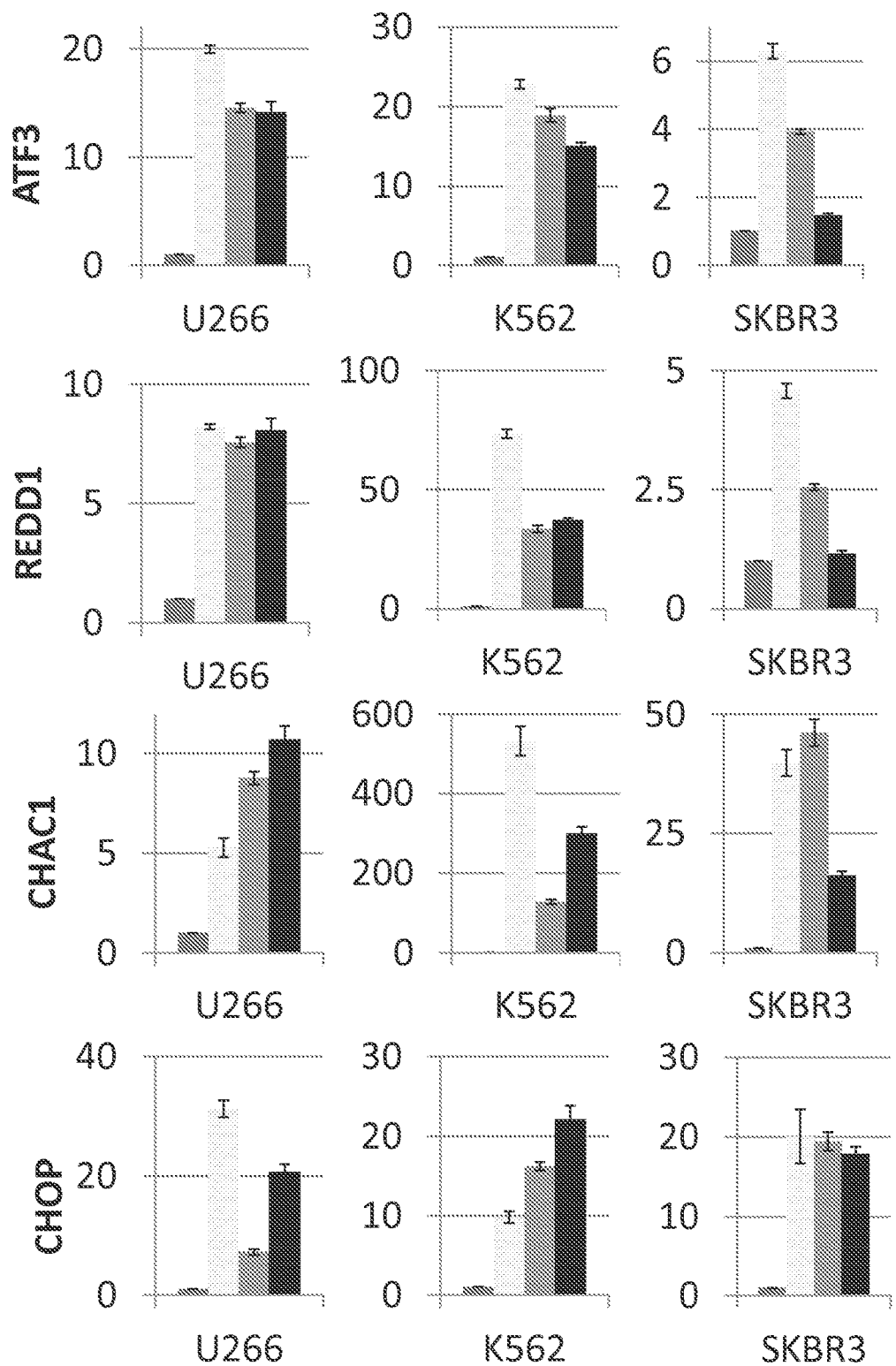
FIG. 40 contains bar graphs quantifying expression of the indicated unfolded protein response (UPR) target genes, which are downstream of ATF4 and upregulated by atovaquone, in U266, K562, and SKBR3 cells treated, from left to right bar in each graph, with vehicle, atovaquone (20, 20, 25 µM respectively), thapsigargin (1 µM), or tunicamycin (5 µg/ml) for 6 hours.
Figure 41:
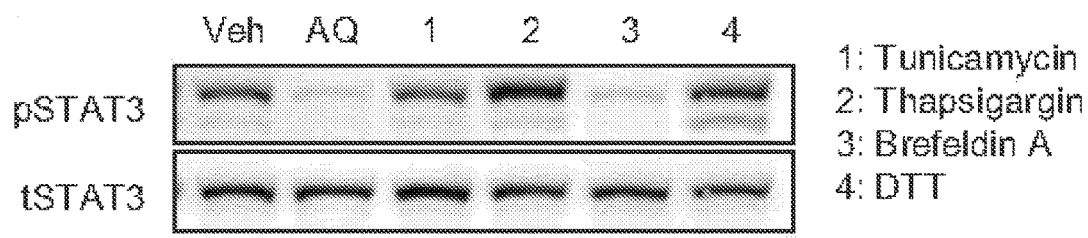
FIG. 41 contains photographs of Western blots of lysates of U266 cells treated with vehicle (Veh), atovaquone (AQ) or the UPR activators tunicamycin (1) (5 µg/ml), thapsigargin (2) (1 µM), and Brefeldin A (3) (3 µg/ml), or with DTT (4) (5 mM) for 2.5 hours, immunoblotted for phospho (p) and total (t) STAT3.

In asking how atovaquone induces REDD1, a possible role for ATF4, which regulates REDD1 expression was considered. ATF4 is regulated mainly at the level of translation and is induced upon phosphorylation of eIF2α. Moreover, in the set of genes consistently induced by atovaquone, ATF3 and CHOP are also ATF4 target genes, and CHAC1 is a target gene of CHOP. Growth-inhibitory and pro-apoptotic functions have been reported for all of these proteins, suggesting they may contribute to the anti-cancer activity of atovaquone. K562 and AML2 cells, which lack STAT3 activation, were treated with rapamycin for 72 hours. Indeed, rapamycin treatment of cancer cells lacking STAT3 activation caused only a modest decrease in viability, indicating that mTOR inhibition alone is not sufficient to fully explain the effects of atovaquone on viability of these cells (FIG. 34). For these reasons, it was hypothesized that atovaquone induces eIF2α phosphorylation, with a resulting increase in ATF4 protein and signaling. U266, K562, and SKBR3 cells were treated with atovaquone (20, 20, 25 µM respectively). It was found that atovaquone induced eIF2α phosphorylation and increased ATF4 protein levels in multiple cell lines, including U266, K562, and SKBR3 (FIG. 35 and FIG. 36). While ATF4 target genes were induced, expression of ATF4 mRNA was unchanged (FIG. 37), demonstrating that the increase in ATF4 protein occurred at the post-transcriptional level. The phospho-eIF2α/ATF4 pathway represents one branch of the UPR, whose other branches consist of ATF6 cleavage and IRE1-mediated XBP1 splicing. Interestingly, however, atovaquone did not induce spliced XBP1 (FIG. 38) or ATF6 cleavage (FIG. 39). Furthermore, in contrast to the UPR activators tunicamycin and thapsigargin, atovaquone did not induce any UPR target genes other than those downstream of ATF4 (FIG. 40). Thus, atovaquone selectively activates the phospho-eIF2α/ATF4 branch of the UPR. Since the UPR has been reported to inhibit IL-6-dependent STAT3 activation, various UPR activators (Tunicamycin, Thapsigargin, and Brefeldin A) were tested to determine if they also inhibit STAT3 phosphorylation in U266 cells. However, only brefeldin A decreased STAT3 phosphorylation (FIG. 41), consistent with its direct effects on cell-surface gp130 and IL-6 receptor. Consequently, atovaquone inhibition of STAT3 is not secondary to UPR activation.

Example 7: Atovaquone Treatment Associates with Improved Cancer Outcomes in Patients This example demonstrates that atovaquone exerts anti-cancer effects in patients.

Atovaquone (trade name Mepron) is used clinically to protect hematological cancer patients against Pneumocystis pneumonia during treatment and after hematopoietic stem cell transplant (HSCT). At many transplant centers, patients receive atovaquone for 20-30 days upon discharge after HSCT, and then are switched to trimethoprim-sulfamethoxazole (TMPSMX; trade name Bactrim) for long-term prophylaxis. However, about 25% of patients are maintained on atovaquone for months or even years due to intolerance of TMP-SMX. In patients taking standard doses of atovaquone, plasma concentrations of 40-80 µM are routinely achieved (235), well within the range needed to inhibit STAT3 and mTOR in vitro. Consequently, retrospective analysis of atovaquone exposure and clinical outcomes after HSCT provides a unique opportunity to investigate the anti-cancer effects of atovaquone in patients. Acute myeloid leukemia (AML) was investigated based on the in vitro data showing the effects of atovaquone in AML cell lines, frequent STAT3 activation in AML patient samples (Schardt J A, et al. (2009) Activation of the unfolded protein response is associated with favorable prognosis in acute myeloid leukemia. Clinical cancer research: an official journal of the American Association for Cancer Research 15(11):3834-3841), association of UPR with better prognosis in AML (Schardt et al. supra), and sufficient sample size.

Figure 42:
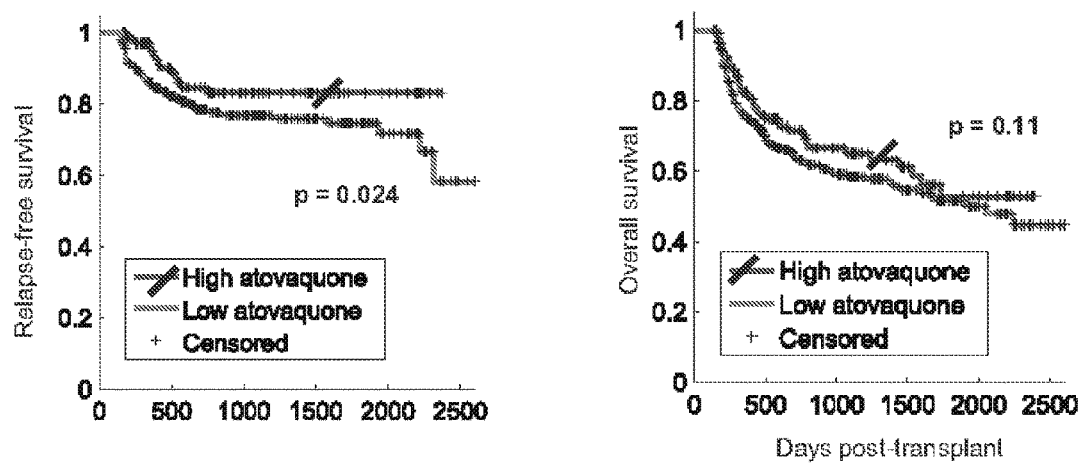
FIG. 42 contains line graphs plotting relapse-free survival (Y-axis) (left graph) or overall survival (right graph) versus time (days post-transplant, X-axis) in AML patients who had high exposure to atovaquone ("high atovaquone"), or who had low exposure to atovaquone ("low atovaquone"), after hematopoietic stem cell transplant (HSCT). The indicated p-values were determined using the log-rank test.
Figure 43:
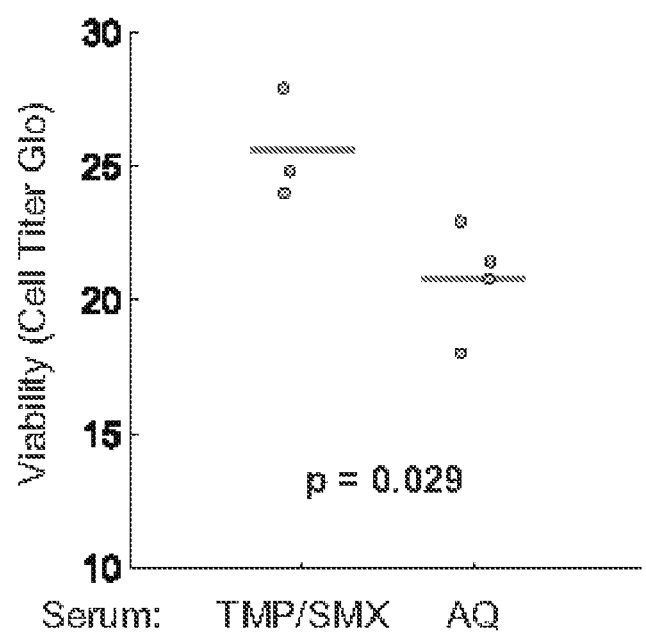
FIG. 43 contains a dot plot quantifying viability of U266 cancer cells grown for 4 days in serum from patients taking trimethoprim/sulfamethoxazole (TMP/SMX) or atovaquone; the indicated p-value was determined using the two-sample t-test.

The patient population consisted of AML patients treated with HSCT at the Dana-Farber Cancer Institute and who survived at least 150 days after transplant without relapse. Patients treated with atovaquone for at least 100 days within the 150-day period were classified as "high atovaquone" exposure, while the remaining patients were classified as "low atovaquone" exposure. Importantly, patients in the "high atovaquone" group had significantly improved relapse-free survival, with a trend toward improved overall survival (FIG. 42). To further investigate the anti-cancer activity of atovaquone in patients, serum samples were collected from patients approximately 100 days following HSCT who were being treated with either TMP-SMX or atovaquone. The serum from the atovaquone-treated patients reduced the viability of U266 cells compared to the serum of patients receiving TMP-SMX (FIG. 43). Atovaquone is a colored compound, and its presence in patient plasma is visibly noticeable. Taken together, these results demonstrate that atovaquone exerts anti-cancer effects in patients.

Example 8: Buparvaquone and Sigma Analog Inhibit STAT-3-Dependent Gene Expression and STAT-3 and S6 Phosphorylation This example demonstrates that the atovaquone analogs, buparvaquone and TDBHN (2-(4-(trans-decahydronaphth-2-yl)butyl)-3-hydroxy-1,4-naphthoquinone) (an analog available from Sigma-Aldrich), inhibit STAT3-dependent reporter gene expression, STAT3 phosphorylation and S6 phosphorylation.

Figure 44:
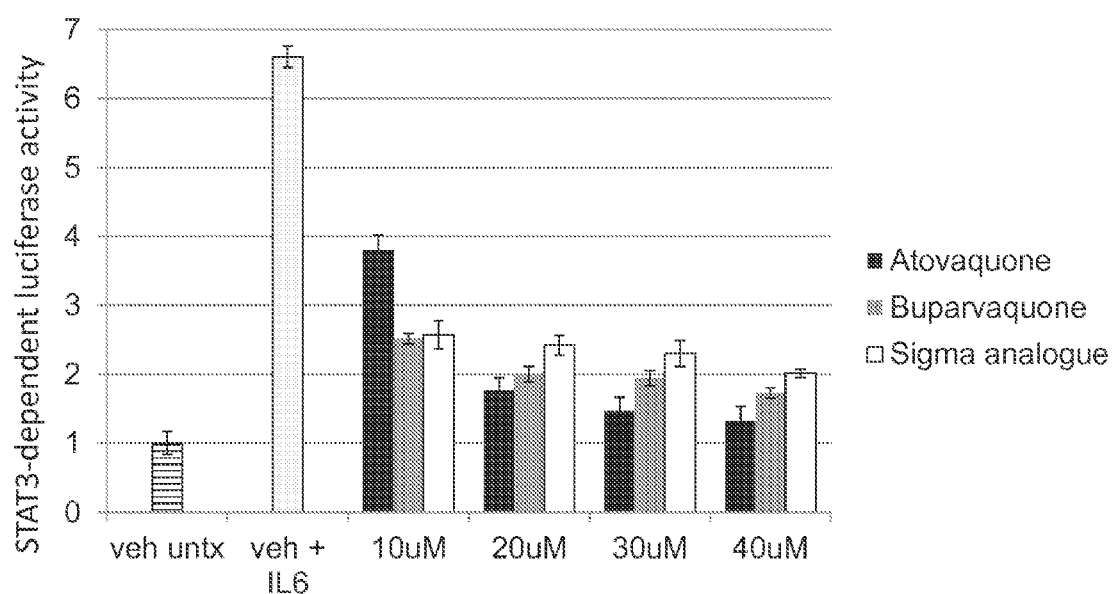
FIG. 44 is a bar graph quantifying the STAT3-dependent firefly luciferase activity in STAT3-luc reporter cells pretreated with the indicated compound at the indicated concentration for 1 hour, then stimulated with IL-6 (10 µg/ml) for 5 hours. Control cells were treated with vehicle with ("veh+IL-6") or without ("veh untx") IL-6.

STAT3-luc reporter cells were pre-treated with atovaquone, buparvaquone or TDBHN (concentration 10, 20, 30, or 40 µM) for 1 hour, then stimulated with IL-6 (10 ng/ml) for 5 hours. The activity of firefly luciferase was measured and normalized by cell viability (Cell Titer Glo). As shown in FIG. 44, all three compounds inhibited STAT-3 reporter gene expression relative to the controls.

Figure 45:
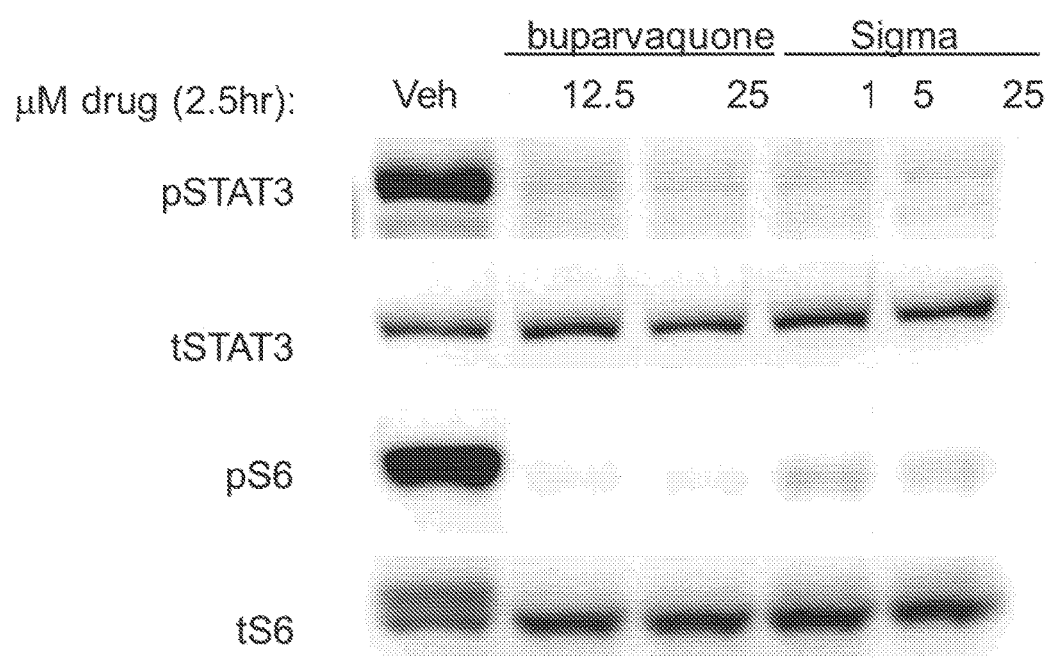
FIG. 45 is a photograph of a Western blot of lysates of U266 cells that were treated with the indicated concentration of drug (buparvaquone or 2-(4-(trans-decahydronaphth-2-yl)butyl)-3-hydroxy-1,4-naphthoquinone ("Sigma") or DMSO vehicle control ("Veh") for 2.5 hours. Blots were immunostained with antibodies for total (t) and phospho (p) STAT3 and total (t) and phospho (p) S6.

Next, U266 cells were treated with 12.5 or 25 µM buparvaquone or 1, 5, or 25 µM 2-(4-(trans-decahydronaphth-2-yl)butyl)-3-hydroxy-1,4-naphthoquinone (Sigma analog), or DMSO vehicle control, for 2.5 hours, after which cells were harvested and immunoblots were performed with antibodies for total and phospho STAT3 and total and phospho S6. As shown in FIG. 45, buparvaquone and the Sigma analog inhibited STAT3 and S6 phosphorylation at all concentrations tested, relative to vehicle control.

Example 9: Effect of Treatment with Atovaquone in an In Vivo Tumor Model

This Example demonstrates that atovaquone treatment reduced tumor growth rate and increased median survival times in a murine model of multiple myeloma.

Figure 46:
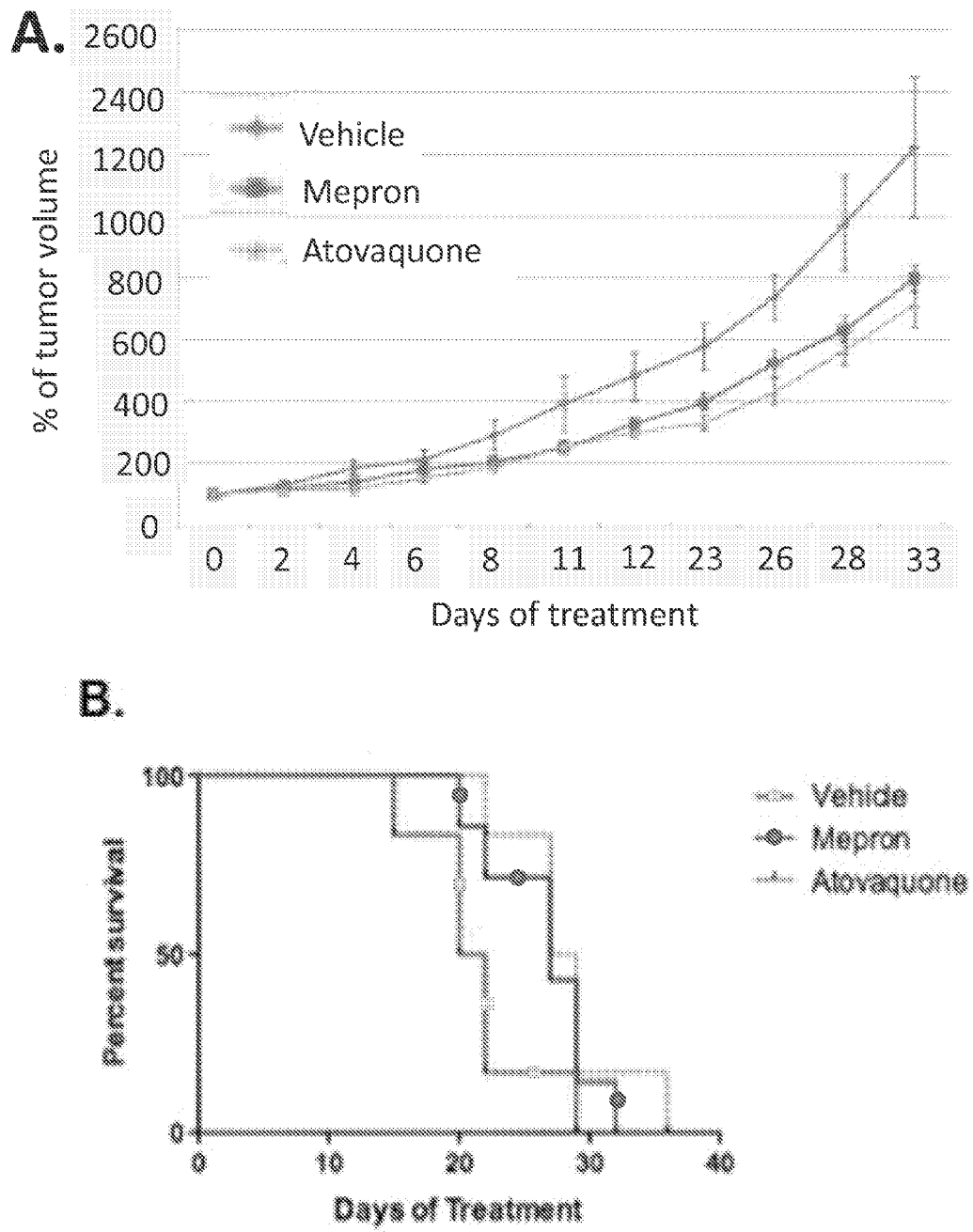
FIG. 46A is a line graph quantifying the percent (%) tumor volume over time (days of treatment)
FIG. 46B is a Kaplan-Meier survival curve plotting percent survival over time (days of treatment), in a mouse model of multiple myeloma. After mice had a tumor volume reaching 100 mm$^3$, the mice received the indicated treatment (Vehicle (5% benzyl alcohol in water), Mepron or Atovaquone) by oral gavage.

To determine whether atovaquone displayed anti-cancer activity in animal models, we utilized xenografts of U266 human multiple myeloma cells (obtained from American Type Culture Collection (ATCC), Manassas, Va.), which display constitutive activation of both STAT3 and mTOR. Female NSG mice (obtained from The Jackson Laboratory, Bar Harbor, Me.) were injected subcutaneously with $5 \times 10^6$ U266 cells in 30% Matrigel, and tumors were allowed to grow to a volume of approximately 100 mm³. At that point, animals were treated daily by oral gavage with either vehicle (5% benzyl alcohol in water), generic atovaquone, or Mepron® brand atovaquone (GlaxoSmithKline LLC, Philadelphia, Pa.) at a dose of 200 mg/kg. Treatment with either form of atovaquone led to a prominent decrease in the growth rate of these tumors (FIG. 46A) as well as an increase in the median survival of the treated animals (FIG. 46B).

Discussion

Upon determining that atovaquone decreased the viability of malignant hematological cell lines, including cells that lacked STAT3 activation, a systematic approach was taken to determine the effects of atovaquone on other intracellular signaling pathways that mediated malignant cell behavior. From these studies, it was found that atovaquone inhibited the mTOR pathway. While it was as efficacious as rapamycin in inhibiting this pathway, the fact that atovaquone required several hours of exposure to inhibit this pathway, and lost activity when cells were treated with a protein synthesis inhibitor, suggested that it was operating by a unique mechanism that required new protein synthesis. Subsequent experimentation revealed that atovaquone induced the phospho-eIF2α/ATF4 pathway and REDD1 expression, which is necessary for atovaquone-induced mTOR inhibition. While not intending to be bound by any one particular theory or mechanism of action, it is believed that this unique manner in which atovaquone is thought to inhibit the mTOR pathway and exert an anti-cancer effect is superior to that of the mTOR inhibitor rapamycin.

It has been discovered, using an unbiased gene expression-based approach, that atovaquone is a novel STAT3 inhibitor. Atovaquone acts by diminishing cell-surface gp130 expression and STAT3 tyrosine phosphorylation. As a consequence, critical STAT3 target genes mediating survival and proliferation are reduced, such as survivin, Bcl-2 family members, and cyclin D1. Moreover, atovaquone inhibits the viability of STAT3-dependent cancer cells by inducing apoptosis and disrupting cell cycle progression. Since atovaquone inhibits STAT3 signaling upstream of JAK kinases, its mechanism predicts that atovaquone will also inhibit phosphorylation of other STATs if they are activated alongside STAT3 by the same upstream events. Indeed, in addition to inhibiting STAT3 phosphorylation, atovaquone inhibited IL-6-dependent phosphorylation of STAT1 in INA-6 and U266 cells and mutant JAK2-dependent phosphorylation of STAT1 and STAT5 in HEL cells. Since STAT5 activation is crucial to cancer pathogenesis caused by JAK2-V617F, the additional inhibition of STAT5 in this context is a desirable effect of atovaquone. By contrast, atovaquone did not inhibit STAT5 phosphorylation in K562 cells, in which STAT5 is activated by BCR-ABL independent of gp130. Because the effects of atovaquone on STAT activation are restricted to gp130-dependent signaling, atovaquone inhibits STATs more selectively than direct pharmacological JAK inhibition. For example, signaling due to growth hormone, erythropoietin, and interferons is abrogated by JAK inhibitors but remains intact under atovaquone, since these hormones and cytokines do not utilize gp130. This reduces the potential side effects of atovaquone, which is already known to be extremely well-tolerated in humans. At the same time, the actions of atovaquone extend to all cytokines that signal through gp130, including LIF and OSM, thereby exerting broader effects than therapies specifically directed against IL-6 or IL-6 receptor, such as monoclonal antibodies. This is also advantageous, since oncogenic effects of LIF and OSM have been reported.

The present Examples demonstrate that IL-6-dependent STAT3 signaling, a key cancer pathway, is effectively inhibited by atovaquone. For example, IL-6 is a critical survival factor in AML and multiple myeloma, which is pertinent to the cell lines used in this study and the findings in AML patients. Moreover, the importance of IL-6 has been established in multiple solid malignancies, including breast, lung, and melanoma. Besides STAT3 activation due to IL-6, it was also demonstrates herein that atovaquone inhibits STAT activation due to mutant JAK2-V617F, which is crucial to myeloproliferative neoplasms. Thus, atovaquone can be used for the treatment of multiple diverse cancers, either as initial therapy or as a second-line option if JAK resistance mutations emerge following JAK inhibitor therapy. Atovaquone can also be combined with a JAK inhibitor to decrease the likelihood of developing resistance. In addition, the present Examples demonstrate that atovaquone activates the phospho-eIF2α/ATF4 branch of the UPR, resulting in induction of REDD1, which mediates mTOR inhibition, and induction of the pro-apoptotic factors CHOP and CHAC1 Inhibiting mTOR has intrinsic anticancer value due to its involvement in tumor cell survival and proliferation. However, recent studies also support specific benefits associated with dual blockade of the JAK/STAT and mTOR pathways, as shown in breast cancer and ALL. Moreover, mTOR is known to phosphorylate STAT3 on serine 727 and increase its transcriptional activity. Although this mode of crosstalk was not observed in this study, it illustrates how the various effects of atovaquone can complement and potentially synergize with one another. While broad UPR activation has variable effects in cancer, the EIF2α/ATF4 pathway has been shown to promote apoptosis in numerous cancer contexts. Additionally, the net effect of UPR activation appears to depend on the balance between induction of pro-survival BiP and pro-apoptotic CHOP. Atovaquone strongly upregulates CHOP with no effect on levels of BiP, supporting the role of the EIF2α/ATF4 pathway in atovaquone-mediated apoptosis. CHAC1, an EIF2α/ATF4 target gene consistently upregulated by atovaquone, is also pro-apoptotic. Thus, atovaquone inhibits the viability of cancer cells through STAT3-related and STAT3-independent mechanisms.

Therefore, in light of all the above findings, the use of atovaquone and related compounds in the treatment of cancer is strongly indicated. Moreover, the risk of side effects is not a great concern given the safe track record of atovaquone use in the clinic.

A number of embodiments of the invention have been described. Nevertheless, it will be understood that various modifications may be made without departing from the spirit and scope of the invention. Accordingly, other embodiments are within the scope of the following claims.

What is claimed is:

1. A method of decreasing the growth of a cancer cell in a cancer, the method comprising delivering to a target cancer cell a growth-inhibitory amount of an atovaquone-related compound, wherein, prior to the delivery, an increased level of activation of the mammalian target of rapamycin (mTOR) pathway in the cancer compared to a control level of activation of the mTOR pathway has been found, wherein the atovaquone-related compound is selected from the group consisting of trans-2-[4-(4-chlorophenyl)cyclohexyl]-3-hydroxy-1,4-naphthalenedione (atovaquone), cis-2-[4-(4-chlorophenyl)cyclohexyl]-3-hydroxy-1,4-naphthoquinone (isomer of atovaquone), 2((4-tert-butylcyclohexyl)methyl)-3-hydroxy-1,4-naphthoquinone (buparvaquone), 3-cyclohexyl-4-hydroxy-naphthalene-1,2-dione (parvaquone), and 2-(4-(trans-decahydronaphth-2-yl)butyl)-3-hydoxy-1,4-naphthoquinone (TDBHN).

2. The method of claim 1, wherein the target cancer cell is in a human subject.

3. The method of claim 2, wherein the delivery comprises administration of the compound to the human subject.

4. The method of claim 1, wherein the level of activation of the mTOR pathway in the cancer was detected in a test cell from the cancer and the control level of activation of the mTOR pathway was detected in a control cell, or
the level of activation of the mTOR pathway in the cancer was detected in microvesicles or exosomes obtained from a test sample of a body fluid of a human subject with the cancer and the control level of activation of the mTOR pathway was detected in microvesicles or exosomes obtained from a control sample of the body fluid from a human subject without the cancer.

5. The method of claim 4, wherein the body fluid is selected from the group consisting of blood, lymph, urine, cerebrospinal fluid (CSF), ascites, and pleural fluid.

6. The method of claim 1, wherein the atovaquone-related compound is atovaquone and the growth-inhibitory amount of the atovaquone is in a range of about 10 to about 40 mg/kg per day.

7. The method of claim 1, wherein the cancer is a hematological tumor selected from the group consisting of acute myeloid leukemia, chronic myeloid leukemia, Hodgkin lymphoma, non-Hodgkin lymphoma, multiple myeloma, acute lymphoblastic leukemia, and chronic lymphocytic leukemia, or
the cancer is a solid tumor selected from the group consisting of breast cancer, endometrial cancer, melanoma, lung cancer, ovarian cancer, pancreatic cancer, colorectal cancer, prostate cancer, brain cancer, gastroesophageal cancer, kidney cancer, non-small cell lung, neuroendocrine cancer, and glioblastoma multiforme.

8. The method of claim 1, wherein the level of activation of the mTOR pathway is determined by detecting the level of phosphorylation of one or more polypeptides selected from the group consisting of mTOR, ribosomal protein S6, S6 kinase, 4E-BP1, and eIF2α.

9. A method comprising,
providing a test sample from a human subject,
detecting an increased level of activation of the mTOR pathway in the test sample compared to a control sample from a human subject without cancer, and
administering a therapeutically effective amount of an atovaquone-related compound to the human subject, wherein the atovaquone-related compound is selected from the group consisting of trans-2-[4-(4-chlorophenyl)cyclohexyl]-3-hydroxy-1,4-naphthalenedione (atovaquone), cis-2-[4-(4-chlorophenyl)cyclohexyl]-3-hydroxy-1,4-naphthoquinone (isomer of atovaquone), 2((4-tert-butylcyclohexyl)methyl)-3-hydroxy-1,4-naphthoquinone (buparvaquone), 3-cyclohexyl-4-hydroxy-naphthalene-1,2-dione (parvaquone), and 2-(4-(trans-decahydronaphth-2-yl)butyl)-3-hydoxy-1,4-naphthoquinone (TDBHN).

10. The method of claim 9, further comprising,
assessing the level of activation of the STAT3 pathway in the test sample or a second test sample from the subject,
detecting an increased level of activation of the STAT3 in the test sample or the second test sample compared to a control sample from a human subject without cancer, and
administering a therapeutically effective amount of the atovaquone-related compound.

11. The method of claim 9, wherein the test sample comprises a cancer cell from the human subject, or
the test sample comprises microvesicles or exosomes obtained from a body fluid of the human subject.

12. The method of claim 10, wherein the second test sample comprises a cancer cell from the human subject, or
the second test sample comprises microvesicles or exosomes obtained from a body fluid of the human subject.

13. The method of claim 12, wherein the body fluid is selected from the group consisting of blood, lymph, urine, CSF, ascites, and pleural fluid.

14. The method of claim 9, wherein the atovaquone-related compound is atovaquone.

15. A method of assessing the success of cancer cell growth inhibitory therapy with an atovaquone-related compound in a human subject, the method comprising,
administering a therapeutically effective amount of an atovaquone-related compound to the human subject, wherein the atovaquone-related compound is selected from the group consisting of trans-2-[4-(4-chlorophenyl)cyclohexyl]-3-hydroxy-1,4-naphthalenedione (atovaquone), cis-2-[4-(4-chlorophenyl)cyclohexyl]-3-hydroxy-1,4-naphthoquinone (isomer of atovaquone), 2((4-tert-butylcyclohexyl)methyl)-3-hydroxy-1,4-naphthoquinone (buparvaquone), 3-cyclohexyl-4-hydroxy-naphthalene-1,2-dione (parvaquone), and 2-(4-(trans-decahydronaphth-2-yl)butyl)-3-hydoxy-1,4-naphthoquinone (TDBHN);

assessing the level of activation of the mTOR or eIF2α/ATF4 pathway in a test sample from the human subject that has been administered with the atovaquone-related compound relative to a control sample.

16. The method of claim 15, further comprising,
assessing the level of activation of the STAT3 pathway in the test sample or a second test sample from the human subject that has been treated with the compound relative to a control sample.

17. The method of claim 15, wherein the test sample comprises a cancer cell from the human subject, or
the test sample comprises microvesicles or exosomes obtained from a body fluid of the human subject.

18. The method of claim 16, wherein the second test sample comprises a cancer cell from the human subject, or
the second sample comprises microvesicles or exosomes obtained from a body fluid of the human subject.

19. The method of claim 15, wherein the control sample was obtained from the human subject prior to the treatment with the atovaquone-related compound.

20. The method of claim 17, wherein the body fluid is selected from the group consisting of blood, lymph, urine, CSF, ascites, and pleural fluid.

21. The method of claim 15, wherein the atovaquone-related compound is atovaquone.

22. The method of claim 15, further comprising determining the level of expression of one or more of CCAAT/-enhancer-binding protein homologous protein (CHOP), cation transport regulator-like 1 protein (CHAC1), and regulated in development and DNA damage responses-1 protein (REDD1).

23. A method of treating cancer in a human subject in need thereof, the method comprising:
administering a therapeutically effective amount of an atovaquone-related compound to the human subject, wherein the atovaquone-related compound is selected from the group consisting of trans-2-[4-(4-chlorophenyl)cyclohexyl]-3-hydroxy-1,4-naphthalenedione (atovaquone), cis-2-[4-(4-chlorophenyl)cyclohexyl]-3-hydroxy-1,4-naphthoquinone (isomer of atovaquone), 2((4-tert-butylcyclohexyl)methyl)-3-hydroxy-1,4-naphthoquinone (buparvaquone), 3-cyclohexyl-4-hydroxy-naphthalene-1,2-dione (parvaquone), and 2-(4-(trans-decahydronaphth-2-yl)butyl)-3-hydoxy-1,4-naphthoquinone (TDBHN); and, after the administration, monitoring the level of activation of the mTOR or eIF2α/ATF4 pathway in a test sample, two or more serial test samples, a second test sample, or a second set of two or more serial test samples from the human subject.

24. The method of claim 23, further comprising, after the administration, monitoring the level of activation of the STAT3 pathway in the test sample, the two or more serial test samples, the second test sample, or the second set of two or more serial test samples from the human subject.

25. The method of claim 23, further comprising continuing the treatment if the level of activation of the mTOR pathway in the test sample, the two or more serial test samples, the second test sample, or the second set of two or more serial test samples is decreased relative to its level of activation in a control sample obtained from the human subject prior to treatment.

26. The method of claim 24, further comprising continuing the treatment if the level of activation of the STAT3 pathway in the test sample, the two or more serial test samples, the second test sample, or the second set of two or more serial test samples is decreased relative to its level of activation in a control sample obtained from the human subject prior to treatment.

27. The method of claim 23, wherein the test sample, each of the two or more serial test samples, the second test sample, or each of the second set of two or more serial test samples comprises a cancer cell from the human subject, or
the test sample, each of the two or more serial test samples, the second test sample, or each of the second set of two or more serial test samples comprises microvesicles or exosomes obtained from a body fluid of the human subject.

28. The method of claim 27, wherein the body fluid is selected from the group consisting of blood, lymph, urine, CSF, ascites, and pleural fluid.

29. The method of claim 23, wherein the atovaquone-related compound is atovaquone and the therapeutically effective amount of the atovaquone is in a range of about 10 to about 40 mg/kg per day.

30. The method of claim 23, further comprising administering an additional therapy to the human subject.

31. The method of claim 30, wherein the additional therapy is selected from the group consisting of chemotherapy, immunotherapy, targeted therapy, radiation therapy, and combinations thereof.

32. The method of claim 23, further comprising determining the level of expression of one or more of CHOP, CHAC1, and REDD1.

33. The method of claim 23, further comprising continuing the treatment if the level of activation of the eIF2α/ATF4 pathway in the test sample, the two or more serial test samples, the second test sample, or the second set of two or more serial test samples is increased relative to its level of activation in a control sample obtained from the patient prior to treatment.

34. A method of decreasing the growth of a cancer cell of a cancer, the method comprising delivering to a target cancer cell a growth-inhibitory amount of an atovaquone-related compound, wherein, prior to the delivery, an increased level of activation of the mammalian target of rapamycin (mTOR) pathway in the cancer compared to a control level of activation of the mTOR pathway has been found, and an increased level of activation of the signal transducer and activator of transcription 3 (STAT3) pathway in the cancer compared to a control level of activation of the STAT3 pathway has been found, wherein the atovaquone-related compound is selected from the group consisting of trans-2-[4-(4-chlorophenyl)cyclohexyl]-3-hydroxy-1,4-naphthalenedione (atovaquone), cis-2-[4-(4-chlorophenyl)cyclohexyl]-3-hydroxy-1,4-naphthoquinone (isomer of atovaquone), 2((4-tert-butylcyclohexyl)methyl)-3-hydroxy-1,4-naphthoquinone (buparvaquone), 3-cyclohexyl-4-hydroxy-naphthalene-1,2-dione (parvaquone), and 2-(4-(trans-decahydronaphth-2-yl)butyl)-3-hydoxy-1,4-naphthoquinone (TDBHN).

35. The method of claim 24, wherein the level of activation of the STAT3 pathway in the cancer was detected in a test cell from the cancer and the control level of activation of the STAT3 pathway was detected in a control cell from a human subject without the cancer, or
the level of activation of the STAT3 pathway in the cancer was detected in microvesicles or exosomes obtained from a test sample of a body fluid of a human subject with the cancer and the control level of activation of the STAT3 pathway was detected in microvesicles or exosomes obtained from a control sample of the body fluid from a human subject without the cancer.

36. The method of claim 24, wherein the level of activation of the STAT3 pathway is determined by detecting the level of one or more of the following markers: STAT3 phosphorylation, nuclear localization of STAT3, STAT3 DNA binding, STAT3-dependent gene expression, and JAK family kinase autophosphorylation.

37. The method of claim 36, wherein the STAT3 phosphorylation comprises phosphorylation of tyrosine 705 of human STAT3.

38. The method of claim 36, wherein detecting STAT3-dependent gene expression comprises determining the expression level of one or more of STAT3 regulated genes encoding polypeptides selected from the group consisting of: myeloid cell leukemia sequence 1 (BCL2-related) (MCL1), jun B proto-oncogene (JUNB), B-cell CLL/lymphoma 6 (BCL6), nuclear factor, interleukin 3 regulated (NFIL3), calpain 2, (m/II) large subunit (CAPN2), early growth response 1 (EGR1), vascular endothelial growth factor A (VEGF), protein tyrosine phosphatase type IVA, member 1 (PTPCAAX1), Kruppel-like factor 4 (KLF4), exostosin glycosyltransferase 1 (EXT1), Niemann-Pick disease, type C1 (NPC1), p21 protein (Cdc42/Rac)-activated kinase 2 (PAK2), pericentrin (PCNT), fibrinogen-like 2 (FGL2), angiopoietin 1 (ANGPT1), GRB10 interacting GYF protein 1 (GIGYF1) (PERQ1), ceroid-lipofuscinosis, neuronal 6, late infantile, variant (CLN6), Brother of CDO (BOC), cysteine dioxygenase (CDO), BCL2-like 1 (BCL2L1) (BCLX), CYCLIN D1, SURVIVIN, and B-cell CLL/lymphoma 2 (BCL2).

39. The method of claim 38, wherein the level of STAT3 pathway activation correlates with the level of expression of one or more of the STAT3-regulated genes encoding polypeptides selected from the group consisting of MCL1, JUNB, BCL6, NFIL3, CAPN2, EGR1, VEGF, PTPCAAX1, KLF4, EXT1, NPC1, PAK2, BCLX, SURVIVIN, and BCL2.

40. The method of claim 38, wherein the level of STAT3 pathway activation correlates inversely with the level of expression of one or more of the STAT3-regulated genes encoding polypeptides selected from the group consisting of PCNT, FGL2, ANGPT1, PERQ1, CLN6, BOC, and CDO.

41. The method of claim 34, wherein the target cancer cell is in a human subject.

42. The method of claim 41, wherein the delivery comprises administration of the compound to the human subject.

43. The method of claim 34, wherein the atovaquone-related compound is atovaquone and the growth-inhibitory amount of the atovaquone is in a range of about 10 to about 40 mg/kg per day.

44. The method of claim 34, wherein the cancer is a hematological tumor selected from the group consisting of acute myeloid leukemia, chronic myeloid leukemia, Hodgkin lymphoma, non-Hodgkin lymphoma, multiple myeloma, acute lymphoblastic leukemia, and chronic lymphocytic leukemia, or the cancer is a solid tumor selected from the group consisting of breast cancer, endometrial cancer, melanoma, lung cancer, ovarian cancer, pancreatic cancer, colorectal cancer, prostate cancer, brain cancer, gastroesophageal cancer, kidney cancer, non-small cell lung, neuroendocrine cancer, and glioblastoma multiforme.

45. A method of treating a STAT3-dependent cancer or a mTOR-dependent cancer in a human subject, the method comprising administering to the human subject a growth-inhibitory amount of a compound selected from the group consisting of trans-2-[4-(4-chlorophenyl)cyclohexyl]-3-hydroxy-1,4-naphthalenedione (atovaquone), cis-2-[4-(4-chlorophenyl)cyclohexyl]-3-hydroxy-1,4-naphthoquinone (isomer of atovaquone), 2((4-tert-butylcyclohexyl)methyl)-3-hydroxy-1,4-naphthoquinone (buparvaquone), 3-cyclohexyl-4-hydroxy-naphthalene-1,2-dione (parvaquone), and 2-(4-(trans-decahydronaphth-2-yl)butyl)-3-hydoxy-1,4-naphthoquinone (TDBHN).

46. The method of claim 45, wherein the human subject is not being treated for pneumocystis pneumonia.

47. The method of claim 45, wherein the compound is atovaquone.

* * * * *

UNITED STATES PATENT AND TRADEMARK OFFICE
CERTIFICATE OF CORRECTION

PATENT NO. : 10,130,590 B2
APPLICATION NO. : 15/025934
DATED : November 20, 2018
INVENTOR(S) : David Frank and Michael Xiang Page 1 of 1

It is certified that error appears in the above-identified patent and that said Letters Patent is hereby corrected as shown below:

In the Claims

In Column 256, Line 56, In Claim 35:
Delete "claim 24," and insert -- claim 34, --, therefor.

In Column 257, Line 1, In Claim 36:
Delete "claim 24," and insert -- claim 34, --, therefor.

Signed and Sealed this
Ninth Day of April, 2019

Andrei Iancu
*Director of the United States Patent and Trademark Office*

SEQUENCE LISTING

<160> NUMBER OF SEQ ID NOS: 58

<210> SEQ ID NO 1
<211> LENGTH: 1752
<212> TYPE: DNA
<213> ORGANISM: Homo sapiens

<400> SEQUENCE: 1
agggcgcagc aggccaaggg ggaggtgcga gcgtggacct gggacgggtc tgggcggctc      60

```
tcggtggttg gcacgggttc gcacacccat tcaagcggca ggacgcactt gtcttagcag      120
ttctcgctga ccgcgctagc tgcggcttct acgctccggc actctgagtt catcagcaaa      180
cgccctggcg tctgtcctca ccatgcctag cctttgggac cgcttctcgt cgtcgtccac      240
ctcctcttcg ccctcgtcct tgccccgaac tcccacccca gatcggccgc cgcgctcagc      300
ctgggggtcg gcgacccggg aggaggggtt tgaccgctcc acgagcctgg agagctcgga      360
ctgcgagtcc ctggacagca gcaacagtgg cttcgggccg gaggaagaca cggcttacct      420
ggatgggtg tcgttgcccg acttcgagct gctcagtgac cctgaggatg aacacttgtg      480
tgccaacctg atgcagctgc tgcaggagag cctggcccag gcgcggctgg gctctcgacg      540
ccctgcgcgc ctgctgatgc ctagccagtt ggtaagccag gtgggcaaag aactactgcg      600
cctggcctac agcgagccgt gcggcctgcg ggggcgctg ctggacgtct gcgtggagca      660
gggcaagagc tgccacagcg tgggccagct ggcactcgac cccagcctgg tgcccacctt      720
ccagctgacc ctcgtgctgc gcctggactc acgactctgg cccaagatcc aggggctgtt      780
tagctccgcc aactctccct tcctccctgg cttcagccag tccctgacgc tgagcactgg      840
cttccgagtc atcaagaaga agctgtacag ctcggaacag ctgctcattg aggagtgttg      900
aacttcaacc tgagggggcc gacagtgccc tccaagacag agacgactga acttttgggg      960
tggagactag aggcaggagc tgagggactg attcctgtgg ttggaaaact gaggcagcca     1020
cctaaggtgg aggtggggga atagtgtttc ccaggaagct cattgagttg tgtgcgggtg     1080
gctgtgcatt ggggacacat accccctcagt actgtagcat gaaacaaagg cttaggggcc     1140
aacaaggctt ccagctggat gtgtgtgtag catgtacctt attattttttg ttactgacag     1200
ttaacagtgg tgtgacatcc agagagcagc tgggctgctc ccgccccagc ccggcccagg     1260
gtgaaggaag aggcacgtgc tcctcagagc agccggaggg agggggggagg tcggaggtcg     1320
tggaggtggt ttgtgtatct tactggtctg aagggaccaa gtgtgtttgt tgtttgtttt     1380
gtatcttgtt tttctgatcg gagcatcact actgacctgt tgtaggcagc tatcttacag     1440
acgcatgaat gtaagagtag aaggggtgg gtgtcaggga tcacttggga tctttgacac     1500
ttgaaaaatt acacctggca gctgcgttta agccttcccc catcgtgtac tgcagagttg     1560
agctggcagg ggaggggctg agagggtggg ggctggaacc cctccccggg aggagtgcca     1620
tctgggtctt ccatctagaa ctgtttacat gaagataaga tactcactgt tcatgaatac     1680
acttgatgtt caagtattaa gacctatgca atatttttta cttttctaat aaacatgttt     1740
gttaaaacag tt                                                         1752
```

<210> SEQ ID NO 2
<211> LENGTH: 232
<212> TYPE: PRT
<213> ORGANISM: Homo sapiens

<400> SEQUENCE: 2

```
Met Pro Ser Leu Trp Asp Arg Phe Ser Ser Ser Thr Ser Ser Ser
 1               5                  10                  15

Pro Ser Ser Leu Pro Arg Thr Pro Thr Pro Asp Arg Pro Pro Arg Ser
            20                  25                  30

Ala Trp Gly Ser Ala Thr Arg Glu Glu Gly Phe Asp Arg Ser Thr Ser
        35                  40                  45

Leu Glu Ser Ser Asp Cys Glu Ser Leu Asp Ser Asn Ser Gly Phe
    50                  55                  60

Gly Pro Glu Glu Asp Thr Ala Tyr Leu Asp Gly Val Ser Leu Pro Asp
```

```
          65                  70                  75                  80
    Phe Glu Leu Leu Ser Asp Pro Glu Asp Glu His Leu Cys Ala Asn Leu
                     85                  90                  95

Met Gln Leu Leu Gln Glu Ser Leu Ala Gln Ala Arg Leu Gly Ser Arg
                    100                 105                 110

Arg Pro Ala Arg Leu Leu Met Pro Ser Gln Leu Val Ser Gln Val Gly
                115                 120                 125

Lys Glu Leu Leu Arg Leu Ala Tyr Ser Glu Pro Cys Gly Leu Arg Gly
    130                 135                 140

Ala Leu Leu Asp Val Cys Val Glu Gln Gly Lys Ser Cys His Ser Val
    145                 150                 155                 160

Gly Gln Leu Ala Leu Asp Pro Ser Leu Val Pro Thr Phe Gln Leu Thr
                    165                 170                 175

Leu Val Leu Arg Leu Asp Ser Arg Leu Trp Pro Lys Ile Gln Gly Leu
                180                 185                 190

Phe Ser Ser Ala Asn Ser Pro Phe Leu Pro Gly Phe Ser Gln Ser Leu
                195                 200                 205

Thr Leu Ser Thr Gly Phe Arg Val Ile Lys Lys Leu Tyr Ser Ser
        210                 215                 220

Glu Gln Leu Leu Ile Glu Glu Cys
    225                 230
```

<210> SEQ ID NO 3
<211> LENGTH: 1081
<212> TYPE: DNA
<213> ORGANISM: Homo sapiens

<400> SEQUENCE: 3

```
gaggtcagag acttaagtct aaggcactga gcgtatcatg ttaaagatga gcgggtggca      60
gcgacagagc caaaatcaga gctggaacct gaggagagag tgttcaagaa ggaagtgtat     120
cttcatacat caccacacct gaaagcagca ccaaagcagc cataaacaat atgtaaataa     180
acagatgtgg ctgtattcca gtacaacttt acctacaaaa acaggcatca gaccagcttg     240
ccaacttgtg gcatagactg tttgctacat ggagcttgtt ccagccactc cccattatcc     300
tgcagatgtg cttttccaga ctgatccaac tgcagagatg cagctgagt cattgccttt      360
ctccttcggg acactgtcca gctgggagct ggaagcctgg tatgaggacc tgcaagaggt     420
cctgtcttca gatgaaaatg ggggtaccta tgtttcacct cctggaaatg aagaggaaga     480
atcaaaaatc ttcaccactc ttgaccctgc ttctctggct tggctgactg aggaggagcc     540
agaaccagca gaggtcacaa gcacctccca gagccctcac tctccagatt ccagtcagag     600
ctccctggct caggaggaag aggaggaaga ccaaggagaa accaggaaac ggaaacagag     660
tggtcattcc ccagcccggg ctggaaagca gcgcatgaag gagaaagaac aggagaatga     720
aggaaagtg gcacagctag ctgaagagaa tgaacggctc aagcaggaaa tcgagcgcct      780
gaccagggaa gtagaggcga ctcgccgagc tctgattgac cgaatggtga atctgccacca    840
agcatgaaca attgggagca tcagtccccc acttgggcca cactacccac ctttcccaga     900
agtggctact gactaccctc tcactagtgc caatgatgtg accctcaatc ccacatacgc     960
aggggggaagg cttggagtag acaaaaggaa aggtctcagc ttgtatatag agattgtaca   1020
tttatttatt actgtcccta tctattaaag tgactttcta tgagccaaaa aaaaaaaaa    1080
a                                                                   1081
```

<210> SEQ ID NO 4
<211> LENGTH: 192
<212> TYPE: PRT
<213> ORGANISM: Homo sapiens

<400> SEQUENCE: 4

Met Glu Leu Val Pro Ala Thr Pro His Tyr Pro Ala Asp Val Leu Phe
1               5                   10                  15

Gln Thr Asp Pro Thr Ala Glu Met Ala Ala Glu Ser Leu Pro Phe Ser
            20                  25                  30

Phe Gly Thr Leu Ser Ser Trp Glu Leu Glu Ala Trp Tyr Glu Asp Leu
        35                  40                  45

Gln Glu Val Leu Ser Ser Asp Glu Asn Gly Gly Thr Tyr Val Ser Pro
    50                  55                  60

Pro Gly Asn Glu Glu Glu Ser Lys Ile Phe Thr Thr Leu Asp Pro
65                  70                  75                  80

Ala Ser Leu Ala Trp Leu Thr Glu Glu Pro Glu Pro Ala Glu Val
                85                  90                  95

Thr Ser Thr Ser Gln Ser Pro His Ser Pro Asp Ser Ser Gln Ser Ser
            100                 105                 110

Leu Ala Gln Glu Glu Glu Glu Asp Gln Gly Arg Thr Arg Lys Arg
        115                 120                 125

Lys Gln Ser Gly His Ser Pro Ala Arg Ala Gly Lys Gln Arg Met Lys
    130                 135                 140

Glu Lys Glu Gln Glu Asn Glu Arg Lys Val Ala Gln Leu Ala Glu Glu
145                 150                 155                 160

Asn Glu Arg Leu Lys Gln Glu Ile Glu Arg Leu Thr Arg Glu Val Glu
                165                 170                 175

Ala Thr Arg Arg Ala Leu Ile Asp Arg Met Val Asn Leu His Gln Ala
            180                 185                 190

<210> SEQ ID NO 5
<211> LENGTH: 1935
<212> TYPE: DNA
<213> ORGANISM: Homo sapiens

<400> SEQUENCE: 5
ggcggaggtg gggttagctt cagttgacca accatgcctt gaggataaat tggatgggat      60
cagatgggaa gatgtgacaa gaagagaaat cctcctctat ataggatgct ctgctgtttc     120
ctaaggattt tcagcacctt gccccaaaat caaaatgatg cttcaacacc caggccaggt     180
ctctgcctcg gaagtgagtg cttctgccat cgtcccctgc ctgtcccctc ctgggtcact     240
ggtgtttgag gattttgcta acctgacgcc ctttgtcaag gaagagctga ggtttgccat     300
ccagaacaag cacctctgcc accggatgtc tctgcgctg gaatcagtca ctgtcagcga     360
cagacccctc ggggtgtcca tcacaaaagc cgaggtagcc cctgaagaag atgaaaggaa     420
aaagaggcga cgagaaagaa ataagattgc agctgcaaag tgccgaaaca agaagaagga     480
gaagacggag tgcctgcaga aagagtcgga gaagctggaa agtgtgaatg ctgaactgaa     540
ggctcagatt gaggagctca agaacgagaa gcagcatttg atatacatgc tcaaccttca     600
tcggcccacg tgtattgtcc gggctcagaa tgggaggact ccagaagatg agagaaacct     660
ctttatccaa cagataaaag aaggaacatt gcagagctaa gcagtcgtgg tatggggcg     720
actggggagt cctcattgaa tcctcatttt atacccaaaa ccctgaagcc attggagagc     780
tgtcttcctg tgtacctcta gaatcccagc agcagagaac catcaaggcg ggagggcctg     840

```
cagtgattca gcaggcccct tccattctgc cccagagtgg gtcttggacc agggcaagtg    900
catctttgcc tcaactccag gatttaggcc ttaacacact ggccattctt atgttccaga    960
tggcccccag ctggtgtcct gcccgccttt catctggatt ctacaaaaaa ccaggatgcc   1020
caccgttagg attcaggcag cagtgtctgt acctcgggtg ggagggatgg ggccatctcc   1080
ttcaccgtgg ctaccattgt cactcgtagg ggatgtggag tgagaacagc atttagtgaa   1140
gttgtgcaac ggccagggtt gtgctttcta gcaaatatgc tgttatgtcc agaaattgtg   1200
tgtgcaagaa aactaggcaa tgtactcttc cgatgtttgt gtcacacaac actgatgtga   1260
cttttatatg cttttttctca gatctggttt ctaagagttt tggggggcgg ggctgtcacc   1320
acgtgcagta tctcaagata ttcaggtggc cagaagagct tgtcagcaag aggaggacag   1380
aattctccca gcgttaacac aaaatccatg gcagtatga tggcaggtcc tctgttgcaa   1440
actcagttcc aaagtcacag gaagaaagca gaaagttcaa cttccaaagg gttaggactc   1500
tccactcaat gtcttaggtc aggagttgtg tctaggctgg aagagccaaa gaatattcca   1560
ttttcctttc cttgtggttg aaaaccacag tcagtggaga gatgtttgga aaccacagtc   1620
agtggagcct gggtggtacc caggctttag cattattgga tgtcaatagc attgttttg    1680 tcatgtagct gttttaagaa atctggccca gggtgtttgc agctgtgaga agtcactcac   1740
actggccaca aggacgctgg ctactgtcta ttaaaattct gatgtttctg tgaaattctc    1800
agagtgttta attgtactca atggtatcat tacaatttc tgtaagagaa aatattactt    1860
atttatccta gtattcctaa cctgtcagaa taataaatat tggaaccaag acatggtaaa    1920
caaaaaaaaa aaaaa                                                    1935
```

<210> SEQ ID NO 6
<211> LENGTH: 181
<212> TYPE: PRT
<213> ORGANISM: Homo sapiens

<400> SEQUENCE: 6

```
Met Met Leu Gln His Pro Gly Gln Val Ser Ala Ser Glu Val Ser Ala
 1               5                  10                  15

Ser Ala Ile Val Pro Cys Leu Ser Pro Gly Ser Leu Val Phe Glu
                20                  25                  30

Asp Phe Ala Asn Leu Thr Pro Phe Val Lys Glu Glu Leu Arg Phe Ala
             35                  40                  45

Ile Gln Asn Lys His Leu Cys His Arg Met Ser Ser Ala Leu Glu Ser
         50                  55                  60

Val Thr Val Ser Asp Arg Pro Leu Gly Val Ser Ile Thr Lys Ala Glu
 65                  70                  75                  80

Val Ala Pro Glu Glu Asp Glu Arg Lys Lys Arg Arg Glu Arg Asn
                 85                  90                  95

Lys Ile Ala Ala Ala Lys Cys Arg Asn Lys Lys Glu Lys Thr Glu
            100                 105                 110

Cys Leu Gln Lys Glu Ser Glu Lys Leu Glu Ser Val Asn Ala Glu Leu
            115                 120                 125

Lys Ala Gln Ile Glu Glu Leu Lys Asn Glu Lys Gln His Leu Ile Tyr
        130                 135                 140

Met Leu Asn Leu His Arg Pro Thr Cys Ile Val Arg Ala Gln Asn Gly
145                 150                 155                 160

Arg Thr Pro Glu Asp Glu Arg Asn Leu Phe Ile Gln Gln Ile Lys Glu
                165                 170                 175
```

Gly Thr Leu Gln Ser
          180

<210> SEQ ID NO 7
<211> LENGTH: 1523
<212> TYPE: DNA
<213> ORGANISM: Homo sapiens

<400> SEQUENCE: 7

| | | | | | |
|---|---|---|---|---|---|
| ccgagcggtg | ccaggccagg | tgtgtgcgtc | cgtcggtctt | ccgtgccca | cgccggagac | 60 |
| cagccccgga | ggccgcctgg | gcctatccct | gtgccaggca | ccatgaagca | ggagtctgca | 120 |
| gccccgaaca | ccccgcccac | ctcgcagtcc | cctacgccgt | ccgctcagtt | ccccccgaaac | 180 |
| gacggcgacc | ctcaagcgct | gtggattttc | gggtacggct | ccctggtgtg | gaggcccgac | 240 |
| ttcgcctaca | gcgacagccg | tgtgggcttc | gtgcgcggct | acagccgccg | tttctggcag | 300 |
| ggagacacct | tccatcgggg | cagcgacaag | atgcctggcc | gtgtggtgac | gctccttgaa | 360 |
| gatcatgagg | gctgcacttg | gggcgtggca | taccaagtgc | aaggggagca | ggtaagcaag | 420 |
| gccctgaagt | acctgaatgt | gcgagaggca | gtgcttggtg | gctacgatac | caaggaggtc | 480 |
| accttctatc | cccaagatgc | tcctgaccaa | ccactgaagg | cattggccta | tgtggccacc | 540 |
| ccacagaacc | ctggttacct | gggccctgcg | cctgaagagg | ccattgccac | gcagatcctg | 600 |
| gcctgccggg | gcttctccgg | ccacaaccct | gaatacttgc | tgcgtctggc | agacttcatg | 660 |
| cagctctgtg | ggcctcaggc | gcaggacgag | cacctggcag | ccatcgtgga | cgctgtgggc | 720 |
| accatgttgc | cctgcttctg | ccccaccgag | caggctctgg | cgctggtgtg | aggggctgag | 780 |
| cccctgcggg | gagtgctcat | gtggacatca | gggccagaca | cccactccag | tgcacaagac | 840 |
| agacttgcga | ccgcttgagc | ccactgagca | gatatggtgg | gtggctggag | gcttctcttt | 900 |
| ctcagtccct | gcctgtctgc | cagcctgcag | ctctcctgct | tgacactgac | ttactacttg | 960 |
| aaactttatt | tattgcacca | tgttggtgtg | gtgggcaggt | ggagggcctg | ccctggacac | 1020 |
| aggggccctg | ctgagcagtg | gccccatcct | ggaacttgac | cagattcccc | ccagtgctgc | 1080 |
| tgctaacccc | acaccaccca | ggcctccacc | tccccaggga | gtctccaaga | gcctcgatcc | 1140 |
| tctgctcact | cagcccagcc | atccatagcc | ctgggaattc | cacctgccaa | ggatcccagc | 1200 |
| aggctggatg | agggatagta | gggcatgagg | agaaggagcc | ctgtaaggac | tgaggccccg | 1260 |
| gccagcccctt | ctcctccacc | agttcccag | agcagagctg | gagctgatgc | ctggacacag | 1320 |
| ctgctgagcc | tggcctgggc | ctcttaccca | cttggttgtt | ttcttgtccc | tctgtctgtc | 1380 |
| tgtctatcta | cttgtctgtc | tgggccactc | ctgcctgtgt | gttggtctat | tcctgggaag | 1440 |
| ctcatcacta | caggccctgg | caaccttccc | agtctgtccc | atactgttac | ccataaaact | 1500 |
| atctctttaa | aaaaaaaaaa | aaa | | | | 1523 |

<210> SEQ ID NO 8
<211> LENGTH: 222
<212> TYPE: PRT
<213> ORGANISM: Homo sapiens

<400> SEQUENCE: 8

Met Lys Gln Glu Ser Ala Ala Pro Asn Thr Pro Thr Ser Gln Ser
1               5                   10                  15

Pro Thr Pro Ser Ala Gln Phe Pro Arg Asn Asp Gly Asp Pro Gln Ala
            20                  25                  30

Leu Trp Ile Phe Gly Tyr Gly Ser Leu Val Trp Arg Pro Asp Phe Ala
        35                  40                  45

```
Tyr Ser Asp Ser Arg Val Gly Phe Val Arg Gly Tyr Ser Arg Arg Phe
 50                  55                  60

Trp Gln Gly Asp Thr Phe His Arg Gly Ser Asp Lys Met Pro Gly Arg
 65                  70                  75                  80

Val Val Thr Leu Leu Glu Asp His Glu Gly Cys Thr Trp Gly Val Ala
                 85                  90                  95

Tyr Gln Val Gln Gly Glu Gln Val Ser Lys Ala Leu Lys Tyr Leu Asn
                100                 105                 110

Val Arg Glu Ala Val Leu Gly Gly Tyr Asp Thr Lys Glu Val Thr Phe
            115                 120                 125

Tyr Pro Gln Asp Ala Pro Asp Gln Pro Leu Lys Ala Leu Ala Tyr Val
        130                 135                 140

Ala Thr Pro Gln Asn Pro Gly Tyr Leu Gly Pro Ala Pro Glu Glu Ala
145                 150                 155                 160

Ile Ala Thr Gln Ile Leu Ala Cys Arg Gly Phe Ser Gly His Asn Leu
                165                 170                 175

Glu Tyr Leu Leu Arg Leu Ala Asp Phe Met Gln Leu Cys Gly Pro Gln
                180                 185                 190

Ala Gln Asp Glu His Leu Ala Ala Ile Val Asp Ala Val Gly Thr Met
            195                 200                 205

Leu Pro Cys Phe Cys Pro Thr Glu Gln Ala Leu Ala Leu Val
210                 215                 220
```

<210> SEQ ID NO 9
<211> LENGTH: 2022
<212> TYPE: DNA
<213> ORGANISM: Homo sapiens

<400> SEQUENCE: 9

```
tttctacttt gcccgcccac agatgtagtt ttctctgcgc gtgtgcgttt tccctcctcc      60
ccgccctcag gtccacggc caccatggcg tattagggc agcagtgcct gcggcagcat       120
tggcctttgc agcggcggca gcagcaccag gctctgcagc ggcaaccccc agcggcttaa     180
gccatggcgt gagtaccggg gcgggtcgtc cagctgtgct cctggggccg gcgcgggttt     240
tggattggtg gggtgcggcc tggggccagg gcggtgccgc caaggggaa gcgatttaac      300
gagcgcccgg gacgcgtggt cttttgcttgg gtgtccccga gacgctcgcg tgcctgggat    360
cgggaaagcg tagtcgggtg cccggactgc ttccccagga gccctacagc cctcggaccc    420
cgagccccgc aagggtccca gggtcttgg ctgttgcccc acgaaacgtg gcaggaacca     480
agatggcggc ggcagggcgg cggcgcgggc gtgagtcaag ggcgggcggt gggcggggcg    540
cggccgccct ggccgtattt ggacgtgggg acggagcgct ttcctcttgg cggccggtgg   600
aagaatcccc tggtctccgt gagcgtccat tttgtggaac ctgagttgca agcagggagg   660
ggcaaataca actgccctgt tcccgattct ctagatggcc gatctagaga agtcccgcct     720
cataagtgga aggatgaaat tctcagaaca gctaacctct aatgggagtt ggcttctgat    780
tctcattcag gcttctcacg gcattcagca gcagcgttgc tgtaaccgac aaagacacct   840
tcgaattaag cacattcctc gattccagca aagcaccgca acatgaccga atgagcttc    900
ctgagcagcg aggtgttggt gggggacttg atgtccccct tcgaccagtc gggtttgggg   960
gctgaagaaa gcctaggtct cttagatgat tacctggagg tggccaagca cttcaaacct 1020
catgggttct ccagcgacaa ggctaaggcg ggctcctccg aatggctggc tgtgatggg    1080
ttggtcagtc cctccaacaa cagcaaggag gatgccttct ccgggacaga ttggatgttg   1140
```

```
gagaaaatgg atttgaagga gttcgacttg gatgccctgt tgggtataga tgacctggaa    1200
accatgccag atgaccttct gaccacgttg gatgacactt gtgatctctt tgcccccta     1260 gtccaggaga ctaataagca gccccccag acggtgaacc caattggcca tctcccagaa     1320
agtttaacaa aacccgacca ggttgccccc ttcaccttct tacaacctct tccccttttcc   1380 ccagggtcc tgtcctccac tccagatcat tcctttagtt tagagctggg cagtgaagtg    1440
gatatcactg aaggagatag gaagccagac tacactgctt acgttgccat gatccctcag    1500
tgcataaagg aggaagacac cccttcagat aatgatagtg gcatctgtat gagcccagag    1560
tcctatctgg ggtctcctca gcacagcccc tctaccaggg gctctccaaa taggagcctc    1620
ccatctccag gtgttctctg tgggtctgcc cgtcccaaac cttacgatcc tcctggagag    1680
aagatggtag cagcaaaagt aaagggtgag aaactggata agaagctgaa aaaaatggag    1740
caaaacaaga cagcagccac taggtaccgc cagaagaaga gggcggagca ggaggctctt    1800
actggtgagt gcaaagagct ggaaaagaag aacgaggctc taaaagagag ggcggattcc    1860
ctggccaagg agatccagta cctgaaagat ttgatagaag aggtccgcaa ggcaagggg    1920 aagaaagg tccctagtt gaggatagtc aggagcgtca atgtgcttgt acatagagtg     1980
ctgtagctgt gtgttccaat aaattatttt gtagggaaag ta                       2022
```

<210> SEQ ID NO 10
<211> LENGTH: 351
<212> TYPE: PRT
<213> ORGANISM: Homo sapiens

<400> SEQUENCE: 10

```
Met Thr Glu Met Ser Phe Leu Ser Ser Glu Val Leu Val Gly Asp Leu
  1               5                  10                  15

Met Ser Pro Phe Asp Gln Ser Gly Leu Gly Ala Glu Glu Ser Leu Gly
             20                  25                  30

Leu Leu Asp Asp Tyr Leu Glu Val Ala Lys His Phe Lys Pro His Gly
         35                  40                  45

Phe Ser Ser Asp Lys Ala Lys Ala Gly Ser Ser Glu Trp Leu Ala Val
     50                  55                  60

Asp Gly Leu Val Ser Pro Ser Asn Asn Ser Lys Glu Asp Ala Phe Ser
 65                  70                  75                  80

Gly Thr Asp Trp Met Leu Glu Lys Met Asp Leu Lys Glu Phe Asp Leu
                 85                  90                  95

Asp Ala Leu Leu Gly Ile Asp Asp Leu Glu Thr Met Pro Asp Asp Leu
            100                 105                 110

Leu Thr Thr Leu Asp Asp Thr Cys Asp Leu Phe Ala Pro Leu Val Gln
        115                 120                 125

Glu Thr Asn Lys Gln Pro Pro Gln Thr Val Asn Pro Ile Gly His Leu
    130                 135                 140

Pro Glu Ser Leu Thr Lys Pro Asp Gln Val Ala Pro Phe Thr Phe Leu
145                 150                 155                 160

Gln Pro Leu Pro Leu Ser Pro Gly Val Leu Ser Ser Thr Pro Asp His
                165                 170                 175

Ser Phe Ser Leu Glu Leu Gly Ser Glu Val Asp Ile Thr Glu Gly Asp
            180                 185                 190

Arg Lys Pro Asp Tyr Thr Ala Tyr Val Ala Met Ile Pro Gln Cys Ile
        195                 200                 205

Lys Glu Glu Asp Thr Pro Ser Asp Asn Asp Ser Gly Ile Cys Met Ser
```

|     |     |     |     |     |     |     |     |     |     |
| --- | --- | --- | --- | --- | --- | --- | --- | --- | --- |
|     |     | 210 |     |     | 215 |     |     | 220 |     |
| Pro | Glu | Ser | Tyr | Leu | Gly | Ser | Pro | Gln | His |
| 225 |     |     |     | 230 |     |     |     | 235 |     |
| Ser | Pro | Thr | Arg | Gly |     |     |     |     |     |
|     |     |     |     | 240 |     |     |     |     |     |
| Ser | Pro | Asn | Arg | Ser | Leu | Pro | Ser | Pro | Gly |
|     |     |     | 245 |     |     |     |     | 250 |     |
| Val | Leu | Cys | Gly | Ser | Ala |     |     |     |     |
|     |     |     |     | 255 |     |     |     |     |     |
| Arg | Pro | Lys | Pro | Tyr | Asp | Pro | Pro | Gly | Glu |
|     |     |     | 260 |     |     |     |     | 265 |     |
| Lys | Met | Val | Ala | Ala | Lys |     |     |     |     |
|     |     |     |     | 270 |     |     |     |     |     |
| Val | Lys | Gly | Glu | Lys | Leu | Asp | Lys | Lys | Leu |
|     |     |     | 275 |     |     |     |     | 280 |     |
| Lys | Met | Glu | Gln | Asn |     |     |     |     |     |
|     |     |     |     | 285 |     |     |     |     |     |
| Lys | Thr | Ala | Ala | Thr | Arg | Tyr | Arg | Gln | Lys |
|     |     |     | 290 |     |     |     |     | 295 |     |
| Lys | Arg | Ala | Glu | Gln | Glu |     |     |     |     |
|     |     |     |     | 300 |     |     |     |     |     |
| Ala | Leu | Thr | Gly | Glu | Cys | Lys | Glu | Leu | Glu |
| 305 |     |     |     | 310 |     |     |     | 315 |     |
| Lys | Lys | Asn | Glu | Ala | Leu |     |     |     |     |
|     |     |     |     | 320 |     |     |     |     |     |
| Lys | Glu | Arg | Ala | Asp | Ser | Leu | Ala | Lys | Glu |
|     |     |     | 325 |     |     |     |     | 330 |     |
| Ile | Gln | Tyr | Leu | Lys | Asp |     |     |     |     |
|     |     |     |     | 335 |     |     |     |     |     |
| Leu | Ile | Glu | Glu | Val | Arg | Lys | Ala | Arg | Gly |
|     |     |     | 340 |     |     |     |     | 345 |     |
| Lys | Lys | Arg | Val | Pro |     |     |     |     |     |
|     |     |     |     | 350 |     |     |     |     |     |

<210> SEQ ID NO 11
<211> LENGTH: 8733
<212> TYPE: DNA
<213> ORGANISM: Homo sapiens

<400> SEQUENCE: 11

```
gctcccggct tagaggacag cggggaaggc gggcggtggg gcaggggggcc tgaagcggcg        60
gtaccggtgc tggcggcggc agctgaggcc ttggccgaag ccgcgcgaac ctcagggcaa       120
gatgcttgga accggacctg ccgccgccac caccgctgcc accacatcta gcaatgtgag       180
cgtcctgcag cagtttgcca gtggcctaaa gagccggaat gaggaaacca gggccaaagc       240
cgccaaggag ctccagcact atgtcaccat ggaactccga gagatgagtc aagaggagtc       300
tactcgcttc tatgaccaac tgaaccatca cattttttgaa ttggtttcca gctcagatgc       360
caatgagagg aaaggtggca tcttggccat agctagcctc ataggagtgg aaggtgggaa       420
tgccaccccga attggcagat tgccaactac tcttcggaac ctcctcccct ccaatgaccc       480
agttgtcatg gaaatggcat ccaaggccat ggccgtcctt gccatggcag ggacacttt       540
taccgctgag tacgtggaat tgaggtgaa gcgagccctg gaatggctgg gtgctgaccg       600
caatgagggc cggagacatg cagctgtcct ggttctccgt gagctggcca tcagcgtccc       660
taccttcttc ttccagcaag tgcaacccct ctttgacaac attttttgtgg ccgtgtggga       720
ccccaaacag gccatccgtg agggagctgt agccgcccct cgtgcctgtc tgattctcac       780
aacccagcgt gagccgaagg agatgcagaa gcctcagtgg tacaggcaca catttgaaga       840
agcagagaag ggatttgatg agaccttggc caaagagaag gcatgaatc gggatgatcg       900
gatccatgga gccttgttga tccttaacga gctggtccga atcagcagca tggagggaga       960
gcgtctgaga gaagaaatgg aagaaatcac acagcagcag ctggtacacg acaagtactg      1020
caaagatctc atgggcttcg gaacaaaacc tcgtcacatt ccccccttca ccagtttcca      1080
ggctgtacag cccccagcagt caaatgcctt ggtggggctg ctggggtaca gctctcacca      1140
aggcctcatg ggatttggga cctccccccag tccagctaag tccaccctgg tggagagccg      1200
gtgttgcaga gacttgatgg aggagaaatt tgatcaggtg tgccagtggg tgctgaaatg      1260
caggaatagc aagaactcgc tgatcccaaat gacaatcctt aatttgttgc ccgcttggc      1320
tgcattccga ccttctgcct tcacagatac ccagtatctc caagatacca tgaaccatgt      1380
```

```
cctaagctgt gtcaagaagg agaaggaacg tacagcggcc ttccaagccc tggggctact   1440
ttctgtggct gtgaggtctg agtttaaggt ctatttgcct cgcgtgctgg acatcatccg   1500
agcggccctg cccccaaagg acttcgccca taagaggcag aaggcaatgc aggtggatgc   1560
cacagtcttc acttgcatca gcatgctggc tcgagcaatg gggccaggca tccagcagga   1620
tatcaaggag ctgctggagc ccatgctggc agtgggacta agccctgccc tcactgcagt   1680
gctctacgac ctgagccgtc agattccaca gctaaagaag gacattcaag atgggctact   1740
gaaaatgctg tccctggtcc ttatgcacaa accccttcgc cacccaggca tgcccaaggg   1800
cctgccccat cagctggcct ctcctggcct cacgaccctc cctgaggcca gcgatgtggg   1860
cagcatcact cttgccctcc gaacgcttgg cagctttgaa tttgaaggcc actctctgac   1920
ccaatttgtt cgccactgtg cggatcattt cctgaacagt gagcacaagg agatccgcat   1980
ggaggctgcc cgcacctgct cccgcctgct cacaccctcc atccacctca tcagtggcca   2040
tgctcatgtg gttagccaga ccgcagtgca agtggtggca gatgtgctta gcaaactgct   2100
cgtagttggg ataacagatc ctgaccctga cattcgctac tgtgtcttgg cgtccctgga   2160
cgagcgcttt gatgcacacc tggcccaggc ggagaacttg caggccttgt tgtggctct    2220 gaatgaccag gtgtttgaga tccgggagct ggccatctgc actgtgggcc gactcagtag   2280
catgaaccct gcctttgtca tgcctttcct gcgcaagatg ctcatccaga ttttgacaga   2340
gttggagcac agtgggattg gaagaatcaa agagcagagt gcccgcatgc tggggcacct   2400
ggtctccaat gccccccgac tcatccgccc ctacatggag cctattctga aggcattaat   2460
tttgaaactg aaagatccag accctgatcc aaacccaggt gtgatcaata atgtcctggc   2520
aacaatagga gaattggcac aggttagtgg cctggaaatg aggaaatggg ttgatgaact   2580
ttttattatc atcatggaca tgctccagga ttcctctttg ttggccaaaa ggcaggtggc   2640
tctgtggacc ctgggacagt tggtggccag cactggctat gtagtagagc cctacaggaa   2700
gtaccctact ttgcttgagg tgctactgaa ttttctgaag actgagcaga accagggtac   2760
acgcagagag gccatccgtg tgttagggct tttaggggct ttggatcctt acaagcacaa   2820
agtgaacatt ggcatgatag accagtcccg ggatgcctct gctgtcagcc tgtcagaatc   2880
caagtcaagt caggattcct ctgactatag cactagtgaa atgctggtca acatgggaaa   2940
cttgcctctg gatgagttct acccagctgt gtccatggtg gccctgatgc ggatcttccg   3000
agaccagtca ctctctcatc atcacaccat ggttgtccag gccatcacct tcatcttcaa   3060
gtccctggga ctcaaatgtg tgcagttcct gccccaggtc atgcccacgt tccttaacgt   3120
cattcgagtc tgtgatgggg ccatccggga atttttgttc cagcagctgg gaatgttggt   3180
gtcctttgtg aagagccaca tcagaccctta tatggatgaa atagtcaccc tcatgagaga   3240
attctgggtc atgaacacct caattcagag cacgatcatt cttctcattg agcaaattgt   3300
ggtagctctt gggggtgaat ttaagctcta cctgccccag ctgatcccac acatgctgcg   3360
tgtcttcatg catgacaaca gcccaggccg cattgtctct atcaagttac tggctgcaat   3420
ccagctgttt ggcgccaacc tggatgacta cctgcattta ctgctgcctc ctattgttaa   3480
gttgtttgat gcccctgaag ctccactgcc atctcgaaag gcagcgctag agactgtgga   3540
ccgcctgacg gagtccctgg atttcactga ctatgcctcc cggatcattc accctattgt   3600
tcgaacactg accagagcc cagaactgcg ctccacagcc atggacacgc tgtcttcact   3660 tgttttttcag ctggggaaga agtaccaaat tttcattcca atggtgaata aagttctggt   3720
```

```
gcgacaccga atcaatcatc agcgctatga tgtgctcatc tgcagaattg tcaagggata    3780
cacacttgct gatgaagagg aggatccttt gatttaccag catcggatgc ttaggagtgg    3840
ccaaggggat gcattggcta gtggaccagt ggaaacagga cccatgaaga aactgcacgt    3900
cagcaccatc aacctccaaa aggcctgggg cgctgccagg agggtctcca agatgactg     3960 gctggaatgg ctgagacggc tgagcctgga gctgctgaag gactcatcat cgccctccct    4020
gcgctcctgc tgggccctgg cacaggccta aacccgatg gccagggatc tcttcaatgc     4080
tgcatttgtg tcctgctggt ctgaactgaa tgaagatcaa caggatgagc tcatcagaag    4140
catcgagttg gccctcacct cacaagacat cgctgaagtc acacagaccc tcttaaactt    4200
ggctgaattc atggaacaca gtgacaaggg ccccctgcca ctgagagatg acaatggcat    4260
tgttctgctg ggtgagagag ctgccaagtc cgagcatat gccaaagcac tacactacaa      4320
agaactggag ttccagaaag gccccacccc tgccattcta gaatctctca tcagcattaa    4380
taataagcta cagcagccgg aggcagcggc cggagtgtta aatatgcca tgaaacactt      4440 tggagagctg gagatccagg ctacctggta tgagaaactg cacgagtggg aggatgccct    4500
tgtggcctat gacaagaaaa tggacaccaa caaggacgac ccagagctga tgctgggccg    4560
catgcgctgc ctcgaggcct tgggggaatg gggtcaactc caccagcagt gctgtgaaaa    4620
gtggaccctg gttaatgatg agacccaagc caagatggcc cggatggctg ctgcagctgc    4680
atggggttta ggtcagtggg acagcatgga agaatacacc tgtatgatcc ctcgggacac    4740
ccatgatggg gcattttata gagctgtgct ggcactgcat caggacctct tctccttggc    4800
acaacagtgc attgacaagg ccagggacct gctggatgct gaattaactg cgatggcagg    4860
agagagttac agtcgggcat atggggccat ggtttcttgc cacatgctgt ccgagctgga    4920
ggaggttatc cagtacaaac ttgtccccga gcgacgagag atcatccgcc agatctggtg    4980
ggagagactg cagggctgcc agcgtatcgt agaggactgg cagaaaatcc ttatggtgcg    5040
gtcccttgtg gtcagccctc atgaagacat gagaacctgg ctcaagtatg caagcctgtg    5100
cggcaagagt ggcaggctgg ctcttgctca taaaaacttta gtgttgctcc tgggagttga   5160
tccgtctcgg caacttgacc atcctctgcc aacagttcac cctcaggtga cctatgccta    5220
catgaaaaac atgtggaaga gtgcccgcaa gatcgatgcc ttccagcaca tgcagcattt    5280
tgtccagacc atgcagcaac aggcccagca tgccatcgct actgaggacc agcagcataa    5340
gcaggaactg cacaagctca tggcccgatg cttcctgaaa cttggagagt ggcagctgaa    5400
tctacagggc atcaatgaga gcacaatccc caaagtgctg cagtactaca gcgccgccac    5460
agagcacgac cgcagctggt acaaggcctg gcatgcgtgg gcagtgatga acttcgaagc    5520
tgtgctacac tacaaacatc agaaccaagc ccgcgatgag aagaagaaac tgcgtcatgc    5580
cagcggggcc aacatcacca cgccaccac tgccgccacc acggccgcca ctgccaccac     5640
cactgccagc accgagggca gcaacagtga gagcgaggcc gagagcaccg agaacagccc    5700
caccccatcg ccgctgcaga agaaggtcac tgaggatctg tccaaaaccc tcctgatgta    5760
cacggtgcct gccgtccagg gcttcttccg ttccatctcc ttgtcacgag caacaacct     5820 ccaggataca ctcagagttc tcaccttatg gtttgattat ggtcactggc cagatgtcaa    5880
tgaggcctta gtgaggggg tgaaagccat ccagattgat acctggctac aggttatacc     5940
tcagctcatt gcaagaattg atacgcccag acccttggtg ggacgtctca ttcaccagct    6000
tctcacagac attggtcggt accaccccca ggccctcatc tacccactga cagtggcttc    6060
taagtctacc acgacagccc ggcacaatgc agccaacaag attctgaaga acatgtgtga    6120
```

```
gcacagcaac accctggtcc agcaggccat gatggtgagc gaggagctga tccgagtggc   6180
catcctctgg catgagatgt ggcatgaagg cctggaagag gcatctcgtt tgtactttgg   6240
ggaaaggaac gtgaaaggca tgtttgaggt gctggagccc ttgcatgcta tgatggaacg   6300
gggcccccag actctgaagg aaacatcctt taatcaggcc tatggtcgag atttaatgga   6360
ggcccaagag tggtgcagga agtacatgaa atcagggaat gtcaaggacc tcacccaagc   6420
ctgggacctc tattatcatg tgttccgacg aatctcaaag cagctgcctc agctcacatc   6480
cttagagctg caatatgttt ccccaaaact tctgatgtgc cgggaccttg aattggctgt   6540
gccaggaaca tatgaccccca accagccaat cattcgcatt cagtccatag caccgtcttt   6600
gcaagtcatc acatccaagc agaggccccg gaaattgaca cttatgggca gcaacggaca   6660
tgagtttgtt ttccttctaa aaggccatga agatctgcgc caggatgagc gtgtgatgca   6720
gctcttcggc ctggttaaca cccttctggc caatgaccca acatctcttc ggaaaaacct   6780
cagcatccag agatacgctg tcatcccttt atcgaccaac tcgggcctca ttggctgggt   6840
tccccactgt gacacactgc acgccctcat ccgggactac agggagaaga agaagatcct   6900
tctcaacatc gagcatcgca tcatgttgcg gatggctccg gactatgacc acttgactct   6960
gatgcagaag gtggaggtgt tgagcatgc cgtcaataat acagctgggg acgacctggc   7020
caagctgctg tggctgaaaa gccccagctc cgaggtgtgg tttgaccgaa gaaccaatta   7080
tacccgttct ttagcggtca tgtcaatggt tgggtatatt ttaggcctgg gagatagaca   7140
cccatccaac ctgatgctgg accgtctgag tgggaagatc ctgcacattg actttgggga   7200
ctgctttgag gttgctatga cccgagagaa gtttccagag aagattccat ttagactaac   7260
aagaatgttg accaatgcta tggaggttac aggcctggat ggcaactaca gaatcacatg   7320
ccacacagtg atggaggtgc tgcgagagca caaggacagt gtcatggccg tgctggaagc   7380 cttttgtctat gacccccttgc tgaactggag gctgatggac acaaataccca aaggcaacaa   7440 gcgatcccga acgaggacgg attcctactc tgctggccag tcagtcgaaa ttttggacgg   7500
tgtggaactt ggagagccag cccataagaa aacggggacc acagtgccag aatctattca   7560
ttctttcatt ggagacggtt tggtgaaacc agaggcccta aataagaaag ctatccagat   7620
tattaacagg gttcgagata agctcactgg tcgggacttc tctcatgatg acactttgga   7680
tgttccaacg caagttgagc tgctcatcaa acaagcgaca tcccatgaaa acctctgcca   7740
gtgctatatt ggctggtgcc ctttctggta actggaggcc cagatgtgcc catcacgttt   7800
tttctgaggc ttttgtactt tagtaaatgc ttccactaaa ctgaaaccat ggtgagaaag   7860
tttgactttg ttaaatattt tgaaatgtaa atgaaaagaa ctactgtata ttaaaagttg   7920
gtttgaacca actttctagc tgctgttgaa gaatatattg tcagaaacac aaggcttgat   7980
ttggttccca ggacagtgaa acatagtaat accacgtaaa tcaagccatt cattttgggg   8040
aacagaagat ccataacttt agaaatacgg gttttgactt aactcacaag gaactcatc   8100 ataagtactt gctgatggaa gaatgaccta gttgctcctc tcaacatggg tacagcaaac   8160
tcagcacagc caagaagcct caggtcgtgg agaacatgga ttaggatcct agactgtaaa   8220
gacacagaag atgctgacct caccctgcc acctatccca agacctcact ggtctgtgga   8280
cagcagcaga aatgtttgca agataggcca aaatgagtac aaaaggtctg tcttccatca   8340
gacccagtga tgctgcgact cacacgcttc aattcaagac ctgaccgcta gtagggaggt   8400
ttattcagat cgctggcagc ctcggctgag cagatgcaca gaggggatca ctgtgcagtg   8460
```

-continued

```
ggaccaccct cactggcctt ctgcagcagg gttctgggat gttttcagtg gtcaaaatac    8520
tctgtttaga gcaagggctc agaaaacaga aatactgtca tggaggtgct gaacacaggg    8580
aaggtctggt acatattgga aattatgagc agaacaaata ctcaactaaa tgcacaaagt    8640
ataaagtgta gccatgtcta gacaccatgt tgtatcagaa taattttgt gccaataaat     8700 gacatcagaa ttttaaacat atgtaaaaaa aaa                                 8733
```

<210> SEQ ID NO 12
<211> LENGTH: 2549
<212> TYPE: PRT
<213> ORGANISM: Homo sapiens

<400> SEQUENCE: 12

```
Met Leu Gly Thr Gly Pro Ala Ala Thr Ala Ala Thr Thr Ser
 1               5                  10                  15

Ser Asn Val Ser Val Leu Gln Gln Phe Ala Ser Gly Leu Lys Ser Arg
             20                  25                  30

Asn Glu Glu Thr Arg Ala Lys Ala Ala Lys Glu Leu Gln His Tyr Val
         35                  40                  45

Thr Met Glu Leu Arg Glu Met Ser Gln Glu Glu Ser Thr Arg Phe Tyr
     50                  55                  60

Asp Gln Leu Asn His His Ile Phe Glu Leu Val Ser Ser Ser Asp Ala
 65                  70                  75                  80

Asn Glu Arg Lys Gly Gly Ile Leu Ala Ile Ala Ser Leu Ile Gly Val
                 85                  90                  95

Glu Gly Gly Asn Ala Thr Arg Ile Gly Arg Phe Ala Asn Tyr Leu Arg
            100                 105                 110

Asn Leu Leu Pro Ser Asn Asp Pro Val Val Met Glu Met Ala Ser Lys
        115                 120                 125

Ala Ile Gly Arg Leu Ala Met Ala Gly Asp Thr Phe Thr Ala Glu Tyr
    130                 135                 140

Val Glu Phe Glu Val Lys Arg Ala Leu Glu Trp Leu Gly Ala Asp Arg
145                 150                 155                 160

Asn Glu Gly Arg Arg His Ala Ala Val Leu Val Leu Arg Glu Leu Ala
                165                 170                 175

Ile Ser Val Pro Thr Phe Phe Phe Gln Gln Val Gln Pro Phe Phe Asp
            180                 185                 190

Asn Ile Phe Val Ala Val Trp Asp Pro Lys Gln Ala Ile Arg Glu Gly
        195                 200                 205

Ala Val Ala Ala Leu Arg Ala Cys Leu Ile Leu Thr Thr Gln Arg Glu
    210                 215                 220

Pro Lys Glu Met Gln Lys Pro Gln Trp Tyr Arg His Thr Phe Glu Glu
225                 230                 235                 240

Ala Glu Lys Gly Phe Asp Glu Thr Leu Ala Lys Glu Lys Gly Met Asn
                245                 250                 255

Arg Asp Asp Arg Ile His Gly Ala Leu Leu Ile Leu Asn Glu Leu Val
            260                 265                 270

Arg Ile Ser Ser Met Glu Gly Glu Arg Leu Arg Glu Glu Met Glu Glu
        275                 280                 285

Ile Thr Gln Gln Gln Leu Val His Asp Lys Tyr Cys Lys Asp Leu Met
    290                 295                 300

Gly Phe Gly Thr Lys Pro Arg His Ile Thr Pro Phe Thr Ser Phe Gln
305                 310                 315                 320

Ala Val Gln Pro Gln Gln Ser Asn Ala Leu Val Gly Leu Leu Gly Tyr
```

|   |   | 325 |   |   |   |   | 330 |   |   |   |   | 335 |   |
|---|---|---|---|---|---|---|---|---|---|---|---|---|---|
| Ser | Ser | His | Gln | Gly | Leu | Met | Gly | Phe | Gly | Thr | Ser | Pro | Ser | Pro | Ala |
|   |   |   | 340 |   |   |   |   | 345 |   |   |   |   | 350 |
| Lys | Ser | Thr | Leu | Val | Glu | Ser | Arg | Cys | Cys | Arg | Asp | Leu | Met | Glu | Glu |
|   |   | 355 |   |   |   |   | 360 |   |   |   |   | 365 |
| Lys | Phe | Asp | Gln | Val | Cys | Gln | Trp | Val | Leu | Lys | Cys | Arg | Asn | Ser | Lys |
|   | 370 |   |   |   |   | 375 |   |   |   |   | 380 |
| Asn | Ser | Leu | Ile | Gln | Met | Thr | Ile | Leu | Asn | Leu | Leu | Pro | Arg | Leu | Ala |
| 385 |   |   |   |   | 390 |   |   |   |   | 395 |   |   |   |   | 400 |
| Ala | Phe | Arg | Pro | Ser | Ala | Phe | Thr | Asp | Thr | Gln | Tyr | Leu | Gln | Asp | Thr |
|   |   |   | 405 |   |   |   |   | 410 |   |   |   |   | 415 |
| Met | Asn | His | Val | Leu | Ser | Cys | Val | Lys | Lys | Glu | Lys | Glu | Arg | Thr | Ala |
|   |   | 420 |   |   |   |   | 425 |   |   |   |   | 430 |
| Ala | Phe | Gln | Ala | Leu | Gly | Leu | Leu | Ser | Val | Ala | Val | Arg | Ser | Glu | Phe |
|   | 435 |   |   |   |   | 440 |   |   |   |   | 445 |
| Lys | Val | Tyr | Leu | Pro | Arg | Val | Leu | Asp | Ile | Ile | Arg | Ala | Ala | Leu | Pro |
|   | 450 |   |   |   |   | 455 |   |   |   |   | 460 |
| Pro | Lys | Asp | Phe | Ala | His | Lys | Arg | Gln | Lys | Ala | Met | Gln | Val | Asp | Ala |
| 465 |   |   |   |   | 470 |   |   |   |   | 475 |   |   |   |   | 480 |
| Thr | Val | Phe | Thr | Cys | Ile | Ser | Met | Leu | Ala | Arg | Ala | Met | Gly | Pro | Gly |
|   |   |   | 485 |   |   |   |   | 490 |   |   |   |   | 495 |
| Ile | Gln | Gln | Asp | Ile | Lys | Glu | Leu | Leu | Glu | Pro | Met | Leu | Ala | Val | Gly |
|   |   |   | 500 |   |   |   |   | 505 |   |   |   |   | 510 |
| Leu | Ser | Pro | Ala | Leu | Thr | Ala | Val | Leu | Tyr | Asp | Leu | Ser | Arg | Gln | Ile |
|   |   | 515 |   |   |   |   | 520 |   |   |   |   | 525 |
| Pro | Gln | Leu | Lys | Lys | Asp | Ile | Gln | Asp | Gly | Leu | Leu | Lys | Met | Leu | Ser |
|   | 530 |   |   |   |   | 535 |   |   |   |   | 540 |
| Leu | Val | Leu | Met | His | Lys | Pro | Leu | Arg | His | Pro | Gly | Met | Pro | Lys | Gly |
| 545 |   |   |   |   | 550 |   |   |   |   | 555 |   |   |   |   | 560 |
| Leu | Ala | His | Gln | Leu | Ala | Ser | Pro | Gly | Leu | Thr | Thr | Leu | Pro | Glu | Ala |
|   |   |   | 565 |   |   |   |   | 570 |   |   |   |   | 575 |
| Ser | Asp | Val | Gly | Ser | Ile | Thr | Leu | Ala | Leu | Arg | Thr | Leu | Gly | Ser | Phe |
|   |   |   | 580 |   |   |   |   | 585 |   |   |   |   | 590 |
| Glu | Phe | Glu | Gly | His | Ser | Leu | Thr | Gln | Phe | Val | Arg | His | Cys | Ala | Asp |
|   |   | 595 |   |   |   |   | 600 |   |   |   |   | 605 |
| His | Phe | Leu | Asn | Ser | Glu | His | Lys | Glu | Ile | Arg | Met | Glu | Ala | Ala | Arg |
|   | 610 |   |   |   |   | 615 |   |   |   |   | 620 |
| Thr | Cys | Ser | Arg | Leu | Leu | Thr | Pro | Ser | Ile | His | Leu | Ile | Ser | Gly | His |
| 625 |   |   |   |   | 630 |   |   |   |   | 635 |   |   |   |   | 640 |
| Ala | His | Val | Val | Ser | Gln | Thr | Ala | Val | Gln | Val | Val | Ala | Asp | Val | Leu |
|   |   |   | 645 |   |   |   |   | 650 |   |   |   |   | 655 |
| Ser | Lys | Leu | Leu | Val | Val | Gly | Ile | Thr | Asp | Pro | Asp | Pro | Asp | Ile | Arg |
|   |   |   | 660 |   |   |   |   | 665 |   |   |   |   | 670 |
| Tyr | Cys | Val | Leu | Ala | Ser | Leu | Asp | Glu | Arg | Phe | Asp | Ala | His | Leu | Ala |
|   |   | 675 |   |   |   |   | 680 |   |   |   |   | 685 |
| Gln | Ala | Glu | Asn | Leu | Gln | Ala | Leu | Phe | Val | Ala | Leu | Asn | Asp | Gln | Val |
|   | 690 |   |   |   |   | 695 |   |   |   |   | 700 |
| Phe | Glu | Ile | Arg | Glu | Leu | Ala | Ile | Cys | Thr | Val | Gly | Arg | Leu | Ser | Ser |
| 705 |   |   |   |   | 710 |   |   |   |   | 715 |   |   |   |   | 720 |
| Met | Asn | Pro | Ala | Phe | Val | Met | Pro | Phe | Leu | Arg | Lys | Met | Leu | Ile | Gln |
|   |   |   | 725 |   |   |   |   | 730 |   |   |   |   | 735 |
| Ile | Leu | Thr | Glu | Leu | Glu | His | Ser | Gly | Ile | Gly | Arg | Ile | Lys | Glu | Gln |
|   |   | 740 |   |   |   |   | 745 |   |   |   |   | 750 |

-continued

Ser Ala Arg Met Leu Gly His Leu Val Ser Asn Ala Pro Arg Leu Ile
        755                 760                 765

Arg Pro Tyr Met Glu Pro Ile Leu Lys Ala Leu Ile Leu Lys Leu Lys
    770                 775                 780

Asp Pro Asp Pro Asp Pro Asn Pro Gly Val Ile Asn Asn Val Leu Ala
785                 790                 795                 800

Thr Ile Gly Glu Leu Ala Gln Val Ser Gly Leu Glu Met Arg Lys Trp
                805                 810                 815

Val Asp Glu Leu Phe Ile Ile Ile Met Asp Met Leu Gln Asp Ser Ser
                820                 825                 830

Leu Leu Ala Lys Arg Gln Val Ala Leu Trp Thr Leu Gly Gln Leu Val
        835                 840                 845

Ala Ser Thr Gly Tyr Val Val Glu Pro Tyr Arg Lys Tyr Pro Thr Leu
850                 855                 860

Leu Glu Val Leu Leu Asn Phe Leu Lys Thr Glu Gln Asn Gln Gly Thr
865                 870                 875                 880

Arg Arg Glu Ala Ile Arg Val Leu Gly Leu Leu Gly Ala Leu Asp Pro
                885                 890                 895

Tyr Lys His Lys Val Asn Ile Gly Met Ile Asp Gln Ser Arg Asp Ala
        900                 905                 910

Ser Ala Val Ser Leu Ser Glu Ser Lys Ser Ser Gln Asp Ser Ser Asp
        915                 920                 925

Tyr Ser Thr Ser Glu Met Leu Val Asn Met Gly Asn Leu Pro Leu Asp
    930                 935                 940

Glu Phe Tyr Pro Ala Val Ser Met Val Ala Leu Met Arg Ile Phe Arg
945                 950                 955                 960

Asp Gln Ser Leu Ser His His His Thr Met Val Val Gln Ala Ile Thr
                965                 970                 975

Phe Ile Phe Lys Ser Leu Gly Leu Lys Cys Val Gln Phe Leu Pro Gln
        980                 985                 990

Val Met Pro Thr Phe Leu Asn Val Ile Arg Val Cys Asp Gly Ala Ile
    995                 1000                1005

Arg Glu Phe Leu Phe Gln Gln Leu Gly Met Leu Val Ser Phe Val Lys
    1010                1015                1020

Ser His Ile Arg Pro Tyr Met Asp Glu Ile Val Thr Leu Met Arg Glu
1025                1030                1035                1040

Phe Trp Val Met Asn Thr Ser Ile Gln Ser Thr Ile Ile Leu Leu Ile
                1045                1050                1055

Glu Gln Ile Val Val Ala Leu Gly Gly Glu Phe Lys Leu Tyr Leu Pro
        1060                1065                1070

Gln Leu Ile Pro His Met Leu Arg Val Phe Met His Asp Asn Ser Pro
    1075                1080                1085

Gly Arg Ile Val Ser Ile Lys Leu Leu Ala Ala Ile Gln Leu Phe Gly
    1090                1095                1100

Ala Asn Leu Asp Asp Tyr Leu His Leu Leu Leu Pro Pro Ile Val Lys
1105                1110                1115                1120

Leu Phe Asp Ala Pro Glu Ala Pro Leu Pro Ser Arg Lys Ala Ala Leu
        1125                1130                1135

Glu Thr Val Asp Arg Leu Thr Glu Ser Leu Asp Phe Thr Asp Tyr Ala
            1140                1145                1150

Ser Arg Ile Ile His Pro Ile Val Arg Thr Leu Asp Gln Ser Pro Glu
        1155                1160                1165

-continued

```
Leu Arg Ser Thr Ala Met Asp Thr Leu Ser Ser Leu Val Phe Gln Leu
1170                1175                1180

Gly Lys Lys Tyr Gln Ile Phe Ile Pro Met Val Asn Lys Val Leu Val
1185                1190                1195                1200

Arg His Arg Ile Asn His Gln Arg Tyr Asp Val Leu Ile Cys Arg Ile
                1205                1210                1215

Val Lys Gly Tyr Thr Leu Ala Asp Glu Glu Asp Pro Leu Ile Tyr
                1220                1225                1230

Gln His Arg Met Leu Arg Ser Gly Gln Gly Asp Ala Leu Ala Ser Gly
                1235                1240                1245

Pro Val Glu Thr Gly Pro Met Lys Lys Leu His Val Ser Thr Ile Asn
1250                1255                1260

Leu Gln Lys Ala Trp Gly Ala Ala Arg Arg Val Ser Lys Asp Asp Trp
1265                1270                1275                1280

Leu Glu Trp Leu Arg Arg Leu Ser Leu Glu Leu Leu Lys Asp Ser Ser
                1285                1290                1295

Ser Pro Ser Leu Arg Ser Cys Trp Ala Leu Ala Gln Ala Tyr Asn Pro
                1300                1305                1310

Met Ala Arg Asp Leu Phe Asn Ala Ala Phe Val Ser Cys Trp Ser Glu
                1315                1320                1325

Leu Asn Glu Asp Gln Gln Asp Glu Leu Ile Arg Ser Ile Glu Leu Ala
                1330                1335                1340

Leu Thr Ser Gln Asp Ile Ala Glu Val Thr Gln Thr Leu Leu Asn Leu
1345                1350                1355                1360

Ala Glu Phe Met Glu His Ser Asp Lys Gly Pro Leu Pro Leu Arg Asp
                1365                1370                1375

Asp Asn Gly Ile Val Leu Leu Gly Glu Arg Ala Ala Lys Cys Arg Ala
                1380                1385                1390

Tyr Ala Lys Ala Leu His Tyr Lys Glu Leu Glu Phe Gln Lys Gly Pro
                1395                1400                1405

Thr Pro Ala Ile Leu Glu Ser Leu Ile Ser Ile Asn Asn Lys Leu Gln
                1410                1415                1420

Gln Pro Glu Ala Ala Ala Gly Val Leu Glu Tyr Ala Met Lys His Phe
1425                1430                1435                1440

Gly Glu Leu Glu Ile Gln Ala Thr Trp Tyr Glu Lys Leu His Glu Trp
                1445                1450                1455

Glu Asp Ala Leu Val Ala Tyr Asp Lys Lys Met Asp Thr Asn Lys Asp
                1460                1465                1470

Asp Pro Glu Leu Met Leu Gly Arg Met Arg Cys Leu Glu Ala Leu Gly
                1475                1480                1485

Glu Trp Gly Gln Leu His Gln Gln Cys Cys Glu Lys Trp Thr Leu Val
                1490                1495                1500

Asn Asp Glu Thr Gln Ala Lys Met Ala Arg Met Ala Ala Ala Ala
1505                1510                1515                1520

Trp Gly Leu Gly Gln Trp Asp Ser Met Glu Glu Tyr Thr Cys Met Ile
                1525                1530                1535

Pro Arg Asp Thr His Asp Gly Ala Phe Tyr Arg Ala Val Leu Ala Leu
                1540                1545                1550

His Gln Asp Leu Phe Ser Leu Ala Gln Gln Cys Ile Asp Lys Ala Arg
                1555                1560                1565

Asp Leu Leu Asp Ala Glu Leu Thr Ala Met Ala Gly Glu Ser Tyr Ser
                1570                1575                1580

Arg Ala Tyr Gly Ala Met Val Ser Cys His Met Leu Ser Glu Leu Glu
```

```
                1585                1590                1595                1600
        Glu Val Ile Gln Tyr Lys Leu Val Pro Glu Arg Arg Glu Ile Ile Arg
                        1605                1610                1615

Gln Ile Trp Trp Glu Arg Leu Gln Gly Cys Gln Arg Ile Val Glu Asp
                        1620                1625                1630

Trp Gln Lys Ile Leu Met Val Arg Ser Leu Val Val Ser Pro His Glu
                        1635                1640                1645

Asp Met Arg Thr Trp Leu Lys Tyr Ala Ser Leu Cys Gly Lys Ser Gly
                        1650                1655                1660

Arg Leu Ala Leu Ala His Lys Thr Leu Val Leu Leu Leu Gly Val Asp
        1665                1670                1675                1680

Pro Ser Arg Gln Leu Asp His Pro Leu Pro Thr Val His Pro Gln Val
                        1685                1690                1695

Thr Tyr Ala Tyr Met Lys Asn Met Trp Lys Ser Ala Arg Lys Ile Asp
                        1700                1705                1710

Ala Phe Gln His Met Gln His Phe Val Gln Thr Met Gln Gln Gln Ala
                        1715                1720                1725

Gln His Ala Ile Ala Thr Glu Asp Gln Gln His Lys Gln Glu Leu His
                        1730                1735                1740

Lys Leu Met Ala Arg Cys Phe Leu Lys Leu Gly Glu Trp Gln Leu Asn
        1745                1750                1755                1760

Leu Gln Gly Ile Asn Glu Ser Thr Ile Pro Lys Val Leu Gln Tyr Tyr
                        1765                1770                1775

Ser Ala Ala Thr Glu His Asp Arg Ser Trp Tyr Lys Ala Trp His Ala
                        1780                1785                1790

Trp Ala Val Met Asn Phe Glu Ala Val Leu His Tyr Lys His Gln Asn
                        1795                1800                1805

Gln Ala Arg Asp Glu Lys Lys Lys Leu Arg His Ala Ser Gly Ala Asn
                        1810                1815                1820

Ile Thr Asn Ala Thr Thr Ala Ala Thr Ala Ala Thr Ala Thr Thr
        1825                1830                1835                1840

Thr Ala Ser Thr Glu Gly Ser Asn Ser Glu Ser Glu Ala Glu Ser Thr
                        1845                1850                1855

Glu Asn Ser Pro Thr Pro Ser Pro Leu Gln Lys Lys Val Thr Glu Asp
                        1860                1865                1870

Leu Ser Lys Thr Leu Leu Met Tyr Thr Val Pro Ala Val Gln Gly Phe
                        1875                1880                1885

Phe Arg Ser Ile Ser Leu Ser Arg Gly Asn Asn Leu Gln Asp Thr Leu
                        1890                1895                1900

Arg Val Leu Thr Leu Trp Phe Asp Tyr Gly His Trp Pro Asp Val Asn
        1905                1910                1915                1920

Glu Ala Leu Val Glu Gly Val Lys Ala Ile Gln Ile Asp Thr Trp Leu
                        1925                1930                1935

Gln Val Ile Pro Gln Leu Ile Ala Arg Ile Asp Thr Pro Arg Pro Leu
                        1940                1945                1950

Val Gly Arg Leu Ile His Gln Leu Leu Thr Asp Ile Gly Arg Tyr His
                        1955                1960                1965

Pro Gln Ala Leu Ile Tyr Pro Leu Thr Val Ala Ser Lys Ser Thr Thr
                        1970                1975                1980

Thr Ala Arg His Asn Ala Ala Asn Lys Ile Leu Lys Asn Met Cys Glu
        1985                1990                1995                2000

His Ser Asn Thr Leu Val Gln Gln Ala Met Met Val Ser Glu Glu Leu
                        2005                2010                2015
```

```
Ile Arg Val Ala Ile Leu Trp His Glu Met Trp His Glu Gly Leu Glu
                2020                2025                2030

Glu Ala Ser Arg Leu Tyr Phe Gly Glu Arg Asn Val Lys Gly Met Phe
                2035                2040                2045

Glu Val Leu Glu Pro Leu His Ala Met Met Glu Arg Gly Pro Gln Thr
                2050                2055                2060

Leu Lys Glu Thr Ser Phe Asn Gln Ala Tyr Gly Arg Asp Leu Met Glu
2065                2070                2075                2080

Ala Gln Glu Trp Cys Arg Lys Tyr Met Lys Ser Gly Asn Val Lys Asp
                2085                2090                2095

Leu Thr Gln Ala Trp Asp Leu Tyr Tyr His Val Phe Arg Arg Ile Ser
                2100                2105                2110

Lys Gln Leu Pro Gln Leu Thr Ser Leu Glu Leu Gln Tyr Val Ser Pro
                2115                2120                2125

Lys Leu Leu Met Cys Arg Asp Leu Glu Leu Ala Val Pro Gly Thr Tyr
                2130                2135                2140

Asp Pro Asn Gln Pro Ile Ile Arg Ile Gln Ser Ile Ala Pro Ser Leu
2145                2150                2155                2160

Gln Val Ile Thr Ser Lys Gln Arg Pro Arg Lys Leu Thr Leu Met Gly
                2165                2170                2175

Ser Asn Gly His Glu Phe Val Phe Leu Leu Lys Gly His Glu Asp Leu
                2180                2185                2190

Arg Gln Asp Glu Arg Val Met Gln Leu Phe Gly Leu Val Asn Thr Leu
                2195                2200                2205

Leu Ala Asn Asp Pro Thr Ser Leu Arg Lys Asn Leu Ser Ile Gln Arg
                2210                2215                2220

Tyr Ala Val Ile Pro Leu Ser Thr Asn Ser Gly Leu Ile Gly Trp Val
2225                2230                2235                2240

Pro His Cys Asp Thr Leu His Ala Leu Ile Arg Asp Tyr Arg Glu Lys
                2245                2250                2255

Lys Lys Ile Leu Leu Asn Ile Glu His Arg Ile Met Leu Arg Met Ala
                2260                2265                2270

Pro Asp Tyr Asp His Leu Thr Leu Met Gln Lys Val Glu Val Phe Glu
                2275                2280                2285

His Ala Val Asn Asn Thr Ala Gly Asp Asp Leu Ala Lys Leu Leu Trp
                2290                2295                2300

Leu Lys Ser Pro Ser Ser Glu Val Trp Phe Asp Arg Arg Thr Asn Tyr
2305                2310                2315                2320

Thr Arg Ser Leu Ala Val Met Ser Met Val Gly Tyr Ile Leu Gly Leu
                2325                2330                2335

Gly Asp Arg His Pro Ser Asn Leu Met Leu Asp Arg Leu Ser Gly Lys
                2340                2345                2350

Ile Leu His Ile Asp Phe Gly Asp Cys Phe Glu Val Ala Met Thr Arg
                2355                2360                2365

Glu Lys Phe Pro Glu Lys Ile Pro Phe Arg Leu Thr Arg Met Leu Thr
                2370                2375                2380

Asn Ala Met Glu Val Thr Gly Leu Asp Gly Asn Tyr Arg Ile Thr Cys
2385                2390                2395                2400

His Thr Val Met Glu Val Leu Arg Glu His Lys Asp Ser Val Met Ala
                2405                2410                2415

Val Leu Glu Ala Phe Val Tyr Asp Pro Leu Leu Asn Trp Arg Leu Met
                2420                2425                2430
```

```
Asp Thr Asn Thr Lys Gly Asn Lys Arg Ser Arg Thr Arg Thr Asp Ser
        2435                2440                2445

Tyr Ser Ala Gly Gln Ser Val Glu Ile Leu Asp Gly Val Glu Leu Gly
        2450                2455                2460

Glu Pro Ala His Lys Lys Thr Gly Thr Thr Val Pro Glu Ser Ile His
2465                2470                2475                2480

Ser Phe Ile Gly Asp Gly Leu Val Lys Pro Glu Ala Leu Asn Lys Lys
        2485                2490                2495

Ala Ile Gln Ile Ile Asn Arg Val Arg Asp Lys Leu Thr Gly Arg Asp
        2500                2505                2510

Phe Ser His Asp Asp Thr Leu Asp Val Pro Thr Gln Val Glu Leu Leu
        2515                2520                2525

Ile Lys Gln Ala Thr Ser His Glu Asn Leu Cys Gln Cys Tyr Ile Gly
        2530                2535                2540

Trp Cys Pro Phe Trp
2545

<210> SEQ ID NO 13
<211> LENGTH: 3648
<212> TYPE: DNA
<213> ORGANISM: Homo sapiens

<400> SEQUENCE: 13
gcgcaaccct ccggaagctg ccgccccttt cccctttat gggaatactt ttttaaaaa      60 aaaagagttc gctggcgcca ccccgtagga ctggccgccc taaaaccgtg ataaaggagc    120
tgctcgccac ttctcacttc cgcttccttc cagtaaggag tcgggtctt ccccagtttt     180 ctcagccagg cggcggcggc gactggcaat gtttggcctc aaaagaaacg cggtaatcgg    240
actcaacctc tactgtgggg gggccggctt ggggccggc agcggcggcg ccacccgccc     300
gggagggcga cttttggcca ccggcgccaa ggacacaaag ccaatgggca ggtctgggc     360 caccagcagg aaggcgctgg agaccttacg acgggttggg gatggcgtgc agcgcaacca    420
cgagacggcc ttccaaggca tgcttcggaa actggacatc aaaaacgaag acgatgtgaa    480
atcgttgtct cgagtgatga tccatgtttt cagcgacggc gtaacaaact ggggcaggat    540
tgtgactctc atttcttttg gtgcctttgt ggctaaacac ttgaagacca taaaccaaga    600
aagctgcatc gaaccattag cagaaagtat cacagacgtt ctcgtaagga caaaacggga    660
ctggctagtt aaacaaagag gctgggatgg gtttgtggag ttcttccatg tagaggacct    720
agaaggtggc atcaggaatg tgctgctggc tttttgcaggt gttgctggag taggagctgg    780
tttggcatat ctaataagat agccttactg taagtgcaat agttgacttt taaccaacca    840
ccaccaccac caaaaccagt ttatgcagtt ggactccaag ctgtaacttc ctagagttgc    900
accctagcaa cctagccaga aaagcaagtg gcaagaggat tatggctaac aagaataaat    960
acatgggaag agtgctcccc attgattgaa gagtcactgt ctgaaagaag caaagttcag   1020
tttcagcaac aaacaaactt tgtttgggaa gctatggagg aggactttta gatttagtga   1080
agatggtagg gtggaaagac ttaatttcct tgttgagaac aggaaagtgg ccagtagcca   1140
ggcaagtcat agaattgatt acccgccgaa ttcattaatt tactgtagtg ttaagagaag   1200
cactaagaat gccagtgacc tgtgtaaaag ttacaagtaa tagaactatg actgtaagcc   1260
tcagtactgt acaagggaag cttttcctct ctctaattag ctttcccagt atacttctta   1320
gaaagtccaa gtgttcagga cttttatacc tgttatactt tggcttggtt tccatgattc   1380
ttactttatt agcctagttt atcaccaata atacttgacg gaaggctcag taattagtta   1440
```

```
tgaatatgga tatcctcaat tcttaagaca gcttgtaaat gtatttgtaa aaattgtata    1500
tatttttaca gaaagtctat ttctttgaaa cgaaggaagt atcgaattta cattagtttt    1560
tttcataccc ttttgaactt tgcaacttcc gtaattagga acctgtttct tacagcdtttt    1620 ctatgctaaa ctttgttctg ttcagttcta gagtgtatac agaacgaatt gatgtgtaac    1680
tgtatgcaga ctggttgtag tggaacaaat ctgataacta tgcaggttta aattttctta    1740
tctgattttg gtaagtattc cttagatagg ttttctttg aaaacctggg attgagaggt     1800
tgatgaatgg aaattctttc acttcattat atgcaagttt tcataatta ggtctaagtg     1860 gagttttaag gttactgatg acttacaaat aatgggctct gattgggcaa tactcatttg    1920
agttccttcc atttgaccta atttaactgg tgaaatttaa agtgaattca tgggctcatc    1980
tttaaagctt ttactaaaag attttcagct gaatggaact cattagctgt gtgcatataa    2040
aaagatcaca tcaggtggat ggagagacat ttgatcccit gtttgcttaa taaattataa    2100
aatgatggct tggaaaagca ggctagtcta accatggtgc tattattagg cttgcttgtt    2160
acacacacag gtctaagcct agtatgtcaa taaagcaaat acttactgtt ttgtttctat    2220
taatgattcc caaaccttgt tgcaagtttt tgcattggca tctttggatt tcagtcttga    2280
tgtttgttct atcagactta acctttattt tcctgtcctt ccttgaaatt gctgattgtt    2340
ctgctccctc tacagatatt tatatcaatt cctacagctt tccctgcca tccctgaact    2400 cttttctagcc cttttagatt ttggcactgt gaaaccctg ctggaaacct gagtgaccct    2460
ccctccccac caagagtcca cagacctttc atctttcacg aacttgatcc tgttagcagg    2520
tggtaatacc atgggtgctg tgacactaac agtcattgag aggtgggagg aagtcccttt    2580
tccttggact ggtatctttt caactattgt tttatcctgt ctttgggggc aatgtgtcaa    2640
aagtcccctc aggaattttc agaggaaaga acattttatg aggctttctc taaagtttcc    2700
tttgtatagg agtatgctca cttaaattta cagaaagagg tgagctgtgt taaacctcag    2760
agtttaaaag ctactgataa actgaagaaa gtgtctatat tggaactagg gtcatttgaa    2820
agcttcagtc tcggaacatg acctttagtc tgtggactcc atttaaaaat aggtatgaat    2880
aagatgacta agaatgtaat ggggaagaac tgccctgcct gcccatctca gagccataag    2940
gtcatctttg ctagagctat ttttacctat gtatttatcg ttcttgatca taagccgctt    3000
atttatatca tgtatctcta aggacctaaa agcactttat gtagttttta attaatctta    3060
agatctggtt acggtaacta aaaaagcctg tctgccaaat ccagtggaaa caagtgcata    3120
gatgtgaatt ggttttagg ggccccactt cccaattcat taggtatgac tgtgaaaata    3180
cagacaagga tcttagttga tattttgggc ttggggcagt gagggcttag gacaccccaa    3240
gtggtttggg aaaggaggag gggagtggtg ggtttatagg gggaggagga ggcaggtggt    3300
ctaagtgctg actggctacg tagttcgggc aaatcctcca aaagggaaag ggaggatttg    3360
cttagaagga tggcgctccc agtgactact ttttgacttc tgtttgtctt acgcttctct    3420
cagggaaaaa catgcagtcc tctagtgttt catgtacatt ctgtgggggg tgaacacctt    3480
ggttctggtt aaacagctgt acttttgata gctgtgccag gaagggttag gaccaactac    3540
aaattaatgt tggttgtcaa atgtagtgtg tttccctaac tttctgtttt tcctgagaaa    3600
aaaaaataaa tcttttattc aaatacaggg aaaaaaaaaa aaaaaaa                  3648
```

<210> SEQ ID NO 14
<211> LENGTH: 197
<212> TYPE: PRT

<213> ORGANISM: Homo sapiens

<400> SEQUENCE: 14

```
Met Phe Gly Leu Lys Arg Asn Ala Val Ile Gly Leu Asn Leu Tyr Cys
 1               5                  10                  15
Gly Gly Ala Gly Leu Gly Ala Gly Ser Gly Ala Thr Arg Pro Gly
            20                  25                  30
Gly Arg Leu Leu Ala Thr Gly Ala Lys Asp Thr Lys Pro Met Gly Arg
            35                  40                  45
Ser Gly Ala Thr Ser Arg Lys Ala Leu Glu Thr Leu Arg Arg Val Gly
    50                  55                  60
Asp Gly Val Gln Arg Asn His Glu Thr Ala Phe Gln Gly Met Leu Arg
65                  70                  75                  80
Lys Leu Asp Ile Lys Asn Glu Asp Asp Val Lys Ser Leu Ser Arg Val
                85                  90                  95
Met Ile His Val Phe Ser Asp Gly Val Thr Asn Trp Gly Arg Ile Val
            100                 105                 110
Thr Leu Ile Ser Phe Gly Ala Phe Val Ala Lys His Leu Lys Thr Ile
            115                 120                 125
Asn Gln Glu Ser Cys Ile Glu Pro Leu Ala Glu Ser Ile Thr Asp Val
        130                 135                 140
Leu Val Arg Thr Lys Arg Asp Trp Leu Val Lys Gln Arg Gly Trp Asp
145                 150                 155                 160
Gly Phe Val Glu Phe Phe His Val Glu Asp Leu Glu Gly Gly Ile Arg
                165                 170                 175
Asn Val Leu Leu Ala Phe Ala Gly Val Ala Gly Val Gly Ala Gly Leu
            180                 185                 190
Ala Tyr Leu Ile Arg
            195
```

<210> SEQ ID NO 15
<211> LENGTH: 1832
<212> TYPE: DNA
<213> ORGANISM: Homo sapiens

<400> SEQUENCE: 15

```
gagcggccag gccagcctcg gagccagcag ggagctggga gctggggaa acgacgccag      60
gaaagctatc gcgccagaga gggcgacggg ggctcgggaa gcctgacagg gcttttgcgc    120
acagctgccg gctggctgct acccgcccgc gccagccccc gagaacgcgc gaccaggcac    180
ccagtccggt caccgcagcg gagagctcgc cgctcgctgc agcgaggccc ggagcggccc    240
cgcagggacc ctccccagac cgcctgggcc gcccggatgt gcactaaaat ggaacagccc    300
ttctaccacg acgactcata cacagctacg ggatacggcc gggcccctgg tggcctctct    360
ctacacgact acaaactcct gaaaccgagc ctggcggtca acctggccga ccctaccgg     420
agtctcaaag cgcctggggc tcgcggaccc ggcccagagg gcggcggtgg cggcagctac    480
tttctggtc agggctcgga caccggcgcg tctctcaagc tcgcctcttc ggagctggaa     540
cgcctgattg tccccaacag caacggcgtg atcacgacga cgcctacacc ccgggacag    600
tactttacc cccgcggggg tggcagcggt ggaggtgcag gggcgcagg gggcggcgtc      660
accgaggagc aggagggctt cgccgacggc tttgtcaaag ccctggacga tctgcacaag   720
atgaaccacg tgcacccccc caacgtgtcc ctgggcgcta ccggggggcc cccggctggg   780
cccgggggcg tctacgccgg cccggagcca cctcccgttt acaccaacct cagcagctac    840
```

-continued

```
tccccagcct ctgcgtcctc gggaggcgcc ggggctgccg tcgggaccgg gagctcgtac    900
ccgacgacca ccatcagcta cctcccacac gcgccgccct tcgccggtgg ccacccggcg    960
cagctgggct tgggccgcgg cgcctccacc ttcaaggagg aaccgcagac cgtgccggag   1020
gcgcgcagcc gggacgccac gccgccggtg tccccatca acatggaaga ccaagagcgc    1080
atcaaagtgg agcgcaagcg gctgcggaac cggctggcgg ccaccaagtg ccggaagcgg   1140
aagctggagc gcatcgcgcg cctggaggac aaggtgaaga cgctcaaggc cgagaacgcg   1200
gggctgtcga gtaccgccgg cctcctccgg gagcaggtgg cccagctcaa acagaaggtc   1260
atgacccacg tcagcaacgg ctgtcagctg ctgcttgggg tcaagggaca cgccttctga   1320
acgtcccctg ccccttttacg acaccccct cgcttggacg gctgggcaca cgcctcccac   1380
tggggtccag ggagcaggcg gtgggcaccc accctgggac ctaggggcgc cgcaaaccac   1440
actggactcc ggccctccta ccctgcgccc agtccttcca cctcgacgtt tacaagcccc   1500
cccttccact tttttttgta tgttttttttt ctgctggaaa cagactcgat tcatattgaa   1560
tataatatat ttgtgtattt aacagggagg ggaagagggg cgatcgcgg cggagctggc    1620
cccgccgcct ggtactcaag cccgcgggga cattgggaag gggaccccg ccccctgccc    1680
tccctctct gcaccgtact gtggaaaaga aacacgcact tagtctctaa agagtttatt   1740
ttaagacgtg tttgtgttttg tgtgtgtttg ttcttttat tgaatctatt taagtaaaaa   1800
aaaaattggt tctttaaaaa aaaaaaaaaa aa                                 1832
```

<210> SEQ ID NO 16
<211> LENGTH: 347
<212> TYPE: PRT
<213> ORGANISM: Homo sapiens

<400> SEQUENCE: 16

```
Met Cys Thr Lys Met Glu Gln Pro Phe Tyr His Asp Asp Ser Tyr Thr
 1               5                  10                  15

Ala Thr Gly Tyr Gly Arg Ala Pro Gly Gly Leu Ser Leu His Asp Tyr
            20                  25                  30

Lys Leu Leu Lys Pro Ser Leu Ala Val Asn Leu Ala Asp Pro Tyr Arg
        35                  40                  45

Ser Leu Lys Ala Pro Gly Ala Arg Gly Pro Gly Pro Glu Gly Gly Gly
    50                  55                  60

Gly Gly Ser Tyr Phe Ser Gly Gln Gly Ser Asp Thr Gly Ala Ser Leu
65                  70                  75                  80

Lys Leu Ala Ser Ser Glu Leu Glu Arg Leu Ile Val Pro Asn Ser Asn
                85                  90                  95

Gly Val Ile Thr Thr Thr Pro Thr Pro Pro Gly Gln Tyr Phe Tyr Pro
            100                 105                 110

Arg Gly Gly Gly Ser Gly Gly Gly Ala Gly Gly Ala Gly Gly Gly Val
        115                 120                 125

Thr Glu Glu Gln Glu Gly Phe Ala Asp Gly Phe Val Lys Ala Leu Asp
    130                 135                 140

Asp Leu His Lys Met Asn His Val Thr Pro Pro Asn Val Ser Leu Gly
145                 150                 155                 160

Ala Thr Gly Gly Pro Pro Ala Gly Pro Gly Gly Val Tyr Ala Gly Pro
                165                 170                 175

Glu Pro Pro Pro Val Tyr Thr Asn Leu Ser Ser Tyr Ser Pro Ala Ser
            180                 185                 190

Ala Ser Ser Gly Gly Ala Gly Ala Ala Val Gly Thr Gly Ser Ser Tyr
```

|  | 195 |  |  |  | 200 |  |  |  | 205 |  |  |
|---|---|---|---|---|---|---|---|---|---|---|---|

Pro Thr Thr Thr Ile Ser Tyr Leu Pro His Ala Pro Pro Phe Ala Gly
210 215 220

Gly His Pro Ala Gln Leu Gly Leu Gly Arg Gly Ala Ser Thr Phe Lys
225 230 235 240

Glu Glu Pro Gln Thr Val Pro Glu Ala Arg Ser Arg Asp Ala Thr Pro
245 250 255

Pro Val Ser Pro Ile Asn Met Glu Asp Gln Glu Arg Ile Lys Val Glu
260 265 270

Arg Lys Arg Leu Arg Asn Arg Leu Ala Ala Thr Lys Cys Arg Lys Arg
275 280 285

Lys Leu Glu Arg Ile Ala Arg Leu Glu Asp Lys Val Lys Thr Leu Lys
290 295 300

Ala Glu Asn Ala Gly Leu Ser Ser Thr Ala Gly Leu Leu Arg Glu Gln
305 310 315 320

Val Ala Gln Leu Lys Gln Lys Val Met Thr His Val Ser Asn Gly Cys
325 330 335

Gln Leu Leu Leu Gly Val Lys Gly His Ala Phe
340 345

<210> SEQ ID NO 17
<211> LENGTH: 3662
<212> TYPE: DNA
<213> ORGANISM: Homo sapiens

<400> SEQUENCE: 17

| gcgagctggt ggttgaagct ggttaaagaa cagcctaggt attccagaag tgtttgagga | 60 |
|---|---|
| tcccttccat gaaggaagag aggaaagttt ttaagtaaac ctcccactcc catgtgtctt | 120 |
| cagctttctt ttgcaaagga gaaaatcctt gaagtttggt aaagaccgag ttagtctatc | 180 |
| tctctttgcc tatctcgagt tgggctgggg agaggaggag ataggttctt ttgtcttttt | 240 |
| ctgtcttctc ccttccccac ttccttccct ccagtcccca ctcactcaca tgcacacact | 300 |
| aaccttggag ccgatgggat tgagtgactg gcacttggga ccacagagaa atgtcagagt | 360 |
| gtttggttac agactcaagg aaacctctca ttttagagtg ctcatttggt tttgagcaaa | 420 |
| attttggact gtgaagcaag gcattggtga agacaaaatg gcctcgccgg ctgacagctg | 480 |
| tatccagttc acccgccatg ccagtgatgt tcttctcaac cttaatcgtc tccggagtcg | 540 |
| agacatcttg actgatgttg tcattgttgt gagccgtgag cagtttagag cccataaaac | 600 |
| ggtcctcatg gcctgcagtg gcctgttcta tagcatcttt acagaccagt tgaaatgcaa | 660 |
| ccttagtgtg atcaatctag atcctgagat caaccctgag ggattctgca tcctcctgga | 720 |
| cttcatgtac acatctcggc tcaatttgcg ggagggcaac atcatggctg tgatggccac | 780 |
| ggctatgtac ctgcagatgg agcatgttgt ggacacttgc cggaagttta ttaaggccag | 840 |
| tgaagcagag atggtttctg ccatcaagcc tcctcgtgaa gagttcctca acagccggat | 900 |
| gctgatgccc caagacatca tggcctatcg gggtcgtgag gtggtggaga caacctgcc | 960 |
| actgaggagc gccctgggt gtgagagcag agcctttgcc cccagcctgt acagtggcct | 1020 |
| gtccacaccg ccagcctctt attccatgta cagccaacctc cctgtcagca gcctcctctt | 1080 |
| ctccgatgag gagtttcggg atgtccggat gcctgtggcc aacccttcc ccaaggagcg | 1140 |
| ggcactccca tgtgatagtg ccaggccagt ccctggtgag tacagccggc cgactttgga | 1200 |
| ggtgtccccc aatgtgtgcc acagcaatat ctattcaccc aaggaaacaa tcccagaaga | 1260 |

```
ggcacgaagt gatatgcact acagtgtggc tgagggcctc aaacctgctg cccctcagc       1320
ccgaaatgcc ccctacttcc cttgtgacaa ggccagcaaa gaagaagaga gaccctcctc      1380
ggaagatgag attgccctgc atttcgagcc ccccaatgca cccctgaacc ggaagggtct      1440
ggttagtcca cagagccccc agaaatctga ctgccagccc aactcgccca cagagtcctg      1500
cagcagtaag aatgcctgca tcctccaggc ttctggctcc cctccagcca agagccccac      1560
tgaccccaaa gcctgcaact ggaagaaata caagttcatc gtgctcaaca gcctcaacca      1620
gaatgccaaa ccagaggggc ctgagcaggc tgagctgggc cgccttccc cacgagccta       1680
cacggcccca cctgcctgcc agccacccat ggagcctgag aaccttgacc tccagtcccc      1740
aaccaagctg agtgccagcg gggaggactc caccatccca caagccagcc ggctcaataa      1800
catcgttaac aggtccatga cgggctctcc ccgcagcagc agcgagagcc actcaccact      1860
ctacatgcac cccccgaagt gcacgtcctg cggctctcag tccccacagc atgcagagat      1920
gtgcctccac accgctggcc ccacgttccc tgaggagatg ggagagaccc agtctgagta      1980
ctcagattct agctgtgaga acggggcctt cttctgcaat gagtgtgact gccgcttctc      2040
tgaggaggcc tcactcaaga ggcacacgct gcagacccac agtgacaaac cctacaagtg      2100
tgaccgctgc caggcctcct tccgctacaa gggcaacctc gccagccaca gaccgtcca      2160
taccggtgag aaacccctatc gttgcaacat ctgtggggcc cagttcaacc ggccagccaa     2220
cctgaaaacc cacactcgaa ttcactctgg agagaagccc tacaaatgcg aaacctgcgg      2280
agccagattt gtacaggtgg cccacctccg tgcccatgtg cttatccaca ctggtgagaa      2340
gccctatccc tgtgaaatct gtggcacccg tttccggcac cttcagactc tgaagagcca      2400
cctgcgaatc cacacaggag agaaaccta ccattgtgag aagtgtaacc tgcatttccg        2460
tcacaaaagc cagctgcgac ttcacttgcg ccagaagcat ggcgccatca ccaacaccaa      2520
ggtgcaatac cgcgtgtcag ccactgacct gcctccggag ctccccaaag cctgctgaag      2580
catggagtgt tgatgctttc gtctccagcc ccttctcaga atctacccaa aggatactgt      2640
aacactttac aatgttcatc ccatgatgta gtgcctcttt catccactag tgcaaatcat      2700
agctggggt tgggggtggt gggggtcggg gcctggggga ctgggagccg cagcagctcc       2760
ccctccccca ctgccataaa acattaagaa aatcatattg cttcttctcc tatgtgtaag      2820
gtgaaccatg tcagcaaaaa gcaaaatcat tttatatgtc aaagcagggg agtatgcaaa      2880
agttctgact tgactttagt ctgcaaaatg aggaatgtat atgttttgtg ggaacagatg      2940
tttcttttgt atgtaaatgt gcattctttt aaaagacaag acttcagtat gttgtcaaag      3000
agagggcttt aatttttta accaaggtg aaggaatata tggcagagtt gtaaatatat        3060
aaatatatat atatataaa taatatata taaacctaaa aagatatat taaaaatata         3120
aaactgcgtt aaaggctcga ttttgtatct gcaggcagac acggatctga gaatctttat     3180
tgagaaagag cacttaagag aatatttaa gtattgcatc tgtataagta agaaaatatt       3240
ttgtctaaaa tgcctcagtg tatttgtatt ttttgcaag tgaaggttta caatttacaa        3300
agtgtgtatt aaaaaaaaca aaagaacaa aaaatctgc agaaggaaaa atgtgtaatt        3360
ttgttctagt tttcagtttg tatatacccg tacaacgtgt cctcacggtg cctttttca       3420
cggaagtttt caatgatggg cgagcgtgca ccatcccttt ttgaagtgta ggcagacaca     3480
gggacttgaa gttgttacta actaaactct ctttgggaat gtttgtctca tcccattctg     3540
cgtcatgctt gtgttataac tactccggag acagggtttg gctgtgtcta aactgcatta    3600
ccgcgttgta aaatatagct gtacaaatat aagaataaaa tgttgaaaag tcaaactgga    3660
``` aa                                                              3662

<210> SEQ ID NO 18
<211> LENGTH: 706
<212> TYPE: PRT
<213> ORGANISM: Homo sapiens

<400> SEQUENCE: 18

```
Met Ala Ser Pro Ala Asp Ser Cys Ile Gln Phe Thr Arg His Ala Ser
  1               5                  10                  15

Asp Val Leu Leu Asn Leu Asn Arg Leu Arg Ser Arg Asp Ile Leu Thr
             20                  25                  30

Asp Val Val Ile Val Ser Arg Glu Gln Phe Arg Ala His Lys Thr
         35                  40                  45

Val Leu Met Ala Cys Ser Gly Leu Phe Tyr Ser Ile Phe Thr Asp Gln
     50                  55                  60

Leu Lys Cys Asn Leu Ser Val Ile Asn Leu Asp Pro Glu Ile Asn Pro
 65                  70                  75                  80

Glu Gly Phe Cys Ile Leu Leu Asp Phe Met Tyr Thr Ser Arg Leu Asn
                 85                  90                  95

Leu Arg Glu Gly Asn Ile Met Ala Val Met Ala Thr Ala Met Tyr Leu
            100                 105                 110

Gln Met Glu His Val Val Asp Thr Cys Arg Lys Phe Ile Lys Ala Ser
        115                 120                 125

Glu Ala Glu Met Val Ser Ala Ile Lys Pro Pro Arg Glu Glu Phe Leu
    130                 135                 140

Asn Ser Arg Met Leu Met Pro Gln Asp Ile Met Ala Tyr Arg Gly Arg
145                 150                 155                 160

Glu Val Val Glu Asn Asn Leu Pro Leu Arg Ser Ala Pro Gly Cys Glu
                165                 170                 175

Ser Arg Ala Phe Ala Pro Ser Leu Tyr Ser Gly Leu Ser Thr Pro Pro
            180                 185                 190

Ala Ser Tyr Ser Met Tyr Ser His Leu Pro Val Ser Ser Leu Leu Phe
        195                 200                 205

Ser Asp Glu Glu Phe Arg Asp Val Arg Met Pro Val Ala Asn Pro Phe
    210                 215                 220

Pro Lys Glu Arg Ala Leu Pro Cys Asp Ser Ala Arg Pro Val Pro Gly
225                 230                 235                 240

Glu Tyr Ser Arg Pro Thr Leu Glu Val Ser Pro Asn Val Cys His Ser
                245                 250                 255

Asn Ile Tyr Ser Pro Lys Glu Thr Ile Pro Glu Glu Ala Arg Ser Asp
            260                 265                 270

Met His Tyr Ser Val Ala Glu Gly Leu Lys Pro Ala Ala Pro Ser Ala
        275                 280                 285

Arg Asn Ala Pro Tyr Phe Pro Cys Asp Lys Ala Ser Lys Glu Glu Glu
    290                 295                 300

Arg Pro Ser Ser Glu Asp Glu Ile Ala Leu His Phe Glu Pro Pro Asn
305                 310                 315                 320

Ala Pro Leu Asn Arg Lys Gly Leu Val Ser Pro Gln Ser Pro Gln Lys
                325                 330                 335

Ser Asp Cys Gln Pro Asn Ser Pro Thr Glu Ser Cys Ser Ser Lys Asn
            340                 345                 350

Ala Cys Ile Leu Gln Ala Ser Gly Ser Pro Pro Ala Lys Ser Pro Thr
        355                 360                 365
```

Asp Pro Lys Ala Cys Asn Trp Lys Lys Tyr Lys Phe Ile Val Leu Asn
        370                 375                 380

Ser Leu Asn Gln Asn Ala Lys Pro Glu Gly Pro Glu Gln Ala Glu Leu
385                 390                 395                 400

Gly Arg Leu Ser Pro Arg Ala Tyr Thr Ala Pro Pro Ala Cys Gln Pro
            405                 410                 415

Pro Met Glu Pro Glu Asn Leu Asp Leu Gln Ser Pro Thr Lys Leu Ser
        420                 425                 430

Ala Ser Gly Glu Asp Ser Thr Ile Pro Gln Ala Ser Arg Leu Asn Asn
            435                 440                 445

Ile Val Asn Arg Ser Met Thr Gly Ser Pro Arg Ser Ser Ser Glu Ser
        450                 455                 460

His Ser Pro Leu Tyr Met His Pro Pro Lys Cys Thr Ser Cys Gly Ser
465                 470                 475                 480

Gln Ser Pro Gln His Ala Glu Met Cys Leu His Thr Ala Gly Pro Thr
            485                 490                 495

Phe Pro Glu Glu Met Gly Glu Thr Gln Ser Glu Tyr Ser Asp Ser Ser
        500                 505                 510

Cys Glu Asn Gly Ala Phe Phe Cys Asn Glu Cys Asp Cys Arg Phe Ser
            515                 520                 525

Glu Glu Ala Ser Leu Lys Arg His Thr Leu Gln Thr His Ser Asp Lys
530                 535                 540

Pro Tyr Lys Cys Asp Arg Cys Gln Ala Ser Phe Arg Tyr Lys Gly Asn
545                 550                 555                 560

Leu Ala Ser His Lys Thr Val His Thr Gly Glu Lys Pro Tyr Arg Cys
            565                 570                 575

Asn Ile Cys Gly Ala Gln Phe Asn Arg Pro Ala Asn Leu Lys Thr His
        580                 585                 590

Thr Arg Ile His Ser Gly Glu Lys Pro Tyr Lys Cys Glu Thr Cys Gly
            595                 600                 605

Ala Arg Phe Val Gln Val Ala His Leu Arg Ala His Val Leu Ile His
        610                 615                 620

Thr Gly Glu Lys Pro Tyr Pro Cys Glu Ile Cys Gly Thr Arg Phe Arg
625                 630                 635                 640

His Leu Gln Thr Leu Lys Ser His Leu Arg Ile His Thr Gly Glu Lys
            645                 650                 655

Pro Tyr His Cys Glu Lys Cys Asn Leu His Phe Arg His Lys Ser Gln
        660                 665                 670

Leu Arg Leu His Leu Arg Gln Lys His Gly Ala Ile Thr Asn Thr Lys
            675                 680                 685

Val Gln Tyr Arg Val Ser Ala Thr Asp Leu Pro Pro Glu Leu Pro Lys
        690                 695                 700

Ala Cys
705

<210> SEQ ID NO 19
<211> LENGTH: 2104
<212> TYPE: DNA
<213> ORGANISM: Homo sapiens

<400> SEQUENCE: 19
acgtagcgcg gcgctcggaa ctgacctact aacacacatc tctccgcgcg gccacggcgc      60
ccgcggaccc ggcgcgcccg cccgcctccc gcgccgcgcc ctcgccgccg cccgcctccc     120

```
gccgcggccc cggaggcccg gcccggcccg agccccgagc gccggcggcc cgactcccgg      180 ccgcccettt ctttctcctc gccggcccga gagcaggaac acgataacga aggaggccca      240
acttcattca ataaggagcc tgacggattt atcccagacg tagaacaaa aggaagaata      300 ttgatggatt ttaaaccaga gttttaaaag agcttgagaa tacggggaaa ttaatttgtt      360
ctcctacaca catagatagg gtaaggttgt ttctgatgca gctgagaaaa atgcagaccg      420
tcaaaaagga gcaggcgtct cttgatgcca gtagcaatgt ggacaagatg atggtccta      480 attctgcttt aacggaagtg tcagaagact ccacaacagg tgaggagctg cttctcagtg      540
aaggaagtgt ggggaagaac aaatcttctg catgtcggag gaaacgggaa ttcattcctg      600
atgaaaagaa agatgctatg tattgggaaa aaaggcggaa aaataatgaa gctgccaaaa      660
gatctcgtga gaagcgtcga ctgaataacc tggttttaga gaacaaacta attgcactgg      720
gagaagaaaa cgccacttta aaagctgagc tgctttcact aaaattaaag tttggtttaa      780
ttagctccac agcatatgct caagagattc agaaactcag taattctaca gctgtgtact      840
ttcaagatta ccagacttcc aaatccaatg tgagttcatt tgtggacgag cacgaaccct      900
cgatggtgtc aagtagttgt atttctgtca ttaaacactc tccacaaagc tcgctgtccg      960
atgtttcaga agtgtcctca gtagaacaca cgcaggagag ctctgtgcag ggaagctgca     1020
gaagtcctga aaacaagttc cagattatca gcaagagcc gatggaatta gagagctaca     1080
caagggagcc aagagatgac cgaggctctt acacagcgtc catctatcaa aactatatgg     1140
ggaattcttt ctctgggtac tcacactctc ccccactact gcaagtcaac cgatcctcca     1200
gcaactcccc gagaacgtcg gaaactgatg atggtgtggt aggaaagtca tctgatggag     1260
aagacgagca acaggtcccc aagggcccca tccattctcc agttgaactc aagcatgtgc     1320
atgcaactgt ggttaaagtt ccagaagtga attcctctgc cttgccacac aagctccgga     1380
tcaaagccaa agccatgcag atcaaagtag aagcctttga taatgaattt gaggccacgc     1440 aaaaacttc ctcacctatt gacatgacat ctaaaagaca tttcgaactc gaaaagcata     1500
gtgccccaag tatggtacat tcttctctta ctcctttctc agtgcaagtg actaacattc     1560
aagattggtc tctcaaatcg gagcactggc atcaaaaaga actgagtggc aaaactcaga     1620
atagtttcaa aactggagtt gttgaaatga agacagtgg ctacaaagtt tctgacccag     1680
agaacttgta tttgaagcag gggatagcaa acttatctgc agaggttgtc tcactcaaga     1740 gacttatage cacacaacca atctctgctt cagactctgg gtaaaattact actgagtaag     1800 agctgggcat ttagaaagat gtcatttgca atagagcagt ccattttgta ttatgctgaa     1860
ttttcactgg acctgtgatg tcatttcact gtgatgtgca catgttgtct gtttggtgtc     1920
tttttgtgca cagattatga tgaagattag attgtgttat cactctgcct gtgtatagtc     1980
agatagtcca tgcgaaggct gtatatattg aacattattt ttgttgttct attataaagt     2040
gtgtaagtta ccagtttcaa taaaggattg gtgacaaaca cagaaaaaaa aaaaaaaaa     2100 aaaa                                                                  2104
```

<210> SEQ ID NO 20
<211> LENGTH: 462
<212> TYPE: PRT
<213> ORGANISM: Homo sapiens

<400> SEQUENCE: 20

```
Met Gln Leu Arg Lys Met Gln Thr Val Lys Lys Glu Gln Ala Ser Leu
 1               5                  10                  15
```

-continued

```
Asp Ala Ser Ser Asn Val Asp Lys Met Met Val Leu Asn Ser Ala Leu
             20                  25                  30

Thr Glu Val Ser Glu Asp Ser Thr Gly Glu Glu Leu Leu Leu Ser
         35                  40                  45

Glu Gly Ser Val Gly Lys Asn Lys Ser Ala Cys Arg Arg Lys Arg
 50                  55                  60

Glu Phe Ile Pro Asp Glu Lys Lys Asp Ala Met Tyr Trp Glu Lys Arg
 65                  70                  75                  80

Arg Lys Asn Asn Glu Ala Ala Lys Arg Ser Arg Glu Lys Arg Arg Leu
                 85                  90                  95

Asn Asp Leu Val Leu Glu Asn Lys Leu Ile Ala Leu Gly Glu Glu Asn
             100                 105                 110

Ala Thr Leu Lys Ala Glu Leu Leu Ser Leu Lys Leu Lys Phe Gly Leu
         115                 120                 125

Ile Ser Ser Thr Ala Tyr Ala Gln Glu Ile Gln Lys Leu Ser Asn Ser
     130                 135                 140

Thr Ala Val Tyr Phe Gln Asp Tyr Gln Thr Ser Lys Ser Asn Val Ser
145                 150                 155                 160

Ser Phe Val Asp Glu His Glu Pro Ser Met Val Ser Ser Cys Ile
             165                 170                 175

Ser Val Ile Lys His Ser Pro Gln Ser Ser Leu Ser Asp Val Ser Glu
         180                 185                 190

Val Ser Val Glu His Thr Gln Glu Ser Ser Val Gln Gly Ser Cys
     195                 200                 205

Arg Ser Pro Glu Asn Lys Phe Gln Ile Ile Lys Gln Glu Pro Met Glu
210                 215                 220

Leu Glu Ser Tyr Thr Arg Glu Pro Arg Asp Asp Arg Gly Ser Tyr Thr
225                 230                 235                 240

Ala Ser Ile Tyr Gln Asn Tyr Met Gly Asn Ser Phe Ser Gly Tyr Ser
             245                 250                 255

His Ser Pro Pro Leu Leu Gln Val Asn Arg Ser Ser Asn Ser Pro
         260                 265                 270

Arg Thr Ser Glu Thr Asp Asp Gly Val Val Gly Lys Ser Ser Asp Gly
     275                 280                 285

Glu Asp Glu Gln Gln Val Pro Lys Gly Pro Ile His Ser Pro Val Glu
290                 295                 300

Leu Lys His Val His Ala Thr Val Val Lys Val Pro Glu Val Asn Ser
305                 310                 315                 320

Ser Ala Leu Pro His Lys Leu Arg Ile Lys Ala Lys Ala Met Gln Ile
             325                 330                 335

Lys Val Glu Ala Phe Asp Asn Glu Phe Glu Ala Thr Gln Lys Leu Ser
         340                 345                 350

Ser Pro Ile Asp Met Thr Ser Lys Arg His Phe Glu Leu Glu Lys His
     355                 360                 365

Ser Ala Pro Ser Met Val His Ser Ser Leu Thr Pro Phe Ser Val Gln
370                 375                 380

Val Thr Asn Ile Gln Asp Trp Ser Leu Lys Ser Glu His Trp His Gln
385                 390                 395                 400

Lys Glu Leu Ser Gly Lys Thr Gln Asn Ser Phe Lys Thr Gly Val Val
             405                 410                 415

Glu Met Lys Asp Ser Gly Tyr Lys Val Ser Asp Pro Glu Asn Leu Tyr
         420                 425                 430

Leu Lys Gln Gly Ile Ala Asn Leu Ser Ala Glu Val Val Ser Leu Lys
```

```
           435                 440                 445
Arg Leu Ile Ala Thr Gln Pro Ile Ser Ala Ser Asp Ser Gly
   450                 455                 460

<210> SEQ ID NO 21
<211> LENGTH: 3270
<212> TYPE: DNA
<213> ORGANISM: Homo sapiens

<400> SEQUENCE: 21
actcagactc tgatggctct gtagctaact ggcccatcct cagagactaa cgcaaaggaa      60
cgaatttcca ggatgttcga ctatgtggag aaaacaaaaa aaaagcaaag aaaaaaatat     120
ttttaaagaa agaaagaagg ccaggtgcag tggctcacgc ctgtaatccc aacactttgg     180
gaggccgagg cagacagatc acctgaggtc aggagttcaa gaccagcctg ccaacatgg      240 agatctgcgc tgaccccag tttatcattg gaggagccac ccgcacagac atctgccaag      300
gagccctggg tgactgctgg ctgctggcag ccattgcctc cctcaccttg aatgaagaaa     360
tcctggctcg agtcgtcccc ctaaaccaga gcttccagga aaactatgca gggatctttc     420
acttccagtt ctggcaatac ggcgagtggg tggaggtggt ggtggatgac aggctgccca     480
ccaaggacgg ggagctgctc tttgtgcatt cagccgaagg gagcgagttc tggagcgccc     540
tgctggagaa ggcatacgcc aagatcaacg gatgctatga gcgctatca ggggtgccaa      600 ccactgaggg cttcgaagac ttcaccggag gcattgctga gtggtatgag ttgaagaagc     660
cccctcccaa cctgttcaag atcatccaga aagctctgca aaaggctct ctccttggct      720 gctccatcga catcaccagc gccgcggact cggaggccat cacgtttcag aagctggtga     780
aggggcacgc gtactcggtc accggagccg aggaggttga agtaacggaa gcctacagaa     840
aactgatccg catccgaaat ccctggggag aagtggagtg gacagggcgg tggaatgaca     900
actgcccaag ctggaacact atagaccag aggagaggga aaggctgacc agacggcatg      960
aagatggaga attctggatg tcttcagtg acttcctgag gcactattcc cgcctggaga    1020 tctgtaaccct gacccccagac actctcacca gcgataccta caagaagtgg aaactcacca     1080
aaatggatgg gaactggagg cggggctcca ccgcgggagg ttgcaggaac tacccgaaca    1140
cattctggat gaaccctcag tacctgatca gctggaggaa ggaggatgag gacgaggagg    1200
atggggagag cggctgcacc ttcctggtgg ggctcattca gaagcaccga cggcggcaga    1260
ggaagatggg cgaggacatg cacaccatcg gctttggcat ctatgaggtt ccagaggagt    1320
taagtgggca gaccaacatc cacctcagca aaaacttctt cctgacgaat cgcgccaggg    1380
agcgctcaga caccttcatc aacctccggg aggtgctcaa ccgcttcaag ctgccgccag    1440
gagagtacat tctcgtgcct tccaccttcg aacccaacaa ggatgggat ttctgcatcc      1500 gggtcttttc tgaaaagaaa gctgactacc aagctgtcga tgatgaaatc gaggccaatc    1560
ttgaagagtt cgacatcagc gaggatgaca ttgatgatgg attcaggaga ctgtttgccc    1620
agttggcagg agaggatgcg gagatctctg cctttgagct gcagaccatc ctgagaaggg    1680
ttctagcaaa gcgccaagat atcaagtcag atggcttcag catcgagaca tgcaaaatta    1740
tggttgacat gctagattcg gacggagtg gcaagctggg gctgaaggag ttctacattc      1800
tctggacgaa gattcaaaaa taccaaaaaa tttaccgaga aatcgacgtt gacaggtctg    1860
gtaccatgaa ttcctatgaa atgcggaagg cattagaaga agcaggtttc aagatgcct      1920 gtcaactcca ccaagtcatc gttgctcggt ttgcagatga ccagctcatc atcgattttg    1980
```

```
ataattttgt tcggtgtttg gttcggctgg aaacgctatt caagatattt aagcagctgg   2040
atcccgagaa tactggaaca atagagctcg accttatctc ttggctctgt ttctcagtac   2100
tttgaagtta taactaatct gcctgaagac ttctcatgat ggaaaatcag ccaaggacta   2160
agcttccata gaaatacact ttgtatctgg acctcaaaat tatgggaaca tttacttaaa   2220
cggatgatca tagctgaaaa taatgatact gtcaatttga gatagcagaa gtttcacaca   2280
tcaaagtaaa agatttgcat atcattatac taaatgcaaa tgagtcgctt aacccttgac   2340
aaggtcaaag aaagctttaa atctgtaaat agtatacact ttttactttt acacactttc   2400
ctgttcatag caatattaaa tcaggaaaaa aaaatgcagg gaggtattta acagctgagc   2460
aaaaacattg agtcgctctc aaaggacacg aggcccttgg cagggaatat ttaaagcaac   2520
ttcaagttta aaatgcagct gttgattcta ccaaacaaca gtccaagatt accatttccc   2580
atgagccaac tgggaaacat ggtatatcat gaagtaatct tgtcaaggca tctggagagt   2640
ccaggagaga agactcacct ctgtcgcttg ggttaaacaa gagacaggtt ttgtagaata   2700
ttgattggta atagtaaatc gttctcctta caatcaagtt cttgacccta ttcggcctta   2760
tacatctggt cttacaaaga ccaaagggat cctgcgcttg atcaactgaa ccagtatgcc   2820
aaaaccaggc atccaatttg taaaccaatt atgataaagg acaaaataag ctgtttgcca   2880
cctcaaaact ttatgaactt caccaccact agtgtctgtc catggagtta gagggacat    2940 cacttagaag ttcttataga aaggacacaa gtttgtttcc tggctttacc ttgggaaaat   3000
gctagcaaca ttatagaaat tttgccttgt tgccttatct tcttccaaat gtactgttaa   3060
ataaaaataa agggttaccc catgcaatca caccatgcca tgttttcctt cctggagggc   3120
agccccacag gacggtttat gagcacacaa ttatagcttg tttctacttt aacaaggtat   3180
gctgcctctg taaattcatg tattcaaagg aaaagacacc ttgcctataa ttaaaatgtg   3240
gaactataaa atttttttaaa atccaaaaaa                                  3270
```

```
<210> SEQ ID NO 22
<211> LENGTH: 622
<212> TYPE: PRT
<213> ORGANISM: Homo sapiens

<400> SEQUENCE: 22

Met Glu Ile Cys Ala Asp Pro Gln Phe Ile Ile Gly Gly Ala Thr Arg
 1               5                  10                  15

Thr Asp Ile Cys Gln Gly Ala Leu Gly Asp Cys Trp Leu Leu Ala Ala
            20                  25                  30

Ile Ala Ser Leu Thr Leu Asn Glu Glu Ile Leu Ala Arg Val Val Pro
        35                  40                  45

Leu Asn Gln Ser Phe Gln Glu Asn Tyr Ala Gly Ile Phe His Phe Gln
    50                  55                  60

Phe Trp Gln Tyr Gly Glu Trp Val Glu Val Val Asp Asp Arg Leu
65                  70                  75                  80

Pro Thr Lys Asp Gly Glu Leu Leu Phe Val His Ser Ala Glu Gly Ser
                85                  90                  95

Glu Phe Trp Ser Ala Leu Leu Glu Lys Ala Tyr Ala Lys Ile Asn Gly
            100                 105                 110

Cys Tyr Glu Ala Leu Ser Gly Gly Ala Thr Thr Glu Gly Phe Glu Asp
        115                 120                 125

Phe Thr Gly Gly Ile Ala Glu Trp Tyr Glu Leu Lys Lys Pro Pro Pro
    130                 135                 140
```

```
Asn Leu Phe Lys Ile Ile Gln Lys Ala Leu Gln Lys Gly Ser Leu Leu
145                 150                 155                 160

Gly Cys Ser Ile Asp Ile Thr Ser Ala Ala Asp Ser Glu Ala Ile Thr
                165                 170                 175

Phe Gln Lys Leu Val Lys Gly His Ala Tyr Ser Val Thr Gly Ala Glu
            180                 185                 190

Glu Val Glu Ser Asn Gly Ser Leu Gln Lys Leu Ile Arg Ile Arg Asn
        195                 200                 205

Pro Trp Gly Glu Val Glu Trp Thr Gly Arg Trp Asn Asp Asn Cys Pro
    210                 215                 220

Ser Trp Asn Thr Ile Asp Pro Glu Glu Arg Glu Arg Leu Thr Arg Arg
225                 230                 235                 240

His Glu Asp Gly Glu Phe Trp Met Ser Phe Ser Asp Phe Leu Arg His
                245                 250                 255

Tyr Ser Arg Leu Glu Ile Cys Asn Leu Thr Pro Asp Thr Leu Thr Ser
                260                 265                 270

Asp Thr Tyr Lys Lys Trp Lys Leu Thr Lys Met Asp Gly Asn Trp Arg
            275                 280                 285

Arg Gly Ser Thr Ala Gly Gly Cys Arg Asn Tyr Pro Asn Thr Phe Trp
        290                 295                 300

Met Asn Pro Gln Tyr Leu Ile Lys Leu Glu Glu Glu Asp Glu Asp Glu
305                 310                 315                 320

Glu Asp Gly Glu Ser Gly Cys Thr Phe Leu Val Gly Leu Ile Gln Lys
                325                 330                 335

His Arg Arg Arg Gln Arg Lys Met Gly Glu Asp Met His Thr Ile Gly
                340                 345                 350

Phe Gly Ile Tyr Glu Val Pro Glu Glu Leu Ser Gly Gln Thr Asn Ile
            355                 360                 365

His Leu Ser Lys Asn Phe Phe Leu Thr Asn Arg Ala Arg Glu Arg Ser
        370                 375                 380

Asp Thr Phe Ile Asn Leu Arg Glu Val Leu Asn Arg Phe Lys Leu Pro
385                 390                 395                 400

Pro Gly Glu Tyr Ile Leu Val Pro Ser Thr Phe Glu Pro Asn Lys Asp
                405                 410                 415

Gly Asp Phe Cys Ile Arg Val Phe Ser Glu Lys Lys Ala Asp Tyr Gln
                420                 425                 430

Ala Val Asp Asp Glu Ile Glu Ala Asn Leu Glu Glu Phe Asp Ile Ser
            435                 440                 445

Glu Asp Asp Ile Asp Asp Gly Phe Arg Arg Leu Phe Ala Gln Leu Ala
    450                 455                 460

Gly Glu Asp Ala Glu Ile Ser Ala Phe Glu Leu Gln Thr Ile Leu Arg
465                 470                 475                 480

Arg Val Leu Ala Lys Arg Gln Asp Ile Lys Ser Asp Gly Phe Ser Ile
                485                 490                 495

Glu Thr Cys Lys Ile Met Val Asp Met Leu Asp Ser Asp Gly Ser Gly
            500                 505                 510

Lys Leu Gly Leu Lys Glu Phe Tyr Ile Leu Trp Thr Lys Ile Gln Lys
        515                 520                 525

Tyr Gln Lys Ile Tyr Arg Glu Ile Asp Val Asp Arg Ser Gly Thr Met
    530                 535                 540

Asn Ser Tyr Glu Met Arg Lys Ala Leu Glu Glu Ala Gly Phe Lys Met
545                 550                 555                 560

Pro Cys Gln Leu His Gln Val Ile Val Ala Arg Phe Ala Asp Asp Gln
```

```
              565                 570                 575
Leu Ile Ile Asp Phe Asp Asn Phe Val Arg Cys Leu Val Arg Leu Glu
            580                 585                 590

Thr Leu Phe Lys Ile Phe Lys Gln Leu Asp Pro Glu Asn Thr Gly Thr
            595                 600                 605

Ile Glu Leu Asp Leu Ile Ser Trp Leu Cys Phe Ser Val Leu
            610                 615                 620

<210> SEQ ID NO 23
<211> LENGTH: 3136
<212> TYPE: DNA
<213> ORGANISM: Homo sapiens

<400> SEQUENCE: 23
gcgcagaact tggggagccg ccgccgccat ccgccgccgc agccagcttc cgccgccgca      60
ggaccggccc ctgccccagc ctccgcagcc gcggcgcgtc cacgcccgcc cgcgcccagg     120
gcgagtcggg gtcgccgcct gcacgcttct cagtgttccc cgcgccccgc atgtaacccg     180
gccaggcccc cgcaactgtg tccectgcag ctccagcccc gggctgcacc ccccgccccc     240
gacaccagct ctccagcctg ctcgtccagg atggccgcgg ccaaggccga gatgcagctg     300
atgtccccgc tgcagatctc tgacccgttc ggatcctttc ctcactcgcc caccatggac     360
aactacccta gctggaggag atgatgctgc tgagcaacg gggctcccca gttcctcggc      420
gccgccgggg ccccagaggg cagcggcagc aacagcagca gcagcagcag cggggcggt     480 ggaggcggcg gggcggcag caacagcagc agcagcagca gcaccttcaa ccctcaggcg     540
gacacgggcg agcagcccta cgagcacctg accgcagagt ctttcctga catctctctg     600 aacaacgaga aggtgctggt ggagaccagt taccccagcc aaaccactcg actgccccc      660 atcacctata ctggccgctt tccctggag cctgcaccca acagtggcaa caccttgtgg     720
cccgagcccc tcttcagctt ggtcagtggc ctagtgagca tgaccaaccc accggcctcc     780
tcgtcctcag caccatctcc agcggcctcc tccgcctccg cctcccagag cccacccctg     840
agctgcgcag tgccatccaa cgacagcagt cccatttact cagcggcacc caccttcccc     900
acgccgaaca ctgacatttt ccctgagcca caaagccagg ccttcccggg ctcggcaggg     960
acagcgctcc agtacccgcc tcctgcctac cctgccgcca agggtggctt ccaggttccc    1020
atgatccccg actacctgtt tccacagcag caggggatc tgggcctggg cacccagac     1080 cagaagccct tccagggcct ggagagccgc acccagcagc cttcgctaac ccctctgtct    1140
actattaagg cctttgccac tcagtcgggc tccaggacc tgaaggccct caataccagc    1200
taccagtccc agctcatcaa cccagccgc atgcgcaagt accccaaccg gcccagcaag    1260 acgcccccc acgaacgccc ttacgcttgc cagtggagt cctgtgatcg ccgcttctcc    1320
cgctccgacg agctcaccc ccacatccgc atccacacag ccagaagcc cttccagtgc    1380 cgcatctgca tgcgcaactt cagccgcagc gaccacctca ccacccacat ccgcacccac    1440
acaggcgaaa agcccttcgc ctgcgacatc tgtggaagaa agtttgccag gagcgatgaa    1500
cgcaagaggc ataccaagat ccacttgcgg cagaaggaca agaaagcaga caaagtgtt     1560 gtggcctctt cggccacctc ctctctctct tcctacccgt ccccggttgc tacctcttac    1620
ccgtccccgg ttactacctc ttatccatcc ccggccacca cctcatacc atcccctgtg    1680 cccacctcct tctcctctcc cggctcctcg acctacccat cccctgtgca cagtggcttc    1740 ccctcccgt cggtggccac cacgtactcc tctgttcccc ctgctttccc ggcccaggtc    1800
```

```
agcagcttcc cttcctcagc tgtcaccaac tccttcagcg cctccacagg gctttcggac   1860
atgacagcaa ccttttctcc caggacaatt gaaatttgct aaagggaaag gggaaagaaa   1920
gggaaaaggg agaaaaagaa acacaagaga cttaaaggac aggaggagga gatggccata   1980
ggagaggagg gttcctctta ggtcagatgg aggttctcag agccaagtcc tccctctcta   2040
ctggagtgga aggtctattg ccaacaatc ctttctgccc acttcccctt ccccaattac    2100
tattcccttt gacttcagct gcctgaaaca gccatgtcca agttcttcac ctctatccaa   2160
agaacttgat ttgcatggat tttggataaa tcatttcagt atcatctcca tcatatgcct   2220 gacccttgc tcccttcaat gctagaaaat cgagttggca aaatgggggtt tgggcccctc   2280 agagccctgc cctgcaccct tgtacagtgt ctgtgccatg gatttcgttt ttcttggggt   2340
actcttgatg tgaagataat ttgcatattc tattgtatta tttggagtta ggtcctcact   2400
tgggggaaaa aaaaaaaaga aaagccaagc aaaccaatgg tgatcctcta ttttgtgatg   2460
atgctgtgac aataagtttg aaccttttt tttgaaacag cagtcccagt attctcagag    2520
catgtgtcag agtgttgttc cgttaacctt tttgtaaata ctgcttgacc gtactctcac   2580
atgtggcaaa atatgtttg gttttctttt tttttttttt ttgaaagtgt ttttctttcg    2640 tcctttggt ttaaaagtt tcacgtcttg gtgccttttg tgtgatgcgc cttgctgatg    2700
gcttgacatg tgcaattgtg agggacatgc tcacctctag ccttaagggg ggcagggagt   2760
gatgatttgg gggaggcttt gggagcaaaa taaggaagag ggctgagctg agcttcggtt   2820
ctccagaatg taagaaaaca aaatctaaaa caaaatctga actctcaaaa gtctattttt   2880
ttaactgaaa atgtaaattt ataaatatat tcaggagttg gaatgttgta gttacctact   2940
gagtaggcgg cgatttttgt atgttatgaa catgcagttc attattttgt ggttctattt   3000
tactttgtac ttgtgtttgc ttaaacaaag tgactgtttg gcttataaac acattgaatg   3060
cgctttattg cccatgggat atgtggtgta tatccttcca aaaattaaa acgaaaataa    3120 agtagctgcg attggg                                                   3136
```

<210> SEQ ID NO 24
<211> LENGTH: 543
<212> TYPE: PRT
<213> ORGANISM: Homo sapiens

<400> SEQUENCE: 24

```
Met Ala Ala Ala Lys Ala Glu Met Gln Leu Met Ser Pro Leu Gln Ile
  1               5                  10                  15

Ser Asp Pro Phe Gly Ser Phe Pro His Ser Pro Thr Met Asp Asn Tyr
             20                  25                  30

Pro Lys Leu Glu Glu Met Met Leu Leu Ser Asn Gly Ala Pro Gln Phe
         35                  40                  45

Leu Gly Ala Ala Gly Ala Pro Glu Gly Ser Gly Ser Asn Ser Ser Ser
     50                  55                  60

Ser Ser Ser Gly Gly Gly Gly Gly Gly Gly Ser Asn Ser Ser
 65                  70                  75                  80

Ser Ser Ser Ser Thr Phe Asn Pro Gln Ala Asp Thr Gly Glu Gln Pro
                 85                  90                  95

Tyr Glu His Leu Thr Ala Glu Ser Phe Pro Asp Ile Ser Leu Asn Asn
            100                 105                 110

Glu Lys Val Leu Val Glu Thr Ser Tyr Pro Ser Gln Thr Thr Arg Leu
        115                 120                 125

Pro Pro Ile Thr Tyr Thr Gly Arg Phe Ser Leu Glu Pro Ala Pro Asn
```

```
            130                 135                 140
Ser Gly Asn Thr Leu Trp Pro Glu Pro Leu Phe Ser Leu Val Ser Gly
145                 150                 155                 160

Leu Val Ser Met Thr Asn Pro Pro Ala Ser Ser Ser Ala Pro Ser
                165                 170                 175

Pro Ala Ala Ser Ser Ala Ser Ala Ser Gln Ser Pro Leu Ser Cys
                180                 185                 190

Ala Val Pro Ser Asn Asp Ser Ser Pro Ile Tyr Ser Ala Ala Pro Thr
                195                 200                 205

Phe Pro Thr Pro Asn Thr Asp Ile Phe Pro Glu Pro Gln Ser Gln Ala
                210                 215                 220

Phe Pro Gly Ser Ala Gly Thr Ala Leu Gln Tyr Pro Pro Pro Ala Tyr
225                 230                 235                 240

Pro Ala Ala Lys Gly Gly Phe Gln Val Pro Met Ile Pro Asp Tyr Leu
                245                 250                 255

Phe Pro Gln Gln Gln Gly Asp Leu Gly Leu Gly Thr Pro Asp Gln Lys
                260                 265                 270

Pro Phe Gln Gly Leu Glu Ser Arg Thr Gln Gln Pro Ser Leu Thr Pro
                275                 280                 285

Leu Ser Thr Ile Lys Ala Phe Ala Thr Gln Ser Gly Ser Gln Asp Leu
290                 295                 300

Lys Ala Leu Asn Thr Ser Tyr Gln Ser Gln Leu Ile Lys Pro Ser Arg
305                 310                 315                 320

Met Arg Lys Tyr Pro Asn Arg Pro Ser Lys Thr Pro Pro His Glu Arg
                325                 330                 335

Pro Tyr Ala Cys Pro Val Glu Ser Cys Asp Arg Arg Phe Ser Arg Ser
                340                 345                 350

Asp Glu Leu Thr Arg His Ile Arg Ile His Thr Gly Gln Lys Pro Phe
                355                 360                 365

Gln Cys Arg Ile Cys Met Arg Asn Phe Ser Arg Ser Asp His Leu Thr
                370                 375                 380

Thr His Ile Arg Thr His Thr Gly Glu Lys Pro Phe Ala Cys Asp Ile
385                 390                 395                 400

Cys Gly Arg Lys Phe Ala Arg Ser Asp Glu Arg Lys Arg His Thr Lys
                405                 410                 415

Ile His Leu Arg Gln Lys Asp Lys Lys Ala Asp Lys Ser Val Val Ala
                420                 425                 430

Ser Ser Ala Thr Ser Ser Leu Ser Ser Tyr Pro Ser Pro Val Ala Thr
                435                 440                 445

Ser Tyr Pro Ser Pro Val Thr Thr Ser Tyr Pro Ser Pro Ala Thr Thr
450                 455                 460

Ser Tyr Pro Ser Pro Val Pro Thr Ser Phe Ser Ser Pro Gly Ser Ser
465                 470                 475                 480

Thr Tyr Pro Ser Pro Val His Ser Gly Phe Pro Ser Pro Ser Val Ala
                485                 490                 495

Thr Thr Tyr Ser Ser Val Pro Pro Ala Phe Pro Ala Gln Val Ser Ser
                500                 505                 510

Phe Pro Ser Ser Ala Val Thr Asn Ser Phe Ser Ala Ser Thr Gly Leu
                515                 520                 525

Ser Asp Met Thr Ala Thr Phe Ser Pro Arg Thr Ile Glu Ile Cys
530                 535                 540
```

<210> SEQ ID NO 25

<211> LENGTH: 3677
<212> TYPE: DNA
<213> ORGANISM: Homo sapiens

<400> SEQUENCE: 25

```
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180
cattttttt taaaactgta ttgtttctcg ttttaattta ttttttgcttg ccattcccca     240
cttgaatcgg gccgacggct tggggagatt gctctacttc cccaaatcac tgtggatttt     300
ggaaaccagc agaaagagga aagaggtagc aagagctcca gagagaagtc gaggaagaga     360
gagacgggt cagagagagc gcgcgggcgt gcgagcagcg aaagcgacag ggcaaagtg       420
agtgacctgc ttttgggggt gaccgccgga gcgcggcgtg agccctcccc cttgggatcc     480
cgcagctgac cagtcgcgct gacggacaga cagacagaca ccgcccccag ccccagctac     540
cacctcctcc ccggccggcg gcggacagtg gacgcggcgg cgagccgcgg gcaggggccg     600
gagcccgcgc ccggaggcgg ggtgggagggg gtcgggctcc gcggcgtcgc actgaaactt     660
ttcgtccaac ttctgggctg ttctcgcttc ggaggagccg tggtccgcgc ggggggaagcc    720
gagccgagcg gagccgcgag aagtgctagc tcgggccggg aggagccgca gccggaggag    780
ggggaggagg aagaagagaa ggaagaggag aggggggccgc agtggcgact cggcgctcgg     840
aagccgggct catggacggg tgaggcggcg gtgtgcgcag acagtgctcc agccgcgcgc     900
gctccccagg ccctggcccg ggcctcgggc cggggaggaa gagtagctcg ccgaggcgcc     960
gaggagagcg ggccgccca cagcccgagc cggagaggga gcgcgagccg cgccggcccc    1020
ggtcgggcct ccgaaaccat gaactttctg ctgtcttggg tgcattggag ccttgccttg    1080
ctgctctacc tccaccatgc caagtggtcc caggctgcac ccatggcaga aggaggaggg    1140
cagaatcatc acgaagtggt gaagttcatg gatgtctatc agcgcagcta ctgccatcca    1200
atcgagaccc tggtggacat cttccaggag taccctgatg agatcgagta catcttcaag    1260
ccatcctgtg tgcccctgat gcgatgcggg ggctgctgca atgacgaggg cctggagtgt    1320
gtgcccactg aggagtccaa catcaccatg cagattatgc ggatcaaacc tcaccaaggc    1380
cagcacatag gagagatgag cttcctacag cacaacaaat gtgaatgcag accaaagaaa    1440
gatagagcaa gacaagaaaa aaaatcagtt cgaggaaagg gaaaggggca aaaacgaaag    1500
cgcaagaaat cccggtataa gtcctggagc gtgtacgttg gtgcccgctg ctgtctaatg    1560
ccctggagcc tccctggccc ccatccctgt gggccttgct cagagcggag aaagcatttg    1620
tttgtacaag atccgcagac gtgtaaatgt tcctgcaaaa acacagactc gcgttgcaag    1680
gcgaggcagc ttgagttaaa cgaacgtact tgcagatgtg acaagccgag gcggtgagcc    1740
gggcaggagg aaggagcctc cctcagggtt tcgggaacca gatctctcac caggaaagac    1800
tgatacagaa cgatcgatac agaaaccacg ctgccgccac cacaccatca ccatcgacag    1860
aacagtcctt aatccagaaa cctgaaatga aggaagagga gactctgcgc agagcacttt    1920
gggtccggag ggcgagactc cggcggaagc attcccgggc gggtgaccca gcacggtccc    1980
tcttggaatt ggattcgcca ttttattttt cttgctgcta aatcaccgag cccggaagat    2040
tagagagttt tatttctggg attcctgtag acacacccac ccacatacat acatttatat    2100
atatatatat tatatatata taaaaataaa tatctctatt ttatatatat aaaatatata    2160
tattcttttt ttaaattaac agtgctaatg ttattggtgt cttcactgga tgtatttgac    2220
```

```
tgctgtggac ttgagttggg aggggaatgt tcccactcag atcctgacag ggaagaggag   2280
gagatgagag actctggcat gatctttttt ttgtcccact tggtggggcc agggtcctct   2340
cccctgccca ggaatgtgca aggccagggc atggggggcaa atatgaccca gttttgggaa  2400
caccgacaaa cccagccctg cgctgagcc tctctacccc aggtcagacg gacagaaaga   2460
cagatcacag gtacagggat gaggacaccg gctctgacca ggagtttggg gagcttcagg   2520
acattgctgt gctttgggga ttccctccac atgctgcacg cgcatctcgc ccccaggggc   2580
actgcctgga agattcagga gcctgggcgg ccttcgctta ctctcacctg cttctgagtt   2640
gcccaggaga ccactggcag atgtcccggc gaagagaaga gacacattgt tggaagaagc   2700
agcccatgac agctccccctt cctgggactc gccctcatcc tcttcctgct cccctttcctg 2760 gggtgcagcc taaaaggacc tatgtcctca caccattgaa accactagtt ctgtcccccc   2820
aggagacctg gttgtgtgtg tgtgagtggt tgaccttcct ccatccctg gtccttccct   2880 tcccttcccg aggcacagag agacagggca ggatccacgt gcccattgtg gaggcagaga   2940
aaagagaaag tgttttatat acggtactta tttaatatcc ctttttaatt agaaattaaa   3000
acagttaatt taattaaaga gtagggtttt ttttcagtat tcttggttaa tatttaattt   3060
caactattta tgagatgtat cttttgctct ctcttgctct cttatttgta ccggttttttg 3120 tatataaaat tcatgtttcc aatctctctc tccctgatcg gtgacagtca ctagcttatc   3180
ttgaacagat atttaatttt gctaacactc agctctgccc tccccgatcc cctggctccc   3240
cagcacacat tcctttgaaa taaggtttca atatacatct acatactata tatatattg   3300 gcaacttgta tttgtgtgta tatatatata tatgttta tgtatatatg tgattctgat   3360
aaaatagaca ttgctattct gtttttata tgtaaaaaca aacaagaaa aaatagagaa    3420 ttctacatac taaatctctc tcctttttta attttaatat ttgttatcat ttatttattg   3480
gtgctactgt ttatccgtaa taattgtggg gaaaagatat taacatcacg tctttgtctc   3540
tagtgcagtt tttcgagata ttccgtagta catatttatt tttaaacaac gacaaagaaa   3600
tacagatata tcttaaaaaa aaaaagcat tttgtattaa agaatttaat tctgatctca   3660
aaaaaaaaaa aaaaaaa                                                 3677
```

<210> SEQ ID NO 26
<211> LENGTH: 412
<212> TYPE: PRT
<213> ORGANISM: Homo sapiens

<400> SEQUENCE: 26

```
Met Thr Asp Arg Gln Thr Asp Thr Ala Pro Ser Pro Ser Tyr His Leu
  1               5                  10                  15

Leu Pro Gly Arg Arg Thr Val Asp Ala Ala Ser Arg Gly Gln
             20                  25                  30

Gly Pro Glu Pro Ala Pro Gly Gly Val Glu Gly Val Gly Ala Arg
             35                  40                  45

Gly Val Ala Leu Lys Leu Phe Val Gln Leu Leu Gly Cys Ser Arg Phe
 50                  55                  60

Gly Gly Ala Val Val Arg Ala Gly Glu Ala Glu Pro Ser Gly Ala Ala
 65                  70                  75                  80

Arg Ser Ala Ser Ser Gly Arg Glu Glu Pro Gln Pro Glu Gly Glu
             85                  90                  95

Glu Glu Glu Glu Lys Glu Glu Glu Arg Gly Pro Gln Trp Arg Leu Gly
            100                 105                 110
```

```
Ala Arg Lys Pro Gly Ser Trp Thr Gly Glu Ala Ala Val Cys Ala Asp
            115                 120                 125

Ser Ala Pro Ala Ala Arg Ala Pro Gln Ala Leu Ala Arg Ala Ser Gly
        130                 135                 140

Arg Gly Gly Arg Val Ala Arg Gly Ala Glu Glu Ser Gly Pro Pro
145                 150                 155                 160

His Ser Pro Ser Arg Arg Gly Ser Ala Ser Ala Gly Pro Gly Arg
                165                 170                 175

Ala Ser Glu Thr Met Asn Phe Leu Leu Ser Trp Val His Trp Ser Leu
            180                 185                 190

Ala Leu Leu Leu Tyr Leu His His Ala Lys Trp Ser Gln Ala Ala Pro
        195                 200                 205

Met Ala Glu Gly Gly Gly Gln Asn His His Glu Val Val Lys Phe Met
    210                 215                 220

Asp Val Tyr Gln Arg Ser Tyr Cys His Pro Ile Glu Thr Leu Val Asp
225                 230                 235                 240

Ile Phe Gln Glu Tyr Pro Asp Glu Ile Glu Tyr Ile Phe Lys Pro Ser
                245                 250                 255

Cys Val Pro Leu Met Arg Cys Gly Gly Cys Cys Asn Asp Glu Gly Leu
            260                 265                 270

Glu Cys Val Pro Thr Glu Glu Ser Asn Ile Thr Met Gln Ile Met Arg
        275                 280                 285

Ile Lys Pro His Gln Gly Gln His Ile Gly Glu Met Ser Phe Leu Gln
    290                 295                 300

His Asn Lys Cys Glu Cys Arg Pro Lys Lys Asp Arg Ala Arg Gln Glu
305                 310                 315                 320

Lys Lys Ser Val Arg Gly Lys Gly Lys Gly Gln Lys Arg Lys Arg Lys
                325                 330                 335

Lys Ser Arg Tyr Lys Ser Trp Ser Val Tyr Val Gly Ala Arg Cys Cys
            340                 345                 350

Leu Met Pro Trp Ser Leu Pro Gly Pro His Pro Cys Gly Pro Cys Ser
        355                 360                 365

Glu Arg Arg Lys His Leu Phe Val Gln Asp Pro Gln Thr Cys Lys Cys
    370                 375                 380

Ser Cys Lys Asn Thr Asp Ser Arg Cys Lys Ala Arg Gln Leu Glu Leu
385                 390                 395                 400

Asn Glu Arg Thr Cys Arg Cys Asp Lys Pro Arg Arg
                405                 410

<210> SEQ ID NO 27
<211> LENGTH: 5093
<212> TYPE: DNA
<213> ORGANISM: Homo sapiens

<400> SEQUENCE: 27
aaagatgacc gtggttaagg cagtagaaag caggctcgac actgagacgc ggttccagcc      60
ctagaaggat tgcattttac gattcaggca aacttcgagt ctcctcatgt gacatgtgtg     120
cactcctgga ccgttttaat tatgagaaac gtggtttgca gcatgattcc ttccagtcga     180
taaatcggaa tctctctcgc tcccaccccct tcttaacttc aggcttcctg catcccggag    240
cactcccggc agcccttcc ctccccccgcc ccggggatgc tccgactcgg cgcttagcca     300
ttcatcaacc ggttcacacc ggcggcggcc gccgcggagt gacgtccgga ggggcgggc     360 ctccgccccc gcctgtcggc tcctggcccg cggttccagg ccgcgattgg tggctggagg    420
```

```
gttgcacgtc gcgccggcta taaaggggag ggcttgtgac gcaagggcgc ctcggcgcgt    480
gtattggctc cttcggctgc gggccggctc ggctacgcgc tctgctccga gccgctcact    540
gcatggtaga gtctggtgcc cccgccgccg cctgcatcgc cgccaccgcc gctccgccac    600
gaccaccgcc gcctcctgcc ctgcagccac cgccaccgcc tgtgtcgccg ccgcctcggg    660
accggctgta tgattaggcc acaatcttca atgagtaaac atattcctca attctgtggt    720
gttcttggtc acacatttat ggagtttctg aagggcagtg gagattactg ccaggcacag    780
cacgacctct atgcagacaa gtgaactgta gaaactgatt actgctccac caagaagccc    840
ccataagagt ggttatcctg gacacagaag tgttgaattg aaatccacag agcattttac    900
aagagttctg acctggatgg ggtaaacctc agtgcacttc ttttctgttg gcctcagtat    960
tactggattt aagaattgct gcttcttgtt aggaggttca tttcacttat cattacttac   1020
aacttcatac tcaaagcact gagaatttca agtggagtat attgaagtag acttcagttt   1080
ctttgcatca tttctgtatt caattttttt aattatttca taccctatt gagtgttttt    1140 taactaaatt aacatggctc gaatgaaccg cccagctcct gtggaagtca catacaagaa   1200
catgagattt cttattacac acaatccaac caatgcgacc ttaaacaaat ttatagagga   1260
acttaagaag tatggagtta ccacaatagt aagagtatgt gaagcaactt atgacactac   1320
tcttgtggag aaagaaggta tccatgttct tgattggcct tttgatgatg gtgcaccacc   1380
atccaaccag attgttgatg actggttaag tcttgtgaaa attaagtttc gtgaagaacc   1440
tggttgttgt attgctgttc attgcgttgc aggccttggg agagctccag tacttgttgc   1500
cctagcatta attgaaggtg aatgaaata cgaagatgca gtacaattca taagacaaaa   1560
gcggcgtgga gcttttaaca gcaagcaact tctgtatttg gagaagtatc gtcctaaaat   1620
gcggctgcgt ttcaaagatt ccaacggtca tagaaacaac tgttgcattc aataaaattg   1680
gggtgcctaa tgctactgga agtggaactt gagatagggc ctaatttgtt atacatatta   1740
gccaacatgt tggcttagta agtctaatga agcttccata ggagtattga aaggcagttt   1800
taccaggcct caagctagac agatttggca acctctgtat ttgggttaca gtcaacctat   1860
ttggatactt ggcaaaagat tcttgctgtc agcatataaa atgtgcttgt catttgtatc   1920
aattgacctt tccccaaatc atgcagtatt gagttatgac ttgttaaatc tattcccatg   1980
ccagaatctt atcaatacat aagaaattta ggaagattag gtgccaaaat acccagcaca   2040
atacttgtat attttagta ccatacagaa gtaaatccc aggaactatg aacactagac    2100
cttatgtggt ttattccttc aatcatttca aacattgaaa gtagggccta catggttatt   2160
tgcctgctca ctttatgttt acatctccca cattcatacc aatatacgtc aggtttgctt   2220
aaccattgat tttttttttt ttttaccaag tcttacagtg attatttac gtgtttccat    2280 gtatctcact ttgtgctgta ttaaaaaaac ctccattttg aaaatctacg ttgtacagaa   2340
gcacatgtct ttaatgtctt cagacaaaaa agccttacat taatttaatg tttgcactct   2400
gaggtgcaac ttaacaggga gggcctgaga aaagaatggg aggggctat taattatttt    2460 tagcaaaatg ttgcctttgt cttgtgcaaa catgtagaat atgctcttta atttagtaaa   2520 atatttttt aaaggtaga gatgcttgt tattgtaatc ataaacttcc tgaaattctt      2580
gtaatttttt tcccatactt atcagaagtg tgtttaccaa cttattttg tttgaaagtg    2640 tgatttttt tttccttccc aacctctctt gcaaaaaaag aaatgggttt ctgctaatga    2700
attgagcaga catctaatat tttatatgcc ttttgagctg tgtaacttaa tatttggata   2760
```

```
cttgacaatt tgttttatta tgtaattgat aaaatggtga tgtgtattaa tgttagttca    2820
accatatatt tatactgtct ggggatgtgt ggttatagtt ctgtgggaga ataattttg    2880 tcagtgttca ccagcttgta aaacttagt gcgagagctg aaacatctaa ataaataatg    2940
acatgcattt atcatcattg agattggttt gcttaaaatt aacttatttt gtagaagaca    3000
aaatgaattg cacttcactt aatgtgtgtc ctcatctttt tacaaataaa tgaaggatta    3060
taaatgatgt cagcatttta gtaaactttt agacaaaatt tgttagggtc attcatgaaa    3120
actttaatac taaaagcact ttccattata tacttttaa aggtctagat aattttgaac     3180
caatttatta ttgtgtactg aggagaaata atgtatagta gaggacagcc ttggtttgta    3240
aagctcagtt ccactagttc atggttttgt gcaacttctg agcctcagtt ttctcctttg    3300
caaattaata attacatacc tttatagatt ttgaaattaa tttaaatatt agtatttggt    3360
acatgaaggc ttaatgttaa gtttccttta atgatccaca ataatccctt tgatcacgtt    3420
aatctaaatc tagatgtctt tgtctaattt ttttgaata gcagttataa atgtaaagga     3480
ctcaaagttt aagtaaaaag tgatactcca ccttgtgttt caagaatttt agttccacct    3540
cttcatacca gtttaacact taatatattt cattggattt tagacagggc aaaaggaaga    3600 acagggggcct ctggaggccc ttggttattt aaatcttgga ttatttgtga tagtaatcac   3660
aaattttggg ctaatttta acctgaggtt ttgtttttt tttaaaggaa atgcagccta      3720
gtcttgagaa cataatttta tataatcaat tactaaatgt taaactatta ccacacagcc    3780
cataaaacag catttgcgtt tattgagaga gaggatgtgc catcatgatt aatgaaaact    3840
atcttttgag tttgaaaaga aattaatttg cagtgtttgg attgtatata tggtgctaaa    3900
aataaattaa tttactttat aaaccttatc tgtacattat acgatgtgat gaaatttgct    3960
ttttatccaa atattttgta tcttgtaaat atggctaatt ataggaatgc ctataataca    4020
tcttagattc cttatatcta ataagagttc aaagagttat gagttgaagt cttgaatgca    4080
ggaaactatc tgatagtgtt ctaaaatttg gttacttggg tttggatacc cttagtggga    4140
tgatgtaaat agaggctagc tacctaggct tgtctatagc aaccataatg ttgatgtaag    4200
taatgcggtt actgaatcat aagaaaatgc catctctttt tagttgaagg aaaactctgg    4260
aagtaggtgc cattggtcat tctgcagtgc actgcaacca ttgtttcccc tagtgccctc    4320 ttttcctag ggcattgctc tcctattccc acgccttaac acagctctat acctagaagc     4380
agccagccca ggcatgcagt cacatttaat cacatccccc ttctagagtg cttcaaaatg    4440
atgtagtccc tcaacttggc taaagaatct caatctcttg aaatttattt ttttaatgtc    4500
atattcatct ggtaaatatc tactgtttgc caggcattta agaatatggc aaagaacata    4560
aaagatggtg tcaccagatt ttggtcacca atgagtaccc gacccgttgc catgattaag    4620
agagaatgct ttctattgga gtttcaggaa atataatttg agaatacttt aaagggaagt    4680
ggaagtataa gtgaatgata tttttctttt acatgtaaac aatgaagtta tttcaaagtt    4740
aagttttaaa caaaatacat gaagtagtgt ctgccataca tgttaatatt ctacattctt    4800
gcttccttaa attaatatgt ttgtgtgtat atatgtgcct cacacctgaa ttgaaaatta    4860
aagactggtt taaagtggt ttaaagtga catttaatgt ttctccatta cgtttggggt      4920
aaccagccta agtggaatct tggaaggaaa gtaagggaaa aacttgtatt tgccttcaat    4980
gaattaaacc agtgatatgt gttaacgtat gaatgaaagg attgatggtg attttataat    5040
tatatatatt gccgcagtaa ccagttaata aattgatagc taccattta aaa            5093
```

<210> SEQ ID NO 28
<211> LENGTH: 173
<212> TYPE: PRT
<213> ORGANISM: Homo sapiens

<400> SEQUENCE: 28

Met Ala Arg Met Asn Arg Pro Ala Pro Val Glu Val Thr Tyr Lys Asn
1               5                   10                  15

Met Arg Phe Leu Ile Thr His Asn Pro Thr Asn Ala Thr Leu Asn Lys
            20                  25                  30

Phe Ile Glu Glu Leu Lys Lys Tyr Gly Val Thr Thr Ile Val Arg Val
        35                  40                  45

Cys Glu Ala Thr Tyr Asp Thr Thr Leu Val Glu Lys Glu Gly Ile His
    50                  55                  60

Val Leu Asp Trp Pro Phe Asp Asp Gly Ala Pro Pro Ser Asn Gln Ile
65                  70                  75                  80

Val Asp Asp Trp Leu Ser Leu Val Lys Ile Lys Phe Arg Glu Glu Pro
                85                  90                  95

Gly Cys Cys Ile Ala Val His Cys Val Ala Gly Leu Gly Arg Ala Pro
            100                 105                 110

Val Leu Val Ala Leu Ala Leu Ile Glu Gly Met Lys Tyr Glu Asp
        115                 120                 125

Ala Val Gln Phe Ile Arg Gln Lys Arg Arg Gly Ala Phe Asn Ser Lys
    130                 135                 140

Gln Leu Leu Tyr Leu Glu Lys Tyr Arg Pro Lys Met Arg Leu Arg Phe
145                 150                 155                 160

Lys Asp Ser Asn Gly His Arg Asn Asn Cys Cys Ile Gln
                165                 170

<210> SEQ ID NO 29
<211> LENGTH: 2949
<212> TYPE: DNA
<213> ORGANISM: Homo sapiens

<400> SEQUENCE: 29

```
agtttcccga ccagagagaa cgaacgtgtc tgcgggcgcg cggggagcag aggcggtggc    60
gggcggcggc ggcaccggga ccgccgagt gaccctcccc cgcccctctg gcccccacc    120
ctcccacccg cccgtggccc gcgcccatgg ccgcgcgcgc tccacacaac tcaccggagt    180
ccgcgccttg cgccgccgac cagttcgcag ctccgcgcca cggcagccag tctcacctgg    240
cggcaccgcc cgcccaccgc ccggccaca gccctgcgc ccacggcagc actcgaggcg    300
accgcgacag tggtggggga cgctgctgag tggaagagag cgcagcccgg ccaccggacc    360
tacttactcg ccttgctgat tgtctatttt tgcgtttaca acttttctaa gaacttttgt    420
atacaaagga acttttaaa aaagacgctt ccaagttata tttaatccaa agaagaagga    480
tctcggccaa tttggggttt tgggttttgg cttcgtttct tctcttcgtt gactttgggg    540
ttcaggtgcc ccagctgctt cgggctgccg aggaccttct gggcccccac attaatgagg    600
cagccacctg gcgagtctga catggctgtc agcgacgcgc tgctcccatc tttctccacg    660
ttcgcgtctg gccggcggg aagggagaag acactgcgtc aagcaggtgc cccgaataac    720
cgctggcggg aggagctctc ccacatgaag cgacttcccc cagtgcttcc cggccgcccc    780
tatgacctgg cggcggcgac cgtggccaca gacctggaga gcggcggagc cggtgcgggct    840
tgcggcggta gcaacctggc gccccctacct cggagagaga ccgaggagtt caacgatctc    900
ctggacctgg actttattct ctccaattcg ctgacccatc ctccggagtc agtggccgcc    960
```

```
accgtgtcct cgtcagcgtc agcctcctct tcgtcgtcgc cgtcgagcag cggccctgcc    1020
agcgcgccct ccacctgcag cttcacctat ccgatccggg ccgggaacga cccgggcgtg    1080
gcgccgggcg gcacgggcgg aggcctcctc tatggcaggg agtccgctcc ccctccgacg    1140
gctcccttca acctggcgga catcaacgac gtgagcccct cgggcggctt cgtggccgag    1200
ctcctgcggc cagaattgga cccggtgtac attccgccgc agcagccgca gccgccaggt    1260
ggcgggctga tgggcaagtt cgtgctgaag gcgtcgctga gcgcccctgg cagcgagtac    1320
ggcagcccgt cggtcatcag cgtcagcaaa ggcagccctg acggcagcca cccggtggtg    1380
gtggcgccct acaacggcgg gccgccgcgc acgtgcccca agatcaagca ggaggcggtc    1440
tcttcgtgca cccacttggg cgctggaccc cctctcagca atggccaccg gccggctgca    1500
cacgacttcc ccctggggcg gcagctcccc agcaggacta ccccgaccct gggtcttgag    1560
gaagtgctga gcagcaggga ctgtcaccct gccctgccgc ttcctcccgg cttccatccc    1620
cacccggggc ccaattaccc atccttcctg cccgatcaga tgcagccgca agtcccgccg    1680
ctccattacc aagagctcat gccacccggt tcctgcatgc cagaggagcc caagccaaag    1740
aggggaagac gatcgtggcc ccggaaaagg accgccaccc acacttgtga ttacgcgggc    1800
tgcggcaaaa cctacacaaa gagttcccat ctcaaggcac acctgcgaac ccacacaggt    1860
gagaaacctt accactgtga ctgggacggc tgtggatgga aattcgcccg ctcagatgaa    1920
ctgaccaggc actaccgtaa acacacgggg caccgcccgt tccagtgcca aaaatgcgac    1980
cgagcatttt ccaggtcgga ccacctcgcc ttacacatga gaggcatttt ttaaatccca    2040
gacagtggat atgacccaca ctgccagaag agaattcagt attttttact tttcacactg    2100
tcttcccgat gagggaagga gcccagccag aaagcactac aatcatggtc aagttcccaa    2160
ctgagtcatc ttgtgagtgg ataatcagga aaaatgagga atccaaaaga caaaaatcaa    2220
agaacagatg gggtctgtga ctggatcttc tatcattcca attctaaatc cgacttgaat    2280
attcctggac ttacaaaatg ccaagggggt gactggaagt tgtggatatc agggtataaa    2340
ttatatccgt gagttggggg agggaagacc agaattccct tgaattgtgt attgatgcaa    2400
tataagcata aagatcacc ttgtattctc tttaccttct aaaagccatt attatgatgt    2460
tagaagaaga ggaagaaatt caggtacaga aacatgtttt aaatagccta atgatggtg    2520
cttggtgagt cttggttcta aaggtaccaa acaaggaagc caaagttttc aaactgctgc    2580
atactttgac aaggaaaatc tatatttgtc ttccgatcaa catttatgac ctaagtcagg    2640
taatatacct ggtttacttc tttagcattt ttatgcagac agtctgttat gcactgtggt    2700
ttcagatgtg caataatttg tacaatggtt tattcccaag tatgccttaa gcagaacaaa    2760
tgtgtttttc tatatagttc cttgccttaa taaatatgta atataaattt aagcaaacgt    2820
ctattttgta tatttgtaaa ctacaaagta aaatgaacat tttgtggagt ttgtattttg    2880
catactcaag gtgagaatta agttttaaat aaacctataa tattttatct gaaaaaaaaa    2940
aaaaaaaaa                                                            2949
```

<210> SEQ ID NO 30
<211> LENGTH: 479
<212> TYPE: PRT
<213> ORGANISM: Homo sapiens

<400> SEQUENCE: 30

Met Arg Gln Pro Pro Gly Glu Ser Asp Met Ala Val Ser Asp Ala Leu
 1               5                  10                  15

```
Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
 50                  55                  60

Leu Ala Ala Ala Thr Val Ala Thr Asp Leu Glu Ser Gly Gly Ala Gly
 65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Gly Pro Ala Ser Ala
130                 135                 140

Pro Ser Thr Cys Ser Phe Thr Tyr Pro Ile Arg Ala Gly Asn Asp Pro
145                 150                 155                 160

Gly Val Ala Pro Gly Thr Gly Gly Leu Leu Tyr Gly Arg Glu
                165                 170                 175

Ser Ala Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Gly Gly Gly
210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
                245                 250                 255

Gly Ser His Pro Val Val Ala Pro Tyr Asn Gly Gly Pro Pro Arg
            260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
            340                 345                 350

Pro Asp Gln Met Gln Pro Gln Val Pro Pro Leu His Tyr Gln Glu Leu
        355                 360                 365

Met Pro Pro Gly Ser Cys Met Pro Glu Glu Pro Lys Pro Lys Arg Gly
370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
            420                 425                 430
```

```
        Cys Gly Trp Lys Phe Ala Arg Ser Asp Glu Leu Thr Arg His Tyr Arg
            435                 440                 445

Lys His Thr Gly His Arg Pro Phe Gln Cys Gln Lys Cys Asp Arg Ala
            450                 455                 460

Phe Ser Arg Ser Asp His Leu Ala Leu His Met Lys Arg His Phe
        465                 470                 475

<210> SEQ ID NO 31
<211> LENGTH: 3376
<212> TYPE: DNA
<213> ORGANISM: Homo sapiens

<400> SEQUENCE: 31
ggcgaccgaa cgcggcggtc ggcagcgttc gcgcggggc ctgcgaagcg ctgctcgggg      60
ccggcactgc ccgcggggag gacgcgccgc cgccgccacc cagcgccgcc gccgccgccg     120
cctccagccg ggccgccgcg cgtcccgggg gccggccccg cgagcgcagg agtaaacacc     180
gccggagtct tggagccgct gcagaaggga ataaagagag atgcagggat tgtgaggtt      240 acggcgcccc agctgcaaga tgcactagcc ggctgaaccc gggatcggct gacttgttgg     300
aaccggagtg ctctgcacgg agagtggtgg atgagttgaa gttgccttcc cggggctcat     360
tttccacgct gccgagagga atccgagagg caaggcaatc acttcgtctt gccattgatt     420
gggtatcggg agcttttttt ttctcccctc tctctttctt ttcctccgtc ttgttgcatg     480
caagaaaatt acagtccgct gctcgcccgc cctgggtgcg agatattcag ccccgctctc     540
tcccgtgcat tgtgcaaccc aaagatgaaa gaccgaaggg gagaaagtta agaaatcgc      600 ccacatgcgc tggatcagtc cacggcttgg ggaaaggcat ccagagaagg tgggagcgga     660
gagtttgaag tctttacagg cgggaagatg gcggactgga gctgaaagtg ttgattggga     720
aacttgggtg attcttgtgt ttatttacaa tcctcttgac ccaggcagga cacatgcagg     780
ccaaaaaacg ctatttcatc ctgctctcag ctggctcttg tctcgcccct ttgttttatt     840
tcggaggctt gcagtttagg gcatcgagga gccacagccg agagaagaa cacagcggta      900 ggaatggctt gcaccacccc agtccggatc atttctggcc ccgcttcccg gacgctctgc     960 gcccttcgt tccttgggat caattggaaa acgaggattc cagcgtgcac atttccccc     1020 ggcagaagcg agatgccaac tccagcatct acaaaggcaa gaagtgccgc atggagtcct    1080
gcttcgattt cacccctttgc aagaaaaacg gcttcaaagt ctacgtatac ccacagcaaa    1140
aaggggagaa aatcgccgaa agttaccaaa acattctagc ggccatcgag ggctccaggt    1200
tctacacctc ggaccccagc caggcgtgcc tctttgtcct gagtctggat actttagaca    1260
gagaccagtt gtcacctcag tatgtgcaca atttgagatc caaagtgcag agtctccact    1320
tgtggaacaa tggtaggaat catttaattt ttaatttata ttccggcact ggcctgact     1380 acaccgagga cgtggggttt gacatcggcc aggcgatgct ggccaaagcc agcatcagta    1440
ctgaaaactt ccgacccaac tttgatgttt ctattcccct cttttctaag gatcatccca    1500
ggacaggagg ggagagggg tttttgaagt tcaacaccat ccctcctctc aggaagtaca    1560
tgctggtatt caaggggaag aggtacctga cagggatagg atcagacacc aggaatgcct    1620
tatatcacgt ccataacggg gaggacgttg tgctcctcac cacctgcaag catggcaaag    1680
actggcaaaa gcacaaggat tctcgctgtg acagagacaa caccgagtat gagaagtatg    1740
attatcggga aatgctgcac aatgccactt tctgtctggt tcctcgtggt cgcaggcttg    1800
ggtccttcag attcctggag gctttgcagg ctgcctgcgt ccctgtgatg ctcagcaatg    1860
```

-continued

```
gatgggagtt gccattctct gaagtgatta attggaacca agctgccgtc ataggcgatg    1920
agagattgtt attacagatt ccttctacaa tcaggtctat tcatcaggat aaaatcctag    1980
cacttagaca gcagacacaa ttcttgtggg aggcttattt ttcttcagtt gagaagattg    2040
tattaactac actagagatt attcaggaca gaatattcaa gcacatatca cgtaacagtt    2100
taatatggaa caaacatcct ggaggattgt tcgtactacc acagtattca tcttatctgg    2160
gagattttcc ttactactat gctaatttag gtttaaagcc ccctccaaa ttcactgcag     2220 tcatccatgc ggtgaccccc ctggtctctc agtcccagcc agtgttgaag cttctcgtgg    2280
ctgcagccaa gtcccagtac tgtgcccaga tcatagttct atggaattgt gacaagcccc    2340
taccagccaa acaccgctgg cctgccactg ctgtgcctgt cgtcgtcatt gaaggagaga    2400
gcaaggttat gagcagccgt tttctgccct acgacaacat catcacagac gccgtgctca    2460
gccttgacga ggacacggtg ctttcaacaa cagaggtgga tttcgccttc acagtgtggc    2520
agagcttccc tgagaggatt gtggggtacc ccgcgcgcag ccacttctgg gataactcta    2580
aggagcggtg gggatacaca tcaaagtgga cgaacgacta ctccatggtg ttgacaggag    2640
ctgctattta ccacaaatat tatcactacc tatactccca ttacctgcca gccagcctga    2700
agaacatggt ggaccaattg gccaattgtg aggacattct catgaacttc ctggtgtctg    2760
ctgtgacaaa attgcctcca atcaaagtga cccagaagaa gcagtataag gagacaatga    2820
tgggacagac ttctcgggct tcccgttggg ctgaccctga ccactttgcc cagcgacaga    2880
gctgcatgaa tacgtttgcc agctggtttg gctacatgcc gctgatccac tctcagatga    2940
ggctcgaccc cgtcctcttt aaagaccagg tctctatttt gaggaagaaa taccgagaca    3000
ttgagcgact ttgaggaatc cggctgagtg ggggagggga agcaagaagg gatggggtc     3060 aagctgctct ctcttcccag tgcagatcca ctcatcagca gagccagatt gtgccaacta    3120
tccaaaaact tagatgagca gaatgacaaa aaaaaaaagg ccaatgagaa ctcaactcct    3180
ggctcctggg actgcaccag actgctccaa actcacctca ctggcttctg tgtcccaaga    3240
ctaggttgtg tacagtttaa ttatggaaca ttaaataatt attttgaaa tgattgctat     3300 gcaggtttaa acttttttaa tgatcaaaac tattaaaaac cagagttctt tgtttaatca    3360
aaaaaaaaaa aaaaaa                                                     3376
```

<210> SEQ ID NO 32
<211> LENGTH: 746
<212> TYPE: PRT
<213> ORGANISM: Homo sapiens

<400> SEQUENCE: 32

```
Met Gln Ala Lys Lys Arg Tyr Phe Ile Leu Leu Ser Ala Gly Ser Cys
  1               5                  10                  15

Leu Ala Leu Leu Phe Tyr Phe Gly Gly Leu Gln Phe Arg Ala Ser Arg
             20                  25                  30

Ser His Ser Arg Arg Glu Glu His Ser Gly Arg Asn Gly Leu His His
         35                  40                  45

Pro Ser Pro Asp His Phe Trp Pro Arg Phe Pro Asp Ala Leu Arg Pro
     50                  55                  60

Phe Val Pro Trp Asp Gln Leu Glu Asn Glu Asp Ser Ser Val His Ile
 65                  70                  75                  80

Ser Pro Arg Gln Lys Arg Asp Ala Asn Ser Ser Ile Tyr Lys Gly Lys
                 85                  90                  95

Lys Cys Arg Met Glu Ser Cys Phe Asp Phe Thr Leu Cys Lys Lys Asn
```

```
                100             105             110
Gly Phe Lys Val Tyr Val Tyr Pro Gln Gln Lys Gly Glu Lys Ile Ala
        115             120             125
Glu Ser Tyr Gln Asn Ile Leu Ala Ala Ile Glu Gly Ser Arg Phe Tyr
        130             135             140
Thr Ser Asp Pro Ser Gln Ala Cys Leu Phe Val Leu Ser Leu Asp Thr
145             150             155             160
Leu Asp Arg Asp Gln Leu Ser Pro Gln Tyr Val His Asn Leu Arg Ser
                165             170             175
Lys Val Gln Ser Leu His Leu Trp Asn Asn Gly Arg Asn His Leu Ile
                180             185             190
Phe Asn Leu Tyr Ser Gly Thr Trp Pro Asp Tyr Thr Glu Asp Val Gly
        195             200             205
Phe Asp Ile Gly Gln Ala Met Leu Ala Lys Ala Ser Ile Ser Thr Glu
        210             215             220
Asn Phe Arg Pro Asn Phe Asp Val Ser Ile Pro Leu Phe Ser Lys Asp
225             230             235             240
His Pro Arg Thr Gly Gly Glu Arg Gly Phe Leu Lys Phe Asn Thr Ile
                245             250             255
Pro Pro Leu Arg Lys Tyr Met Leu Val Phe Lys Gly Lys Arg Tyr Leu
                260             265             270
Thr Gly Ile Gly Ser Asp Thr Arg Asn Ala Leu Tyr His Val His Asn
                275             280             285
Gly Glu Asp Val Val Leu Leu Thr Thr Cys Lys His Gly Lys Asp Trp
        290             295             300
Gln Lys His Lys Asp Ser Arg Cys Asp Arg Asp Asn Thr Glu Tyr Glu
305             310             315             320
Lys Tyr Asp Tyr Arg Glu Met Leu His Asn Ala Thr Phe Cys Leu Val
                325             330             335
Pro Arg Gly Arg Arg Leu Gly Ser Phe Arg Phe Leu Glu Ala Leu Gln
                340             345             350
Ala Ala Cys Val Pro Val Met Leu Ser Asn Gly Trp Glu Leu Pro Phe
        355             360             365
Ser Glu Val Ile Asn Trp Asn Gln Ala Ala Val Ile Gly Asp Glu Arg
        370             375             380
Leu Leu Leu Gln Ile Pro Ser Thr Ile Arg Ser Ile His Gln Asp Lys
385             390             395             400
Ile Leu Ala Leu Arg Gln Gln Thr Gln Phe Leu Trp Glu Ala Tyr Phe
                405             410             415
Ser Ser Val Glu Lys Ile Val Leu Thr Thr Leu Glu Ile Ile Gln Asp
                420             425             430
Arg Ile Phe Lys His Ile Ser Arg Asn Ser Leu Ile Trp Asn Lys His
                435             440             445
Pro Gly Gly Leu Phe Val Leu Pro Gln Tyr Ser Ser Tyr Leu Gly Asp
        450             455             460
Phe Pro Tyr Tyr Tyr Ala Asn Leu Gly Leu Lys Pro Pro Ser Lys Phe
465             470             475             480
Thr Ala Val Ile His Ala Val Thr Pro Leu Val Ser Gln Ser Gln Pro
                485             490             495
Val Leu Lys Leu Leu Val Ala Ala Lys Ser Gln Tyr Cys Ala Gln
                500             505             510
Ile Ile Val Leu Trp Asn Cys Asp Lys Pro Leu Pro Ala Lys His Arg
        515             520             525
```

Trp Pro Ala Thr Ala Val Pro Val Val Ile Glu Gly Glu Ser Lys
            530                 535                 540

Val Met Ser Ser Arg Phe Leu Pro Tyr Asp Asn Ile Ile Thr Asp Ala
545                 550                 555                 560

Val Leu Ser Leu Asp Glu Asp Thr Val Leu Ser Thr Thr Glu Val Asp
                565                 570                 575

Phe Ala Phe Thr Val Trp Gln Ser Phe Pro Glu Arg Ile Val Gly Tyr
            580                 585                 590

Pro Ala Arg Ser His Phe Trp Asp Asn Ser Lys Glu Arg Trp Gly Tyr
        595                 600                 605

Thr Ser Lys Trp Thr Asn Asp Tyr Ser Met Val Leu Thr Gly Ala Ala
        610                 615                 620

Ile Tyr His Lys Tyr Tyr His Tyr Leu Tyr Ser His Tyr Leu Pro Ala
625                 630                 635                 640

Ser Leu Lys Asn Met Val Asp Gln Leu Ala Asn Cys Glu Asp Ile Leu
                645                 650                 655

Met Asn Phe Leu Val Ser Ala Val Thr Lys Leu Pro Pro Ile Lys Val
            660                 665                 670

Thr Gln Lys Lys Gln Tyr Lys Glu Thr Met Met Gly Gln Thr Ser Arg
        675                 680                 685

Ala Ser Arg Trp Ala Asp Pro Asp His Phe Ala Gln Arg Gln Ser Cys
690                 695                 700

Met Asn Thr Phe Ala Ser Trp Phe Gly Tyr Met Pro Leu Ile His Ser
705                 710                 715                 720

Gln Met Arg Leu Asp Pro Val Leu Phe Lys Asp Gln Val Ser Ile Leu
                725                 730                 735

Arg Lys Lys Tyr Arg Asp Ile Glu Arg Leu
            740                 745

<210> SEQ ID NO 33
<211> LENGTH: 4827
<212> TYPE: DNA
<213> ORGANISM: Homo sapiens

<400> SEQUENCE: 33
gaagggcaac acgggaccct tgaagcgggg tcgcggcggc gccccagccc gggccaggga      60
gtcccggcag cggcacctcc cagaaagggc ggagccgacg acgccttctt ccttcctgac     120
cggcgcgcgc agcctgctgc cgcggtcagc gcctgctcct gctcctccgc tcctcctgcg     180
cggggtgctg aaacagcccg ggaagtagag ccgcctccg gggagcccaa ccagccgaac      240
gccgccggcg tcagcagcct tgcgcggcca cagcatgacc gctcgcggcc tggcccttgg     300
cctcctcctg ctgctactgt gtccagcgca ggtgttttca cagtcctgtg tttggtatgg     360
agagtgtgga attgcatatg gggacaagag gtacaattgc gaatattctg cgcccaccaa     420
accattgcca aaggatggat atgacttagt gcaggaactc tgtccaggat tcttctttgg     480
caatgtcagt ctctgttgtg atgttcggca gcttcagaca ctaaaagaca acctgcagct     540
gcctctacag tttctgtcca gatgtccatc ctgtttttat aacctactga acctgttttg     600
tgagctgaca tgtagccctc gacagagtca gttttgaat gttacagcta ctgaagatta     660
tgttgatcct gttacaaacc agacgaaaac aaatgtgaaa gagttacaat actacgtcgg     720
acagagtttt gccaatgcaa tgtacaatgc ctgccgggat gtggaggccc cctcaagtaa     780
tgacaaggcc ctgggactcc tgtgtgggaa ggacgctgac gcctgtaatg ccaccaactg     840

```
gattgaatac atgttcaata aggacaatgg acaggcacct tttaccatca ctcctgtgtt    900
ttcagatttt ccagtccatg ggatggagcc catgaacaat gccaccaaag gctgtgacga    960
gtctgtggat gaggtcacag caccatgtag ctgccaagac tgctctattg tctgtggccc   1020
caagccccag cccccacctc ctcctgctcc ctggacgatc cttggcttgg acgccatgta   1080
tgtcatcatg tggatcacct acatggcgtt tttgcttgtg ttttttggag cattttttgc   1140
agtgtggtgc tacagaaaac ggtattttgt ctccgagtac actcccatcg atagcaatat   1200
agcttttttct gttaatgcaa gtgacaaagg agaggcgtcc tgctgtgacc ctgtcagcgc   1260
agcatttgag ggctgcttga ggcggctgtt cacacgctgg gggtcttttct gcgtccgaaa   1320
ccctggctgt gtcattttct tctcgctggt cttcattact gcgtgttcgt caggcctggt   1380
gtttgtccgg gtcacaacca atccagttga cctctggtca gccccagca gccaggctcg   1440
cctggaaaaa gagtactttg accagcactt tgggcctttc ttccggacgg agcagctcat   1500
catccgggcc cctctcactg acaaacacat ttaccagcca tacccttcgg gagctgatgt   1560
accctttgga cctccgcttg acatacgagat actgcaccag gttcttgact acaaatagc   1620
catcgaaaac attactgcct cttatgacaa tgagactgtg acacttcaag acatctgctt   1680
ggccctctt tcaccgtata acacgaactg caccattttg agtgtgttaa attacttcca   1740
gaacagccat tccgtgctgg accacaagaa aggggacgac ttctttgtgt atgccgatta   1800
ccacacgcac tttctgtact gcgtacgggc tcctgcctct ctgaatgata caagtttgct   1860
ccatgaccct tgtctgggta cgtttggtgg accagtgttc ccgtggcttg tgttgggagg   1920
ctatgatgat caaaactaca ataacgccac tgcccttgtg attaccttcc ctgtcaataa   1980
ttactataat gatacagaga agctccagag ggcccaggcc tgggaaaaag agtttattaa   2040
ttttgtgaaa aactacaaga atcccaatct gaccatttcc ttcactgctg aacgaagtat   2100
tgaagatgaa ctaaatcgtg aaagtgacag tgatgtcttc accgttgtaa ttagctatgc   2160
catcatgttt ctatatatt ccctagcctt ggggcacatg aaaagctgtc gcaggcttct   2220
ggtggattcg aaggtctcac taggcatcgc gggcatcttg atcgtgctga gctcggtggc   2280
ttgctccttg ggtgtcttca gctacattgg gttgcccttg accctcattg tgattgaagt   2340
catcccgttc ctggtgctgg ctgttggagt ggacaacatc ttcattctgg tgcaggccta   2400
ccagagagat gaacgtcttc aagggggaaac cctggatcag cagctgggca gggtcctagg   2460
agaagtggct cccagtatgt tcctgtcatc cttttctgag actgtagcat ttttcttagg   2520
agcattgtcc gtgatgccag ccgtgcacac ctttctctctc tttgcgggat tggcagtctt   2580
cattgacttt cttctgcaga ttacctgttt cgtgagtctc ttggggttag acattaaacg   2640
tcaagagaaa aatcggctag acatcttttg ctgtgtcaga ggtgctgaag atggaacaag   2700
cgtccaggcc tcagagagct gtttgtttcg cttcttcaaa aactcctatt ctccacttct   2760
gctaaaggac tggatgagac caattgtgat agcaatattt gtgggtgttc tgtcattcag   2820
catcgcagtc ctgaacaaag tagatattgg attggatcag tctctttcga tgccagatga   2880
ctcctacatg gtggattatt tcaaatccat cagtcagtac ctgcatgcgg gtccgcctgt   2940
gtactttgtc ctggaggaag ggcacgacta cacttcttcc aaggggcaga acatggtgtg   3000
cggcggcatg ggctgcaaca atgattccct ggtgcagcag atatttaacg cggcgcagct   3060
ggacaactat acccgaatag gcttcgcccc ctcgtcctgg atcgacgatt atttcgactg   3120
ggtgaagcca cagtcgtctt gctgtcgagt ggacaatatc actgaccagt tctgcaatgc   3180
ttcagtggtt gaccctgcct gcgttcgctg caggcctctg actccggaag gcaaacagag   3240
```

```
gcctcagggg ggagacttca tgagattcct gcccatgttc ctttcggata accctaaccc    3300
caagtgtggc aaaggggggac atgctgccta tagttctgca gttaacatcc tccttggcca   3360
tggcaccagg gtcggagcca cgtacttcat gacctaccac accgtgctgc agacctctgc   3420
tgactttatt gacgctctga agaaagcccg acttatagcc agtaatgtca ccgaaaccat   3480
gggcattaac ggcagtgcct accgagtatt tccttacagt gtgttttatg tcttctacga   3540
acagtacctg accatcattg acgacactat cttcaacctc ggtgtgtccc tgggcgcgat   3600
atttctggtg accatggtcc tcctgggctg tgagctctgg tctgcagtca tcatgtgtgc   3660
caccatcgcc atggtcttgg tcaacatgtt tggagttatg tggctctggg gcatcagtct   3720
gaacgctgta tccttggtca acctggtgat gagctgtggc atctccgtgg agttctgcag   3780
ccacataacc agagcgttca cggtgagcat gaaaggcagc cgcgtggagc gcgcggaaga   3840
ggcacttgcc cacatgggca gctccgtgtt cagtggaatc acacttacaa aatttggagg   3900
gattgtggtg ttggcttttg ccaaatctca aattttccag atattctact tcaggatgta   3960
tttggccatg gtcttactgg gagccactca cggattaata tttctccctg tcttactcag   4020
ttacataggg ccatcagtaa ataaagccaa aagttgtgcc actgaagagc gatacaaagg   4080
aacagagcgc gaacggcttc taaatttcta gccctctcgc agggcatcct gactgaactg   4140
tgtctaaggg tcggtcggtt taccactgga cgggtgctgc atcggcaagg ccaagttgaa   4200
caccggatgg tgccaaccat cggttgtttg gcagcagctt tgaacgtagc gcctgtgaac   4260
tcaggaatgc acagttgact tgggaagcag tattactaga tctggaggca accacaggac   4320
actaaacttc tcccagcctc ttcaggaaag aaacctcatt ctttggcaag caggaggtga   4380
cactagatgg ctgtgaatgt gatccgctca ctgacactct gtaaaggcca atcaatgcac   4440
tgtctgtctc tcctttttagg agtaagccat cccacaagtt ctataccata ttttagtga    4500
cagttgaggt tgtagataca ctttataaca ttttatagtt taaagagctt tattaatgca   4560
ataaattaac tttgtacaca tttttatata aaaaaacagc aagtgatttc agaatgttgt   4620
aggcctcatt agagcttggt ctccaaaaat ctgtttgaaa aaagcaacat gttcttcaca   4680
gtgttcccct agaaaggaag agatttaatt gccagttaga tgtggcatga atgagggac    4740
aaagaaagca tctcgtaggt gtgtctactg ggttttaact tattttctt taataaaata    4800
cattgttttc ctaaaaaaaa aaaaaaa                                        4827
```

<210> SEQ ID NO 34
<211> LENGTH: 1278
<212> TYPE: PRT
<213> ORGANISM: Homo sapiens

<400> SEQUENCE: 34

Met Thr Ala Arg Gly Leu Ala Leu Gly Leu Leu Leu Leu Leu Leu Cys
1               5                   10                  15

Pro Ala Gln Val Phe Ser Gln Ser Cys Val Trp Tyr Gly Glu Cys Gly
            20                  25                  30

Ile Ala Tyr Gly Asp Lys Arg Tyr Asn Cys Glu Tyr Ser Gly Pro Pro
        35                  40                  45

Lys Pro Leu Pro Lys Asp Gly Tyr Asp Leu Val Gln Glu Leu Cys Pro
    50                  55                  60

Gly Phe Phe Phe Gly Asn Val Ser Leu Cys Cys Asp Val Arg Gln Leu
65                  70                  75                  80

Gln Thr Leu Lys Asp Asn Leu Gln Leu Pro Leu Gln Phe Leu Ser Arg

-continued

```
                85                  90                  95
Cys Pro Ser Cys Phe Tyr Asn Leu Leu Asn Leu Phe Cys Glu Leu Thr
            100                 105                 110

Cys Ser Pro Arg Gln Ser Gln Phe Leu Asn Val Thr Ala Thr Glu Asp
            115                 120                 125

Tyr Val Asp Pro Val Thr Asn Gln Thr Lys Thr Asn Val Lys Glu Leu
130                 135                 140

Gln Tyr Tyr Val Gly Gln Ser Phe Ala Asn Ala Met Tyr Asn Ala Cys
145                 150                 155                 160

Arg Asp Val Glu Ala Pro Ser Ser Asn Asp Lys Ala Leu Gly Leu Leu
            165                 170                 175

Cys Gly Lys Asp Ala Asp Ala Cys Asn Ala Thr Asn Trp Ile Glu Tyr
            180                 185                 190

Met Phe Asn Lys Asp Asn Gly Gln Ala Pro Phe Thr Ile Thr Pro Val
            195                 200                 205

Phe Ser Asp Phe Pro Val His Gly Met Glu Pro Met Asn Asn Ala Thr
210                 215                 220

Lys Gly Cys Asp Glu Ser Val Asp Glu Val Thr Ala Pro Cys Ser Cys
225                 230                 235                 240

Gln Asp Cys Ser Ile Val Cys Gly Pro Lys Pro Gln Pro Pro Pro Pro
            245                 250                 255

Pro Ala Pro Trp Thr Ile Leu Gly Leu Asp Ala Met Tyr Val Ile Met
            260                 265                 270

Trp Ile Thr Tyr Met Ala Phe Leu Leu Val Phe Phe Gly Ala Phe Phe
            275                 280                 285

Ala Val Trp Cys Tyr Arg Lys Arg Tyr Phe Val Ser Glu Tyr Thr Pro
            290                 295                 300

Ile Asp Ser Asn Ile Ala Phe Ser Val Asn Ala Ser Asp Lys Gly Glu
305                 310                 315                 320

Ala Ser Cys Cys Asp Pro Val Ser Ala Ala Phe Glu Gly Cys Leu Arg
            325                 330                 335

Arg Leu Phe Thr Arg Trp Gly Ser Phe Cys Val Arg Asn Pro Gly Cys
            340                 345                 350

Val Ile Phe Phe Ser Leu Val Phe Ile Thr Ala Cys Ser Ser Gly Leu
            355                 360                 365

Val Phe Val Arg Val Thr Thr Asn Pro Val Asp Leu Trp Ser Ala Pro
370                 375                 380

Ser Ser Gln Ala Arg Leu Glu Lys Glu Tyr Phe Asp Gln His Phe Gly
385                 390                 395                 400

Pro Phe Phe Arg Thr Glu Gln Leu Ile Ile Arg Ala Pro Leu Thr Asp
            405                 410                 415

Lys His Ile Tyr Gln Pro Tyr Pro Ser Gly Ala Asp Val Pro Phe Gly
            420                 425                 430

Pro Pro Leu Asp Ile Gln Ile Leu His Gln Val Leu Asp Leu Gln Ile
            435                 440                 445

Ala Ile Glu Asn Ile Thr Ala Ser Tyr Asp Asn Glu Thr Val Thr Leu
            450                 455                 460

Gln Asp Ile Cys Leu Ala Pro Leu Ser Pro Tyr Asn Thr Asn Cys Thr
465                 470                 475                 480

Ile Leu Ser Val Leu Asn Tyr Phe Gln Asn Ser His Ser Val Leu Asp
            485                 490                 495

His Lys Lys Gly Asp Asp Phe Phe Val Tyr Ala Asp Tyr His Thr His
            500                 505                 510
```

```
Phe Leu Tyr Cys Val Arg Ala Pro Ala Ser Leu Asn Asp Thr Ser Leu
        515                 520                 525

Leu His Asp Pro Cys Leu Gly Thr Phe Gly Gly Pro Val Phe Pro Trp
        530                 535                 540

Leu Val Leu Gly Gly Tyr Asp Asp Gln Asn Tyr Asn Asn Ala Thr Ala
545                 550                 555                 560

Leu Val Ile Thr Phe Pro Val Asn Asn Tyr Tyr Asn Asp Thr Glu Lys
        565                 570                 575

Leu Gln Arg Ala Gln Ala Trp Glu Lys Glu Phe Ile Asn Phe Val Lys
        580                 585                 590

Asn Tyr Lys Asn Pro Asn Leu Thr Ile Ser Phe Thr Ala Glu Arg Ser
        595                 600                 605

Ile Glu Asp Glu Leu Asn Arg Glu Ser Asp Ser Asp Val Phe Thr Val
        610                 615                 620

Val Ile Ser Tyr Ala Ile Met Phe Leu Tyr Ile Ser Leu Ala Leu Gly
625                 630                 635                 640

His Met Lys Ser Cys Arg Arg Leu Leu Val Asp Ser Lys Val Ser Leu
                    645                 650                 655

Gly Ile Ala Gly Ile Leu Ile Val Leu Ser Ser Val Ala Cys Ser Leu
                    660                 665                 670

Gly Val Phe Ser Tyr Ile Gly Leu Pro Leu Thr Leu Ile Val Ile Glu
                    675                 680                 685

Val Ile Pro Phe Leu Val Leu Ala Val Gly Val Asp Asn Ile Phe Ile
                    690                 695                 700

Leu Val Gln Ala Tyr Gln Arg Asp Glu Arg Leu Gln Gly Glu Thr Leu
705                 710                 715                 720

Asp Gln Gln Leu Gly Arg Val Leu Gly Glu Val Ala Pro Ser Met Phe
                    725                 730                 735

Leu Ser Ser Phe Ser Glu Thr Val Ala Phe Phe Leu Gly Ala Leu Ser
                    740                 745                 750

Val Met Pro Ala Val His Thr Phe Ser Leu Phe Ala Gly Leu Ala Val
                    755                 760                 765

Phe Ile Asp Phe Leu Leu Gln Ile Thr Cys Phe Val Ser Leu Leu Gly
                    770                 775                 780

Leu Asp Ile Lys Arg Gln Glu Lys Asn Arg Leu Asp Ile Phe Cys Cys
785                 790                 795                 800

Val Arg Gly Ala Glu Asp Gly Thr Ser Val Gln Ala Ser Glu Ser Cys
                    805                 810                 815

Leu Phe Arg Phe Phe Lys Asn Ser Tyr Ser Pro Leu Leu Leu Lys Asp
                    820                 825                 830

Trp Met Arg Pro Ile Val Ile Ala Ile Phe Val Gly Val Leu Ser Phe
                    835                 840                 845

Ser Ile Ala Val Leu Asn Lys Val Asp Ile Gly Leu Asp Gln Ser Leu
850                 855                 860

Ser Met Pro Asp Asp Ser Tyr Met Val Asp Tyr Phe Lys Ser Ile Ser
865                 870                 875                 880

Gln Tyr Leu His Ala Gly Pro Pro Val Tyr Phe Val Leu Glu Glu Gly
                    885                 890                 895

His Asp Tyr Thr Ser Ser Lys Gly Gln Asn Met Val Cys Gly Gly Met
                    900                 905                 910

Gly Cys Asn Asn Asp Ser Leu Val Gln Gln Ile Phe Asn Ala Ala Gln
                    915                 920                 925
```

```
Leu Asp Asn Tyr Thr Arg Ile Gly Phe Ala Pro Ser Ser Trp Ile Asp
    930                 935                 940

Asp Tyr Phe Asp Trp Val Lys Pro Gln Ser Ser Cys Cys Arg Val Asp
945                 950                 955                 960

Asn Ile Thr Asp Gln Phe Cys Asn Ala Ser Val Val Asp Pro Ala Cys
            965                 970                 975

Val Arg Cys Arg Pro Leu Thr Pro Glu Gly Lys Gln Arg Pro Gln Gly
        980                 985                 990

Gly Asp Phe Met Arg Phe Leu Pro Met Phe Leu Ser Asp Asn Pro Asn
            995                1000                1005

Pro Lys Cys Gly Lys Gly His Ala Ala Tyr Ser Ser Ala Val Asn
    1010                1015                1020

Ile Leu Leu Gly His Gly Thr Arg Val Gly Ala Thr Tyr Phe Met Thr
1025                1030                1035                1040

Tyr His Thr Val Leu Gln Thr Ser Ala Asp Phe Ile Asp Ala Leu Lys
                1045                1050                1055

Lys Ala Arg Leu Ile Ala Ser Asn Val Thr Glu Thr Met Gly Ile Asn
        1060                1065                1070

Gly Ser Ala Tyr Arg Val Phe Pro Tyr Ser Val Phe Tyr Val Phe Tyr
    1075                1080                1085

Glu Gln Tyr Leu Thr Ile Ile Asp Asp Thr Ile Phe Asn Leu Gly Val
    1090                1095                1100

Ser Leu Gly Ala Ile Phe Leu Val Thr Met Val Leu Gly Cys Glu
1105                1110                1115                1120

Leu Trp Ser Ala Val Ile Met Cys Ala Thr Ile Ala Met Val Leu Val
            1125                1130                1135

Asn Met Phe Gly Val Met Trp Leu Trp Gly Ile Ser Leu Asn Ala Val
    1140                1145                1150

Ser Leu Val Asn Leu Val Met Ser Cys Gly Ile Ser Val Glu Phe Cys
        1155                1160                1165

Ser His Ile Thr Arg Ala Phe Thr Val Ser Met Lys Gly Ser Arg Val
    1170                1175                1180

Glu Arg Ala Glu Glu Ala Leu Ala His Met Gly Ser Ser Val Phe Ser
1185                1190                1195                1200

Gly Ile Thr Leu Thr Lys Phe Gly Gly Ile Val Val Leu Ala Phe Ala
            1205                1210                1215

Lys Ser Gln Ile Phe Gln Ile Phe Tyr Phe Arg Met Tyr Leu Ala Met
        1220                1225                1230

Val Leu Leu Gly Ala Thr His Gly Leu Ile Phe Leu Pro Val Leu Leu
    1235                1240                1245

Ser Tyr Ile Gly Pro Ser Val Asn Lys Ala Lys Ser Cys Ala Thr Glu
1250                1255                1260

Glu Arg Tyr Lys Gly Thr Glu Arg Glu Arg Leu Leu Asn Phe
1265                1270                1275

<210> SEQ ID NO 35
<211> LENGTH: 6139
<212> TYPE: DNA
<213> ORGANISM: Homo sapiens

<400> SEQUENCE: 35
gtcttcctcc cccagggttg tggccacgcg cagcggcggc ggttgttccg cttccctcc      60 ggcccgggcc gtcgccattg ccgaaggctc cctcccctcc cctccctggc gtgcgcagga    120
ctccgccgcc gctgggccta gcggtagcag cggctgctcc agcgcggcgt ctcttcccgc    180
```

-continued

```
cccgcttccc cttccctccc ctcccctccc cgcaccgcgc gctagcccgg ggcggctccg    240
cagcccgccg ggagctctga ccgaggcgcc tcgctgggc ggggaccttg ccttgcccgg     300
ggccatttca taattctgaa tcatgtctga taacggagaa ctggaagata agcctccagc    360
acctcctgtg cgaatgagca gcaccatctt tagcactgga ggcaaagacc ctttgtcagc    420
caatcacagt ttgaaacctt tgccctctgt tccagaagag aaaaagccca ggcataaaat    480
catctccata ttctcaggca cagagaaagg aagtaaaaag aaagaaaagg aacggccaga    540
aatttctcct ccatctgatt ttgagcacac catccatgtt ggctttgatg ctgttactgg    600
agaattcact ggcatgccag aacagtgggc tcgattacta cagacctcca atatcaccaa    660
actagagcaa aagaagaatc ctcaggctgt gctggatgtc ctaaagttct acgactccaa    720
cacagtgaag cagaaatatc tgagctttac tcctcctgag aaagatggct tccttctgg    780 aacaccagca ctgaatgcca agggaacaga agcacccgca gtagtgacag aggaggagga    840
tgatgatgaa gagactgctc ctcccgttat tgccccgcga ccggatcata cgaaatcaat    900
ttacacacgg tctgtaattg accctgttcc tgcaccagtt ggtgattcac atgttgatgg    960
tgctgccaag tctttagaca aacagaaaaa gaagactaag atgacagatg aagagattat   1020
ggagaaatta agaactatcg tgagcatagg tgaccctaag aaaaaatata caagatatga   1080
aaaaattgga caaggggctt ctggtacagt tttcactgct actgacgttg cactgggaca   1140
ggaggttgct atcaaacaaa ttaatttaca gaaacagcca agaaggaac tgatcattaa    1200 cgagattctg gtgatgaaag aattgaaaaa tcccaacatc gttaactttt tggacagtta   1260
cctggtagga gatgaattgt ttgtggtcat ggaatacctt gctgggggt cactcactga    1320 tgtggtaaca gaaacgtgca tggatgaagc acagattgct gctgtatgca gagagtgttt   1380
acaggcattg gagttttac atgctaatca agtgatccac agagacatca aaagtgacaa    1440
tgtacttttg ggaatggaag gatctgttaa gctcactgac tttggtttct gtgcccagat    1500 caccctgag cagagcaaac gcagtaccat ggtcggaacg ccatactgga tggcaccaga    1560
ggtggttaca cggaaagctt atggccctaa agtcgacata tggtctctgg gtatcatggc    1620
tattgagatg gtagaaggag agcctccata cctcaatgaa atcccttga gggccttgta    1680 cctaatagca actaatggaa ccccagaact tcagaatcca gagaaacttt ccccaatatt    1740
tcgggatttc ttaaatcgat gtttggaaat ggatgtggaa aaagggggtt cagccaaaga    1800
attattacag catcctttcc tgaaactggc caaaccgtta tctagcttga caccactgat    1860
catggcagct aaagaagcaa tgaagagtaa ccgttaacat cactgctgtg gcctcatact    1920
ctttttccca ttttctacaa gaagcctttt agtatatgaa aattattact cttttttgggg   1980 tttaaagaaa tggtctgcat aacctgaatg aaagaagcaa atgactattc tctgaagaca    2040
accaagagaa aattgcaaaa agacaagtat gacttttata tgaaccccctt ctttagggtc    2100 cagaaggaat tgtggactga atcactagcc ttaggtcttt cagcaaacag cctatcaggg    2160
ccatttatca tgtgtgagat ttgcatttta ctttgctgac tttgttgtaa tagatcccat    2220
tcattgtccc ctttggggta tttccaatac ttgaatggca gattggagtt tttcagagta    2280 tgtgttcat ctgctagtct ttctctcctt catagcttt cttttcctgg acttgctcct     2340
tttgagttgc ttttgcgttt ctcatgccta ggcaagtgta atagaaatta tgtagctcct    2400
tatgttggca aaggagctct atatagtttc acttttgtata aaagttagga ccagctgttg    2460
ttacatgtaa tattttagtt cagaacttga cctgaaggaa gggaagaaaa gtatgtgatt    2520
```

```
tttacctttt ttaacaaatg tgaaaaagtc agttttagaa atttcgtggt agtaagttcg    2580
gcatttgtta catgtataga gagaagacta ataatctcta tttataacta aatcattgag    2640
atagaaaaag attcccattg actgtagact tcttcccatt ttgtcttccc ttctgcctgt    2700
ttccccttca ggcttggctc taggaaccaa agtgatttgt tgttgttcca acctgggctt    2760
tgtgactttg gttagtgcca ctaccttctt ccctcctttc cccttcaat ttggaaataa    2820 atttctgtat atgttgcaat tttaggttta ggtttgttct ttttcttttt cattaatcct    2880
ctctcacctc acagataccc cctcccatgg caaataatat aataaccagt gaattttcag    2940
gaatttaaaa attagctttt ttccacttaa aggagaaaaa tatttgggac tagcagcaga    3000
ggcagtaaga gatgtgaacc ttggtgagct ctgatacagt gagaagagat tatactcatg    3060
aaagagaatg ttagtgttac agagaagcag ccgatagcaa atcgactgta gagacttggc    3120
ggcggtggca ttgccccagg tcgtcagcag tgtggtatta tctatgagaa cttgagcgac    3180
agagtatttc ttgatgaatt tatagatcat ttgagatgtt gagttacttt agtttagttt    3240
tgttttgttt tttcaaataa gtagagacta ttgtaaaaaa cgagaaagga aaatgaaatg    3300
tgcgtgttga tagcaataat ttgtttcttt taaagattct aaaaggtctg agacctgtag    3360
cattaattat ttgagtgccc tcccttctcc cctcccctcc cttttctctt ctcttttttc    3420
ctctcctctt cttctccttt attcattgtt ttgcttttgg agtgggtgtt gttcaagtat    3480
ctgtggtttg gttctggcat tttgttccca ccatccccctt cccccattaa cttccccccct   3540 gcttgccatc ctgcagtagt ataaatcatg aataaaaaat aattttgctg ttgtagtata    3600
cattggagaa actggcaggt tttatttcca ttattttatt tccactatat ctatgataag    3660
atgcaattat aaggagagaa gtgactgttt tttattgata aggcaagatt ttcagaaaaa    3720
tgagtaaaat aattaatgaa acatatttag agcacttaat ggtctctgtt ttcaatataa    3780
ttcttgattt cattttttctc tggaatatat tggccttcta cagctattac tgaattatag    3840
aaactggttt atttctggca gaaagctgca gtgccacctg agttccaaat tttaccattc    3900
tttgtaaaca gttggatgga ttatgataaa gaagatgcta ccaatgaaat agaaaaccaa    3960
cgagatgaga agactgtgat cctcatgtac tcagaggcac ttccctccta agtcaaagac    4020
catcctcact gactatgtgc caacgcctcg tttcaggctt gtgactcaac aaagggcttt    4080
tccattgata gaagcagttt gggatttgta gttgcgactt cttcgatagt tacctgcacg    4140
tccattgctg gcaactgact tgtcattaaa acctggctct ttggttaagg gagctacgct    4200
gtggtttatt cttaagttac gtggataaac taacctctaa cagaaatata ctttggttaa    4260
ttttgaaatg tgtcattttt aaacaatctt aaaagtaata cagaattgtg atttattaat    4320
tttaaaacat tcagaacttg ttgaaagaaa aattatatct gaatcaagat tcatgttttt    4380 tattttatt tttttgata cagagtctca ctctgtcact caggctggag tgcagtgaca    4440
tgatctcagc tcactgcaac ctccgcttcc tgggttcaag caattctcat gcctcagcct    4500
cctgagtagc tgagaccaca ggcacccgcc accacaccca gctatttttt tgtattttta    4560
gtagagacag agtctcacca cattgcccag gctggtctcc aactcctgag ctcaggcagt    4620
ctgcccacct tggcctccca agtgctgca gttacaggcg tgagccactg cacctggcct    4680
catgtttttt aaataattgc cttttatatt tacccttttt gtcatcactt tagaatgaaa    4740
attcccattt aaatctgaaa gttaccttaa tagtcctctt gtgttattag gacagtatta    4800
ttatagtact tatttatttt attttagatt taaagttatc ttctcttttt ctttttctt    4860 ctgctgcttt tagggacaat taaaactggg aaactatgaa acatggaaca ttttatccta    4920
```

```
cctgaaagta aacgagtaat tgtgaagcat aagacactga ggctaataca actctgtctt    4980
catgtgttga ctgcctggca catagtattc attctcttcc ctttaacata gaagtgtcca    5040
gctgcgtaca gtctagtaac cagcaactgt aaacgaacct gtgcctctaa caagcgattc    5100
taaaccacct atgagtattt cttttagggc tcacttaaat acatgtttgt atatactgta    5160
ttctagccag aataatttta gatctgatca ggtagtagct aaaattagaa aaaacaaaa     5220 tagatgctta aagaatttgc atccattttt gagtctaaat cttttaaaat atactgagat    5280
ccacatctag tgaaatgtca gtgtcaaaat attatagatt atagctaaaa tccagattaa    5340
tactcatttg gggttttta tagtggaact tcatagtaat acaaaaagca gattgtcttc     5400
ctgtctccgc tgctcccaca gtaggtattg aaactggtaa aatcagtttt ttgatagtgt    5460
gtgtatataa gaaaaaatag atacacacat tcttttttct cagtcaacac attgattgaa    5520
cactctggca agatgctgt ggtggatgag gttggagttc gaaagaagaa gcaagcgctg      5580
gcctggcctt gaaagaaccg aagtctttcc cattcacttc tctagaaagc tgccaagaca    5640
gaggcagaaa gaaatggatg atagttctgt caagcacact tctgttctct tagaacttag    5700
aagtgtttct aagagaacag aagtaataag agaaacagtt acgtgtggaa ttcaacatct    5760
ttggttggaa cgcattggct ttttttttct tgttttgata gaaatggaat taagcaaaag    5820 tagttttgt cttttctgtt gtcttcaaat tttatgcctt ttattttaa tttaatcccg       5880 ttcaattatt taattgttat acattgacat taactgctgt attttgactt tgttcaataa    5940
ttttgttctt tcagggctag aaataaactt tttaaaaaaa gtgtgcattt ttcccttttcc   6000 taaactttta ttctttcttt tgatcagcgt aaaagaatat tttaatgtct tttgatagca    6060
taaaagaata tttaaatgtc ttaataggtt ttcaaagaac atttagtatt tttagtgata    6120
aatgttttaa acctttaa                                                  6139
```

<210> SEQ ID NO 36
<211> LENGTH: 524
<212> TYPE: PRT
<213> ORGANISM: Homo sapiens

<400> SEQUENCE: 36

```
Met Ser Asp Asn Gly Glu Leu Glu Asp Lys Pro Pro Ala Pro Pro Val
1               5                   10                  15

Arg Met Ser Ser Thr Ile Phe Ser Thr Gly Gly Lys Asp Pro Leu Ser
            20                  25                  30

Ala Asn His Ser Leu Lys Pro Leu Pro Ser Val Pro Glu Glu Lys Lys
        35                  40                  45

Pro Arg His Lys Ile Ile Ser Ile Phe Ser Gly Thr Glu Lys Gly Ser
    50                  55                  60

Lys Lys Lys Glu Lys Glu Arg Pro Glu Ile Ser Pro Pro Ser Asp Phe
65                  70                  75                  80

Glu His Thr Ile His Val Gly Phe Asp Ala Val Thr Gly Glu Phe Thr
                85                  90                  95

Gly Met Pro Glu Gln Trp Ala Arg Leu Leu Gln Thr Ser Asn Ile Thr
            100                 105                 110

Lys Leu Glu Gln Lys Lys Asn Pro Gln Ala Val Leu Asp Val Leu Lys
        115                 120                 125

Phe Tyr Asp Ser Asn Thr Val Lys Gln Lys Tyr Leu Ser Phe Thr Pro
    130                 135                 140

Pro Glu Lys Asp Gly Phe Pro Ser Gly Thr Pro Ala Leu Asn Ala Lys
```

| | | | | | | | | | | | | | | |
|---|---|---|---|---|---|---|---|---|---|---|---|---|---|---|
| 145 | | | | 150 | | | | 155 | | | | 160 | | |

Gly Thr Glu Ala Pro Ala Val Val Thr Glu Glu Asp Asp Glu
                          165                      170                      175

Glu Thr Ala Pro Pro Val Ile Ala Pro Arg Pro Asp His Thr Lys Ser
           180                      185                      190

Ile Tyr Thr Arg Ser Val Ile Asp Pro Val Pro Ala Pro Val Gly Asp
           195                      200                      205

Ser His Val Asp Gly Ala Ala Lys Ser Leu Asp Lys Gln Lys Lys Lys
       210                      215                      220

Thr Lys Met Thr Asp Glu Glu Ile Met Glu Lys Leu Arg Thr Ile Val
225                    230                      235                      240

Ser Ile Gly Asp Pro Lys Lys Tyr Thr Arg Tyr Glu Lys Ile Gly
               245                      250                      255

Gln Gly Ala Ser Gly Thr Val Phe Thr Ala Thr Asp Val Ala Leu Gly
             260                      265                      270

Gln Glu Val Ala Ile Lys Gln Ile Asn Leu Gln Lys Gln Pro Lys Lys
       275                      280                      285

Glu Leu Ile Ile Asn Glu Ile Leu Val Met Lys Glu Leu Lys Asn Pro
290                    295                      300

Asn Ile Val Asn Phe Leu Asp Ser Tyr Leu Val Gly Asp Glu Leu Phe
305                    310                      315                      320

Val Val Met Glu Tyr Leu Ala Gly Gly Ser Leu Thr Asp Val Val Thr
             325                      330                      335

Glu Thr Cys Met Asp Glu Ala Gln Ile Ala Ala Val Cys Arg Glu Cys
           340                      345                      350

Leu Gln Ala Leu Glu Phe Leu His Ala Asn Gln Val Ile His Arg Asp
       355                      360                      365

Ile Lys Ser Asp Asn Val Leu Leu Gly Met Glu Gly Ser Val Lys Leu
           370                      375                      380

Thr Asp Phe Gly Phe Cys Ala Gln Ile Thr Pro Glu Gln Ser Lys Arg
385                    390                      395                      400

Ser Thr Met Val Gly Thr Pro Tyr Trp Met Ala Pro Glu Val Val Thr
             405                      410                      415

Arg Lys Ala Tyr Gly Pro Lys Val Asp Ile Trp Ser Leu Gly Ile Met
           420                      425                      430

Ala Ile Glu Met Val Glu Gly Glu Pro Pro Tyr Leu Asn Glu Asn Pro
       435                      440                      445

Leu Arg Ala Leu Tyr Leu Ile Ala Thr Asn Gly Thr Pro Glu Leu Gln
450                    455                      460

Asn Pro Glu Lys Leu Ser Pro Ile Phe Arg Asp Phe Leu Asn Arg Cys
465                    470                      475                      480

Leu Glu Met Asp Val Glu Lys Arg Gly Ser Ala Lys Glu Leu Leu Gln
           485                      490                      495

His Pro Phe Leu Lys Leu Ala Lys Pro Leu Ser Ser Leu Thr Pro Leu
           500                      505                      510

Ile Met Ala Ala Lys Glu Ala Met Lys Ser Asn Arg
           515                      520

<210> SEQ ID NO 37
<211> LENGTH: 10573
<212> TYPE: DNA
<213> ORGANISM: Homo sapiens

<400> SEQUENCE: 37

```
gcgggggag  ggcgagccca  agcgcggggg  agggagtgta  aatagagcga  aggctgctct    60
gtgtcagccc  cgtcaccgcc  gggcggcccg  cgcggagtct  gagggagatg  gaagttgagc   120
aagagcagcg  gcgcagaaag  gtggaggccg  ggaggacgaa  gcttgctcac  ttccgacaga   180
gaaaaacaaa  aggtgacagt  tcgcattcgg  agaaaaagac  ggcgaagagg  aagggctcgg   240
ctgtcgatgc  gtctgtccag  gaggagagtc  cggtaaccaa  ggaggacagc  gcactctgtg   300
gaggagggga  catttgcaaa  agcacatcat  gtgacgacac  ccctgatggg  gcaggagggg   360
cctttgcagc  tcagccggag  gactgtgatg  gagagaagag  agaggacttg  aacagctgc    420
agcagaagca  agtcaatgac  catcctccag  agcagtgtgg  gatgttcaca  gtcagtgacc   480
acccaccaga  acagcatggg  atgttcacag  tcggtgacca  cccaccagaa  cagcgtggga   540
tgttcacagt  cagtgaccac  ccaccagaac  agcatgggat  gttcacagtc  agtgaccacc   600
caccagaaca  gcgtgggatg  ttcacaatca  gtgaccacca  accggaacag  cgtgggatgt   660
tcacagtcag  tgaccacaca  ccagaacagc  gtgggatctt  cacaatcagt  gaccacccag   720
cagaacagcg  tgggatgttc  acaaaggagt  gtgaacaaga  atgtgaactt  gccattactg   780
acctggagag  cggccgtgaa  gatgaggctg  gcctgcatca  gagtcaggcc  gtgcatggcc   840
ttgagctgga  ggcgctgcgc  ctgagtctga  gcaacatgca  cacggcgcag  ctggagctga   900
cacaggccaa  cctccagaag  gagaaggaga  cggcattgac  ggagctgcgg  gagatgctca   960
acagccggcg  tgcccaggag  ctggccctgc  tacagagcag  gcagcagcac  gagctggagc  1020
tcctcaggga  gcagcacgca  cgggagaagg  aggaggtggt  gctcaggtgt  ggacaggaag  1080
cagctgagct  gaaggagaag  ttacaatcag  aaatggagaa  aaacgcccag  atagtaaaga  1140
ccctgaagga  agattgggaa  tctgaaaaag  atttatgttt  agaaaatcta  cgcaaagaac  1200
tgtctgcaaa  gcatcaatca  gaaatggagg  atttacaaaa  ccagtttcag  aaagaattgg  1260
cagaacagag  agctgagttg  agaagatttt  tcaagacaa   aaaccaggct  gaacgggccc  1320
ttaggaacct  ggagagtcat  catcaagcag  ccattgagaa  gttacgtgaa  gacctgcagt  1380
ccgagcacgg  ccggtgttta  aagacttgg   agttcaagtt  caaagagagc  gagaaagaaa  1440
aacagctgga  gttagagaat  cttcaagcat  catatgaaga  cctgaaggca  caatcacaag  1500
aagagatcag  gcgcttgtgg  tcccagcttg  attctgccag  gaccagtaga  caggaattga  1560
gtgagctaca  tgagcaactc  ctggcgcgca  cctctcgtgt  ggaagattta  gaacagctga  1620
agcagcgaga  aaaaacccag  catgagtccg  aactggagca  actgaggatt  tattttgaaa  1680
agaagttaag  ggatgctgag  aaaacttacc  aagaagacct  aaccctgtta  cagcagaggc  1740
tgcagggggc  gagggaagat  gctcttctgg  actctgtgga  agttgggttg  tcctgtgtgg  1800
gtttagaaga  gaaacctgag  aaaggaagaa  aagatcacgt  tgatgaactc  gagcctgagc  1860
gacataagga  gagcctgcca  cgcttccagg  cggagttaga  agaaagccac  aggcaccagc  1920
tggaagcgct  ggagtctccc  ctctgcatcc  agcacgaggg  gcatgtctca  gacagatgct  1980
gcgtagagac  ttcagcattg  ggacacgagt  ggcgtctgga  accctctgaa  gggcacagcc  2040
aagagcttcc  ctgggtgcat  ctccagggtg  tgcaggacgg  ggacttggag  gccgacacag  2100
agcgggcagc  cagagtcttg  ggtctggaaa  ctgagcacaa  ggtgcaactt  tcgcttcttc  2160
agactgagct  caaagaagaa  attgaactcc  taaaaataga  aaatagaaat  ttgtatggga  2220
agttgcagca  tgaaactcgt  ctgaaggacg  atttggagaa  ggtaaaacac  aatctaattg  2280
aagaccacca  gaaggaacta  aataatgcta  agcaaaagac  tgagctgatg  aaacaggaat  2340
tccaaagaaa  agaaacggac  tggaaagtta  tgaaggagga  gctacagcgg  gaagctgagg  2400
```

```
agaagttaac attgatgcta cttgaactga gagaaaaggc tgaatccgag aaacagacca   2460
tcataaacaa gtttgagctt cgagaagctg aaatgaggca gcttcaggac caacaggcag   2520
cccagatcct ggatctggag aggtccttga cggagcagca gggccgcctg cagcagctgg   2580
aacaggacct cacttcagac gacgccctgc attgcagcca gtgtgggcgg gagccgccca   2640
cagcccagga cggggagctt gctgcgctcc acgtgaagga agactgcgcc ctgcagctga   2700
tgctggcccg gagcaggttt ttagaggaac gtaaagagat caccgagaaa ttcagtgcgg   2760
aacaagatgc cttcctgcag gaggcccagg agcagcatgc ccgtgagctg cagctcctcc   2820
aggagagaca ccagcagcag ctcctgtcag tgacggcgga gctcgaggcc agacaccagg   2880
ccgcgttggg cgagctgaca gcctccttag agagcaagca gggggctctg ctggctgcac   2940
gtgtggccga actgcagaca aaacacgctg ccgacctcgg cgctctggag accagacatc   3000
tgtccagcct tgattctttg gaatcctgtt acctctctga atttcagacc atccgtgagg   3060
agcacaggca ggccctagag ctcttacgag cagactttga ggaacaactg tggaaaaagg   3120
actctcttca ccaaacgatt ttgactcaag agttggagaa actgaagcgg aaacacgaag   3180
gggagctaca gtctgtgcgg gaccacctgc gaaccgaagt gagcacagag ctcgccggaa   3240
ccgtggctca cgagctgcag ggagtgcacc agggtgaatt tggaagtgaa aagaaaactg   3300 cttttgcatga aaaagaggag acacttcggc ttcagagtgc acaggcacag cctttcacc    3360 aagaggagaa agagtctttg tctctgcagc ttcaaaagaa gaatcaccaa gtccagcagc   3420
tgaaagacca ggttttatcc ttaagtcacg agatagaaga gtgccgctcc gagttggagg   3480
tgctgcagca gaggcgggag cgggagaacc gggaaggcgc aaacctcctc tccatgctca   3540
aggccgacgt caacctgtcc cacagcgaaa gaggggccct ccaggacgcc ctgcgcaggc   3600
tgctgggttt gtttggagag acgctgaggg cagccgtcac cctgaggagc cggatcgggg   3660
agcgcgtggg gctctgcctg gatgacgcgg gcgcaggcct ggccctgtcg acagctccgg   3720
cgctggagga gacatggtct gatgtggccc tcccggagtt ggacagaact ttgtctgaat   3780
gtgcagagat gtcttccgtg gctgaaatta gcagccacat gcgtgaaagc tttctcatga   3840
gcccagaaag tgtgcgggag tgtgagcagc ccatccggag ggtcttccag agcctcagcc   3900
tggccgtgga cggcctcatg gagatggccc tggactccag caggcagctg aagaagcac    3960 gccaaattca ttctcgtttt gaaaagaat ttagtttta gaatgaggag acagcacagg    4020
ttgtcaggaa gcaccaggag ctgctggagt gtttgaagga ggagagcgca gcaaaggcag   4080
agctggcgct ggagctgcac aagactcagg gtacccttga gggattcaag gtggagcag    4140 cagatctgaa ggaggtgctg gccgggaagg aggattccga gcaccgtctg gtgctggagc   4200
tggagagcct gagacggcag ctgcagcagg cggcccagga gcaggcggcg ctgagggagg   4260
agtgcacccg tctgtggagt cgggggggagg ccacagccac ggacgccgag gccagagaag   4320
ctgctctccg gaaggaagtg gaggatctga ccaaagaaca gtcggagacc aggaagcagg   4380
ctgagaagga ccgctcagcc ctgctctccc agatgaagat tttggagtct gagttagaag   4440
aacagctgtc tcagcatcgc gggtgtgcca gcaggcgga ggccgtcact gccctggaac     4500
agcaggtggc atctctggac aagcatttgc gcaaccagcg gcaattcatg gatgagcagg   4560
cagccgagcg ggagcacgag cgcgaggagt tccagcagga gattcagagg ctggaggggc   4620
agctccgcca ggcggccaag ccgcagccct ggggccctcg cgacagccag caggcgccgc   4680
tggatggaga ggttgagttg ttacaacaaa agttgagaga aaagttggat gaatttaatg   4740
```

-continued

```
aattggctat acagaaagag tcggcagata gacaagtgtt aatgcaggaa gaagaaatta    4800
aacgtctgga ggagatgaac atcaacatca ggaaaaaagt ggcccagctc caggaagaag    4860
tggaaaaaca gaaaaacatc gtgaaagggc tggaacagga taaagaggtg ttaaagaaac    4920
agcagatgag tagcttgctt ctggcgtcca cgttgcagtc tacactagat gcaggcagat    4980
gtcccgagcc tccttcgggc agccctcctg agggtccaga aatacagtta gaggtgacac    5040
agagagcact cctgcggcgc gagagcgagg ttttggactt aaaagaacag ctagaaaaga    5100
tgaaaggtga cttagaaagt aaaaatgaag aaatactaca tctgaactta aaattggaca    5160
tgcagaacag ccagactgct gtcagcctca gagaacttga ggaagagaac acgagcttga    5220
aggtcatata taccagaagt tctgagattg aagagctgaa agccactatt gaaaatctgc    5280
aagagaatca gaaacgatta caaaaggaga agcagagga aattgaacaa ctccatgaag    5340
tcattgagaa gctgcagcac gagctgtccc tcatggggcc tgtggtgcac gaagtcagcg    5400
acagtcaggc tggcagtctg cagagcgagc tgctctgctc ccaggccggg ggccctcgtg    5460
ggcaggccct acagggcgag ctcgaggctg cgctggaagc caaggaggcc ctgagccggc    5520
tgctggctga ccaggagcgc aggcacagcc aggccctgga ggccctgcag cagcgcctcc    5580
agggcgcaga ggaggctgcg gagctacagc tggctgagct ggagcgcaat gtagccctca    5640
gggaggctga ggtcgaagac atggcctccc ggatccagga gttcgaagcg ccctgaaag    5700
caaaggaagc gacgattgcc gagagaaatt tagaaatcga cgctctgaac cagcggaagg    5760
cggcccactc tgccgagctg gaggccgtcc tgttggcctt ggcccgcatc cgccgcgccc    5820
tggagcagca gccccctggca gccggggcgg cgcctcccga gctgcagtgg ctccgagcgc    5880
agtgtgcccg cctcagccgc cagctgcagg tgctgcacca gcggttcctg aggtgccagg    5940
tggagctgga caggcggcag gcccgcagag ccacagctca cacagggtg cccggggccc    6000
acccacagcc tcgcatggat ggtggcgcca aggcccaggt caccggcgac gtggaggcct    6060
cccatgatgc tgctttggag ccggttgtcc ctgacccaca gggtgatctg cagcctgtcc    6120
tggtgacgtt gaaggatgca cctctctgca agcaagaagg cgtgatgtca gtgctcaccg    6180
tctgccagag gcagctgcag tcggagctgc tcttggtgaa aaatgaaatg cgcctgagtc    6240
tggaggacgg cggcaagggt aaagaaaaag tactggaaga ttgtcagctg ccgaaggtcg    6300
atctcgtagc tcaggtgaaa cagcttcagg aaaaactgaa ccgtttgctg tattccatga    6360
ccttccagaa tgtggatgct gccgacacca atctctgtg gcccatggcc tcagcacacc    6420
tgttggagag cagctggagt gatgattcct gtgacggaga agagcctgac atatcaccc    6480
acatagacac atgtgatgcc aatacagcca cggggggtgt aactgatgtt atcaaaaatc    6540
aggccataga cgcgtgtgat gccaatacaa ccccaggggg tgtaactgat gttatcaaaa    6600
attgggattc cttgatacca gatgaaatgc cagattctcc cattcaagaa aaatcagaat    6660
gtcaggacat gtctctttct tcaccgacca gcgtacttgg tggctcccgc caccagagcc    6720
acactgcaga ggctgggccc cggaagagcc cggtcgggat gctggacctg tcttcctgga    6780
gctcccctga ggtcctcagg aaggactgga ccctggagcc ctggcccagc ctccccgtga    6840
cacccccactc aggagccctg agcctgtgca gtgccgacac atccctgggg gacagggcgg    6900
acacctcgct gccacagacc caggggccgg ggctgctttg ttccccaggc gtgtctgcag    6960
cagcgctggc actgcagtgg gccgagtctc cgccggctga cgaccaccat gtgcagagga    7020
cggctgtgga gaaagatgtc gaagatttta tcacaacatc ctttgattct caagaaacat    7080
taagttcacc tcctcctgga ttagaaggaa aagctgatag aagtgagaaa agtgacggct    7140
```

```
cgggttttgg agcaagactg agcccggggt caggaggccc tgaggctcaa actgctggtc    7200
ctgtgacccc tgcttccatc tctggaaggt ttcagccgct gccggaagcc atgaaggaga    7260
aggaagtgcg tccgaagcac gtgaaggctt tactgcagat ggtgcgtgac gagagccacc    7320
agatcctggc gctgtcagaa ggccttgcac ccccaagcgg cgagccacac ccaccccgga    7380
aggaagacga gatacaggac atctcgctcc atggggaaa gacgcaggaa gtgcccaccg    7440
cgtgccccga ttggagaggg gaccttctgc aggttgtgca agaggccttt gaaaaagagc    7500
aggagatgca gggggttgag ctgcagcccc gactcagtgg ctcagatctg ggggtcaca    7560
gctccctgct cgaaaggctg gagaagatca tccgtgagca gggagacctg caggaaaagt    7620
ccctggagca tcttcgcttg ccggaccgga gcagcctgct gtccgagatc caggcgctgc    7680
gtgcccagct gcgcatgacg cacctgcaga accaggagaa gctgcagcac ttgcgcacgg    7740
cgctgacaag cgcagaggcg cgcgggagcc agcaggagca ccagctgcgc aggcaggttg    7800
aactgctggc ttataaagta gagcaggaga agtgcattgc tggtgacttg cagaagacgc    7860
tgagtgaaga gcaagagaag gcaaacagcg tgcagaagct cctggcggcg gagcagactg    7920
tagtgcgaga tttgaagtcc gacctctgtg agagcaggca gaagagcgaa cagctgtccc    7980
ggtccctctg cgaggtgcag caggaggtcc tccagctgag atccatgctg agcagtaagg    8040
agaacgagct gaaggccgcg cttcaggagc tggagagtga gcaggggaag gggcgtgccc    8100
tgcagagcca gctggaggag gagcagctgc ggcacctgca gagggagagc cagagtgcca    8160
aggccctgga ggagctgcgg gcgtctttgg agacacagcg tgctcagagc agtcgactct    8220
gcgtggcact gaaacacgag cagacggcca aggacaacct gcagaaggag ctgcgtatcg    8280
agcactcacg ctgcgaggcc ttgctggctc aggagcggag ccagctctct gagctccaga    8340
aggaccttgc ggctgagaag agccgcaccc tggagctgtc agaggccttg cggcacgagc    8400
ggctcctgac cgagcagctg agccagagga cacaggaggc ttgcgtgcac caggacacac    8460
aggcccatca cgctctgctg cagaagctga aggaggaga gtcccgggtg gtggacttgc    8520
aagcgatgct tgaaaaggtg cagcagcaag ccctgcattc tcagcagcag cttgaggctg    8580
aggctcagaa gcactgtgag gcgctcagga gagaagga ggtaagtgcc acactgaagt    8640
cgacggtgga agccctgcac acccaaaaac gagagctgag atgctctctg gagagagaga    8700
gggagaaacc agcgtggttg caggcagaat tagagcagtc acaccacgg ttgaaagagc    8760
aagaaggacg caaggctgcg aggaggagcg cggaggccag gcagagccca gcggctgcgg    8820
agcagtggag gaagtggcag agagacaagg agaagctgcg agaattagaa ctgcagcgtc    8880
agcgtgactt gcataagatc aagcagcttc agcagacagt gagagacctg gagtcgaagg    8940
acgaggtgcc tggcagccgc ctccacctag gttctgcccg cagggctgcc ggctcggatg    9000
cggaccacct ccgggaacag cagcgagagc tggaggcgat gaggcagcgg ctgctctctg    9060
ccgcccggct tctcaccagc ttcaccagcc aggccgtgga caggacagtt aatgattgga    9120
cgtcatccaa tgagaaagca gtgatgtctt tactgcacac gttggaggag ctgaagtctg    9180
acttgagcag gccccacctcc tcccagaaaa aatggcagc agagctgcag ttccagtttg    9240
tggacgtcct gctgaaagac aatgtttccc tcacaaaagc gctcagcacg gtgacccagg    9300
agaagctgga gctgagcaga gccgtgtcta gcttgagaa gttgctgaag caccatctgc    9360
agaagggctg cagcccaagc aggtcggaaa ggtctgcttg gaagcagac gaaacggctc    9420
cacagagttc cctgaggcgc ccagacccg gccggcttcc accagctgcc agcgaggaag    9480
```

```
cacacaccag caatgtcaag atggaaaaat tgtacctgca ttacttgaga gcagagagct    9540
ttagaaaagc tctgatttat caaaagaagt atcttttgct gttgattggt ggattccagg    9600
attctgaaca agaaacactc tccatgattg cccatttggg ggtatttcct tccaaagcag    9660
aacggaaaat cacatctcgt cctttcacca ggttccgcac ggccgtcagg gtggtcattg    9720
caatattaag attacgtttt ttggttaaga aatggcaaga agtagatcgg aaaggagctc    9780
tggcacaagg caaagcccct cgcccagggc cccgagcacg acagccgcag tctccaccca    9840
gaaccagaga gtcccccca acccgggatg taccctctgg ccacaccagg gaccctgcca    9900
gaggccgcag actggcagca gcagcctccc cacacagtgg gggaagagcc actccatccc    9960
caaattcaag attagaaaga tccctgactg cttctcaaga tccagaacat tccttgacag   10020
agtatattca ccatttagaa gtgatccagc aaagattggg aggggtacta ccagattcta   10080
cttcaaagaa atcctgccac ccgatgatta aacagtgaat aaaatgtcat ggctctttcc   10140
tgcgacaatt ctatttgagg aaaagatttg ttttccctt ttcccaagga agctcgtggg   10200
acagcatggg cactactctt catgtgcggt gacaccagcc cccagatgcc ttgaattaag   10260
tgtcctcacc tttatgcatg actgcaaagc cagctggagc attttctatg gagcctccgt   10320
atgttttagg cccatgacct tcgtgaggtg acgggcactc actcccatga gccctggctg   10380
tgtgctgttg tgtgcctatc ggcagatcca tccttcctgc ctccaaggag gatacacaga   10440
gaatggcttc ctgttgtttt gtttattttc ttaacgtgta cagatggaaa cttcatttaa   10500
aaataaaaac aaaacaactc aaaaaggaat aaaatttaat cactgttttg tttgtgaata   10560
aaaaaaaaaa aaa                                                       10573

<210> SEQ ID NO 38
<211> LENGTH: 3336
<212> TYPE: PRT
<213> ORGANISM: Homo sapiens

<400> SEQUENCE: 38

Met Glu Val Glu Gln Glu Gln Arg Arg Lys Val Glu Ala Gly Arg
  1               5                  10                  15

Thr Lys Leu Ala His Phe Arg Gln Arg Lys Thr Lys Gly Asp Ser Ser
                 20                  25                  30

His Ser Glu Lys Lys Thr Ala Lys Arg Lys Gly Ser Ala Val Asp Ala
             35                  40                  45

Ser Val Gln Glu Glu Ser Pro Val Thr Lys Glu Asp Ser Ala Leu Cys
         50                  55                  60

Gly Gly Gly Asp Ile Cys Lys Ser Thr Ser Cys Asp Asp Thr Pro Asp
 65                  70                  75                  80

Gly Ala Gly Gly Ala Phe Ala Ala Gln Pro Glu Asp Cys Asp Gly Glu
                 85                  90                  95

Lys Arg Glu Asp Leu Glu Gln Leu Gln Gln Lys Gln Val Asn Asp His
                100                 105                 110

Pro Pro Glu Gln Cys Gly Met Phe Thr Val Ser Asp His Pro Pro Glu
            115                 120                 125

Gln His Gly Met Phe Thr Val Gly Asp His Pro Glu Gln Arg Gly
        130                 135                 140

Met Phe Thr Val Ser Asp His Pro Pro Glu Gln His Gly Met Phe Thr
145                 150                 155                 160

Val Ser Asp His Pro Pro Glu Gln Arg Gly Met Phe Thr Ile Ser Asp
                165                 170                 175
```

```
His Gln Pro Glu Gln Arg Gly Met Phe Thr Val Ser Asp His Thr Pro
            180                 185                 190
Glu Gln Arg Gly Ile Phe Thr Ile Ser Asp His Pro Ala Glu Gln Arg
            195                 200                 205
Gly Met Phe Thr Lys Glu Cys Glu Gln Glu Cys Glu Leu Ala Ile Thr
    210                 215                 220
Asp Leu Glu Ser Gly Arg Glu Asp Glu Ala Gly Leu His Gln Ser Gln
225                 230                  235                 240
Ala Val His Gly Leu Glu Leu Glu Ala Leu Arg Leu Ser Leu Ser Asn
                245                 250                 255
Met His Thr Ala Gln Leu Glu Leu Thr Gln Ala Asn Leu Gln Lys Glu
            260                 265                 270
Lys Glu Thr Ala Leu Thr Glu Leu Arg Glu Met Leu Asn Ser Arg Arg
            275                 280                 285
Ala Gln Glu Leu Ala Leu Leu Gln Ser Arg Gln Gln His Glu Leu Glu
            290                 295                 300
Leu Leu Arg Glu Gln His Ala Arg Glu Lys Glu Glu Val Val Leu Arg
305                 310                 315                 320
Cys Gly Gln Glu Ala Ala Glu Leu Lys Glu Lys Leu Gln Ser Glu Met
                325                 330                 335
Glu Lys Asn Ala Gln Ile Val Lys Thr Leu Lys Glu Asp Trp Glu Ser
            340                 345                 350
Glu Lys Asp Leu Cys Leu Glu Asn Leu Arg Lys Glu Leu Ser Ala Lys
            355                 360                 365
His Gln Ser Glu Met Glu Asp Leu Gln Asn Gln Phe Gln Lys Glu Leu
            370                 375                 380
Ala Glu Gln Arg Ala Glu Leu Glu Lys Ile Phe Gln Asp Lys Asn Gln
385                 390                 395                 400
Ala Glu Arg Ala Leu Arg Asn Leu Glu Ser His His Gln Ala Ala Ile
            405                 410                 415
Glu Lys Leu Arg Glu Asp Leu Gln Ser Glu His Gly Arg Cys Leu Glu
            420                 425                 430
Asp Leu Glu Phe Lys Phe Lys Glu Ser Glu Lys Glu Lys Gln Leu Glu
            435                 440                 445
Leu Glu Asn Leu Gln Ala Ser Tyr Glu Asp Leu Lys Ala Gln Ser Gln
            450                 455                 460
Glu Glu Ile Arg Arg Leu Trp Ser Gln Leu Asp Ser Ala Arg Thr Ser
465                 470                 475                 480
Arg Gln Glu Leu Ser Glu Leu His Glu Gln Leu Leu Ala Arg Thr Ser
            485                 490                 495
Arg Val Glu Asp Leu Glu Gln Leu Lys Gln Arg Glu Lys Thr Gln His
            500                 505                 510
Glu Ser Glu Leu Glu Gln Leu Arg Ile Tyr Phe Glu Lys Lys Leu Arg
            515                 520                 525
Asp Ala Glu Lys Thr Tyr Gln Glu Asp Leu Thr Leu Leu Gln Gln Arg
            530                 535                 540
Leu Gln Gly Ala Arg Glu Asp Ala Leu Leu Asp Ser Val Glu Val Gly
545                 550                 555                 560
Leu Ser Cys Val Gly Leu Glu Glu Lys Pro Glu Lys Gly Arg Lys Asp
                565                 570                 575
His Val Asp Glu Leu Glu Pro Glu Arg His Lys Glu Ser Leu Pro Arg
            580                 585                 590
Phe Gln Ala Glu Leu Glu Glu Ser His Arg His Gln Leu Glu Ala Leu
```

-continued

```
              595                 600                 605
        Glu Ser Pro Leu Cys Ile Gln His Glu Gly His Val Ser Asp Arg Cys
            610                 615                 620
        Cys Val Glu Thr Ser Ala Leu Gly His Glu Trp Arg Leu Glu Pro Ser
        625                 630                 635                 640
        Glu Gly His Ser Gln Glu Leu Pro Trp Val His Leu Gln Gly Val Gln
                            645                 650                 655
        Asp Gly Asp Leu Glu Ala Asp Thr Glu Arg Ala Ala Arg Val Leu Gly
                        660                 665                 670
        Leu Glu Thr Glu His Lys Val Gln Leu Ser Leu Leu Gln Thr Glu Leu
                    675                 680                 685
        Lys Glu Glu Ile Glu Leu Leu Lys Ile Glu Asn Arg Asn Leu Tyr Gly
                690                 695                 700
        Lys Leu Gln His Glu Thr Arg Leu Lys Asp Asp Leu Glu Lys Val Lys
        705                 710                 715                 720
        His Asn Leu Ile Glu Asp His Gln Lys Glu Leu Asn Asn Ala Lys Gln
                            725                 730                 735
        Lys Thr Glu Leu Met Lys Gln Glu Phe Gln Arg Lys Glu Thr Asp Trp
                        740                 745                 750
        Lys Val Met Lys Glu Glu Leu Gln Arg Glu Ala Glu Glu Lys Leu Thr
                    755                 760                 765
        Leu Met Leu Leu Glu Leu Arg Glu Lys Ala Glu Ser Glu Lys Gln Thr
                770                 775                 780
        Ile Ile Asn Lys Phe Glu Leu Arg Glu Ala Glu Met Arg Gln Leu Gln
        785                 790                 795                 800
        Asp Gln Gln Ala Ala Gln Ile Leu Asp Leu Glu Arg Ser Leu Thr Glu
                            805                 810                 815
        Gln Gln Gly Arg Leu Gln Leu Glu Gln Asp Leu Thr Ser Asp Asp
                        820                 825                 830
        Ala Leu His Cys Ser Gln Cys Gly Arg Glu Pro Pro Thr Ala Gln Asp
                    835                 840                 845
        Gly Glu Leu Ala Ala Leu His Val Lys Glu Asp Cys Ala Leu Gln Leu
                850                 855                 860
        Met Leu Ala Arg Ser Arg Phe Leu Glu Glu Arg Lys Glu Ile Thr Glu
        865                 870                 875                 880
        Lys Phe Ser Ala Glu Gln Asp Ala Phe Leu Gln Glu Ala Gln Glu Gln
                            885                 890                 895
        His Ala Arg Glu Leu Gln Leu Leu Gln Glu Arg His Gln Gln Gln Leu
                        900                 905                 910
        Leu Ser Val Thr Ala Glu Leu Glu Ala Arg His Gln Ala Ala Leu Gly
                    915                 920                 925
        Glu Leu Thr Ala Ser Leu Glu Ser Lys Gln Gly Ala Leu Leu Ala Ala
                930                 935                 940
        Arg Val Ala Glu Leu Gln Thr Lys His Ala Ala Asp Leu Gly Ala Leu
        945                 950                 955                 960
        Glu Thr Arg His Leu Ser Ser Leu Asp Ser Leu Glu Ser Cys Tyr Leu
                            965                 970                 975
        Ser Glu Phe Gln Thr Ile Arg Glu Glu His Arg Gln Ala Leu Glu Leu
                        980                 985                 990
        Leu Arg Ala Asp Phe Glu Glu Gln Leu Trp Lys Lys Asp Ser Leu His
                    995                 1000                1005
        Gln Thr Ile Leu Thr Gln Glu Leu Glu Lys Leu Lys Arg Lys His Glu
                1010                1015                1020
```

```
Gly Glu Leu Gln Ser Val Arg Asp His Leu Arg Thr Glu Val Ser Thr
1025                1030                1035                1040

Glu Leu Ala Gly Thr Val Ala His Glu Leu Gln Gly Val His Gln Gly
                1045                1050                1055

Glu Phe Gly Ser Glu Lys Lys Thr Ala Leu His Glu Lys Glu Glu Thr
                1060                1065                1070

Leu Arg Leu Gln Ser Ala Gln Ala Gln Pro Phe His Gln Glu Glu Lys
                1075                1080                1085

Glu Ser Leu Ser Leu Gln Leu Gln Lys Lys Asn His Gln Val Gln Gln
                1090                1095                1100

Leu Lys Asp Gln Val Leu Ser Leu Ser His Glu Ile Glu Glu Cys Arg
1105                1110                1115                1120

Ser Glu Leu Glu Val Leu Gln Gln Arg Arg Glu Arg Glu Asn Arg Glu
                1125                1130                1135

Gly Ala Asn Leu Leu Ser Met Leu Lys Ala Asp Val Asn Leu Ser His
                1140                1145                1150

Ser Glu Arg Gly Ala Leu Gln Asp Ala Leu Arg Arg Leu Leu Gly Leu
                1155                1160                1165

Phe Gly Glu Thr Leu Arg Ala Ala Val Thr Leu Arg Ser Arg Ile Gly
                1170                1175                1180

Glu Arg Val Gly Leu Cys Leu Asp Asp Ala Gly Ala Gly Leu Ala Leu
1185                1190                1195                1200

Ser Thr Ala Pro Ala Leu Glu Glu Thr Trp Ser Asp Val Ala Leu Pro
                1205                1210                1215

Glu Leu Asp Arg Thr Leu Ser Glu Cys Ala Glu Met Ser Ser Val Ala
                1220                1225                1230

Glu Ile Ser Ser His Met Arg Glu Ser Phe Leu Met Ser Pro Glu Ser
                1235                1240                1245

Val Arg Glu Cys Glu Gln Pro Ile Arg Arg Val Phe Gln Ser Leu Ser
                1250                1255                1260

Leu Ala Val Asp Gly Leu Met Glu Met Ala Leu Asp Ser Ser Arg Gln
1265                1270                1275                1280

Leu Glu Glu Ala Arg Gln Ile His Ser Arg Phe Glu Lys Glu Phe Ser
                1285                1290                1295

Phe Lys Asn Glu Glu Thr Ala Gln Val Val Arg Lys His Gln Glu Leu
                1300                1305                1310

Leu Glu Cys Leu Lys Glu Glu Ser Ala Ala Lys Ala Glu Leu Ala Leu
                1315                1320                1325

Glu Leu His Lys Thr Gln Gly Thr Leu Glu Gly Phe Lys Val Glu Thr
                1330                1335                1340

Ala Asp Leu Lys Glu Val Leu Ala Gly Lys Glu Asp Ser Glu His Arg
1345                1350                1355                1360

Leu Val Leu Glu Leu Glu Ser Leu Arg Arg Gln Leu Gln Gln Ala Ala
                1365                1370                1375

Gln Glu Gln Ala Ala Leu Arg Glu Glu Cys Thr Arg Leu Trp Ser Arg
                1380                1385                1390

Gly Glu Ala Thr Ala Thr Asp Ala Glu Ala Arg Glu Ala Ala Leu Arg
                1395                1400                1405

Lys Glu Val Glu Asp Leu Thr Lys Glu Gln Ser Glu Thr Arg Lys Gln
                1410                1415                1420

Ala Glu Lys Asp Arg Ser Ala Leu Leu Ser Gln Met Lys Ile Leu Glu
1425                1430                1435                1440
```

```
Ser Glu Leu Glu Glu Gln Leu Ser Gln His Arg Gly Cys Ala Lys Gln
            1445                1450                1455

Ala Glu Ala Val Thr Ala Leu Glu Gln Gln Val Ala Ser Leu Asp Lys
        1460                1465                1470

His Leu Arg Asn Gln Arg Gln Phe Met Asp Glu Gln Ala Ala Glu Arg
        1475                1480                1485

Glu His Glu Arg Glu Glu Phe Gln Gln Glu Ile Gln Arg Leu Glu Gly
        1490                1495                1500

Gln Leu Arg Gln Ala Ala Lys Pro Gln Pro Trp Gly Pro Arg Asp Ser
1505                1510                1515                1520

Gln Gln Ala Pro Leu Asp Gly Glu Val Glu Leu Leu Gln Gln Lys Leu
            1525                1530                1535

Arg Glu Lys Leu Asp Glu Phe Asn Glu Leu Ala Ile Gln Lys Glu Ser
            1540                1545                1550

Ala Asp Arg Gln Val Leu Met Gln Glu Glu Ile Lys Arg Leu Glu
            1555                1560                1565

Glu Met Asn Ile Asn Ile Arg Lys Lys Val Ala Gln Leu Gln Glu Glu
            1570                1575                1580

Val Glu Lys Gln Lys Asn Ile Val Lys Gly Leu Glu Gln Asp Lys Glu
1585                1590                1595                1600

Val Leu Lys Lys Gln Gln Met Ser Ser Leu Leu Ala Ser Thr Leu
            1605                1610                1615

Gln Ser Thr Leu Asp Ala Gly Arg Cys Pro Glu Pro Pro Ser Gly Ser
            1620                1625                1630

Pro Pro Glu Gly Pro Glu Ile Gln Leu Glu Val Thr Gln Arg Ala Leu
            1635                1640                1645

Leu Arg Arg Glu Ser Glu Val Leu Asp Leu Lys Glu Gln Leu Glu Lys
            1650                1655                1660

Met Lys Gly Asp Leu Glu Ser Lys Asn Glu Glu Ile Leu His Leu Asn
1665                1670                1675                1680

Leu Lys Leu Asp Met Gln Asn Ser Gln Thr Ala Val Ser Leu Arg Glu
            1685                1690                1695

Leu Glu Glu Glu Asn Thr Ser Leu Lys Val Ile Tyr Thr Arg Ser Ser
            1700                1705                1710

Glu Ile Glu Glu Leu Lys Ala Thr Ile Glu Asn Leu Gln Glu Asn Gln
            1715                1720                1725

Lys Arg Leu Gln Lys Glu Lys Ala Glu Glu Ile Glu Gln Leu His Glu
            1730                1735                1740

Val Ile Glu Lys Leu Gln His Glu Leu Ser Leu Met Gly Pro Val Val
1745                1750                1755                1760

His Glu Val Ser Asp Ser Gln Ala Gly Ser Leu Gln Ser Glu Leu Leu
            1765                1770                1775

Cys Ser Gln Ala Gly Gly Pro Arg Gly Gln Ala Leu Gln Gly Glu Leu
            1780                1785                1790

Glu Ala Ala Leu Glu Ala Lys Glu Ala Leu Ser Arg Leu Leu Ala Asp
            1795                1800                1805

Gln Glu Arg Arg His Ser Gln Ala Leu Glu Ala Leu Gln Gln Arg Leu
            1810                1815                1820

Gln Gly Ala Glu Glu Ala Glu Leu Gln Leu Ala Glu Leu Glu Arg
1825                1830                1835                1840

Asn Val Ala Leu Arg Glu Ala Glu Val Glu Asp Met Ala Ser Arg Ile
            1845                1850                1855

Gln Glu Phe Glu Ala Ala Leu Lys Ala Lys Glu Ala Thr Ile Ala Glu
```

```
                1860              1865              1870
Arg Asn Leu Glu Ile Asp Ala Leu Asn Gln Arg Lys Ala Ala His Ser
            1875              1880              1885

Ala Glu Leu Glu Ala Val Leu Leu Ala Leu Ala Arg Ile Arg Arg Ala
            1890              1895              1900

Leu Glu Gln Gln Pro Leu Ala Ala Gly Ala Ala Pro Pro Glu Leu Gln
1905              1910              1915              1920

Trp Leu Arg Ala Gln Cys Ala Arg Leu Ser Arg Gln Leu Gln Val Leu
            1925              1930              1935

His Gln Arg Phe Leu Arg Cys Gln Val Glu Leu Asp Arg Arg Gln Ala
            1940              1945              1950

Arg Arg Ala Thr Ala His Thr Arg Val Pro Gly Ala His Pro Gln Pro
            1955              1960              1965

Arg Met Asp Gly Gly Ala Lys Ala Gln Val Thr Gly Asp Val Glu Ala
            1970              1975              1980

Ser His Asp Ala Ala Leu Glu Pro Val Val Pro Asp Pro Gln Gly Asp
1985              1990              1995              2000

Leu Gln Pro Val Leu Val Thr Leu Lys Asp Ala Pro Leu Cys Lys Gln
            2005              2010              2015

Glu Gly Val Met Ser Val Leu Thr Val Cys Gln Arg Gln Leu Gln Ser
            2020              2025              2030

Glu Leu Leu Leu Val Lys Asn Glu Met Arg Leu Ser Leu Glu Asp Gly
            2035              2040              2045

Gly Lys Gly Lys Glu Lys Val Leu Glu Asp Cys Gln Leu Pro Lys Val
            2050              2055              2060

Asp Leu Val Ala Gln Val Lys Gln Leu Gln Glu Lys Leu Asn Arg Leu
2065              2070              2075              2080

Leu Tyr Ser Met Thr Phe Gln Asn Val Asp Ala Ala Asp Thr Lys Ser
            2085              2090              2095

Leu Trp Pro Met Ala Ser Ala His Leu Leu Glu Ser Ser Trp Ser Asp
            2100              2105              2110

Asp Ser Cys Asp Gly Glu Glu Pro Asp Ile Ser Pro His Ile Asp Thr
            2115              2120              2125

Cys Asp Ala Asn Thr Ala Thr Gly Gly Val Thr Asp Val Ile Lys Asn
            2130              2135              2140

Gln Ala Ile Asp Ala Cys Asp Ala Asn Thr Thr Pro Gly Gly Val Thr
2145              2150              2155              2160

Asp Val Ile Lys Asn Trp Asp Ser Leu Ile Pro Asp Glu Met Pro Asp
            2165              2170              2175

Ser Pro Ile Gln Glu Lys Ser Glu Cys Gln Asp Met Ser Leu Ser Ser
            2180              2185              2190

Pro Thr Ser Val Leu Gly Gly Ser Arg His Gln Ser His Thr Ala Glu
            2195              2200              2205

Ala Gly Pro Arg Lys Ser Pro Val Gly Met Leu Asp Leu Ser Ser Trp
            2210              2215              2220

Ser Ser Pro Glu Val Leu Arg Lys Asp Trp Thr Leu Glu Pro Trp Pro
2225              2230              2235              2240

Ser Leu Pro Val Thr Pro His Ser Gly Ala Leu Ser Leu Cys Ser Ala
            2245              2250              2255

Asp Thr Ser Leu Gly Asp Arg Ala Asp Thr Ser Leu Pro Gln Thr Gln
            2260              2265              2270

Gly Pro Gly Leu Leu Cys Ser Pro Gly Val Ser Ala Ala Ala Leu Ala
            2275              2280              2285
```

-continued

Leu Gln Trp Ala Glu Ser Pro Pro Ala Asp Asp His His Val Gln Arg
    2290                2295                2300

Thr Ala Val Glu Lys Asp Val Glu Asp Phe Ile Thr Thr Ser Phe Asp
2305                2310                2315                2320

Ser Gln Glu Thr Leu Ser Ser Pro Pro Gly Leu Glu Gly Lys Ala
                2325                2330                2335

Asp Arg Ser Glu Lys Ser Asp Gly Ser Gly Phe Gly Ala Arg Leu Ser
                2340                2345                2350

Pro Gly Ser Gly Gly Pro Glu Ala Gln Thr Ala Gly Pro Val Thr Pro
                2355                2360                2365

Ala Ser Ile Ser Gly Arg Phe Gln Pro Leu Pro Glu Ala Met Lys Glu
    2370                2375                2380

Lys Glu Val Arg Pro Lys His Val Lys Ala Leu Leu Gln Met Val Arg
2385                2390                2395                2400

Asp Glu Ser His Gln Ile Leu Ala Leu Ser Glu Gly Leu Ala Pro Pro
                2405                2410                2415

Ser Gly Glu Pro His Pro Pro Arg Lys Glu Asp Glu Ile Gln Asp Ile
                2420                2425                2430

Ser Leu His Gly Gly Lys Thr Gln Glu Val Pro Thr Ala Cys Pro Asp
    2435                2440                2445

Trp Arg Gly Asp Leu Leu Gln Val Val Gln Glu Ala Phe Glu Lys Glu
    2450                2455                2460

Gln Glu Met Gln Gly Val Glu Leu Gln Pro Arg Leu Ser Gly Ser Asp
2465                2470                2475                2480

Leu Gly Gly His Ser Ser Leu Leu Glu Arg Leu Glu Lys Ile Ile Arg
                2485                2490                2495

Glu Gln Gly Asp Leu Gln Glu Lys Ser Leu Glu His Leu Arg Leu Pro
                2500                2505                2510

Asp Arg Ser Ser Leu Leu Ser Glu Ile Gln Ala Leu Arg Ala Gln Leu
                2515                2520                2525

Arg Met Thr His Leu Gln Asn Gln Glu Lys Leu Gln His Leu Arg Thr
    2530                2535                2540

Ala Leu Thr Ser Ala Glu Ala Arg Gly Ser Gln Gln Glu His Gln Leu
2545                2550                2555                2560

Arg Arg Gln Val Glu Leu Leu Ala Tyr Lys Val Glu Gln Glu Lys Cys
                2565                2570                2575

Ile Ala Gly Asp Leu Gln Lys Thr Leu Ser Glu Glu Gln Lys Ala
                2580                2585                2590

Asn Ser Val Gln Lys Leu Leu Ala Ala Glu Gln Thr Val Val Arg Asp
    2595                2600                2605

Leu Lys Ser Asp Leu Cys Glu Ser Arg Gln Lys Ser Glu Gln Leu Ser
    2610                2615                2620

Arg Ser Leu Cys Glu Val Gln Gln Glu Val Leu Gln Leu Arg Ser Met
2625                2630                2635                2640

Leu Ser Ser Lys Glu Asn Glu Leu Lys Ala Ala Leu Gln Glu Leu Glu
                2645                2650                2655

Ser Glu Gln Gly Lys Gly Arg Ala Leu Gln Ser Gln Leu Glu Glu Glu
                2660                2665                2670

Gln Leu Arg His Leu Gln Arg Glu Ser Gln Ser Ala Lys Ala Leu Glu
            2675                2680                2685

Glu Leu Arg Ala Ser Leu Glu Thr Gln Arg Ala Gln Ser Ser Arg Leu
    2690                2695                2700

```
Cys Val Ala Leu Lys His Glu Gln Thr Ala Lys Asp Asn Leu Gln Lys
2705                2710                2715                2720

Glu Leu Arg Ile Glu His Ser Arg Cys Glu Ala Leu Leu Ala Gln Glu
            2725                2730                2735

Arg Ser Gln Leu Ser Glu Leu Gln Lys Asp Leu Ala Ala Glu Lys Ser
        2740                2745                2750

Arg Thr Leu Glu Leu Ser Glu Ala Leu Arg His Glu Arg Leu Leu Thr
    2755                2760                2765

Glu Gln Leu Ser Gln Arg Thr Gln Glu Ala Cys Val His Gln Asp Thr
2770                2775                2780

Gln Ala His His Ala Leu Leu Gln Lys Leu Lys Glu Glu Lys Ser Arg
2785                2790                2795                2800

Val Val Asp Leu Gln Ala Met Leu Glu Lys Val Gln Gln Gln Ala Leu
            2805                2810                2815

His Ser Gln Gln Gln Leu Glu Ala Glu Ala Gln Lys His Cys Glu Ala
        2820                2825                2830

Leu Arg Arg Glu Lys Glu Val Ser Ala Thr Leu Lys Ser Thr Val Glu
    2835                2840                2845

Ala Leu His Thr Gln Lys Arg Glu Leu Arg Cys Ser Leu Glu Arg Glu
2850                2855                2860

Arg Glu Lys Pro Ala Trp Leu Gln Ala Glu Leu Glu Gln Ser His Pro
2865                2870                2875                2880

Arg Leu Lys Glu Gln Glu Gly Arg Lys Ala Ala Arg Ser Ala Glu
            2885                2890                2895

Ala Arg Gln Ser Pro Ala Ala Ala Glu Gln Trp Arg Lys Trp Gln Arg
        2900                2905                2910

Asp Lys Glu Lys Leu Arg Glu Leu Glu Leu Gln Arg Gln Arg Asp Leu
    2915                2920                2925

His Lys Ile Lys Gln Leu Gln Gln Thr Val Arg Asp Leu Glu Ser Lys
2930                2935                2940

Asp Glu Val Pro Gly Ser Arg Leu His Leu Gly Ser Ala Arg Arg Ala
2945                2950                2955                2960

Ala Gly Ser Asp Ala Asp His Leu Arg Glu Gln Gln Arg Glu Leu Glu
            2965                2970                2975

Ala Met Arg Gln Arg Leu Leu Ser Ala Ala Arg Leu Leu Thr Ser Phe
        2980                2985                2990

Thr Ser Gln Ala Val Asp Arg Thr Val Asn Asp Trp Thr Ser Ser Asn
    2995                3000                3005

Glu Lys Ala Val Met Ser Leu Leu His Thr Leu Glu Glu Leu Lys Ser
3010                3015                3020

Asp Leu Ser Arg Pro Thr Ser Ser Gln Lys Lys Met Ala Ala Glu Leu
3025                3030                3035                3040

Gln Phe Gln Phe Val Asp Val Leu Leu Lys Asp Asn Val Ser Leu Thr
            3045                3050                3055

Lys Ala Leu Ser Thr Val Thr Gly Glu Lys Leu Glu Leu Ser Arg Ala
        3060                3065                3070

Val Ser Lys Leu Glu Lys Leu Leu Lys His His Leu Gln Lys Gly Cys
    3075                3080                3085

Ser Pro Ser Arg Ser Glu Arg Ser Ala Trp Lys Pro Asp Glu Thr Ala
3090                3095                3100

Pro Gln Ser Ser Leu Arg Arg Pro Asp Pro Gly Arg Leu Pro Pro Ala
3105                3110                3115                3120

Ala Ser Glu Glu Ala His Thr Ser Asn Val Lys Met Glu Lys Leu Tyr
```

```
                    3125                3130                3135
Leu His Tyr Leu Arg Ala Glu Ser Phe Arg Lys Ala Leu Ile Tyr Gln
            3140                3145                3150

Lys Lys Tyr Leu Leu Leu Ile Gly Gly Phe Gln Asp Ser Glu Gln
        3155                3160                3165

Glu Thr Leu Ser Met Ile Ala His Leu Gly Val Phe Pro Ser Lys Ala
    3170                3175                3180

Glu Arg Lys Ile Thr Ser Arg Pro Phe Thr Arg Phe Arg Thr Ala Val
3185                3190                3195                3200

Arg Val Val Ile Ala Ile Leu Arg Leu Arg Phe Leu Val Lys Lys Trp
                3205                3210                3215

Gln Glu Val Asp Arg Lys Gly Ala Leu Ala Gln Gly Lys Ala Pro Arg
            3220                3225                3230

Pro Gly Pro Arg Ala Arg Gln Pro Gln Ser Pro Arg Thr Arg Glu
        3235                3240                3245

Ser Pro Pro Thr Arg Asp Val Pro Ser Gly His Thr Arg Asp Pro Ala
    3250                3255                3260

Arg Gly Arg Arg Leu Ala Ala Ala Ser Pro His Ser Gly Gly Arg
3265                3270                3275                3280

Ala Thr Pro Ser Pro Asn Ser Arg Leu Glu Arg Ser Leu Thr Ala Ser
                3285                3290                3295

Gln Asp Pro Glu His Ser Leu Thr Glu Tyr Ile His Leu Glu Val
            3300                3305                3310

Ile Gln Gln Arg Leu Gly Gly Val Leu Pro Asp Ser Thr Ser Lys Lys
        3315                3320                3325

Ser Cys His Pro Met Ile Lys Gln
    3330                3335

<210> SEQ ID NO 39
<211> LENGTH: 4268
<212> TYPE: DNA
<213> ORGANISM: Homo sapiens

<400> SEQUENCE: 39
gccctgcgca ctccctgctg gggtgagcag cactgtaaag atgaagctgg ctaactggta      60
ctggctgagc tcagctgttc ttgccactta cggttttttg gttgtggcaa acaatgaaac     120
agaggaaatt aaagatgaaa gagcaaagga tgtctgccca gtgagactag aaagcagagg     180
gaaatgcgaa gaggcagggg agtgccccta ccaggtaagc ctgcccccct tgactattca     240
gctcccgaag caattcagca ggatcgagga ggtgttcaaa gaagtccaaa acctcaagga     300
aatcgtaaat agtctaaaga aatcttgcca agactgcaag ctgcaggctg atgacaacgg     360
agacccaggc agaaacggac tgttgttacc cagtacagga gccccgggag aggttggtga     420
taacagagtt agagaattag agagtgaggt taacaagctg tcctctgagc taagaatgc      480 caaagaggag atcaatgtac ttcatggtcg cctggagaag ctgaatcttg taaatatgaa     540
caacatagaa aattatgttg acagcaaagt ggcaaatcta acatttgttg tcaatagttt     600
ggatggcaaa tgttcaaagt gtcccagcca agaacaaata cagtcacgtc cagttcaaca     660
tctaatatat aaagattgct ctgactacta cgcaataggc aaaagaagca gtgagaccta     720
cagagttaca cctgatccca aaaatagtag ctttgaagtt tactgtgaca tggagaccat     780 gggggaggc tggacagtgc tgcaggcacg tctcgatggg agcaccaact tcaccagaac     840
atggcaagac tacaaagcag gctttggaaa cctcagaagg gaattttggc tggggaacga     900
```

```
taaaattcat cttctgacca agagtaagga aatgattctg agaatagatc ttgaagactt      960
taatggtgtc gaactatatg ccttgtatga tcagttttat gtggctaatg agtttctcaa     1020
atatcgttta cacgttggta actataatgg cacagctgga gatgcattac gtttcaacaa     1080
acattacaac cacgatctga agtttttcac cactccagat aaagacaatg atcgatatcc     1140
ttctgggaac tgtgggctgt actacagttc aggctggtgg tttgatgcat gtctttctgc     1200
aaacttaaat ggcaaatatt atcaccaaaa atacagaggt gtccgtaatg ggattttctg     1260
gggtacctgg cctggtgtaa gtgaggcaca ccctggtggc tacaagtcct ccttcaaaga     1320
ggctaagatg atgatcagac ccaagcactt taagccataa atcactctgt tcattcctcc     1380
aggtattcgt tatctaatag ggcaattaat tccttcagca ctttagaata tgccttgttt     1440
catatttttc atagctaaaa aatgatgtct gacggctagg ttcttatgct acacagcatt     1500
tgaaataaag ctgaaaaaca atgcatttta aaggagtcct ttgttgttat gctgttatcc     1560
aatgaacact tgcaagcaat tagcaatatt gagaattata cattagattt acaattcttt     1620
taatttctat tgaaactttt tctattgctt gtattacttg ctgtatttaa aaataattg      1680 ttggctgggt gtggtagctc acgcctgtaa tcccagcact ttggaatgtc aaggcaggca     1740
gatcacttga ggtcaggagt ttgagaccag cctggccaaa catgtgaaac gctgtctcta     1800
ttaaaaatac aaaaattagc cgggcatggt ggtacatgcc tgtaatccta gctacttggg     1860
aggctgaggc aggagaatcg cttgaacctg agaggaagag gttgcagtga gccaagactg     1920
agccactgca ctccagcatg ggtgacagag aaaactctgt ctcaaacaaa aaaataataa     1980
aatttattca gtaggctgga ttctacacaa agtaatctgt atttgggcca tgatttaagc     2040
acatctgaag gtatatcact cttttcaggc tataattatt tgggtaatct tcattctgag     2100
acaaacttaa tctatatcat ttactttgca acagaacaac cctacagcat tttggttccc     2160
agactaaggg aactaatatc tatataatta aacttgttca tttatcattc atgaaatata     2220
aaatacttgt catttaaacc gtttaaaaat gtggtagcat aatgtcaccc caaaaagcat     2280
tcagaaagca atgtaactgt gaagaccagg gtttaaaggt aattcattta tagtttataa     2340
ctccttagat gtttgatgtt gaaaactgct ttaacatgaa aattatcttc ctctgctctg     2400
tgtgaacaat agcttttaat ttaagattgc tcactactgt actagactac tggtaggttt     2460 ttttggggg ggtgggtagg gatatgtggg taatgaagca tttacttaca ggctatcata     2520
ctctgaggcc aatttttatct ccaaagcaat aatatcatta agtgattcac ttcatagaag     2580
gctaagtttc tctaggacag atagaaaaca tgaattttga aatatataga acagtagtta     2640
aaatactata tatttcaacc ctggctggta gattgcttat tttactatca gaaactaaaa     2700
gatagatttt tacccaaaca gaagtatctg taatttttat aattcatcaa ttctggaatg     2760
ctatatataa tatttaaaag acttttttaaa tgtgtttaat ttcatcatcg taaaagggga     2820
tcatctcaga gagaacagca gtattctgcg tattttaaa aatgctctag agtaacattt     2880
gaagtaattc actgtagtgt atgccagtcc tagaaataat tttttaatt tctggtgtct     2940 gtttctaata cactaaccaa gttttcaaaa tatatttaca aagatgcatc tttacccatt     3000
attttaaaat gattaaggag gatagttgct tcagtaaca agctaatttt tcaaatatta     3060
ggcccttaca gaactattta gtcaaaaagt aagatattcc tttaaaatat ataacccaaa     3120
gctttcagtt aaacatgata tatcacaaat actattaaaa tgttaaagag aaatgcaaat     3180
agcattaaat gatgaccaaa atgtaaaata ttgtagattt caaaagctgt gtctctatta     3240
ggtgggatac caaatgtaaa tgatgtaact gacgttgttt tttactttt actttttaaa     3300
```

-continued

```
aaagactaaa aacgttttga tattatacaa tgtatttgtt tcagataagg tcattgtcat    3360
ttagtatata taattaatat atgtacaagt ttaagtaaat tcctgtgagt aaaaatggac    3420
ttatcacaaa acatagttct aaagaaaggt atatgctcat atacacggtg tccattaatt    3480
taatgggaac taggtataac ttcaggagaa tttggcaaat aattcattaa tccatgtaaa    3540
tattcaaaag cttgttctat ccacattatt tcaagggatc actttatttt tcattatact    3600
ttcacagcac ttttctagta aattctgtaa cacagaaatt ccattttgga atcatttcat    3660
gttaccaata attctagact tttataacat ttaacatgtt gatggaaata gattacatct    3720
gctagaacct tttgccttaa ctattcacca atatatgcta atattcataa atatggattg    3780
actgtttaca acattagaa tcttgtcttg gttccatttt gatggctaat atttgttatc     3840
ttaattaaga ctatttctga ggtcatgatt acttgaaaat attgactaaa actgggtcct    3900
tagaaattcc aggtggagct gatttaccta tgactgaggg gaaaaaaaaa tcaaatttta    3960
ctgataatag taatgctcca aatgaattaa tgacacatct gttcaataaa taaagagctt    4020
aaatatacaa aacataagaa atctgggcaa caaaacttgt ggtctttact tttgaatagc    4080
tacccaagaa aaggttttaa aggtaaaagt tatgagtaat gtcatcacaa taagctcttg    4140
tttaaaattc ttttctttta tgtataatta ggtttatgtt tcatgtcttt ttaaaacctt    4200 ataaagatt taattatcac atctattctt caatgtggaa atattaaata ttgttggttg     4260
taaaataa                                                             4268
```

<210> SEQ ID NO 40
<211> LENGTH: 439
<212> TYPE: PRT
<213> ORGANISM: Homo sapiens

<400> SEQUENCE: 40

```
Met Lys Leu Ala Asn Trp Tyr Trp Leu Ser Ser Ala Val Leu Ala Thr
  1               5                  10                  15

Tyr Gly Phe Leu Val Val Ala Asn Asn Glu Thr Glu Glu Ile Lys Asp
             20                  25                  30

Glu Arg Ala Lys Asp Val Cys Pro Val Arg Leu Glu Ser Arg Gly Lys
         35                  40                  45

Cys Glu Glu Ala Gly Glu Cys Pro Tyr Gln Val Ser Leu Pro Pro Leu
     50                  55                  60

Thr Ile Gln Leu Pro Lys Gln Phe Ser Arg Ile Glu Glu Val Phe Lys
 65                  70                  75                  80

Glu Val Gln Asn Leu Lys Glu Ile Val Asn Ser Leu Lys Lys Ser Cys
                 85                  90                  95

Gln Asp Cys Lys Leu Gln Ala Asp Asp Asn Gly Asp Pro Gly Arg Asn
            100                 105                 110

Gly Leu Leu Leu Pro Ser Thr Gly Ala Pro Gly Glu Val Gly Asp Asn
        115                 120                 125

Arg Val Arg Glu Leu Glu Ser Glu Val Asn Lys Leu Ser Ser Glu Leu
    130                 135                 140

Lys Asn Ala Lys Glu Glu Ile Asn Val Leu His Gly Arg Leu Glu Lys
145                 150                 155                 160

Leu Asn Leu Val Asn Met Asn Asn Ile Glu Asn Tyr Val Asp Ser Lys
                165                 170                 175

Val Ala Asn Leu Thr Phe Val Val Asn Ser Leu Asp Gly Lys Cys Ser
            180                 185                 190
```

```
Lys Cys Pro Ser Gln Glu Gln Ile Gln Ser Arg Pro Val Gln His Leu
            195                 200                 205

Ile Tyr Lys Asp Cys Ser Asp Tyr Tyr Ala Ile Gly Lys Arg Ser Ser
        210                 215                 220

Glu Thr Tyr Arg Val Thr Pro Asp Pro Lys Asn Ser Ser Phe Glu Val
225                 230                 235                 240

Tyr Cys Asp Met Glu Thr Met Gly Gly Trp Thr Val Leu Gln Ala
                245                 250                 255

Arg Leu Asp Gly Ser Thr Asn Phe Thr Arg Thr Trp Gln Asp Tyr Lys
                260                 265                 270

Ala Gly Phe Gly Asn Leu Arg Arg Glu Phe Trp Leu Gly Asn Asp Lys
            275                 280                 285

Ile His Leu Leu Thr Lys Ser Lys Glu Met Ile Leu Arg Ile Asp Leu
        290                 295                 300

Glu Asp Phe Asn Gly Val Glu Leu Tyr Ala Leu Tyr Asp Gln Phe Tyr
305                 310                 315                 320

Val Ala Asn Glu Phe Leu Lys Tyr Arg Leu His Val Gly Asn Tyr Asn
                325                 330                 335

Gly Thr Ala Gly Asp Ala Leu Arg Phe Asn Lys His Tyr Asn His Asp
                340                 345                 350

Leu Lys Phe Phe Thr Thr Pro Asp Lys Asp Asn Asp Arg Tyr Pro Ser
        355                 360                 365

Gly Asn Cys Gly Leu Tyr Tyr Ser Ser Gly Trp Trp Phe Asp Ala Cys
        370                 375                 380

Leu Ser Ala Asn Leu Asn Gly Lys Tyr Tyr His Gln Lys Tyr Arg Gly
385                 390                 395                 400

Val Arg Asn Gly Ile Phe Trp Gly Thr Trp Pro Gly Val Ser Glu Ala
                405                 410                 415

His Pro Gly Gly Tyr Lys Ser Ser Phe Lys Glu Ala Lys Met Met Ile
                420                 425                 430

Arg Pro Lys His Phe Lys Pro
        435

<210> SEQ ID NO 41
<211> LENGTH: 4338
<212> TYPE: DNA
<213> ORGANISM: Homo sapiens

<400> SEQUENCE: 41
ggggcacact catgcattcc tgtcaagtca tcttgtgaaa ggctgcctgc ttccagcttg    60
gcttggatgt gcaaccttaa taaaactcac tgaggtctgg gagaaaatag cagatctgca   120
gcagataggg tagaggaaag ggtctagaat atgtacacgc agctgactca ggcaggctcc   180
atgctgaacg gtcacacaga gaggaaacaa taaatctcag ctactatgca ataaatatct   240
caagttttaa cgaagaaaaa catcattgca gtgaaataaa aaattttaaa atttttagaac  300 aaagctaaca aatggctagt tttctatgat tcttcttcaa acgctttctt tgaggggggaa  360 agagtcaaac aaacaagcag ttttacctga aataaagaac tagttttaga ggtcagaaga   420
aaggagcaag ttttgcgaga ggcacggaag gagtgtgctg cagtacaat gacagttttc    480 ctttcctttg ctttcctcgc tgccattctg actcacatag ggtgcagcaa tcagcgccga   540
agtccagaaa acagtgggag aagatataac cggattcaac atgggcaatg tgcctacact   600
ttcattcttc cagaacacga tggcaactgt cgtgagagta cgacagacca gtacaacaca   660
aacgctctgc agagagatgc tccacacgtg gaaccggatt tctcttccca gaaacttcaa   720
```

-continued

```
catctggaac atgtgatgga aaattatact cagtggctgc aaaaacttga gaattacatt    780
gtggaaaaca tgaagtcgga gatggcccag atacagcaga atgcagttca gaaccacacg    840
gctaccatgc tggagatagg aaccagcctc ctctctcaga ctgcagagca gaccagaaag    900
ctgacagatg ttgagaccca ggtactaaat caaacttctc gacttgagat acagctgctg    960
gagaattcat tatccaccta caagctagag aagcaacttc ttcaacagac aaatgaaatc   1020
ttgaagatcc atgaaaaaaa cagtttatta gaacataaaa tcttagaaat ggaaggaaaa   1080
cacaaggaag agttggacac cttaaaggaa gagaaagaga accttcaagg cttggttact   1140
cgtcaaacat atataatcca ggagctgaaa agcaattaa acagagctac caccaacaac    1200
agtgtccttc agaagcagca actggagctg atggacacag tccacaacct tgtcaatctt   1260
tgcactaaag aaggtgtttt actaaaggga ggaaaaagag aggaagagaa accatttaga   1320
gactgtgcag atgtatatca agctggtttt aataaaagtg gaatctacac tatttatatt   1380
aataatatgc cagaacccaa aaaggtgttt tgcaatatgg atgtcaatgg gggaggttgg   1440
actgtaatac aacatcgtga agatggaagt ctagatttcc aaagaggctg gaaggaatat   1500
aaaatgggtt ttggaaatcc ctccggtgaa tattggctgg ggaatgagtt tattttttgcc  1560
attaccagtc agaggcagta catgctaaga attgagttaa tggactggga agggaaccga   1620
gcctattcac agtatgacag attccacata ggaaatgaaa agcaaaacta taggttgtat   1680
ttaaaaggtc acactgggac agcaggaaaa cagagcagcc tgatcttaca cggtgctgat   1740
ttcagcacta aagatgctga taatgacaac tgtatgtgca aatgtgccct catgttaaca   1800
ggaggatggt ggtttgatgc ttgtggcccc tccaatctaa atggaatgtt ctatactgcg   1860
ggacaaaacc atggaaaact gaatgggata aagtggcact acttcaaagg gcccagttac   1920
tccttacgtt ccacaactat gatgattcga cctttagatt tttgaaagcg caatgtcaga   1980
agcgattatg aaagcaacaa agaaatccgg agaagctgcc aggtgagaaa ctgtttgaaa   2040
acttcagaag caaacaatat tgtctcccct ccagcaataa gtggtagtta tgtgaagtca   2100
ccaaggttct tgaccgtgaa tctggagccg tttgagttca caagagtctc tacttggggt   2160
gacagtgctc acgtggctcg actatagaaa actccactga ctgtcgggct ttaaaaaggg   2220
aagaaactgc tgagcttgct gtgcttcaaa ctactactgg accttatttt ggaactatgg   2280
tagccagatg ataaatatgg ttaatttcat gtaaaacaga aaaaagagt gaaaagaga    2340
atatacatga agaatagaaa caagcctgcc ataatccttt ggaaaagatg tattatacca   2400
gtgaaaaggt gttatatcta tgcaaaccta ctaacaaatt atactgttgc acaatttga    2460
taaaaattta gaacagcatt gtcctctgag ttggttaaat gttaatggat ttcagaagcc   2520
taattccagt atcatactta ctagttgatt tctgcttacc catcttcaaa tgaaaattcc   2580
atttttgtaa gccataatga actgtagtac atggacaata agtgtgtggt agaaacaaac   2640
tccattactc tgattttga tacagttttc agaaaaagaa atgaacataa tcaagtaagg    2700
atgtatgtgg tgaaaactta ccaccccat actatggttt tcatttactc taaaaactga    2760
ttgaatgata tataaatata tttatagcct gagtaaagtt aaaagaatgt aaaatatatc   2820
atcaagttct taaataata tacatgcatt taatatttcc tttgatatta tacaggaaag    2880
caatatttg gagtatgtta agttgaagta aaagcaagta ctctggagca gttcatttta    2940
cagtatctac ttgcatgtgt atacatacat gtaacttcat tatttaaaaa atattttag    3000
aactccaata ctcaccctgt tatgtcttgc taatttaaat tttgctaatt aactgaaaca   3060
```

```
tgcttaccag attcacactg ttccagtgtc tataaagaa acactttgaa gtctataaaa      3120
aataaaataa ttataaatat cattgtacat agcatgttta tatctgcaaa aaacctaata      3180
gctaattaat ctggaatatg caacattgtc cttaattgat gcaaataaca caaatgctca      3240
aagaaatcta ctatatccct taatgaaata catcattctt catatatttc tccttcagtc      3300 cattcccta ggcaattttt aatttttaaa aattattatc aggggagaaa aattggcaaa       3360
actattatat gtaagggaaa tatatacaaa aagaaaatta atcatagtca cctgactaag      3420
aaattctgac tgctagttgc cataaataac tcaatggaaa tattcctatg ggataatgta      3480
ttttaagtga atttttgggg tgcttgaagt tactgcatta ttttatcaag aagtcttctc      3540
tgcctgtaag tgtccaaggt tatgacagta aacagttttt attaaaacat gagtcactat      3600
gggatgagaa aattgaaata aagctactgg gcctcctctc ataaaagaga cagttgttgg      3660
caaggtagca ataccagttt caaacttggt gacttgatcc actatgcctt aatggtttcc      3720
tccatttgag aaaataaagc tattcacatt gttaagaaaa atactttta aagtttacca       3780 tcaagtcttt tttatattta tgtgtctgta ttctaccct ttttgcctta caagtgatat       3840
ttgcaggtat tataccatt ttctattctt ggtggcttct tcatagcagg taagcctctc       3900
cttctaaaaa cttctcaact gttttcattt aagggaaaga aaatgagtat tttgtcctt       3960 tgtgttccta cagacacttt cttaaaccag ttttggata aagaatacta tttccaaact       4020
catattacaa aaacaaaata aaataataaa aaaagaaagc atgatattta ctgttttgtt      4080
gtctgggttt gagaaatgaa atattgtttc caattattta taataaatca gtataaaatg      4140
ttttatgatt gttatgtgta ttatgtaata cgtacatgtt tatggcaatt taacatgtgt      4200 attctttta ttgtttcaga ataggataat taggtattcg aattttgtct ttaaaattca      4260
tgtggtttct atgcaaagtt cttcatatca tcacaacatt atttgattta aataaaattg      4320
aaagtaatat ttgtgcaa                                                    4338
```

<210> SEQ ID NO 42
<211> LENGTH: 498
<212> TYPE: PRT
<213> ORGANISM: Homo sapiens

<400> SEQUENCE: 42

Met Thr Val Phe Leu Ser Phe Ala Phe Leu Ala Ala Ile Leu Thr His
1               5                   10                  15

Ile Gly Cys Ser Asn Gln Arg Arg Ser Pro Glu Asn Ser Gly Arg Arg
            20                  25                  30

Tyr Asn Arg Ile Gln His Gly Gln Cys Ala Tyr Thr Phe Ile Leu Pro
        35                  40                  45

Glu His Asp Gly Asn Cys Arg Glu Ser Thr Thr Asp Gln Tyr Asn Thr
    50                  55                  60

Asn Ala Leu Gln Arg Asp Ala Pro His Val Glu Pro Asp Phe Ser Ser
65                  70                  75                  80

Gln Lys Leu Gln His Leu Glu His Val Met Glu Asn Tyr Thr Gln Trp
                85                  90                  95

Leu Gln Lys Leu Glu Asn Tyr Ile Val Glu Asn Met Lys Ser Glu Met
            100                 105                 110

Ala Gln Ile Gln Gln Asn Ala Val Gln Asn His Thr Ala Thr Met Leu
        115                 120                 125

Glu Ile Gly Thr Ser Leu Leu Ser Gln Thr Ala Glu Gln Thr Arg Lys
    130                 135                 140

| Leu | Thr | Asp | Val | Glu | Thr | Gln | Val | Leu | Asn | Gln | Thr | Ser | Arg | Leu | Glu |
| 145 | | | | 150 | | | | | 155 | | | | | 160 | |

| Ile | Gln | Leu | Leu | Glu | Asn | Ser | Leu | Ser | Thr | Tyr | Lys | Leu | Glu | Lys | Gln |
| | | | | 165 | | | | | 170 | | | | | 175 | |

| Leu | Leu | Gln | Gln | Thr | Asn | Glu | Ile | Leu | Lys | Ile | His | Glu | Lys | Asn | Ser |
| | | | 180 | | | | | 185 | | | | | 190 | | |

| Leu | Leu | Glu | His | Lys | Ile | Leu | Glu | Met | Glu | Gly | Lys | His | Lys | Glu | Glu |
| | | 195 | | | | | 200 | | | | | 205 | | | |

| Leu | Asp | Thr | Leu | Lys | Glu | Glu | Lys | Glu | Asn | Leu | Gln | Gly | Leu | Val | Thr |
| | 210 | | | | | 215 | | | | | 220 | | | | |

| Arg | Gln | Thr | Tyr | Ile | Ile | Gln | Glu | Leu | Glu | Lys | Gln | Leu | Asn | Arg | Ala |
| 225 | | | | 230 | | | | | 235 | | | | | 240 | |

| Thr | Thr | Asn | Asn | Ser | Val | Leu | Gln | Lys | Gln | Gln | Leu | Glu | Leu | Met | Asp |
| | | | | 245 | | | | | 250 | | | | | 255 | |

| Thr | Val | His | Asn | Leu | Val | Asn | Leu | Cys | Thr | Lys | Glu | Gly | Val | Leu | Leu |
| | | | 260 | | | | | 265 | | | | | 270 | | |

| Lys | Gly | Gly | Lys | Arg | Glu | Glu | Lys | Pro | Phe | Arg | Asp | Cys | Ala | Asp |
| | | 275 | | | | | 280 | | | | | 285 | | |

| Val | Tyr | Gln | Ala | Gly | Phe | Asn | Lys | Ser | Gly | Ile | Tyr | Thr | Ile | Tyr | Ile |
| | 290 | | | | | 295 | | | | | 300 | | | | |

| Asn | Asn | Met | Pro | Glu | Pro | Lys | Lys | Val | Phe | Cys | Asn | Met | Asp | Val | Asn |
| 305 | | | | 310 | | | | | 315 | | | | | 320 | |

| Gly | Gly | Gly | Trp | Thr | Val | Ile | Gln | His | Arg | Glu | Asp | Gly | Ser | Leu | Asp |
| | | | | 325 | | | | | 330 | | | | | 335 | |

| Phe | Gln | Arg | Gly | Trp | Lys | Glu | Tyr | Lys | Met | Gly | Phe | Gly | Asn | Pro | Ser |
| | | | 340 | | | | | 345 | | | | | 350 | | |

| Gly | Glu | Tyr | Trp | Leu | Gly | Asn | Glu | Phe | Ile | Phe | Ala | Ile | Thr | Ser | Gln |
| | | 355 | | | | | 360 | | | | | 365 | | | |

| Arg | Gln | Tyr | Met | Leu | Arg | Ile | Glu | Leu | Met | Asp | Trp | Glu | Gly | Asn | Arg |
| | 370 | | | | | 375 | | | | | 380 | | | | |

| Ala | Tyr | Ser | Gln | Tyr | Asp | Arg | Phe | His | Ile | Gly | Asn | Glu | Lys | Gln | Asn |
| 385 | | | | 390 | | | | | 395 | | | | | 400 | |

| Tyr | Arg | Leu | Tyr | Leu | Lys | Gly | His | Thr | Gly | Thr | Ala | Gly | Lys | Gln | Ser |
| | | | | 405 | | | | | 410 | | | | | 415 | |

| Ser | Leu | Ile | Leu | His | Gly | Ala | Asp | Phe | Ser | Thr | Lys | Asp | Ala | Asp | Asn |
| | | | 420 | | | | | 425 | | | | | 430 | | |

| Asp | Asn | Cys | Met | Cys | Lys | Cys | Ala | Leu | Met | Leu | Thr | Gly | Gly | Trp | Trp |
| | | 435 | | | | | 440 | | | | | 445 | | | |

| Phe | Asp | Ala | Cys | Gly | Pro | Ser | Asn | Leu | Asn | Gly | Met | Phe | Tyr | Thr | Ala |
| | 450 | | | | | 455 | | | | | 460 | | | | |

| Gly | Gln | Asn | His | Gly | Lys | Leu | Asn | Gly | Ile | Lys | Trp | His | Tyr | Phe | Lys |
| 465 | | | | 470 | | | | | 475 | | | | | 480 | |

| Gly | Pro | Ser | Tyr | Ser | Leu | Arg | Ser | Thr | Thr | Met | Met | Ile | Arg | Pro | Leu |
| | | | | 485 | | | | | 490 | | | | | 495 | |

Asp Phe

<210> SEQ ID NO 43
<211> LENGTH: 6329
<212> TYPE: DNA
<213> ORGANISM: Homo sapiens

<400> SEQUENCE: 43

```
gattgggggc ggtggtctgg gtgtgattcc tgtgggggaa accagcccga ggtgccttgg      60
ctcaggcttg cctgcctgga gtccttgtcg tgtacccgtc tgtggcccta gagtcacctc     120
```

-continued

```
ctgctcctttt tcactgggtt tctccccaga ccaagccct  ggatttgagc ttctgagcag    180
ccaactgatt  ttttcatga  gggaaagaat tttgctccta gatttatttc taatccttt    240 ctccgtaact  gacctttct  ctgtaagcta tttgtggctc tagtgggttt ttgtttgctt    300
gcttgttttt  gttttatctt tgccctgaac gtccatcctg gcctcggctg cctccctccc    360
cgagttcttc  actacacctc ctgtctcagc ctcccagaga gggtggcgag ggtgctgatg    420
cccagagaca  ccatccggcg aatgacctc  tcctgtcatg cggggcaggg cagggctgcc    480
ggcagagcca  tgtcctgaac cctccctcct cccccctgct ctccttaagg gtctttccca    540
gatgtgaagg  tccctcccag gctctactga ggtcagacca attcccagtg gcttgggtac    600
cctcgttcac  tccagcacca gccctgccc  tccttcttcc cgggccaggc tgccaggtga    660
gccccgggcc  aagggtggtt gccctgctga ggccgaaagg actcgagctt cccatctcct    720 cgcctcccc   aggtctttca ccgtctggac tcatctctgg gtaactcatg gtgtgagtgg    780
ccacgtggct  ggctcaggtg agtccttta  accccaggt  gacccaccag ctagtccggg    840
gcccattgtt  gtgcccacta ggatgtcccc catggtgtcc tccctgcgct taaagttct    900 ccttcgtgtg  ctgttcttca tggccctgt  tccccacag  gtgtttggac agtgaacgcc    960 aggtccctc   ctccccaccc ccggcctctc aaacacgccc agccacga   tggcagcaga   1020 gacactcaac  tttgggcctg agtggctcag ggcctgtcc  gggggcggca gcgtggcctc   1080 cccaccccg   tccctgcca  tgcccaaata aagctggct  gactaccgtt atgggcgaga   1140
ggaaatgctg  gctctctacg tcaaggagaa caaggtcccg gaagagctgc aggacaagga   1200
gttcgccgcg  gtgctgcagg acgagccact gcagccctg  gctctggagc cgctgactga   1260
ggaggaacag  agaaacttct ccctgtcagt gaacagcgtg gctgtgctga ggctgatggg   1320
gaaaggggct  ggcccccccc tggctggcac ctcccgaggc aggggcagca cgcggagccg   1380
aggccgcggc  cgtggtgaca gctgcttta  ccaaagaagc atcgaagaag gcgatgggc   1440 ctttggacga  agcccccggg aaatccagcg cagccagagc tgggatgaca gaggcgagag   1500
gcggtttgag  aagtcagcaa ggcgggatgg agcacgatgt ggctttgagg agggagggc   1560 tggcccaagg  aaggagcacg cccgctcaga cagcgagaac tggcgctccc tacgggagga   1620
acaggaggag  gaggaggagg gcagctggag gctcggagca gggccccggc gagacggcga   1680
ccgctggcgc  tccgccagcc ctgatggtgg tccccgctct gctggctggc gggaacatgg   1740
ggaacggcgg  cgcaagtttg aatttgattt gcgaggggat cgaggagggt gtggtgaaga   1800
ggaggggcgg  ggaggggagg gcagctctca cctgcggcgg tgccgagcgc ctgaaggctt   1860
tgaggaggac  aaggatgggc tcccagagtg gtgcctggac gatgaggatg aagaaatggg   1920
cacctttgat  gcctctgggg ccttcttgcc tctcaagaag ggcccaagg  agcccattcc   1980 tgaggagcag  gagctggact tccaaggggtt ggaggaggag gaggaacctt ccgaagggct   2040
agaggaggaa  gggcctgagg caggtgggaa agagctgacc ccactgcctc tcaggagga   2100 gaagtccagc  tccccatccc cactgcccac cctgggccca ctctggggga caaacgggga   2160 tgggacgaa   actgcagaga aagagccccc agcggccgaa gatgatattc ggggatcca   2220 gctgagtccc  ggggtgggct cctctgctgg cccacccgga gatctggagg atgatgaagg   2280
cttgaagcac  ctgcagcagg aggcggagaa gctggtggcc tccctgcagg acagctcctt   2340
ggaggaggag  cagttcacgg ctgccatgca gaccaggc   ctgcgccact ctgcagccgc   2400
cactgccctc  ccgctcagcc atggggctgc ccggaagtgg ttctacaagg acccacaggg   2460
```

```
cgagatccaa ggcccctcca cgacacagga gatggcagag tggttccagg ccggctactt   2520
ttccatgtca ctgctggtga agcggggctg cgatgagggc ttccagccgc tgggcgaggt   2580
gatcaagatg tggggccgcg tgcccttgc cccagggccc tcacctcccc cactgctggg    2640
aaacatggac caggagcggc tgaagaagca acaggagctg gccgcggcgg ccttgtacca   2700
gcagctgcag caccagcagt tctccagct ggtcagcagc cgccagctcc cacagtgcgc    2760
gctccgagaa aaggcagctc tggggacct gacaccgcca ccaccgccgc cgccacagca    2820
gcagcagcag cagctcacgg cattcctgca gcagctccag gcgctcaaac ccccagagg    2880 cggggaccag aacctgctcc cgacgatgag ccggtccttg tcggtgccag attcgggccg   2940
cctctgggac gtacatacct cagcctcatc acagtcaggt ggtgaggcca gtctttggga   3000
cataccaatt aactcttcga ctcagggtcc aattctagaa caactccagc tgcaacataa   3060
attccaggag cgcagagaag tggagctcag ggcgaagcgg aggaagagg aacgcaagcg    3120 tcgagaggaa aagcgccgcc agcagcagca ggaggagcag aagcggcggc aggaggagga   3180
agagctgttt cggcgcaagc acgtgcgcca gcaggagcta ttgctgaagt tgctacagca   3240
gcagcaggcg gtccctgtgc ccccgcacc cagctccccg ccccactct gggctggcct     3300 ggccaagcag gggctgtcca tgaagacgct cctggagttg cagctggagg gcgagcggca   3360
gctgcacaaa cagcccccac ctcgggagcc agctcgggcc caggccccca accaccgagt   3420
gcagcttggg ggcctgggca ctgccccct gaaccagtgg gtgtctgagg ctgggccact    3480
gtggggcggg ccagacaaga gtgggggcgg cagcagcggc ctgggctct gggaggacac    3540 ccccaagagc ggcgggagcc tggtccgtgg cctcggcctg aagaacagcc ggagcagccc   3600
atctctcagt gactcataca gccacctatc gggtcggccc attcgcaaaa agacggagga   3660
agaagagaag ctgctgaagc tgctgcaggg cattcccagg ccccaggacg gcttcaccca   3720
gtggtgcgag cagatgctgc acacgctgag cgccacgggc agcctggacg tgcccatggc   3780
tgtagcgatc ctcaaggagg tggaatcccc ctatgatgtc cacgattata tccgttcctg   3840
cctgggggac acgctggaag ccaaagaatt tgccaaacaa ttcctggagc ggagggccaa   3900
gcagaaagcc agccagcagc ggcagcagca gcaggaggca tggctgagca cgcctcgct   3960 gcagacggcc ttccaggcca accacagcac caaactcggc cccggggagg gcagcaaggc   4020
caagaggcgg gcactgatgc tgcactcaga ccccagcatc ctggggtact ccctgcacgg   4080
atcttctggt gagatcgaga gcgtggatga ctactgacca gcccggaccc ccagcccctg   4140
ggctgtaggc cagggcagcc acagcggcgt ggaccgaggg tccagcctg caggctcccc    4200 gcagagagca caggaagagg caggggcggg gtccccagca cttgttacaa acacacgatg   4260
caccttaact cacccaccac gaggcacttt acagactggg ggaggggtt tttcttttta    4320 ttttttttt taattttaaa cgactgaaga aaacattagg agaggcaaaa atattgttaa    4380
aaactagact ctaaacaccc cttcctgctg tgaggatagt gggtgtgaca atggaaggtc   4440
cacagaggtt tttgttttt ggttttttt ttttttaa gaaaaaaga tgaaaatga         4500 aaaaaaaat ggttaggagg ctgaaagaaa aaacacactg ttattttggg gcagtgggga   4560
cacaggcccc gtgacctgt cctgcctggc cccaaggcc atacttaccc cccagaaggc    4620
gggccatggg gtaactggaa gctggggcc agcagtttgc acaggaggcc tgtctgagcc   4680
ccacccgcca gacctgttgt gagcagctcc tgtcactgag gctggctgag gtgtccgggg   4740
tggggccaaa gtagcccctt ggcttcgctg ctttggggga cagttgcaca aattggacga   4800
gtggccccag ctctctggct gccatcttgt gctggccgag tagacgggag gggccaagcc   4860
```

```
gtgccaacct ctctggctgg cagggtgggg cagcaggact ctggttctgg tgagggcgt    4920 ctcccactgc tgccattttg ggggacaccc tgggtttgaa cctgaaagcc ccagctctct    4980
gccttgccac gtgaatgtat tctttgggcc acaagccccc gcctcacccc tgcctgagct    5040
gcctcacccc tgtgagcggc gggggtggat gattgctcca gaggctgcag agagaaggct    5100
gagctgtttc tccagtgaag ggggcaggag gaggggcctc aaaggcaagg agtgggtggc    5160
tttgggctta gggttgcagt agaggggctg ccgcccgggg ccccaacctg tagccagctc    5220
gtaagatgtg gaccacccag ctctgcacct gacccttccg ctgaccaaat gggagaggag    5280
caggtggcct tccgggtctg atatgatgcg cttttttaccg ttgggtaagg ttggggtgaa    5340
gagaagtgtg cggctcctgg gtcagaggag gctgcccctt ctattgctca cccacttctt    5400
attcccggtc ccctacttgg gttcgtctcc gcccattttg ggttttgtaa cagttttgtc    5460
ttttgggttt ctcatccagc tcctcccatt gacctcattg ctcagagtgc agtattaggg    5520
caaggcttcg ccactgcctc cctccatgaa tgtatttctc cctcctgccc tggggacatg    5580
gggagtggcc cgtttctttc cccatctagt cccagaaaga tggtgtttgg ttttctgttg    5640
ttggattttt ttttttttttt tttttttttt gcaccaaagt ggcaactagg tcagtgttgg    5700
gggatcaagc tggcctcggg gtgggggggcc cccacctgcc tctccctggt tccacagtg    5760 ttagcgtccc tgaaaagaca atattctctc taaagcaata aggggtgacg ggccgggggg    5820
agtgtttgct gctgctggcc cccagctccc cttccctctt gccaggtgtg ggggagactc    5880
ctgttgtgac tgaatgtaac cccccacccc ctgccgcagc caatgcaggg gaaggggac    5940 actcttcctg tctcttctcc ccagctaaag agactttgga cttaggggggc ccatgagcct    6000 ggagaggcct taaccctgtg aggaagtata gggggagccc tctcccaccc ccatcccctt    6060
ctgagagtgg tcaatgttta caagcccctg agccccctg cccagggact cagaccctgt    6120
tgctgtcctt ccccggcccc ggtcttcctg ggccctcgct gctccctgc ccttcctggg    6180 gttggggtgg gtgcaggggt caccgtgttc cctgtctgcc ttgtacccac agtctccccg    6240 cccctctcc accctgtgtg acttccctct cttttacctg ctcctgtaaa tactcccttc    6300
tcccaataaa acttggtgtg tgttctccc                                       6329
```

<210> SEQ ID NO 44
<211> LENGTH: 1035
<212> TYPE: PRT
<213> ORGANISM: Homo sapiens

<400> SEQUENCE: 44

```
Met Ala Ala Glu Thr Leu Asn Phe Gly Pro Glu Trp Leu Arg Ala Leu
  1               5                  10                  15

Ser Gly Gly Gly Ser Val Ala Ser Pro Pro Ser Pro Ala Met Pro
                 20                  25                  30

Lys Tyr Lys Leu Ala Asp Tyr Arg Tyr Gly Arg Glu Glu Met Leu Ala
             35                  40                  45

Leu Tyr Val Lys Glu Asn Lys Val Pro Glu Glu Leu Gln Asp Lys Glu
         50                  55                  60

Phe Ala Ala Val Leu Gln Asp Glu Pro Leu Gln Pro Leu Ala Leu Glu
     65                  70                  75                  80

Pro Leu Thr Glu Glu Glu Gln Arg Asn Phe Ser Leu Ser Val Asn Ser
                 85                  90                  95

Val Ala Val Leu Arg Leu Met Gly Lys Gly Ala Gly Pro Pro Leu Ala
                100                 105                 110
```

```
Gly Thr Ser Arg Gly Arg Gly Ser Thr Arg Ser Arg Gly Arg Gly Arg
            115                 120                 125

Gly Asp Ser Cys Phe Tyr Gln Arg Ser Ile Glu Glu Gly Asp Gly Ala
            130                 135                 140

Phe Gly Arg Ser Pro Arg Glu Ile Gln Arg Ser Gln Ser Trp Asp Asp
145                 150                 155                 160

Arg Gly Glu Arg Arg Phe Glu Lys Ser Ala Arg Arg Asp Gly Ala Arg
                165                 170                 175

Cys Gly Phe Glu Glu Gly Ala Gly Pro Arg Lys Glu His Ala Arg
                180                 185                 190

Ser Asp Ser Glu Asn Trp Arg Ser Leu Arg Glu Glu Gln Glu Glu
            195                 200                 205

Glu Glu Gly Ser Trp Arg Leu Gly Ala Gly Pro Arg Arg Asp Gly Asp
            210                 215                 220

Arg Trp Arg Ser Ala Ser Pro Asp Gly Gly Pro Arg Ser Ala Gly Trp
225                 230                 235                 240

Arg Glu His Gly Glu Arg Arg Lys Phe Glu Asp Leu Arg Gly
                245                 250                 255

Asp Arg Gly Gly Cys Gly Glu Glu Gly Arg Gly Gly Gly Ser
            260                 265                 270

Ser His Leu Arg Arg Cys Arg Ala Pro Glu Gly Phe Glu Asp Lys
            275                 280                 285

Asp Gly Leu Pro Glu Trp Cys Leu Asp Asp Glu Asp Glu Glu Met Gly
            290                 295                 300

Thr Phe Asp Ala Ser Gly Ala Phe Leu Pro Leu Lys Lys Gly Pro Lys
305                 310                 315                 320

Glu Pro Ile Pro Glu Glu Gln Glu Leu Asp Phe Gln Gly Leu Glu Glu
                325                 330                 335

Glu Glu Glu Pro Ser Glu Gly Leu Glu Glu Gly Pro Glu Ala Gly
            340                 345                 350

Gly Lys Glu Leu Thr Pro Leu Pro Pro Gln Glu Glu Lys Ser Ser Ser
            355                 360                 365

Pro Ser Pro Leu Pro Thr Leu Gly Pro Leu Trp Gly Thr Asn Gly Asp
            370                 375                 380

Gly Asp Glu Thr Ala Glu Lys Glu Pro Ala Ala Glu Asp Asp Ile
385                 390                 395                 400

Arg Gly Ile Gln Leu Ser Pro Gly Val Gly Ser Ser Ala Gly Pro Pro
                405                 410                 415

Gly Asp Leu Glu Asp Asp Glu Gly Leu Lys His Leu Gln Gln Glu Ala
            420                 425                 430

Glu Lys Leu Val Ala Ser Leu Gln Asp Ser Ser Leu Glu Glu Glu Gln
            435                 440                 445

Phe Thr Ala Ala Met Gln Thr Gln Gly Leu Arg His Ser Ala Ala Ala
450                 455                 460

Thr Ala Leu Pro Leu Ser His Gly Ala Ala Arg Lys Trp Phe Tyr Lys
465                 470                 475                 480

Asp Pro Gln Gly Glu Ile Gln Gly Pro Phe Thr Thr Gln Glu Met Ala
                485                 490                 495

Glu Trp Phe Gln Ala Gly Tyr Phe Ser Met Ser Leu Leu Val Lys Arg
                500                 505                 510

Gly Cys Asp Glu Gly Phe Gln Pro Leu Gly Glu Val Ile Lys Met Trp
                515                 520                 525
```

```
Gly Arg Val Pro Phe Ala Pro Gly Pro Ser Pro Pro Leu Leu Gly
    530                 535                 540

Asn Met Asp Gln Glu Arg Leu Lys Lys Gln Gln Glu Leu Ala Ala Ala
545                 550                 555                 560

Ala Leu Tyr Gln Gln Leu Gln His Gln Gln Phe Leu Gln Leu Val Ser
            565                 570                 575

Ser Arg Gln Leu Pro Gln Cys Ala Leu Arg Glu Lys Ala Ala Leu Gly
        580                 585                 590

Asp Leu Thr Pro Pro Pro Pro Pro Pro Gln Gln Gln Gln Gln
        595                 600                 605

Leu Thr Ala Phe Leu Gln Gln Leu Gln Ala Leu Lys Pro Pro Arg Gly
    610                 615                 620

Gly Asp Gln Asn Leu Leu Pro Thr Met Ser Arg Ser Leu Ser Val Pro
625                 630                 635                 640

Asp Ser Gly Arg Leu Trp Asp Val His Thr Ser Ala Ser Ser Gln Ser
            645                 650                 655

Gly Gly Glu Ala Ser Leu Trp Asp Ile Pro Ile Asn Ser Ser Thr Gln
        660                 665                 670

Gly Pro Ile Leu Glu Gln Leu Gln Leu Gln His Lys Phe Gln Glu Arg
    675                 680                 685

Arg Glu Val Glu Leu Arg Ala Lys Arg Glu Glu Glu Arg Lys Arg
    690                 695                 700

Arg Glu Glu Lys Arg Arg Gln Gln Gln Glu Gln Lys Arg Arg
705                 710                 715                 720

Gln Glu Glu Glu Glu Leu Phe Arg Arg Lys His Val Arg Gln Gln Glu
                725                 730                 735

Leu Leu Leu Lys Leu Leu Gln Gln Gln Ala Val Pro Val Pro Pro
            740                 745                 750

Ala Pro Ser Ser Pro Pro Leu Trp Ala Gly Leu Ala Lys Gln Gly
    755                 760                 765

Leu Ser Met Lys Thr Leu Leu Glu Leu Gln Leu Glu Gly Glu Arg Gln
770                 775                 780

Leu His Lys Gln Pro Pro Pro Arg Glu Pro Ala Arg Ala Gln Ala Pro
785                 790                 795                 800

Asn His Arg Val Gln Leu Gly Gly Leu Gly Thr Ala Pro Leu Asn Gln
            805                 810                 815

Trp Val Ser Glu Ala Gly Pro Leu Trp Gly Gly Pro Asp Lys Ser Gly
        820                 825                 830

Gly Gly Ser Ser Gly Leu Gly Leu Trp Glu Asp Thr Pro Lys Ser Gly
    835                 840                 845

Gly Ser Leu Val Arg Gly Leu Gly Leu Lys Asn Ser Arg Ser Ser Pro
850                 855                 860

Ser Leu Ser Asp Ser Tyr Ser His Leu Ser Gly Arg Pro Ile Arg Lys
865                 870                 875                 880

Lys Thr Glu Glu Glu Lys Leu Leu Lys Leu Leu Gln Gly Ile Pro
                885                 890                 895

Arg Pro Gln Asp Gly Phe Thr Gln Trp Cys Glu Gln Met Leu His Thr
    900                 905                 910

Leu Ser Ala Thr Gly Ser Leu Asp Val Pro Met Ala Val Ala Ile Leu
        915                 920                 925

Lys Glu Val Glu Ser Pro Tyr Asp Val His Asp Tyr Ile Arg Ser Cys
930                 935                 940

Leu Gly Asp Thr Leu Glu Ala Lys Glu Phe Ala Lys Gln Phe Leu Glu
```

```
                945                 950                 955                 960
Arg Arg Ala Lys Gln Lys Ala Ser Gln Gln Arg Gln Gln Gln Glu
                    965                 970                 975
Ala Trp Leu Ser Ser Ala Ser Leu Gln Thr Ala Phe Gln Ala Asn His
                980                 985                 990
Ser Thr Lys Leu Gly Pro Gly Glu Gly Ser Lys Ala Lys Arg Arg Ala
            995                 1000                1005
Leu Met Leu His Ser Asp Pro Ser Ile Leu Gly Tyr Ser Leu His Gly
        1010                1015                1020
Ser Ser Gly Glu Ile Glu Ser Val Asp Asp Tyr
1025                1030                1035

<210> SEQ ID NO 45
<211> LENGTH: 2258
<212> TYPE: DNA
<213> ORGANISM: Homo sapiens

<400> SEQUENCE: 45
```

| | | | | | |
|---|---|---|---|---|---|
| gtccgcagcc | ccgcctgttc | ctcccgaggg | ccgcgcgctc | tcgccggccc | gccccgaacc | 60 |
| gccccgcgct | gggaatttgc | ggcggcctcc | gccggggcag | ccgagctgaa | ccggtctctt | 120 |
| cctcggaaag | gcagggccga | ggggcctgcg | ggcagccat | ggaggcgacg | cggaggcggc | 180 |
| agcacctggg | agcgacgggc | ggcccaggcg | cgcagctggg | cgcctccttc | ctgcaggcca | 240 |
| ggcatggctc | tgtgagcgct | gatgaggctg | cccgcacggc | tcccttccac | ctcgacctct | 300 |
| ggttctactt | cacactgcag | aactgggttc | tggactttgg | gcgtcccatt | gccatgctgg | 360 |
| tattccctct | cgagtggttt | ccactcaaca | agcccagtgt | tggggactac | ttccacatgg | 420 |
| cctacaacgt | catcacgccc | tttctcttgc | tcaagctcat | cgagcggtcc | ccccgcaccc | 480 |
| tgccacgctc | catcacgtac | gtgagcatca | tcatcttcat | catgggtgcc | agcatccacc | 540 |
| tggtgggtga | ctctgtcaac | caccgcctgc | tcttcagtgg | ctaccagcac | acctgtctg | 600 |
| tccgtgagaa | ccccatcatc | aagaatctca | agccggagac | gctgatcgac | tcctttgagc | 660 |
| tgctctacta | ttatgatgag | tacctgggtc | actgcatgtg | gtacatcccc | ttcttcctca | 720 |
| tcctcttcat | gtacttcagc | ggctgcttta | ctgcctctaa | agctgagagc | ttgattccag | 780 |
| ggcctgccct | gctcctggtg | gcacccagtg | gcctgtacta | ctggtacctg | gtcaccgagg | 840 |
| gccagatctt | catcctcttc | atcttcacct | tcttcgccat | gctggccctc | gtcctgcacc | 900 |
| agaagcgcaa | cgcctcttc | ctggacagca | acggcctctt | cctcttctcc | tccttcgcac | 960 |
| tgaccctctt | gcttgtggcg | ctctgggtcg | cctggctgtg | gaatgaccct | gttctcagga | 1020 |
| agaagtaccc | gggtgtcatc | tacgtccctg | agccctgggc | tttctacacc | cttcacgtca | 1080 |
| gcagtcggca | ctgagtccct | ggcaccaggc | tctggcgctc | tgctgggtgg | agggtgggc | 1140 |
| catggagggc | atctgaatac | aggagtaggg | ggggtgtggg | tgtgtaacca | gagaccgaga | 1200 |
| gcatgagtgg | ggtgtgcctc | gtgtgcgtgg | attcgtgtgt | gtgtgtgtgt | gtgtcttgta | 1260 |
| tatgtgtgcg | cagagtgcat | cattttcaga | ctctactatt | tccgtcaagt | ttctgtttga | 1320 |
| tttggatcat | ctcaggatcg | gattctgttt | tagagtgttt | ctgggccagg | atccgggccc | 1380 |
| ctgccctcct | ctgcacctga | ccacactccc | tactcagggc | tagtctgttc | ttcccggaca | 1440 |
| tcttctggta | gccgtgcagg | agagggctgg | gtggggcaga | ggccaggagg | ggacctggtg | 1500 |
| tgtcacctgc | ccaccacctg | gctcatccct | caggcccacc | ctgacccta | attacatagg | 1560 |
| ttacgtcagc | ctactgtggc | tgttgagcaa | agcatttctc | ctttctgggc | ctcatttgca | 1620 |

-continued

```
ctagatgggc ctgtggtccc aaagtaggtc agtaggttgg ggttgctgac accccttggg    1680
tgcagctttg ggacagatga gtggctctgt cctgtcactg ccctctccct gcctggggc     1740 tatgtgcact ccagacccct gcccaggctc aggcccatga ggtatggaga caccctggcc    1800
cccaggagct ggaggcaccg cccactcccc tggcattcca gctttgcagg tgaccctcct    1860
ctacccaaag ctctgtcccc ctgctcccac tccagaagaa ctgcggcacg cgcttcgggc    1920
agcctagcca caggctttga gcgcctgcat tcctgggggc tggagggtgg ggtgccaaag    1980
gccctgagca aaagccagag ctcctctcat caaagccttt acaaggtgct gggcccagag    2040
gctttgcctt gacagagtgg cccagggttt caagggagga ggaacctccc cctacctagg    2100
acccttcctg tgggggtct acagagtcag ggacagaagg gaagggaccc acaggaagtc     2160
acagtggtgc ccagggatgt gtcagccccc agccacgggg acgcgggatt caagaatgaa    2220
gtaaatacag tcacagcccc aaaaaaaaaa aaaaaaa                             2258
```

<210> SEQ ID NO 46
<211> LENGTH: 311
<212> TYPE: PRT
<213> ORGANISM: Homo sapiens

<400> SEQUENCE: 46

```
Met Glu Ala Thr Arg Arg Gln His Leu Gly Ala Thr Gly Gly Pro
1               5                   10                  15

Gly Ala Gln Leu Gly Ala Ser Phe Leu Gln Ala Arg His Gly Ser Val
            20                  25                  30

Ser Ala Asp Glu Ala Ala Arg Thr Ala Pro Phe His Leu Asp Leu Trp
        35                  40                  45

Phe Tyr Phe Thr Leu Gln Asn Trp Val Leu Asp Phe Gly Arg Pro Ile
    50                  55                  60

Ala Met Leu Val Phe Pro Leu Glu Trp Phe Pro Leu Asn Lys Pro Ser
65                  70                  75                  80

Val Gly Asp Tyr Phe His Met Ala Tyr Asn Val Ile Thr Pro Phe Leu
                85                  90                  95

Leu Leu Lys Leu Ile Glu Arg Ser Pro Arg Thr Leu Pro Arg Ser Ile
            100                 105                 110

Thr Tyr Val Ser Ile Ile Ile Phe Ile Met Gly Ala Ser Ile His Leu
        115                 120                 125

Val Gly Asp Ser Val Asn His Arg Leu Leu Phe Ser Gly Tyr Gln His
    130                 135                 140

His Leu Ser Val Arg Glu Asn Pro Ile Ile Lys Asn Leu Lys Pro Glu
145                 150                 155                 160

Thr Leu Ile Asp Ser Phe Glu Leu Leu Tyr Tyr Tyr Asp Glu Tyr Leu
                165                 170                 175

Gly His Cys Met Trp Tyr Ile Pro Phe Phe Leu Ile Leu Phe Met Tyr
            180                 185                 190

Phe Ser Gly Cys Phe Thr Ala Ser Lys Ala Glu Ser Leu Ile Pro Gly
        195                 200                 205

Pro Ala Leu Leu Leu Val Ala Pro Ser Gly Leu Tyr Tyr Trp Tyr Leu
    210                 215                 220

Val Thr Glu Gly Gln Ile Phe Ile Leu Phe Ile Phe Thr Phe Phe Ala
225                 230                 235                 240

Met Leu Ala Leu Val Leu His Gln Lys Arg Lys Arg Leu Phe Leu Asp
                245                 250                 255

Ser Asn Gly Leu Phe Leu Phe Ser Ser Phe Ala Leu Thr Leu Leu Leu
```

```
            260                 265                 270
Val Ala Leu Trp Val Ala Trp Leu Trp Asn Asp Pro Val Leu Arg Lys
            275                 280                 285

Lys Tyr Pro Gly Val Ile Tyr Val Pro Glu Pro Trp Ala Phe Tyr Thr
            290                 295                 300

Leu His Val Ser Ser Arg His
305                 310
```

<210> SEQ ID NO 47
<211> LENGTH: 4293
<212> TYPE: DNA
<213> ORGANISM: Homo sapiens

<400> SEQUENCE: 47

| | | | | | |
|---|---|---|---|---|---|
| gtttctcata | gttggcgtct | tctaaaggaa | aaacactaaa | atgaggaact | cagcggaccg | 60 |
| ggagcgacgc | agcttgaggg | aagcatccct | agctgttggc | gcagaggggc | gaggctgaag | 120 |
| ccgagtggcc | cgaggtgtct | gaggggctgg | ggcaaaggtg | aaagagtttc | agaacaagct | 180 |
| tcctggaacc | catgacccat | gaagtcttgt | cgacatttat | accgtctgag | ggtagcagct | 240 |
| cgaaagtaga | agaagtggag | tgttgccagg | acggcagta | tctctttgtg | tgaccctggc | 300 |
| ggcttatggg | acgttggctt | cagacctttg | tgatacacca | tgctgcgtgg | gacgatgacg | 360 |
| gcgtggagag | gaatgaggcc | tgaggtcaca | ctggcttgcc | cctcctagc | cacagcaggc | 420 |
| tgctttgctg | acttgaacga | ggtccctcag | gtcaccgtcc | agcctgcgtc | caccgtccag | 480 |
| aagcccggag | gcactgtgat | cttgggctgc | gtggtggaac | ctccaaggat | gaatgtaacc | 540 |
| tggcgcctga | atggaaagga | gctgaatggc | tcggatgatg | ctctgggtgt | cctcatcacc | 600 |
| cacgggaccc | tcgtcatcac | tgcccttaac | aaccacactg | tgggacggta | ccagtgtgtg | 660 |
| gcccggatgc | ctgcgggggc | tgtggccagc | gtgccagcca | ctgtgacact | agccaatctc | 720 |
| caggacttca | agttagatgt | gcagcacgtg | attgaagtgg | atgagggaaa | cacagcagtc | 780 |
| attgcctgcc | acctgcctga | gagccacccc | aaagcccagg | tccggtacag | cgtcaaacaa | 840 |
| gagtggctgg | aggcctccag | aggtaactac | ctgatcatgc | cctcagggaa | cctccagatt | 900 |
| gtgaatgcca | gccaggagga | cgagggcatg | tacaagtgtg | cagcctacaa | cccagtgacc | 960 |
| caggaagtga | aaacctccgg | ctccagcgac | aggctacgtg | tgcgccgctc | caccgctgag | 1020 |
| gctgcccgca | tcatctaccc | cccagaggcc | caaaccatca | tcgtcaccaa | aggccagagt | 1080 |
| ctcattctgg | agtgtgtggc | cagtggaatc | ccaccccac | gggtcacctg | gccaaggat | 1140 |
| gggtccagtg | tcaccggcta | caacaagacg | cgcttcctgc | tgagcaacct | cctcatcgac | 1200 |
| accaccagcg | aggaggactc | aggcacctac | cgctgcatgg | ccgacaatgg | ggttgggcag | 1260 |
| cccgggggcag | cggtcatcct | ctacaatgtc | caggtgtttg | aaccccctga | ggtcaccatg | 1320 |
| gagctatccc | agctggtcat | cccctgggc | cagagtgcca | agcttacctg | tgaggtgcgt | 1380 |
| gggaacccc | cgcctccgt | gctgtggctg | aggaatgctg | tgcccctcat | ctccagccag | 1440 |
| cgcctccggc | tctcccgcag | ggccctgcgc | gtgctcagca | tggggcctga | ggacgaaggc | 1500 |
| gtctaccagt | gcatggccga | gaacgaggtt | gggagcgccc | atgccgtagt | ccagctgcgg | 1560 |
| acctccaggc | caagcataac | cccaaggcta | tggcaggatg | ctgagctggc | tactggcaca | 1620 |
| cctcctgtat | caccctccaa | actcggcaac | cctgagcaga | tgctgagggg | gcaaccggcg | 1680 |
| ctccccagac | cccaacgtc | agtggggcct | gcttccccgc | agtgtccagg | agagaagggg | 1740 |
| caggggctc | ccgccgaggc | tcccatcatc | ctcagctcgc | cccgcacctc | caagacagac | 1800 |

-continued

```
tcatatgaac tggtgtggcg gcctcggcat gagggcagtg gccgggcgcc aatcctctac    1860
tatgtggtga acaccgcaa ggtcacaaat tcctctgacg attggaccat ctctggcatt    1920
ccagccaacc agcaccgcct gaccctcacc agacttgacc ccgggagctt gtatgaagtg    1980
gagatggcag cttacaactg tgcgggagag ggccagacag ccatggtcac cttccgaact    2040
ggacggcggc ccaaacccga gatcatggcc agcaaagagc agcagatcca gagagacgac    2100
cctggagcca gtcccagag cagcagccag ccagaccacg gccgcctctc cccccagaa    2160 gctcccgaca ggcccaccat ctccacggcc tccgagacct cagtgtacgt gacctggatt    2220
ccccgtggga atggtgggtt cccaatccag tccttccgtg tggagtacaa gaagctaaag    2280
aaagtgggag actggattct ggccaccagc gccatccccc catcgcggct gtccgtggag    2340
atcacgggcc tagagaaagg cacctcctac aagtttcgag tccgggctct gaacatgctg    2400
ggggagagcg agcccagcgc ccctctcgg ccctacgtgg tgtcgggcta cagcggtcgc    2460
gtgtacgaga ggcccgtggc aggtccttat atcaccttca cggatgcggt caatgagacc    2520
accatcatgc tcaagtggat gtacatccca gcaagtaaca caacacccc aatccatggc    2580 ttttatatct attatcgacc cacagacagt gacaatgata gtgactacaa gaaggatatg    2640
gtggaagggg acaagtactg gcactccatc agccacctgc agccagagac ctcctacgac    2700
attaagatgc agtgcttcaa tgaaggaggg gagagcgagt tcagcaacgt gatgatctgt    2760
gagaccaaag ctcggaagtc ttctggccag cctggtcgac tgccacccc aactctggcc    2820 ccaccacagc cgcccctcc tgaaaccata gagcggccgg tgggcactgg ggccatggtg    2880
gctcgctcca gcgacctgcc ctatctgatt gtcggggtcg tcctgggctc catcgttctc    2940
atcatcgtca ccttcatccc cttctgcttg tggagggcct ggtctaagca aaacataca    3000 acagacctgg gttttcctcg aagtgccctt ccaccctcct gcccgtatac tatggtgcca    3060 tgggaggac tcccaggcca ccaggccagt ggacagccct acctcagtgg catcagtgga    3120
cgggcctgtg ctaatgggat ccacatgaat aggggctgcc cctcggctgc agtgggctac    3180
ccgggcatga agccccagca gcactgccca ggcgagcttc agcagcagag tgacaccagc    3240
agcctgctga ggcagaccca tcttggcaat ggatatgacc cccaaagtca ccagatcacg    3300
aggggtccca gtctagcccc ggacgagggc tctttcttat acacactgcc cgacgactcc    3360
actcaccagc tgctgcagcc ccatcacgac tgctgccaac gccaggagca gcctgctgct    3420
gtgggccagt cagggggtgag gagagccccc gacagtcctg tcctggaagc agtgtgggac    3480
cctccatttc actcagggcc cccatgctgc ttgggccttg tgccagttga agaggtggac    3540
agtcctgact cctgccaagt gagtggagga gactggtgtc cccagcaccc cgtagggcc    3600 tacgtaggac aggaacctgg aatgcagctc tccccggggc cactggtgcg tgtgtctttt    3660
gaaacaccac ctctcacaat ttaggcagaa gctgatatcc cagaaagact atatattgtt    3720
ttttttttaa aaaaaaag aagaaaaag agacagagaa aattggtatt tattttctta    3780
ttatagccat atttatatat ttatgcactt gtaaataaat gtatatgttt tataattctg    3840
gagagacata aggagtccta cccgttgagg ttggagaggg aaaataaaga agctgccacc    3900
taacaggagt cacccaggaa agcaccgcac aggctggcgc gggacagact cctaacctgg    3960
ggcctctgca gtggcaggcg aggctgcagg aggcccacag ataagctggc aagaggaagg    4020
atcccaggca catggttcat cacgagcatg agggaacagc aaggggcacg gtatcacagc    4080
ctggagacac ccacacagat ggctggatcc ggtgctacgg gaaacatttt cctaagatgc    4140
ccatgagaac agaccaagat gtgtacagca ctatgagcat taaaaaacct tccagaatca    4200
```

```
ataatccgtg gcaacatatc tctgtaaaaa caaacactgt aacttctaaa taaatgttta    4260
gtcttccctg taaccttcaa aaaaaaaaaa aaa                                 4293
```

<210> SEQ ID NO 48
<211> LENGTH: 1114
<212> TYPE: PRT
<213> ORGANISM: Homo sapiens

<400> SEQUENCE: 48

```
Met Leu Arg Gly Thr Met Thr Ala Trp Arg Gly Met Arg Pro Glu Val
 1               5                  10                  15

Thr Leu Ala Cys Leu Leu Leu Ala Thr Ala Gly Cys Phe Ala Asp Leu
            20                  25                  30

Asn Glu Val Pro Gln Val Thr Val Gln Pro Ala Ser Thr Val Gln Lys
        35                  40                  45

Pro Gly Gly Thr Val Ile Leu Gly Cys Val Val Glu Pro Pro Arg Met
 50                  55                  60

Asn Val Thr Trp Arg Leu Asn Gly Lys Glu Leu Asn Gly Ser Asp Asp
 65                  70                  75                  80

Ala Leu Gly Val Leu Ile Thr His Gly Thr Leu Val Ile Thr Ala Leu
                85                  90                  95

Asn Asn His Thr Val Gly Arg Tyr Gln Cys Val Ala Arg Met Pro Ala
            100                 105                 110

Gly Ala Val Ala Ser Val Pro Ala Thr Val Thr Leu Ala Asn Leu Gln
        115                 120                 125

Asp Phe Lys Leu Asp Val Gln His Val Ile Glu Val Asp Glu Gly Asn
130                 135                 140

Thr Ala Val Ile Ala Cys His Leu Pro Glu Ser His Pro Lys Ala Gln
145                 150                 155                 160

Val Arg Tyr Ser Val Lys Gln Glu Trp Leu Glu Ala Ser Arg Gly Asn
                165                 170                 175

Tyr Leu Ile Met Pro Ser Gly Asn Leu Gln Ile Val Asn Ala Ser Gln
            180                 185                 190

Glu Asp Glu Gly Met Tyr Lys Cys Ala Ala Tyr Asn Pro Val Thr Gln
        195                 200                 205

Glu Val Lys Thr Ser Gly Ser Ser Asp Arg Leu Arg Val Arg Arg Ser
    210                 215                 220

Thr Ala Glu Ala Ala Arg Ile Ile Tyr Pro Pro Glu Ala Gln Thr Ile
225                 230                 235                 240

Ile Val Thr Lys Gly Gln Ser Leu Ile Leu Glu Cys Val Ala Ser Gly
                245                 250                 255

Ile Pro Pro Pro Arg Val Thr Trp Ala Lys Asp Gly Ser Ser Val Thr
            260                 265                 270

Gly Tyr Asn Lys Thr Arg Phe Leu Leu Ser Asn Leu Leu Ile Asp Thr
        275                 280                 285

Thr Ser Glu Glu Asp Ser Gly Thr Tyr Arg Cys Met Ala Asp Asn Gly
    290                 295                 300

Val Gly Gln Pro Gly Ala Ala Val Ile Leu Tyr Asn Val Gln Val Phe
305                 310                 315                 320

Glu Pro Pro Glu Val Thr Met Glu Leu Ser Gln Leu Val Ile Pro Trp
                325                 330                 335

Gly Gln Ser Ala Lys Leu Thr Cys Glu Val Arg Gly Asn Pro Pro Pro
            340                 345                 350
```

-continued

Ser Val Leu Trp Leu Arg Asn Ala Pro Leu Ile Ser Gln Arg
          355                 360             365

Leu Arg Leu Ser Arg Arg Ala Leu Arg Val Leu Ser Met Gly Pro Glu
    370                 375                 380

Asp Glu Gly Val Tyr Gln Cys Met Ala Glu Asn Glu Val Gly Ser Ala
385                 390                 395                 400

His Ala Val Val Gln Leu Arg Thr Ser Arg Pro Ser Ile Thr Pro Arg
                405                 410                 415

Leu Trp Gln Asp Ala Glu Leu Ala Thr Gly Thr Pro Val Ser Pro
                420                 425                 430

Ser Lys Leu Gly Asn Pro Glu Gln Met Leu Arg Gly Gln Pro Ala Leu
        435                 440                 445

Pro Arg Pro Pro Thr Ser Val Gly Pro Ala Ser Pro Gln Cys Pro Gly
    450                 455                 460

Glu Lys Gly Gln Gly Ala Pro Ala Glu Ala Pro Ile Ile Leu Ser Ser
465                 470                 475                 480

Pro Arg Thr Ser Lys Thr Asp Ser Tyr Glu Leu Val Trp Arg Pro Arg
                485                 490                 495

His Glu Gly Ser Gly Arg Ala Pro Ile Leu Tyr Tyr Val Val Lys His
            500                 505                 510

Arg Lys Val Thr Asn Ser Ser Asp Asp Trp Thr Ile Ser Gly Ile Pro
        515                 520                 525

Ala Asn Gln His Arg Leu Thr Leu Thr Arg Leu Asp Pro Gly Ser Leu
    530                 535                 540

Tyr Glu Val Glu Met Ala Ala Tyr Asn Cys Ala Gly Glu Gly Gln Thr
545                 550                 555                 560

Ala Met Val Thr Phe Arg Thr Gly Arg Arg Pro Lys Pro Glu Ile Met
                565                 570                 575

Ala Ser Lys Glu Gln Gln Ile Gln Arg Asp Asp Pro Gly Ala Ser Pro
            580                 585                 590

Gln Ser Ser Ser Gln Pro Asp His Gly Arg Leu Ser Pro Pro Glu Ala
        595                 600                 605

Pro Asp Arg Pro Thr Ile Ser Thr Ala Ser Glu Thr Ser Val Tyr Val
    610                 615                 620

Thr Trp Ile Pro Arg Gly Asn Gly Phe Pro Ile Gln Ser Phe Arg
625                 630                 635                 640

Val Glu Tyr Lys Lys Leu Lys Lys Val Gly Asp Trp Ile Leu Ala Thr
                645                 650                 655

Ser Ala Ile Pro Pro Ser Arg Leu Ser Val Glu Ile Thr Gly Leu Glu
            660                 665                 670

Lys Gly Thr Ser Tyr Lys Phe Arg Val Arg Ala Leu Asn Met Leu Gly
        675                 680                 685

Glu Ser Glu Pro Ser Ala Pro Ser Arg Pro Tyr Val Val Ser Gly Tyr
    690                 695                 700

Ser Gly Arg Val Tyr Glu Arg Pro Val Ala Gly Pro Tyr Ile Thr Phe
705                 710                 715                 720

Thr Asp Ala Val Asn Glu Thr Thr Ile Met Leu Lys Trp Met Tyr Ile
                725                 730                 735

Pro Ala Ser Asn Asn Asn Thr Pro Ile His Gly Phe Tyr Ile Tyr Tyr
            740                 745                 750

Arg Pro Thr Asp Ser Asp Asn Asp Ser Asp Tyr Lys Lys Asp Met Val
        755                 760                 765

Glu Gly Asp Lys Tyr Trp His Ser Ile Ser His Leu Gln Pro Glu Thr

```
                    770                 775                 780
Ser  Tyr  Asp  Ile  Lys  Met  Gln  Cys  Phe  Asn  Glu  Gly  Gly  Glu  Ser  Glu
785                 790                 795                 800

Phe  Ser  Asn  Val  Met  Ile  Cys  Glu  Thr  Lys  Ala  Arg  Lys  Ser  Ser  Gly
                    805                 810                 815

Gln  Pro  Gly  Arg  Leu  Pro  Pro  Thr  Leu  Ala  Pro  Gln  Pro  Pro
                    820                 825                 830

Leu  Pro  Glu  Thr  Ile  Glu  Arg  Pro  Val  Gly  Thr  Gly  Ala  Met  Val  Ala
                    835                 840                 845

Arg  Ser  Ser  Asp  Leu  Pro  Tyr  Leu  Ile  Val  Gly  Val  Leu  Gly  Ser
850                 855                 860

Ile  Val  Leu  Ile  Ile  Val  Thr  Phe  Ile  Pro  Phe  Cys  Leu  Trp  Arg  Ala
865                 870                 875                 880

Trp  Ser  Lys  Gln  Lys  His  Thr  Thr  Asp  Leu  Gly  Phe  Pro  Arg  Ser  Ala
                    885                 890                 895

Leu  Pro  Pro  Ser  Cys  Pro  Tyr  Thr  Met  Val  Pro  Leu  Gly  Gly  Leu  Pro
                    900                 905                 910

Gly  His  Gln  Ala  Ser  Gly  Gln  Pro  Tyr  Leu  Ser  Gly  Ile  Ser  Gly  Arg
                    915                 920                 925

Ala  Cys  Ala  Asn  Gly  Ile  His  Met  Asn  Arg  Gly  Cys  Pro  Ser  Ala  Ala
930                 935                 940

Val  Gly  Tyr  Pro  Gly  Met  Lys  Pro  Gln  Gln  His  Cys  Pro  Gly  Glu  Leu
945                 950                 955                 960

Gln  Gln  Gln  Ser  Asp  Thr  Ser  Ser  Leu  Leu  Arg  Gln  Thr  His  Leu  Gly
                    965                 970                 975

Asn  Gly  Tyr  Asp  Pro  Gln  Ser  His  Gln  Ile  Thr  Arg  Gly  Pro  Lys  Ser
                    980                 985                 990

Ser  Pro  Asp  Glu  Gly  Ser  Phe  Leu  Tyr  Thr  Leu  Pro  Asp  Asp  Ser  Thr
                    995                 1000                1005

His  Gln  Leu  Leu  Gln  Pro  His  His  Asp  Cys  Cys  Gln  Arg  Gln  Glu  Gln
                    1010                1015                1020

Pro  Ala  Ala  Val  Gly  Gln  Ser  Gly  Val  Arg  Arg  Ala  Pro  Asp  Ser  Pro
1025                1030                1035                1040

Val  Leu  Glu  Ala  Val  Trp  Asp  Pro  Pro  Phe  His  Ser  Gly  Pro  Pro  Cys
                    1045                1050                1055

Cys  Leu  Gly  Leu  Val  Pro  Val  Glu  Glu  Val  Asp  Ser  Pro  Asp  Ser  Cys
                    1060                1065                1070

Gln  Val  Ser  Gly  Gly  Asp  Trp  Cys  Pro  Gln  His  Pro  Val  Gly  Ala  Tyr
                    1075                1080                1085

Val  Gly  Gln  Glu  Pro  Gly  Met  Gln  Leu  Ser  Pro  Gly  Pro  Leu  Val  Arg
                    1090                1095                1100

Val  Ser  Phe  Glu  Thr  Pro  Pro  Leu  Thr  Ile
1105                1110

<210> SEQ ID NO 49
<211> LENGTH: 1627
<212> TYPE: DNA
<213> ORGANISM: Homo sapiens

<400> SEQUENCE: 49
attcctagtg actccaagcg cttaaaaggg gcccgggagg atgaaccccca cagatctgaa      60 cctgatttgt gtgtgcaccg cgtctccagc gatcccggat ccactgcgct gccaggggcc     120
tgggggtggg tctcttgctg tctctgcgac gacatcctta cgtttcggca ctctaatgct     180
```

```
gggtttgtgc gtgtgtgtct gcttagcggt ctagcgggct gttaggctcc ctcgccccca    240
gctccttggc tcgctcagct cctccaccgc agcccagcag tgagacgcgc gcgcagccag    300
ctccccacga gatggaacag accgaagtgc tgaagccacg gaccctggct gatctgatcc    360
gcatcctgca ccagctcttt gccggcgatg aggtcaatgt agaggaggtg caggccatca    420
tggaagccta cgagagcgac cccaccgagt gggcaatgta cgccaagttc gaccagtaca    480
ggtatacccg aaatcttgtg gatcaaggaa atggaaaatt taatctgatg attctctgtt    540
ggggtgaagg acatggcagc agtattcatg atcataccaa ctcccactgc tttctgaaga    600
tgctacaggg aaatctaaag gagacattat ttgcctggcc tgacaaaaaa tccaatgaga    660
tggtcaagaa gtctgaaaga gtcttgaggg aaaaccagtg tgcctacatc aatgattcca    720
ttggcttaca tcgagtagag aacatcagcc atacggaacc tgctgtgagc cttcacttgt    780
acagtccacc ttttgataca tgccatgcct ttgatcaaag aacaggacat aaaaacaaag    840
tcacaatgac attccatagt aaatttggaa tcagaactcc aaatgcaact tcgggctcgc    900
tggagaacaa ctaaggggca ccaaaccctc tgaggtttta ctttaaggtt cgctgtatgt    960
ttgccttgga caaaaaggct acctaccacg tgctatccag taatatactt aaataagcca   1020
atacttagat ctactgtaag gcagatgcta attataaggc attaagtaag caaatagtgc   1080
cctcagctac tgcagaagaa aagtcccact gaggaaaaga agtcttgtg attttttaaag   1140
gcaagttttc aagtgctctc atagttctat cctctaattc cattaaatcc atactaggag   1200
cgtcagtgag ggttttcata gcttttggaa atactttggt ctctgaactg taattagcaa   1260
gaagtaaaaa cagaaacgtc aaacgtcaaa tgtttgcttt gttacctgga ggactaaatg   1320
tagatgtctt tagtatactt tgtatgttct taatattgga agataatttt gtgaatctgt   1380
agattttatt ttttcagtct taccttacaa atttcttttc tatgaataat agaggaactt   1440
acggcactct gccatttgtt aatgaaagga agtgcagagg atttagaaaa gtacatgatc   1500
cccagaccac aacaaaccaa aacataaact catgtctgtg tcccatggtc atagtcaaag   1560
attttgtact gctaaaatta ccaaataatt taaataaagt ggatttgaac acaaaaaaaa   1620
aaaaaaa                                                             1627
```

<210> SEQ ID NO 50
<211> LENGTH: 200
<212> TYPE: PRT
<213> ORGANISM: Homo sapiens

<400> SEQUENCE: 50

```
Met Glu Gln Thr Glu Val Leu Lys Pro Arg Thr Leu Ala Asp Leu Ile
 1               5                  10                  15

Arg Ile Leu His Gln Leu Phe Ala Gly Asp Glu Val Asn Val Glu Glu
            20                  25                  30

Val Gln Ala Ile Met Glu Ala Tyr Glu Ser Asp Pro Thr Glu Trp Ala
        35                  40                  45

Met Tyr Ala Lys Phe Asp Gln Tyr Arg Tyr Thr Arg Asn Leu Val Asp
    50                  55                  60

Gln Gly Asn Gly Lys Phe Asn Leu Met Ile Leu Cys Trp Gly Glu Gly
65                  70                  75                  80

His Gly Ser Ser Ile His Asp His Thr Asn Ser His Cys Phe Leu Lys
                85                  90                  95

Met Leu Gln Gly Asn Leu Lys Glu Thr Leu Phe Ala Trp Pro Asp Lys
           100                 105                 110
```

```
Lys Ser Asn Glu Met Val Lys Lys Ser Glu Arg Val Leu Arg Glu Asn
            115                 120                 125
Gln Cys Ala Tyr Ile Asn Asp Ser Ile Gly Leu His Arg Val Glu Asn
        130                 135                 140
Ile Ser His Thr Glu Pro Ala Val Ser Leu His Leu Tyr Ser Pro Pro
145                 150                 155                 160
Phe Asp Thr Cys His Ala Phe Asp Gln Arg Thr Gly His Lys Asn Lys
                165                 170                 175
Val Thr Met Thr Phe His Ser Lys Phe Gly Ile Arg Thr Pro Asn Ala
            180                 185                 190
Thr Ser Gly Ser Leu Glu Asn Asn
            195                 200

<210> SEQ ID NO 51
<211> LENGTH: 2575
<212> TYPE: DNA
<213> ORGANISM: Homo sapiens

<400> SEQUENCE: 51
ggaggaggaa gcaagcgagg gggctggttc ctgagcttcg caattcctgt gtcgccttct      60
gggctcccag cctgccgggt cgcatgatcc ctccggccgg agctggtttt tttgccagcc     120
accgcgaggc cggctgagtt accggcatcc ccgcagccac ctcctctccc gacctgtgat     180
acaaaagatc ttccggggc tgcacctgcc tgcctttgcc taaggcgat ttgaatctct      240
ttctctccct tcagaatctt atcttggctt tggatcttag aagagaatca ctaaccagag     300
acgagactca gtgagtgagc aggtgttttg dacaatggac tggttgagcc catccctatt     360
ataaaaatgt ctcagagcaa ccgggagctg gtggttgact ttctctccta caagcttttcc    420
cagaaaggat acagctggag tcagtttagt gatgtgaaag agaacaggac tgaggcccca     480
gaagggactg aatcggagat ggagaccccc agtgccatca atggcaaccc atcctggcac     540
ctggcagaca gccccgcggt gaatggagcc actggccaca gcagcagtt ggatgcccgg      600
gaggtgatcc ccatggcagc agtaaagcaa gcgctgaggg aggcaggcga cgagtttgaa     660
ctgcggtacc ggcgggcatt cagtgacctg acatcccagc tccacatcac cccagggaca     720
gcatatcaga gctttgaaca ggtagtgaat gaactcttcc gggatggggt aaactggggt     780
cgcattgtgg cctttttctc cttcggcggg gcactgtgcg tggaaagcgt agacaaggag     840
atgcaggtat tggtgagtcg gatcgcagct tggatggcca cttacctgaa tgaccaccta     900
gagccttgga tccaggagaa cggcggctgg gatacttttg tggaactcta tgggaacaat     960
gcagcagccg agagccgaaa gggccaggaa cgcttcaacc gctggttcct gacgggcatg    1020
actgtggccg gcgtggttct gctgggctca ctcttcagtc ggaaatgacc agacactgac    1080
catccactct accctcccac cccttctct gctccaccac atcctccgtc cagccgccat     1140
tgccaccagg agaaccacta catgcagccc atgcccacct gcccatcaca gggttgggcc    1200
cagatctggt cccttgcagc tagttttcta gaatttatca cacttctgtg agaccccccac   1260
acctcagttc ccttggcctc agaattcaca aaatttccac aaaatctgtc caaaggaggc    1320
tggcaggtat ggaagggttt gtggctgggg gcaggagggc cctacctgat tggtgcaacc    1380
cttacccctt agcctccctg aaaatgtttt tctgccaggg agcttgaaag ttttcagaac    1440
ctcttcccca gaaaggagac tagattgcct ttgttttgat gtttgtggcc tcagaattga    1500
tcattttccc cccactctcc ccacactaac ctgggttccc tttccttcca tccctacccc    1560
ctaagagcca tttaggggcc acttttgact agggattcag gctgcttggg ataaagatgc    1620
```

-continued

```
aaggaccagg actccctcct cacctctgga ctggctagag tcctcactcc cagtccaaat    1680
gtcctccaga agcctctggc tagaggccag ccccacccag gagggagggg gctatagcta    1740
caggaagcac cccatgccaa agctagggtg gcccttgcag ttcagcacca ccctagtccc    1800
ttcccctccc tggctcccat gaccatactg agggaccaac tgggcccaag acagatgccc    1860
cagagctgtt tatggcctca gctgcctcac ttcctacaag agcagcctgt ggcatctttg    1920
ccttgggctg ctcctcatgg tgggttcagg ggactcagcc ctgaggtgaa agggagctat    1980
caggaacagc tatgggagcc ccagggtctt ccctacctca ggcaggaagg gcaggaagga    2040
gagcctgctg catggggtgg ggtagggctg actagaaggg ccagtcctgc ctggccaggc    2100
agatctgtgc cccatgcctg tccagcctgg gcagccaggc tgccaaggcc agagtggcct    2160
ggccaggagc tcttcaggcc tccctctctc ttctgctcca cccttggcct gtctcatccc    2220
caggggtccc agccaccccg ggctctctgc tgtacatatt tgagactagt ttttattcct    2280
tgtgaagatg atatactatt tttgttaagc gtgtctgtat ttatgtgtga ggagctgctg    2340
gcttgcagtg cgcgtgcacg tggagagctg gtgcccggag attggacggc ctgatgctcc    2400 ctccctgcc ctggtccagg gaagctggcc gagggtcctg gctcctgagg ggcatctgcc     2460
cctcccccaa cccccacccc acacttgttc cagctctttg aaatagtctg tgtgaaggtg    2520
aaagtgcagt tcagtaataa actgtgttta ctcagtgaaa aaaaaaaaa aaaaa          2575
```

<210> SEQ ID NO 52
<211> LENGTH: 233
<212> TYPE: PRT
<213> ORGANISM: Homo sapiens

<400> SEQUENCE: 52

```
Met Ser Gln Ser Asn Arg Glu Leu Val Val Asp Phe Leu Ser Tyr Lys
 1               5                  10                  15

Leu Ser Gln Lys Gly Tyr Ser Trp Ser Gln Phe Ser Asp Val Glu Glu
            20                  25                  30

Asn Arg Thr Glu Ala Pro Glu Gly Thr Glu Ser Glu Met Glu Thr Pro
        35                  40                  45

Ser Ala Ile Asn Gly Asn Pro Ser Trp His Leu Ala Asp Ser Pro Ala
    50                  55                  60

Val Asn Gly Ala Thr Gly His Ser Ser Ser Leu Asp Ala Arg Glu Val
65                  70                  75                  80

Ile Pro Met Ala Ala Val Lys Gln Ala Leu Arg Glu Ala Gly Asp Glu
                85                  90                  95

Phe Glu Leu Arg Tyr Arg Arg Ala Phe Ser Asp Leu Thr Ser Gln Leu
            100                 105                 110

His Ile Thr Pro Gly Thr Ala Tyr Gln Ser Phe Glu Gln Val Val Asn
        115                 120                 125

Glu Leu Phe Arg Asp Gly Val Asn Trp Gly Arg Ile Val Ala Phe Phe
    130                 135                 140

Ser Phe Gly Gly Ala Leu Cys Val Glu Ser Val Asp Lys Glu Met Gln
145                 150                 155                 160

Val Leu Val Ser Arg Ile Ala Ala Trp Met Ala Thr Tyr Leu Asn Asp
                165                 170                 175

His Leu Glu Pro Trp Ile Gln Glu Asn Gly Gly Trp Asp Thr Phe Val
            180                 185                 190

Glu Leu Tyr Gly Asn Asn Ala Ala Ala Glu Ser Arg Lys Gly Gln Glu
        195                 200                 205
```

Arg Phe Asn Arg Trp Phe Leu Thr Gly Met Thr Val Ala Gly Val Val
    210                 215                 220

Leu Leu Gly Ser Leu Phe Ser Arg Lys
225                 230

<210> SEQ ID NO 53
<211> LENGTH: 4304
<212> TYPE: DNA
<213> ORGANISM: Homo sapiens

<400> SEQUENCE: 53

| | | | | |
|---|---|---|---|---|
| cacacggact | acaggggagt | tttgttgaag | ttgcaaagtc | ctggagcctc cagagggctg | 60 |
| tcggcgcagt | agcagcgagc | agcagagtcc | gcacgctccg | gcgaggggca gaagagcgcg | 120 |
| agggagcgcg | gggcagcaga | agcgagagcc | gagcgcggac | ccagccagga cccacagccc | 180 |
| tccccagctg | cccaggaaga | gccccagcca | tggaacacca | gctcctgtgc tgcgaagtgg | 240 |
| aaaccatccg | ccgcgcgtac | cccgatgcca | acctcctcaa | cgaccgggtg ctgcgggcca | 300 |
| tgctgaaggc | ggaggagacc | tgcgcgccct | cggtgtccta | cttcaaatgt gtgcagaagg | 360 |
| aggtcctgcc | gtccatgcgg | aagatcgtcg | ccacctggat | gctggaggtc tgcgaggaac | 420 |
| agaagtgcga | ggaggaggtc | ttcccgctgg | ccatgaacta | cctggaccgc ttcctgtcgc | 480 |
| tggagcccgt | gaaaaagagc | cgcctgcagc | tgctgggggc | cacttgcatg ttcgtggcct | 540 |
| ctaagatgaa | ggagaccatc | cccctgacgg | ccgagaagct | gtgcatctac accgacaact | 600 |
| ccatccggcc | cgaggagctg | ctgcaaatgg | agctgctcct | ggtgaacaag ctcaagtgga | 660 |
| acctggccgc | aatgacccccg | cacgatttca | ttgaacactt | cctctccaaa atgccagagg | 720 |
| cggaggagaa | caaacagatc | atccgcaaac | acgcgcagac | cttcgttgcc ctctgtgcca | 780 |
| cagatgtgaa | gttcatttcc | aatccgccct | ccatggtggc | agcggggagc gtggtggccg | 840 |
| cagtgcaagg | cctgaacctg | aggagcccca | acaacttcct | gtcctactac cgcctcacac | 900 |
| gcttcctctc | cagagtgatc | aagtgtgacc | cggactgcct | ccgggcctgc caggagcaga | 960 |
| tcgaagccct | gctggagtca | agcctgcgcc | aggcccagca | gaacatggac cccaaggccg | 1020 |
| ccgaggagga | ggaagaggag | gaggaggagg | tggacctggc | ttgcacaccc accgacgtgc | 1080 |
| gggacgtgga | catctgaggg | cgccaggcag | gcgggcgcca | ccgccacccg cagcgagggc | 1140 |
| ggagccggcc | ccaggtgctc | ccctgacagt | ccctcctctc | cggagcattt tgataccaga | 1200 |
| agggaaagct | tcattctcct | tgttgttggt | tgttttttcc | tttgctcttt ccccccttcca | 1260 |
| tctctgactt | aagcaaaaga | aaaagattac | ccaaaaactg | tctttaaaag agagagagag | 1320 |
| aaaaaaaaaa | tagtatttgc | ataaccctga | gcggtggggg | aggagggttg tgctacagat | 1380 |
| gatagaggat | tttatacccc | aataatcaac | tcgtttttat | attaatgtac ttgtttctct | 1440 |
| gttgtaagaa | taggcattaa | cacaaaggag | gcgtctcggg | agaggattag gttccatcct | 1500 |
| ttacgtgttt | aaaaaaaagc | ataaaaacat | tttaaaaaca | tagaaaaatt cagcaaacca | 1560 |
| tttttaaagt | agaagagggt | tttaggtaga | aaaacatatt | cttgtgcttt tcctgataaa | 1620 |
| gcacagctgt | agtgggggttc | taggcatctc | tgtactttgc | ttgctcatat gcatgtagtc | 1680 |
| actttataag | tcattgtatg | ttattatatt | ccgtaggtag | atgtgtaacc tcttcacctt | 1740 |
| attcatggct | gaagtcacct | cttggttaca | gtagcgtagc | gtgcccgtgt gcatgtcctt | 1800 |
| tgcgcctgtg | accaccaccc | caacaaacca | tccagtgaca | aaccatccag tggaggtttg | 1860 |
| tcgggcacca | gccagcgtag | cagggtcggg | aaaggccacc | tgtcccactc ctacgatacg | 1920 |

```
ctactataaa gagaagacga aatagtgaca taatatattc tatttttata ctcttcctat    1980
ttttgtagtg acctgtttat gagatgctgg ttttctaccc aacggccctg cagccagctc    2040
acgtccaggt tcaacccaca gctacttggt ttgtgttctt cttcatattc taaaaccatt    2100
ccatttccaa gcactttcag tccaataggt gtaggaaata gcgctgtttt tgttgtgtgt    2160
gcagggaggg cagttttcta atggaatggt ttgggaatat ccatgtactt gtttgcaagc    2220
aggactttga ggcaagtgtg ggccactgtg gtggcagtgg aggtgggtg tttgggaggc     2280 tgcgtgccag tcaagaagaa aaaggtttgc attctcacat tgccaggatg ataagttcct    2340
ttccttttct ttaaagaagt tgaagtttag gaatcctttg gtgccaactg gtgtttgaaa    2400
gtagggacct cagaggttta cctagagaac aggtggtttt taagggttat cttagatgtt    2460
tcacaccgga aggttttaa acactaaaat atataattta tagttaaggc taaaaagtat     2520
atttattgca gaggatgttc ataaggccag tatgatttat aaatgcaatc tccccttgat    2580
ttaaacacac agatacacac acacacacac acacacacaa accttctgcc tttgatgtta    2640
cagatttaat acagtttatt tttaaagata gatccttta taggtgagaa aaaacaatc      2700 tggaagaaaa aaaccacaca aagacattga ttcagcctgt ttggcgtttc ccagagtcat    2760
ctgattggac aggcatgggt gcaaggaaaa ttagggtact caacctaagt tcggttccga    2820
tgaattctta tccctgccc cttcctttaa aaaacttagt gacaaaatag acaatttgca     2880
catcttggct atgtaattct tgtaattttt atttaggaag tgttgaaggg aggtggcaag    2940
agtgtggagg ctgacgtgtg agggaggaca ggcgggagga ggtgtgagga ggaggctccc    3000
gaggggaagg ggcggtgccc acaccgggga caggccgcag ctccattttc ttattgcgct    3060
gctaccgttg acttccaggc acggtttgga aatattcaca tcgcttctgt gtatctcttt    3120
cacattgttt gctgctattg gaggatcagt tttttgtttt acaatgtcat atactgccat    3180
gtactagttt tagttttctc ttagaacatt gtattacaga tgccttttt gtagtttttt     3240 ttttttttat gtgatcaatt ttgacttaat gtgattactg ctctattcca aaaaggttgc    3300
tgtttcacaa tacctcatgc ttcacttagc catggtggac ccagcgggca ggttctgcct    3360
gctttggcgg gcagacacgc gggcgcgatc ccacacaggc tggcggggc cggccccgag     3420 gccgcgtgcg tgagaaccgc gccggtgtcc ccagagacca ggctgtgtcc ctcttctctt    3480
ccctgcgcct gtgatgctgg gcacttcatc tgatcggggg cgtagcatca tagtagtttt    3540
tacagctgtg ttattctttg cgtgtagcta tggaagttgc ataattatta ttattattat    3600
tataacaagt gtgtcttacg tgccaccacg gcgttgtacc tgtaggactc tcattcggga    3660
tgattggaat agcttctgga atttgttcaa gttttgggta tgtttaatct gttatgtact    3720
agtgttctgt ttgttattgt tttgttaatt acaccataat gctaatttaa agagactcca    3780
aatctcaatg aagccagctc acagtgctgt gtgccccggt cacctagcaa gctgccgaac    3840
caaaagaatt tgcaccccgc tgcgggccca cgtggttggg gccctgccct ggcagggtca    3900
tcctgtgctc ggaggccatc tcgggcacag gcccaccccg ccccacccct ccagaacacg    3960
gctcacgctt acctcaacca tcctggctgc ggcgtctgtc tgaaccacgc ggggggccttg   4020 agggacgctt tgtctgtcgt gatggggcaa gggcacaagt cctggatgtt gtgtgtatcg    4080
agaggccaaa ggctggtggc aagtgcacgg ggcacagcgg agtctgtcct gtgacgcgca    4140
agtctgaggg tctgggcggc gggcggctgg gtctgtgcat ttctggttgc accgcggcgc    4200
ttcccagcac caacatgtaa ccggcatgtt tccagcagaa gacaaaaaga caaacatgaa    4260
agtctagaaa taaaactggt aaaaccccaa aaaaaaaaaa aaaa                     4304
```

<210> SEQ ID NO 54
<211> LENGTH: 295
<212> TYPE: PRT
<213> ORGANISM: Homo sapiens

<400> SEQUENCE: 54

```
Met Glu His Gln Leu Leu Cys Cys Glu Val Glu Thr Ile Arg Arg Ala
1               5                   10                  15

Tyr Pro Asp Ala Asn Leu Leu Asn Asp Arg Val Leu Arg Ala Met Leu
            20                  25                  30

Lys Ala Glu Glu Thr Cys Ala Pro Ser Val Ser Tyr Phe Lys Cys Val
        35                  40                  45

Gln Lys Glu Val Leu Pro Ser Met Arg Lys Ile Val Ala Thr Trp Met
    50                  55                  60

Leu Glu Val Cys Glu Glu Gln Lys Cys Glu Glu Val Phe Pro Leu
65                  70                  75                  80

Ala Met Asn Tyr Leu Asp Arg Phe Leu Ser Glu Pro Val Lys Lys
                85                  90                  95

Ser Arg Leu Gln Leu Leu Gly Ala Thr Cys Met Phe Val Ala Ser Lys
            100                 105                 110

Met Lys Glu Thr Ile Pro Leu Thr Ala Glu Lys Leu Cys Ile Tyr Thr
        115                 120                 125

Asp Asn Ser Ile Arg Pro Glu Glu Leu Leu Gln Met Glu Leu Leu Leu
    130                 135                 140

Val Asn Lys Leu Lys Trp Asn Leu Ala Ala Met Thr Pro His Asp Phe
145                 150                 155                 160

Ile Glu His Phe Leu Ser Lys Met Pro Glu Ala Glu Glu Asn Lys Gln
                165                 170                 175

Ile Ile Arg Lys His Ala Gln Thr Phe Val Ala Leu Cys Ala Thr Asp
            180                 185                 190

Val Lys Phe Ile Ser Asn Pro Pro Ser Met Val Ala Ala Gly Ser Val
        195                 200                 205

Val Ala Ala Val Gln Gly Leu Asn Leu Arg Ser Pro Asn Asn Phe Leu
    210                 215                 220

Ser Tyr Tyr Arg Leu Thr Arg Phe Leu Ser Arg Val Ile Lys Cys Asp
225                 230                 235                 240

Pro Asp Cys Leu Arg Ala Cys Gln Glu Gln Ile Glu Ala Leu Leu Glu
                245                 250                 255

Ser Ser Leu Arg Gln Ala Gln Gln Asn Met Asp Pro Lys Ala Ala Glu
            260                 265                 270

Glu Glu Glu Glu Glu Glu Glu Glu Val Asp Leu Ala Cys Thr Pro Thr
        275                 280                 285

Asp Val Arg Asp Val Asp Ile
    290                 295
```

<210> SEQ ID NO 55
<211> LENGTH: 2655
<212> TYPE: DNA
<213> ORGANISM: Homo sapiens

<400> SEQUENCE: 55

```
cccagaaggc cgcgggggt ggaccgccta agagggcgtg cgctcccgac atgccccgcg     60
gcgcgccatt aaccgccaga tttgaatcgc gggacccgtt ggcagaggtg gcggcggcgg    120
catgggtgcc ccgacgttgc ccctgcctg gcagcccttt ctcaaggacc accgcatctc    180
```

```
tacattcaag aactggccct tcttggaggg ctgcgcctgc accccggagc ggatggccga    240
ggctggcttc atccactgcc ccactgagaa cgagcccagc ttggcccagt gtttcttctg    300
cttcaaggag ctggaaggct gggagccaga tgacgacccc atagaggaac ataaaaagca    360
ttcgtccggt tgcgctttcc tttctgtcaa gaagcagttt gaagaattaa cccttggtga    420 attttgaaa ctggacagag aaagagccaa gaacaaaatt gcaaggaaa ccaacaataa      480 gaagaaagaa tttgaggaaa ctgcggagaa agtgcgccgt gccatcgagc agctggctgc    540
catggattga ggcctctggc cggagctgcc tggtcccaga gtggctgcac cacttccagg    600
gtttattccc tggtgccacc agccttcctg tgggcccctt agcaatgtct taggaaagga    660
gatcaacatt ttcaaattag atgtttcaac tgtgctcttg ttttgtcttg aaagtggcac    720
cagaggtgct tctgcctgtg cagcgggtgc tgctggtaac agtggctgct tctctctctc    780
tctctctttt ttgggggctc attttgctg ttttgattcc cgggcttacc aggtgagaag    840
tgagggagga agaaggcagt gtcccttttg ctagagctga cagctttgtt cgcgtgggca    900
gagccttcca cagtgaatgt gtctggacct catgttgttg aggctgtcac agtcctgagt    960
gtggacttgg caggtgcctg ttgaatctga gctgcaggtt ccttatctgt cacacctgtg    1020
cctcctcaga ggacagtttt tttgttgttg tgtttttttg tttttttttt tttggtagat    1080
gcatgacttg tgtgtgatga gagaatggag acagagtccc tggctcctct actgtttaac    1140
aacatggctt tcttattttg tttgaattgt taattcacag aatagcacaa actacaatta    1200
aaactaagca caaagccatt ctaagtcatt ggggaaacgg ggtgaacttc aggtggatga    1260
ggagacagaa tagagtgata ggaagcgtct ggcagatact ccttttgcca ctgctgtgtg    1320
attagacagg cccagtgagc cgcggggcac atgctggccg ctcctccctc agaaaaaggc    1380
agtggcctaa atccttttta aatgacttgg ctcgatgctg tggggactg gctgggctgc     1440 tgcaggccgt gtgtctgtca gcccaacctt cacatctgtc acgttctcca cacgggggag    1500
agacgcagtc cgcccaggtc cccgctttct ttggaggcag cagctcccgc agggctgaag    1560
tctggcgtaa gatgatggat ttgattcgcc ctcctccctg tcatagagct gcagggtgga    1620
ttgttacagc ttcgctggaa acctctggag gtcatctcgg ctgttcctga gaaataaaaa    1680
gcctgtcatt tcaaacactg ctgtggaccc tactgggttt ttaaaatatt gtcagttttt    1740
catcgtcgtc cctagcctgc caacagccat ctgcccagac agccgcagtg aggatgagcg    1800
tcctggcaga gacgcagttg tctctgggcg cttgccagag ccacgaaccc cagacctgtt    1860
tgtatcatcc gggctccttc cgggcagaaa caactgaaaa tgcacttcag acccactat    1920 ttctgccaca tctgagtcgg cctgagatag acttttccct ctaaactggg agaatatcac    1980
agtggttttt gttagcagaa aatgcactcc agcctctgta tcatctaag ctgcttattt     2040 ttgatatttg tgtcagtctg taaatggata cttcactta ataactgttg cttagtaatt     2100
ggctttgtag agaagctgga aaaaatggt tttgtcttca actcctttgc atgccaggcg     2160
gtgatgtgga tctcggcttc tgtgagcctg tgctgtgggc agggctgagc tggagccgcc    2220
cctctcagcc cgcctgccac ggcctttcct taaaggccat ccttaaaacc agaccctcat    2280
ggctaccagc acctgaaagc ttcctcgaca tctgttaata aagccgtagg cccttgtcta    2340
agtgcaaccg cctagacttt cttcagata catgtccaca tgtccatttt tcaggttctc     2400
taagttggag tggagtctgg gaagggttgt gaatgaggct tctgggctat gggtgaggtt    2460
ccaatggcag gttagagccc ctcgggccaa ctgccatcct ggaaagtaga gacagcagtg    2520
```

```
cccgctgccc agaagagacc agcaagccaa actggagccc ccattgcagg ctgtcgccat    2580
gtggaaagag taactcacaa ttgccaataa agtctcatgt ggttttatct aaaaaaaaaa    2640
aaaaaaaaaa aaaaa                                                     2655
```

<210> SEQ ID NO 56
<211> LENGTH: 142
<212> TYPE: PRT
<213> ORGANISM: Homo sapiens

<400> SEQUENCE: 56

```
Met Gly Ala Pro Thr Leu Pro Pro Ala Trp Gln Pro Phe Leu Lys Asp
 1               5                  10                  15

His Arg Ile Ser Thr Phe Lys Asn Trp Pro Phe Leu Glu Gly Cys Ala
            20                  25                  30

Cys Thr Pro Glu Arg Met Ala Glu Ala Gly Phe Ile His Cys Pro Thr
        35                  40                  45

Glu Asn Glu Pro Asp Leu Ala Gln Cys Phe Phe Cys Phe Lys Glu Leu
    50                  55                  60

Glu Gly Trp Glu Pro Asp Asp Asp Pro Ile Glu Glu His Lys Lys His
65                  70                  75                  80

Ser Ser Gly Cys Ala Phe Leu Ser Val Lys Lys Gln Phe Glu Glu Leu
                85                  90                  95

Thr Leu Gly Glu Phe Leu Lys Leu Asp Arg Glu Arg Ala Lys Asn Lys
            100                 105                 110

Ile Ala Lys Glu Thr Asn Asn Lys Lys Lys Glu Phe Glu Glu Thr Ala
        115                 120                 125

Glu Lys Val Arg Arg Ala Ile Glu Gln Leu Ala Ala Met Asp
    130                 135                 140
```

<210> SEQ ID NO 57
<211> LENGTH: 6492
<212> TYPE: DNA
<213> ORGANISM: Homo sapiens

<400> SEQUENCE: 57

```
tttctgtgaa gcagaagtct gggaatcgat ctggaaatcc tcctaatttt tactccctct     60
ccccgcgact cctgattcat tgggaagttt caaatcagct ataactggag agtgctgaag    120
attgatggga tcgttgcctt atgcatttgt tttggtttta caaaaggaa acttgacaga     180 ggatcatgct gtacttaaaa aatacaacat cacagaggaa gtagactgat attaacaata    240
cttactaata ataacgtgcc tcatgaaata agatccgaa aggaattgga ataaaaattt      300
cctgcatctc atgccaaggg ggaaacacca gaatcaagtg ttccgcgtga ttgaagacac    360
cccctcgtcc aagaatgcaa agcacatcca ataaaatagc tggattataa ctcctcttct    420
ttctctgggg gccgtggggt gggagctggg gcgagaggtg ccgttggccc ccgttgcttt    480
tcctctggga aggatggcgc acgctgggag aacagggtac gataaccggg agatagtgat    540
gaagtacatc cattataagc tgtcgcagag gggctacgag tgggatgcgg gagatgtggg    600
cgccgcgccc ccgggggccg ccccgcacc gggcatcttc tcctcccagc ccgggcacac    660
gccccatcca gccgcatccc gggacccggt cgccaggacc tcgccgctgc agaccccggc    720 tgccccggc gccgccgcgg ggcctgcgct cagcccggtg ccacctgtgg tccacctgac    780
cctccgccag gccggcgacg acttctcccg ccgctaccgc gcgacttcg ccagagatgtc    840 cagccagctg cacctgacgc ccttcaccgc gcggggacgc tttgccacgg tggtgggagga   900
```

-continued

```
gctcttcagg gacggggtga actggggag gattgtggcc ttctttgagt tcggtggggt    960
catgtgtgtg gagagcgtca accgggagat gtcgccctg gtggacaaca tcgccctgtg   1020
gatgactgag tacctgaacc ggcacctgca cacctggatc caggataacg gaggctggga   1080
tgcctttgtg gaactgtacg gccccagcat gcggcctctg tttgatttct cctggctgtc   1140
tctgaagact ctgctcagtt tggccctggt gggagcttgc atcaccctgg gtgcctatct   1200
gggccacaag tgaagtcaac atgcctgccc caaacaaata tgcaaaaggt tcactaaagc   1260
agtagaaata atatgcattg tcagtgatgt accatgaaac aaagctgcag gctgtttaag   1320
aaaaaataac acacatataa acatcacaca cacagacaga cacacacaca caacaatt    1380 aacagtcttc aggcaaaacg tcgaatcagc tatttactgc caagggaaa tatcatttat   1440 ttttacatt attaagaaaa aaagatttat ttatttaaga cagtcccatc aaaactcctg    1500
tctttggaaa tccgaccact aattgccaag caccgcttcg tgtggctcca cctggatgtt   1560
ctgtgcctgt aaacatagat tcgctttcca tgttgttggc cggatcacca tctgaagagc   1620
agacggatgg aaaaaggacc tgatcattgg ggaagctggc tttctggctg ctggaggctg   1680
gggagaaggt gttcattcac ttgcatttct ttgccctggg ggctgtgata ttaacagagg   1740
gagggttcct gtggggggaa gtccatgcct ccctggcctg aagaagagac tctttgcata   1800
tgactcacat gatgcatacc tggtgggagg aaaagagttg ggaacttcag atggacctag   1860
tacccactga gatttccacg ccgaaggaca gcgatgggaa aaatgcccctt aaatcatagg   1920 aaagtatttt tttaagctac caattgtgcc gagaaaagca ttttagcaat ttatacaata   1980
tcatccagta ccttaagccc tgattgtgta tattcatata ttttggatac gcaccccca   2040 actcccaata ctggctctgt ctgagtaaga acagaatcc tctggaactt gaggaagtga   2100
acatttcggt gacttccgca tcaggaaggc tagagttacc cagagcatca ggccgccaca   2160
agtgcctgct tttaggagac cgaagtccgc agaacctgcc tgtgtcccag cttggaggcc   2220
tggtcctgga actgagccgg ggccctcact ggcctcctcc agggatgatc aacagggcag   2280
tgtggtctcc gaatgtctgg aagctgatgg agctcagaat tccactgtca agaaagagca   2340
gtagaggggt gtggctgggc ctgtcaccct ggggccctcc aggtaggccc gttttcacgt   2400
ggagcatggg agccacgacc cttcttaaga catgtatcac tgtagaggga aggaacagag   2460
gccctgggcc cttcctatca gaaggacatg gtgaaggctg ggaacgtgag gagaggcaat   2520
ggccacggcc cattttggct gtagcacatg gcacgttggc tgtgtggcct tggcccacct   2580
gtgagtttaa agcaaggctt taaatgactt tggagagggt cacaaatcct aaaagaagca   2640
ttgaagtgag gtgtcatgga ttaattgacc cctgtctatg gaattacatg taaaacatta   2700
tcttgtcact gtagtttggt tttatttgaa aacctgacaa aaaaaagtt ccaggtgtgg   2760 aatatggggg ttatctgtac atcctggggc attaaaaaaa aatcaatgg tggggaacta   2820 taaagaagta acaaaagaag tgacatcttc agcaaataaa ctaggaaatt tttttttctt   2880
ccagtttaga atcagccttg aaacattgat ggaataactc tgtggcatta ttgcattata   2940
taccatttat ctgtattaac tttggaatgt actctgttca atgtttaatg ctgtggttga   3000
tatttcgaaa gctgctttaa aaaaatacat gcatctcagc gttttttgt ttttaattgt    3060 atttagttat ggcctataca ctatttgtga gcaaggtga tcgttttctg tttgagattt    3120
ttatctcttg attcttcaaa agcattctga gaaggtgaga taagccctga gtctcagcta   3180
cctaagaaaa acctggatgt cactggccac tgaggagctt tgtttcaacc aagtcatgtg   3240
catttccacg tcaacagaat tgtttattgt gacagttata tctgttgtcc ctttgacctt   3300
```

```
gtttcttgaa ggtttcctcg tccctgggca attccgcatt taattcatgg tattcaggat    3360
tacatgcatg tttggttaaa cccatgagat tcattcagtt aaaaatccag atggcaaatg    3420
accagcagat tcaaatctat ggtggtttga cctttagaga gttgctttac gtggcctgtt    3480
tcaacacaga cccacccaga gccctcctgc cctccttccg cggggcttt ctcatggctg     3540 tccttcaggg tcttcctgaa atgcagtggt gcttacgctc caccaagaaa gcaggaaacc    3600
tgtggtatga agccagacct ccccggcggg cctcagggaa cagaatgatc agacctttga    3660
atgattctaa tttttaagca aaatattatt ttatgaaagg tttacattgt caaagtgatg    3720
aatatggaat atccaatcct gtgctgctat cctgccaaaa tcattttaat ggagtcagtt    3780
tgcagtatgc tccacgtggt aagatcctcc aagctgcttt agaagtaaca atgaagaacg    3840
tggacgtttt taatataaag cctgttttgt cttttgttgt tgttcaaacg ggattcacag    3900
agtatttgaa aaatgtatat atattaagag gtcacggggg ctaattgctg gctggctgcc    3960
ttttgctgtg gggttttgtt acctggtttt aataacagta aatgtgccca gcctcttggc    4020
cccagaactg tacagtattg tggctgcact tgctctaaga gtagttgatg ttgcattttc    4080
cttattgtta aaaacatgtt agaagcaatg aatgtatata aaagcctcaa ctagtcattt    4140
ttttctcctc ttctttttt tcattatatc taattatttt gcagttgggc aacagagaac     4200
catccctatt ttgtattgaa gagggattca catctgcatc ttaactgctc tttatgaatg    4260
aaaaaacagt cctctgtatg tactcctctt tacactggcc agggtcagag ttaaatagag    4320
tatatgcact ttccaaattg gggacaaggg ctctaaaaaa agccccaaaa ggagaagaac    4380
atctgagaac ctcctcggcc ctcccagtcc ctcgctgcac aaatactccg caagagaggc    4440
cagaatgaca gctgacaggg tctatggcca tcgggtcgtc tccgaagatt tggcagggggc   4500 agaaaactct ggcaggctta agatttggaa taaagtcaca gaattaagga agcacctcaa    4560
tttagttcaa acaagacgcc aacattctct ccacagctca cttacctctc tgtgttcaga    4620
tgtggccttc catttatatg tgatctttgt tttattagta aatgcttatc atctaaagat    4680
gtagctctgg cccagtggga aaaattagga agtgattata atcgagagg agttataata     4740 atcaagatta aatgtaaata atcagggcaa tcccaacaca tgtctagctt tcacctccag    4800
gatctattga gtgaacagaa ttgcaaatag tctctatttg taattgaact tatcctaaaa    4860
caaatagttt ataaatgtga acttaaactc taattaattc caactgtact tttaaggcag    4920
tggctgtttt tagactttct tatcacttat agttagtaat gtacacctac tctatcagag    4980
aaaaacagga aaggctcgaa atacaagcca ttctaaggaa attagggagt cagttgaaat    5040
tctattctga tcttattctg tggtgtcttt tgcagcccag acaaatgtgg ttacacactt    5100
tttaagaaat acaattctac attgtcaagc ttatgaaggt tccaatcaga tctttattgt    5160
tattcaattt ggatctttca gggatttttt ttttaaatta ttatgggaca aggacatttt    5220
gttggagggg tgggagggag gaagaatttt taaatgtaaa acattcccaa gtttggatca    5280
gggagttgga agttttcaga ataaccagaa ctaagggtat gaaggacctg tattgggggtc   5340 gatgtgatgc ctctgcgaag aaccttgtgt gacaaatgag aaacattttg aagtttgtgg    5400
tacgaccttt agattccaga gacatcagca tggctcaaag tgcagctccg tttggcagtg    5460
caatggtata aatttcaagc tggatatgtc taatgggtat ttaaacaata aatgtgcagt    5520
tttaactaac aggatattta atgacaacct tctggttggt agggacatct gtttctaaat    5580
gtttattatg tacaatacag aaaaaaattt tataaaatta agcaatgtga aactgaattg    5640
```

```
gagagtgata atacaagtcc tttagtctta cccagtgaat cattctgttc catgtctttg    5700
gacaaccatg accttggaca atcatgaaat atgcatctca ctggatgcaa agaaaatcag    5760
atggagcatg aatggtactg taccggttca tctggactgc cccagaaaaa taacttcaag    5820
caaacatcct atcaacaaca aggttgttct gcataccaag ctgagcacag aagatgggaa    5880
cactggtgga ggatggaaag gctcgctcaa tcaagaaaat tctgagacta ttaataaata    5940
agactgtagt gtagatactg agtaaatcca tgcacctaaa ccttttggaa aatctgccgt    6000
gggccctcca gatagctcat ttcattaagt ttttccctcc aaggtagaat ttgcaagagt    6060
gacagtggat tgcatttctt ttggggaagc tttcttttgg tggttttgtt tattataccct   6120 tcttaagttt tcaaccaagg tttgcttttg ttttgagtta ctggggttat ttttgtttta    6180
aataaaaata agtgtacaat aagtgttttt gtattgaaag cttttgttat caagattttc    6240
atacttttac cttccatggc tcttttttaag attgatactt ttaagaggtg gctgatattc   6300
tgcaacactg tacacataaa aaatacggta aggatacttt acatggttaa ggtaaagtaa    6360
gtctccagtt ggccaccatt agctataatg gcactttgtt tgtgttgttg gaaaagtca    6420 cattgccatt aaactttcct tgtctgtcta gttaatattg tgaagaaaaa taaagtacag    6480
tgtgagatac tg                                                       6492
```

<210> SEQ ID NO 58
<211> LENGTH: 239
<212> TYPE: PRT
<213> ORGANISM: Homo sapiens

<400> SEQUENCE: 58

```
Met Ala His Ala Gly Arg Thr Gly Tyr Asp Asn Arg Glu Ile Val Met
 1               5                  10                  15

Lys Tyr Ile His Tyr Lys Leu Ser Gln Arg Gly Tyr Glu Trp Asp Ala
            20                  25                  30

Gly Asp Val Gly Ala Ala Pro Pro Gly Ala Ala Pro Ala Pro Gly Ile
        35                  40                  45

Phe Ser Ser Gln Pro Gly His Thr Pro His Pro Ala Ala Ser Arg Asp
    50                  55                  60

Pro Val Ala Arg Thr Ser Pro Leu Gln Thr Pro Ala Ala Pro Gly Ala
65                  70                  75                  80

Ala Ala Gly Pro Ala Leu Ser Pro Val Pro Pro Val Val His Leu Thr
                85                  90                  95

Leu Arg Gln Ala Gly Asp Asp Phe Ser Arg Arg Tyr Arg Arg Asp Phe
            100                 105                 110

Ala Glu Met Ser Ser Gln Leu His Leu Thr Pro Phe Thr Ala Arg Gly
        115                 120                 125

Arg Phe Ala Thr Val Val Glu Glu Leu Phe Arg Asp Gly Val Asn Trp
    130                 135                 140

Gly Arg Ile Val Ala Phe Phe Glu Phe Gly Gly Val Met Cys Val Glu
145                 150                 155                 160

Ser Val Asn Arg Glu Met Ser Pro Leu Val Asp Asn Ile Ala Leu Trp
                165                 170                 175

Met Thr Glu Tyr Leu Asn Arg His Leu His Thr Trp Ile Gln Asp Asn
            180                 185                 190
```

| | | | | | | | | | | | | | | |
|---|---|---|---|---|---|---|---|---|---|---|---|---|---|---|
| Gly | Gly | Trp | Asp | Ala | Phe | Val | Glu | Leu | Tyr | Gly | Pro | Ser | Met | Arg | Pro |
| | | 195 | | | | | 200 | | | | | 205 | | | |
| Leu | Phe | Asp | Phe | Ser | Trp | Leu | Ser | Leu | Lys | Thr | Leu | Leu | Ser | Leu | Ala |
| | | 210 | | | | | 215 | | | | | 220 | | | |
| Leu | Val | Gly | Ala | Cys | Ile | Thr | Leu | Gly | Ala | Tyr | Leu | Gly | His | Lys | |
| 225 | | | | | 230 | | | | | 235 | | | | | |